(12) United States Patent
Shukla et al.

(10) Patent No.: US 9,163,001 B2
(45) Date of Patent: Oct. 20, 2015

(54) SUBSTITUTED CHROMAN COMPOUNDS AS CALCIUM SENSING RECEPTOR MODULATORS

(71) Applicant: LUPIN LIMITED, Mumbai, Maharashtra (IN)

(72) Inventors: Manojkumar Ramprasad Shukla, Pune (IN); Ankush Gangaram Sarde, Pune (IN); Rajeshkumar Maganlal Loriya, Pune (IN); Vipul Dilip Pachpute, Pune (IN); Navnath Bajirao Walke, Pune (IN); Talha Hussain Khan, Pune (IN); Sanjeev Anant Kulkarni, Pune (IN); Venkata P. Palle, Pune (IN); Rajender Kumar Kamboj, Pune (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/380,632

(22) PCT Filed: Feb. 22, 2013

(86) PCT No.: PCT/IB2013/051445
§ 371 (c)(1),
(2) Date: Aug. 22, 2014

(87) PCT Pub. No.: WO2013/124828
PCT Pub. Date: Aug. 29, 2013

(65) Prior Publication Data
US 2015/0038546 A1   Feb. 5, 2015

(30) Foreign Application Priority Data

Feb. 24, 2012 (IN) .............................. 178/KOL/2012
Sep. 7, 2012 (IN) .......................... 1030/KOL/2012

(51) Int. Cl.
| | | |
|---|---|---|
| C07D 311/58 | (2006.01) | |
| A61K 31/353 | (2006.01) | |
| C07D 405/10 | (2006.01) | |
| A61K 31/4025 | (2006.01) | |

(52) U.S. Cl.
CPC ............ *C07D 311/58* (2013.01); *A61K 31/353* (2013.01); *A61K 31/4025* (2013.01); *C07D 405/10* (2013.01)

(58) Field of Classification Search
None
See application file for complete search history.

(56) References Cited

U.S. PATENT DOCUMENTS

| | | |
|---|---|---|
| 2003/0199497 A1 | 10/2003 | Rual et al. |
| 2011/0028452 A1 | 2/2011 | Didivk et al. |

FOREIGN PATENT DOCUMENTS

| | | |
|---|---|---|
| WO | WO 02/12181 A1 | 2/2002 |
| WO | WO 2004/069793 A2 | 8/2004 |
| WO | WO 2004/106280 A1 | 12/2004 |
| WO | WO 2006/123725 A1 | 11/2006 |
| WO | WO 2007/123941 A2 | 11/2007 |
| WO | WO 2008/059854 A1 | 5/2008 |
| WO | WO 2009/065406 A2 | 5/2009 |
| WO | WO 2010/038895 A1 | 4/2010 |
| WO | WO 2010/042642 A | 4/2010 |
| WO | WO 2010/136037 A1 | 12/2010 |
| WO | WO 2010/150837 A1 | 12/2010 |
| WO | WO 2012/069402 A1 | 5/2012 |
| WO | WO 2012/069419 A1 | 5/2012 |
| WO | WO 2012/069421 A1 | 5/2012 |
| WO | WO 2012/120476 A1 | 9/2012 |
| WO | WO 2012/127385 A1 | 9/2012 |
| WO | WO 2012/127388 A1 | 9/2012 |

OTHER PUBLICATIONS

International Search Report for corresponding International Patent Application No. PC/IB2013/051445 mailed May 23, 2013.
Kiefer, L. et al. "Design and synthesis of cyclic sulfonamides and sulfamates as new calcium sensing receptor agonists", *Bioorganic & Medicinal Chemistry Letters*, 20(24): 7483-7487 (2010).
Kiefer, L. et al. "Novel calcium sensing receptor ligands: a patent survey", *Expert Opin. Ther. Patents*, 681-698 (2011).
Thalén, L. et al. "A Chemoenzymatic Approach to Enantiomerically Pure Amines Using Dynamic Kinetic Resolution: Application to the Synthesis of Norsertraline", *Chem. Eur. J.*, 15: 3403-3410 (2009).
Kessler, A. et al. "$N^1$-Benzoyl-$N^2$-[1-naphthyl)ethyl]-*trans*-1,2-diaminocyclohexanes: Development of 4-Chlorophenylcarboxamide (Calhex 231) as a New Calcium Sensing Receptor Ligand Demonstrating Potent Calcilytic Activity", *J. Med. Chem.*, 49: 5119-5128 (2006).

Primary Examiner — Michael Barker
(74) Attorney, Agent, or Firm — Merchant & Gould P.C.

(57) ABSTRACT

The present invention provides calcium sensing receptor modulators (CaSR). In particular, the compounds described herein are useful for treating, managing, and/or lessening the severity of diseases, disorders, syndromes and/or conditions associated with the modulation of calcium sensing receptors (CaSR). The invention also provides herein the pharmaceutical compositions thereof, and methods for treating, managing, and/or lessening the severity of diseases, disorders, syndromes and/or conditions associated with the modulation of CaSR. The invention also relates to process for the preparation of the compounds of the invention.

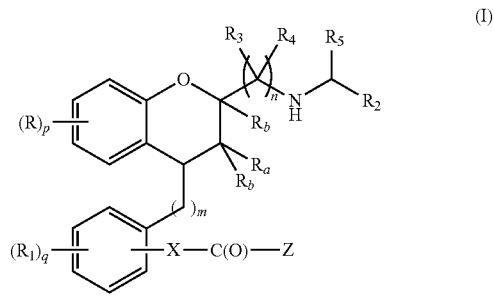

29 Claims, No Drawings

SUBSTITUTED CHROMAN COMPOUNDS AS CALCIUM SENSING RECEPTOR MODULATORS

RELATED APPLICATIONS

The present application is a National Stage Application of PCT/IB2013/051445, filed Feb. 22, 2013, which claims the benefit of priority to Indian Provisional Patent Application Nos. 0178/KOL/2012, filed on Feb. 24, 2012 and 1030/KOL/2012, filed on Sep. 7, 2012. The entire provisional specifications are incorporated herein by reference. To the extent appropriate, a claim of priority is made to each of the above disclosed applications.

FIELD OF THE INVENTION

The present invention relates to substituted chroman compounds, pharmaceutically acceptable salts thereof and pharmaceutical compositions for the treatment, management, and/or lessening the severity of diseases, disorders, syndromes or conditions associated with the modulation of calcium sensing receptors (CaSR). The invention also relates to methods of treating, managing and/or lessening the severity of diseases disorders, syndromes or conditions associated with the modulation of calcium sensing receptors (CaSR). The invention also relates to processes for the preparation of the compounds of the invention.

BACKGROUND OF THE INVENTION $Ca^{2+}$ is known to be an intracellular second messenger, with the molecular identification of an extracellular calcium sensing receptor (CaSR), it has further opened the possibility that $Ca^{2+}$ might also function as a messenger outside the cells. Information about the local changes in extracellular concentration of $Ca^{2+}$ is conveyed to the interior of many types of cells through this unique receptor.

Calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily Structurally, CaSR has an exceptionally large amino-terminal extracellular (ECD) domain (about 600 amino acids), a feature that is shared by all of the members of the family C GPCRs.

In mammals, the expression of CaSR is quite ubiquitous and its presence in the parathyroid gland plays an important role in the secretion of parathyroid hormone (PTH). The reduction in serum calcium leads to the secretion of PTH. Consequently, PTH secretion leads to conservation of serum $Ca^{2+}$ by increasing kidney retention and intestinal absorption of $Ca^{2+}$. This happens indirectly through the PTH-induced synthesis of the active vitamin D metabolite, 25-dihydroxyvitamin D. In addition, the pulsatile action of PTH has anabolic effects on bone development and its sustained levels can lead to catabolic effects, in which the bones breakdown releasing $Ca^{2+}$ as in the case of osteoporosis. All these systems converge in maintenance of baseline serum $Ca^{2+}$ and it involves a tight regulation between serum PTH and extracellular calcium which is mediated by the remarkable receptor CaSR.

In conditions such as primary and secondary hyperparathyroidism, there is excessive secretion of parathyroid hormone due to hyperplasia of the glands. The most common cause of primary hyperparathyroidism (PHPT) is parathyroid adenoma resulting from clonal mutations (~97%) and associated hypercalcemia. In the case of secondary hyperparathyroidism (SHPT), it is most commonly seen in patients with chronic renal failure. The kidneys fail to convert enough vitamin D to its active form and also does not adequately excrete phosphorous. Excess phosphorous further depletes serum calcium forming calcium phosphate (kidney stones) leading to hypocalcemia.

Small molecules that are positive allosteric modulators called calcimimetics modulate and improve the receptors sensitivity to the already existing milieu of extracellular ionic calcium. This would eventually translate in lowering plasma PTH levels thereby improving conditions of hyperparathyroidism, calcium homeostasis and bone metabolism. WO 2012/127388, WO 2012/120476, WO 2012/127385, WO 2012/069421, WO 2012/069419, WO 2012/069402, US 2011/0028452, WO 2010/150837, WO 2010/136037, WO 2010/042642, WO 2010/038895, WO 2009/065406, WO 2008/059854, WO 2006/123725, WO 2004/106280, WO 2004/069793, WO 2002/012181 and US 2003/0199497 applications disclose the compounds related to calcium sensing receptors (CaSR) for the treatment of various diseases mediated by CaSR. And also J. Med. Chem. (2006), 49, 5119-5128 discloses the compounds related to calcium sensing receptors (CaSR).

SUMMARY OF THE INVENTION

In accordance with one aspect, the invention provides compounds having the structure of Formula (I),

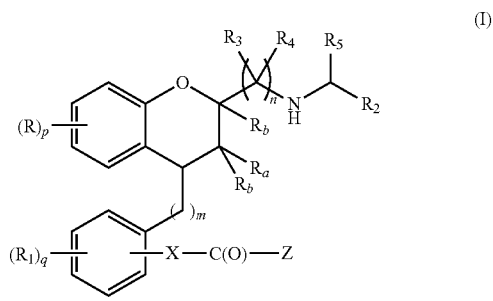

wherein, $R_a$ is selected from hydrogen, halogen, substituted or unsubstituted alkyl, cyano, substituted or unsubstituted cycloalkyl and substituted or unsubstituted haloalkyl;

$R_b$, which may be same or different at each occurrence, is independently selected from hydrogen, halogen, substituted or unsubstituted alkyl, substituted or unsubstituted cycloalkyl and substituted or unsubstituted haloalkyl;

R, which may be same or different at each occurrence, is independently selected from halogen, hydroxy, substituted or unsubstituted alkyl, substituted or unsubstituted haloalkyl, substituted or unsubstituted alkenyl, substituted or unsubstituted alkynyl, substituted or unsubstituted cycloalkyl, $OR_6$, nitro, cyano, —C(O)OR$_6$, —(CH$_2$)$_r$—C(O)OR$_6$, —O—C(O)OR$_6$, —O(CH$_2$)$_r$—C(O)OR$_6$, —NR$_7$R$_8$, —(CH$_2$)$_r$NR$_7$R$_8$—, —C(O)R$_9$, —C(O)NR$_7$R$_8$, —(CH$_2$)$_r$—C(O)NR$_7$R$_8$, —NR$_7$C(O)R$_9$, —S(O)$_{0-2}$R$_6$, —S(O)$_2$NR$_7$R$_8$, and —NR$_7$S(O)$_2$R$_9$;

X is selected from a bond, —(CR$_c$R$_d$)$_r$—, —O—, —NR$_7$—, —NR$_7$(CR$_c$R$_d$)$_r$—, —O(CR$_c$R$_d$)$_r$—, —C(O)NR$_7$—, —C(O)NR$_7$(CR$_c$R$_d$)$_r$—, —(CR$_c$R$_d$)$_r$NR$_7$(CR$_c$R$_d$)$_r$—, —(CR$_c$R$_d$)$_r$cycloalkylene-, cycloalkylene, -cycloalkylene(CR$_c$R$_d$)$_r$— and —O-cycloalkylene where cycloalkylene may be substituted or unsubstituted;

$R_c$ and $R_d$, which may be same or different at each occurrence, are independently selected from hydrogen, halogen, hydroxy, cyano, nitro, substituted or unsubstituted alkyl, substituted or unsubstituted haloalkyl and substituted or unsubstituted cycloalkyl; or $R_c$ and $R_d$, together with the carbon atom to which they are attached, may form a substituted or unsubstituted 3 to 7 membered saturated carbocyclic ring;

Z is $-OR_6$ or $-NR_{10}R_{11}$;

$R_1$, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, substituted or unsubstituted cycloalkyl, $-OR_6$, $-C(O)R_9$, $-NR_7R_8$, $-(CH_2)_r-NR_7R_8-$, $-(CH_2)_r-C(O)OR_6$, $-O-C(O)OR_6$, $-O(CH_2)_r-C(O)OR_6$, $-C(O)NR_7R_8$, $-(CH_2)_r-C(O)NR_7R_8$, $-NR_7C(O)R_9$, $-S(O)_{0-2}R_7$, $-S(O)_2NR_7R_8$ and $-NR_7S(O)_2R_9$;

$R_2$ is selected from substituted or unsubstituted aryl, substituted or unsubstituted heteroaryl and substituted or unsubstituted heterocyclyl;

$R_3$ and $R_4$ may be same or different and are independently selected from hydrogen, halogen, substituted or unsubstituted alkyl, substituted or unsubstituted haloalkyl, substituted or unsubstituted alkenyl, substituted or unsubstituted alkynyl, substituted or unsubstituted alkoxy, substituted or unsubstituted haloalkoxy and substituted or unsubstituted cycloalkyl;

$R_5$ is substituted or unsubstituted alkyl;

$R_6$, which may be same or different at each occurrence, is independently selected from hydrogen, substituted or unsubstituted alkyl, substituted or unsubstituted haloalkyl, substituted or unsubstituted alkenyl, substituted or unsubstituted alkynyl, and substituted or unsubstituted aryl;

$R_7$ and $R_8$, which may be same or different at each occurrence, are independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; or $R_7$ and $R_8$, together with the nitrogen atom to which they are attached, may form a substituted or unsubstituted, saturated or unsaturated 3 to 12 membered cyclic ring, wherein the unsaturated cyclic ring may have one or two double bonds;

at each occurrence, $R_9$ is substituted or unsubstituted alkyl or substituted or unsubstituted aryl;

$R_{10}$ and $R_{11}$ may be same or different and are independently selected from hydrogen, substituted or unsubstituted alkyl, substituted or unsubstituted alkenyl, substituted or unsubstituted alkynyl, $-(CR_cR_d)_r-C(O)OR_6$, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; or $R_{10}$ and $R_{11}$, together with the nitrogen atom to which they are attached, may form a substituted or unsubstituted, saturated or unsaturated 3 to 12 membered cyclic ring, wherein the unsaturated cyclic ring may have one or two double bonds;

'n' is an integer ranging from 1 to 3, both inclusive;
'm' is an integer ranging from 0 to 3, both inclusive;
'p' is an integer ranging from 0 to 4, both inclusive;
'q' is an integer ranging from 0 to 3, both inclusive; and
'r' is an integer ranging from 1 to 3, both inclusive;
or its pharmaceutically acceptable salt thereof.

According to one embodiment, there are provided compounds having the structure of Formula (II):

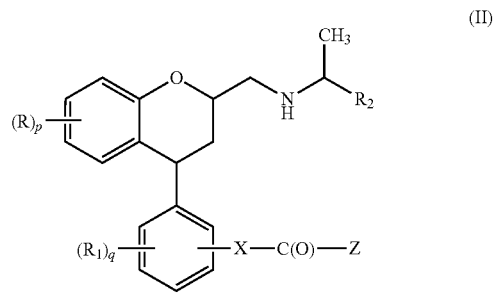

or its pharmaceutically acceptable salt thereof;
wherein,
$R_2$ is substituted or unsubstituted phenyl or substituted or unsubstituted naphthyl;
R, $R_1$, X, Z, 'p' and 'q' are as defined in Formula (I).

According to another embodiment, there are provided compounds having the structure of Formula (III):

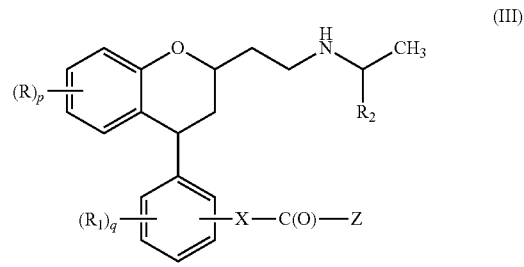

or its pharmaceutically acceptable salt thereof;
wherein,
$R_2$ is substituted or unsubstituted phenyl or substituted or unsubstituted naphthyl;
R, $R_1$, X, Z, 'p' and 'q' are as defined in Formula (I).

According to another embodiment, there are provided compounds having the structure of Formula (IV):

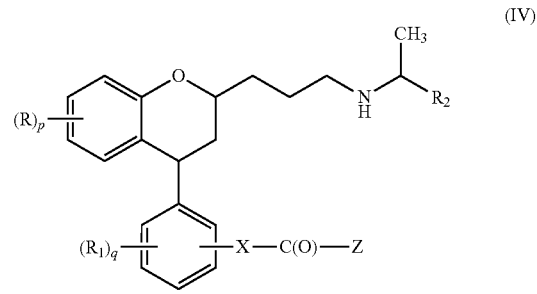

or its pharmaceutically acceptable salt thereof;
wherein,
$R_2$ is substituted or unsubstituted phenyl or substituted or unsubstituted naphthyl;
R, $R_1$, X, Z, 'p' and 'q' are as defined in Formula (I).

According to another embodiment, there are provided compounds having the structure of Formula (V):

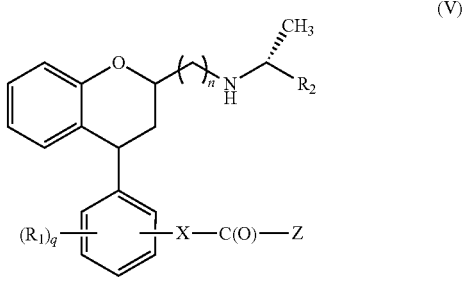

or its pharmaceutically acceptable salt thereof;
wherein,
$R_2$ is substituted or unsubstituted phenyl or substituted or unsubstituted naphthyl;
$R_1$, X, Z, 'n', and 'q' are as defined in Formula (I).

It should be understood that the Formula (I), Formula (II), Formula (III), Formula (IV) and Formula (V) structurally encompasses all tautomers, stereoisomers, enantiomers and diastereomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims.

According to another embodiment, there are provided compounds of Formula (I) in which 'n' is 1.

According to another embodiment, there are provided compounds of Formula (I) in which 'n' is 2.

According to another embodiment, there are provided compounds of Formula (I) in which 'n' is 3.

According to another embodiment, there are provided compounds of Formula (I), in which 'm' is 0.

According to another embodiment, there are provided compounds of Formula (I), in which 'p' is 0.

According to another embodiment, there are provided compounds of Formulae (I), (II), (III), (IV) and/or (V) in which $R_1$ is selected from halogen, substituted or unsubstituted alkyl, substituted or unsubstituted haloalkyl, substituted or unsubstituted cycloalkyl, cyano, —$OR_6$, —C(O)alkyl; wherein $R_6$ is hydrogen, substituted or unsubstituted alkyl, substituted or unsubstituted haloalkyl, or substituted or unsubstituted cycloalkyl; and 'q' is 0, 1, or 2.

According to another embodiment, there are provided compounds of Formulae (I), (II), (III), (IV) and/or (V) in which $R_2$ is substituted or unsubstituted aryl, wherein the aryl is substituted or unsubstituted phenyl or substituted or unsubstituted naphthyl. In this embodiment the substituent(s) on $R_2$ may be one or more and are independently selected from halogen, hydroxyl, substituted or unsubstituted alkyl, substituted or unsubstituted haloalkyl, and substituted or unsubstituted alkoxy.

According to another embodiment, there are provided compounds of Formulae (I), (II), (III), (IV) and/or (V) in which X is selected from a bond, —$(CR_cR_d)_r$—, —O—, —$NR_7$—, —$NR_7(CR_cR_d)_r$—, —$O(CR_cR_d)_r$—, —C(O)$NR_7$—, —C(O)$NR_7(CR_cR_d)_r$—, —$(CR_cR_d)_rNR_7(CR_cR_d)_r$—, —$(CR_cR_d)_r$cycloalkylene-, cycloalkylene, -cycloalkylene($CR_cR_d)_r$— and —O-cycloalkylene where cycloalkylene may be substituted or unsubstituted; $R_7$ is hydrogen or substituted or unsubstituted alkyl; $R_c$ and $R_d$ are hydrogen or substituted or unsubstituted alkyl and 'r' is 1, 2 or 3.

According to another embodiment, there are provided compounds of Formulae (I), (II), (III), (IV) and/or (V) in which Z is —$OR_6$ wherein $R_6$ is selected from hydrogen, substituted or unsubstituted alkyl, substituted or unsubstituted haloalkyl, substituted or unsubstituted aryl or substituted or unsubstituted arylalkyl.

According to another embodiment, there are provided compounds of Formulae (I), (II), (III), (IV) and/or (V) in which Z is $NR_{10}R_{11}$ wherein $R_{10}$ and $R_{11}$ may be same or different and are independently selected from hydrogen, substituted or unsubstituted alkyl, —$(CR_cR_d)_r$—C(O)OH, —$(CR_cR_d)_r$—C(O)O-alkyl, substituted or unsubstituted cycloalkyl, substituted or unsubstituted aryl or substituted or unsubstituted arylalkyl wherein $R_c$ and $R_d$ are hydrogen or substituted or unsubstituted alkyl and 'r' is 1, 2 or 3; or $R_{10}$ and $R_{11}$, together with the nitrogen atom to which they are attached, may form a saturated or unsaturated 3 to 12 membered cyclic ring, where the unsaturated cyclic ring may have one or two double bonds.

According to another embodiment, there are provided compounds of Formula (I) in which $R_a$ is hydrogen; $R_b$ is hydrogen; $R_1$ is selected from halogen, substituted or unsubstituted alkyl, substituted or unsubstituted haloalkyl, substituted or unsubstituted cycloalkyl, cyano, —$OR_6$, —C(O)alkyl wherein $R_6$ is hydrogen, substituted or unsubstituted alkyl, substituted or unsubstituted haloalkyl, or substituted or unsubstituted cycloalkyl; 'q' is 0, 1, or 2; $R_2$ is substituted or unsubstituted aryl; $R_3$ is hydrogen; $R_4$ is hydrogen; $R_5$ is substituted or unsubstituted alkyl; X is selected from a bond, —$(CR_cR_d)_r$—, —O—, —$NR_7$—, —$NR_7(CR_cR_d)_r$—, —$O(CR_cR_d)_r$—, —C(O)$NR_7$—, —C(O)$NR_7(CR_cR_d)_r$— wherein $R_7$ is hydrogen or substituted or unsubstituted alkyl, $R_c$ and $R_d$ are hydrogen or substituted or unsubstituted alkyl; and 'r' is 1, 2, or 3; Z is —$OR_6$ or $NR_{10}R_{11}$ wherein $R_6$ is selected from hydrogen, substituted or unsubstituted alkyl, substituted or unsubstituted haloalkyl, substituted or unsubstituted aryl or substituted or unsubstituted arylalkyl; $R_{10}$ and $R_{11}$ may be same or different and are independently selected from hydrogen, substituted or unsubstituted alkyl, —$(CR_cR_d)_r$—C(O)OH, —$(CR_cR_d)_r$—C(O)O-alkyl, substituted or unsubstituted cycloalkyl or $R_{10}$ and $R_{11}$ together may form a substituted or unsubstituted, saturated or unsaturated 3 to 12 membered cyclic ring, where the unsaturated cyclic ring may have one or two double bonds, 'n' is 1, 2 or 3; 'm' is 0 or 1; and 'p' is 0;

or its pharmaceutically acceptable salt thereof.

According to another embodiment, there are provided compounds of Formula (V) in which $R_1$ is selected from halogen, substituted or unsubstituted alkyl, substituted or unsubstituted haloalkyl, substituted or unsubstituted cycloalkyl, cyano, —$OR_6$, —C(O)alkyl wherein $R_6$ is hydrogen, substituted or unsubstituted alkyl, substituted or unsubstituted haloalkyl, or substituted or unsubstituted cycloalkyl; 'q' is 0, 1, or 2; $R_2$ is substituted or unsubstituted aryl; X is selected from a bond, —$(CR_cR_d)_r$—, —O—, —$NR_7$—, —$NR_7(CR_cR_d)_r$—, —$O(CR_cR_d)_r$—, —C(O)$NR_7$—, —C(O)$NR_7(CR_cR_d)_r$— wherein $R_7$ is hydrogen or substituted or unsubstituted alkyl, $R_c$ and $R_d$ are hydrogen or substituted or unsubstituted alkyl, 'r' is 1, 2, or 3; Z is —$OR_6$ or $NR_{10}R_{11}$ wherein $R_6$ is selected from hydrogen, substituted or unsubstituted alkyl, substituted or unsubstituted haloalkyl, substituted or unsubstituted aryl or substituted or unsubstituted arylalkyl; $R_{10}$ and $R_{11}$ are independently selected from hydrogen, substituted or unsubstituted alkyl, —$(CR_cR_d)_r$—C(O)OH, —$(CR_cR_d)_r$—C(O)O-alkyl, substituted or unsubstituted cycloalkyl or $R_{10}$ and $R_{11}$ together may form a substituted or unsubstituted, saturated or unsaturated 3 to 12 membered cyclic ring, where the unsaturated cyclic ring may have one or two double bonds, 'n' is 1, 2 or 3;
or its pharmaceutically acceptable salt thereof.

According to another embodiment, there are provided compounds of Formula (I) or pharmaceutically acceptable salt; wherein the pharmaceutically acceptable salt is hydrochloride salt.

According to another embodiment, there are provided compounds of Formula (I) structurally encompasses stereoisomers including enantiomers and diastereomers.

Below are the representative compounds, which are illustrative in nature only and are not intended to limit to the scope of the invention.

Methyl 2-fluoro-5-((2R,4R)-2-((((R)-1-(naphthalen-1-yl) ethyl)amino)methyl)chroman-4-yl)benzoate;
Methyl 2-fluoro-5-((2R,4S)-2-((((R)-1-(naphthalen-1-yl) ethyl)amino)methyl)chroman-4-yl)benzoate;
Methyl-3-((2R,4S)-2-((((R)-1-(naphthalen-1-yl)ethyl) amino)methyl)chroman-4-yl)benzoate;
Methyl 2-methyl-3-((2R,4S)-2-((((R)-1-(naphthalen-1-yl) ethyl)amino)methyl)chroman-4-yl)benzoate;
Methyl 3-methyl-5-((2R,4S)-2-((((R)-1-(naphthalen-1-yl) ethyl)amino)methyl)chroman-4-yl)benzoate;
Methyl 4-methyl-3-((2R,4S)-2-((((R)-1-(naphthalen-1-yl) ethyl)amino)methyl)chroman-4-yl)benzoate;
Methyl 2-ethyl-5-((2R,4R)-2-((((R)-1-(naphthalen-1-yl) ethyl)amino)methyl)chroman-4-yl)benzoate;
Methyl 2-ethyl-5-((2R,4S)-2-((((R)-1-(naphthalen-1-yl) ethyl)amino)methyl)chroman-4-yl)benzoate;
Methyl 2-isopropyl-5-((2R,4S)-2-((((R)-1-(naphthalen-1-yl) ethyl)amino)methyl)chroman-4-yl)benzoate;
Methyl 2-cyclopropyl-5-((2R,4R)-2-((((R)-1-(naphthalen-1-yl)ethyl)amino)methyl)chroman-4-yl)benzoate;
Methyl 2-cyclopropyl-5-((2R,4S)-2-((((R)-1-(naphthalen-1-yl)ethyl)amino)methyl)chroman-4-yl)benzoate;
Methyl 2,6-difluoro-3-((2R,4R)-2-((((R)-1-(naphthalen-1-yl)ethyl)amino)methyl)chroman-4-yl)benzoate;
Methyl 4-fluoro-2-methyl-3-((2R,4R)-2-((((R)-1-(naphthalen-1-yl)ethyl)amino) methyl)chroman-4-yl)benzoate;
Methyl 4-fluoro-2-methyl-3-((2R,4S)-2-((((R)-1-(naphthalen-1-yl)ethyl)amino) methyl)chroman-4-yl)benzoate;
Methyl 2,3-dimethyl-5-((2R,4S)-2-((((R)-1-(naphthalen-1-yl)ethyl)amino)methyl)chroman-4-yl)benzoate;
Methyl 5-((2R,4S)-2-((((R)-1-(naphthalen-1-yl)ethyl) amino)methyl)chroman-4-yl)-2-(trifluoromethyl)benzoate;
Methyl 2-methyl-5-((2R,4R)-2-((((R)-1-(naphthalen-1-yl) ethyl)amino)methyl)chroman-4-yl)benzoate;
Methyl 2-methyl-5-((2R,4S)-2-((((R)-1-(naphthalen-1-yl) ethyl)amino)methyl)chroman-4-yl)benzoate;
Methyl 2-fluoro-3-((2R,4R)-2-((((R)-1-(naphthalen-1-yl) ethyl)amino)methyl)chroman-4-yl)benzoate;
Methyl 3-fluoro-5-((2R,4S)-2-((((R)-1-(naphthalen-1-yl) ethyl)amino)methyl)chroman-4-yl)benzoate;
Methyl 4-fluoro-3-((2R,4R)-2-((((R)-1-(naphthalen-1-yl) ethyl)amino)methyl)chroman-4-yl)benzoate;
Methyl 2-methoxy-5-((2R,4S)-2-((((R)-1-(naphthalen-1-yl) ethyl)amino)methyl)chroman-4-yl)benzoate;
Methyl 2-methoxy-3-((2R,4R)-2-((((R)-1-(naphthalen-1-yl) ethyl)amino)methyl)chroman-4-yl)benzoate;
Methyl 2-methoxy-3-((2R,4S)-2-((((R)-1-(naphthalen-1-yl) ethyl)amino)methyl)chroman-4-yl)benzoate;
Methyl 4-methoxy-3-((2R,4R)-2-((((R)-1-(naphthalen-1-yl) ethyl)amino)methyl)chroman-4-yl)benzoate;
Methyl 2-(2-methyl-5-((2R,4S)-2-((((R)-1-(naphthalen-1-yl)ethyl)amino)methyl)chroman-4-yl)phenoxy)acetate;
Methyl 2-(3-methyl-5-((2R,4S)-2-((((R)-1-(naphthalen-1-yl)ethyl)amino)methyl)chroman-4-yl)phenoxy)acetate;
Methyl 2-(2-fluoro-5-((2R,4R)-2-((((R)-1-(naphthalen-1-yl) ethyl)amino)methyl)chroman-4-yl)phenoxy)acetate;
Methyl 2-(2-fluoro-5-((2R,4S)-2-((((R)-1-(naphthalen-1-yl) ethyl)amino)methyl)chroman-4-yl)phenoxy)acetate;
Methyl 2-(2-fluoro-3-((2R,4R)-2-((((R)-1-(naphthalen-1-yl) ethyl)amino)methyl)chroman-4-yl)phenoxy)acetate;
Methyl 2-(3-fluoro-5-((2R,4R)-2-((((R)-1-(naphthalen-1-yl) ethyl)amino)methyl)chroman-4-yl)phenoxy)acetate;
Methyl 2-(3-fluoro-5-((2R,4S)-2-((((R)-1-(naphthalen-1-yl) ethyl)amino)methyl)chroman-4-yl)phenoxy)acetate;
Methyl 2-(4-fluoro-3-((2R,4R)-2-((((R)-1-(naphthalen-1-yl) ethyl)amino)methyl)chroman-4-yl)phenoxy)acetate;
Methyl 2-methyl-2-(3-((2R,4S)-2-((((R)-1-(naphthalen-1-yl)ethyl)amino)methyl)chroman-4-yl)phenoxy)propanoate;
Methyl 4-((2R,4R)-2-((((R)-1-(naphthalen-1-yl)ethyl) amino)methyl)chroman-4-yl)benzoate;
Methyl 4-((2R,4S)-2-((((R)-1-(naphthalen-1-yl)ethyl) amino)methyl)chroman-4-yl)benzoate;
Methyl 2-methyl-4-((2R,4R)-2-((((R)-1-(naphthalen-1-yl) ethyl)amino)methyl)chroman-4-yl)benzoate;
Methyl 2-methyl-4-((2R,4S)-2-((((R)-1-(naphthalen-1-yl) ethyl)amino)methyl)chroman-4-yl)benzoate;
Methyl 4-((2R,4R)-2-((((R)-1-(naphthalen-1-yl)ethyl) amino)methyl)chroman-4-yl)-2-(trifluoromethyl)benzoate;
Methyl 4-((2R,4S)-2-((((R)-1-(naphthalen-1-yl)ethyl) amino)methyl)chroman-4-yl)-2-(trifluoromethyl)benzoate;
Methyl 2,6-difluoro-4-((2R,4S)-2-((((R)-1-(naphthalen-1-yl)ethyl)amino)methyl)chroman-4-yl)benzoate;
Methyl 3-methoxy-4-((2R,4R)-2-((((R)-1-(naphthalen-1-yl) ethyl)amino)methyl)chroman-4-yl)benzoate;
Methyl 3-methoxy-4-((2R,4S)-2-((((R)-1-(naphthalen-1-yl) ethyl)amino)methyl)chroman-4-yl)benzoate;
Methyl 3-fluoro-4-((2R,4R)-2-((((R)-1-(naphthalen-1-yl) ethyl)amino)methyl)chroman-4-yl)benzoate;
Methyl 2-fluoro-4-((2R,4S)-2-((((R)-1-(naphthalen-1-yl) ethyl)amino)methyl)chroman-4-yl)benzoate;
Methyl 2-(4-((2R,4R)-2-((((R)-1-(naphthalen-1-yl)ethyl) amino)methyl)chroman-4-yl)phenoxy)acetate;
Methyl 2-(4-((2R,4S)-2-((((R)-1-(naphthalen-1-yl)ethyl) amino)methyl)chroman-4-yl)phenoxy)acetate;
Methyl 2-(2-fluoro-4-((2R,4R)-2-((((R)-1-(naphthalen-1-yl) ethyl)amino)methyl)chroman-4-yl)phenoxy)acetate;
Methyl 2-(2-fluoro-4-((2R,4S)-2-((((R)-1-(naphthalen-1-yl) ethyl)amino)methyl)chroman-4-yl)phenoxy)acetate;
Methyl 2-(4-((2R,4R)-2-((((R)-1-(naphthalen-1-yl)ethyl) amino)methyl)chroman-4-yl)phenyl)acetate;
Methyl 2-(4-((2R,4S)-2-((((R)-1-(naphthalen-1-yl)ethyl) amino)methyl)chroman-4-yl)phenyl)acetate;
Methyl 2-methyl-2-(4-((2R,4R)-2-((((R)-1-(naphthalen-1-yl)ethyl)amino)methyl)chroman-4-yl)phenyl)propanoate;
Methyl 2-methyl-2-(4-((2R,4S)-2-((((R)-1-(naphthalen-1-yl)ethyl)amino)methyl)chroman-4-yl)phenyl)propanoate;
Methyl 3-methyl-4-((2R,4S)-2-((((R)-1-(naphthalen-1-yl) ethyl)amino)methyl)chroman-4-yl)benzoate;
Methyl 2-fluoro-5-((2S,4R)-2-((((R)-1-(naphthalen-1-yl) ethyl)amino)methyl)chroman-4-yl)benzoate;
Methyl 3-((2S,4R)-2-((((R)-1-(naphthalen-1-yl)ethyl) amino)methyl)chroman-4-yl)benzoate;
Methyl 2-methyl-5-((2S,4R)-2-((((R)-1-(naphthalen-1-yl) ethyl)amino)methyl)chroman-4-yl)benzoate;

Methyl 2-methyl-5-((2S,4S)-2-((((R)-1-(naphthalen-1-yl)ethyl)amino)methyl)chroman-4-yl)benzoate;
Methyl 2-(4-((2S,4R)-2-((((R)-1-(naphthalen-1-yl)ethyl)amino)methyl)chroman-4-yl)phenoxy)acetate;
Methyl 2-(4-((2S,4S)-2-((((R)-1-(naphthalen-1-yl)ethyl)amino)methyl)chroman-4-yl)phenoxy)acetate;
Methyl 5-((2R,4R)-2-((((R)-1-(4-fluoronaphthalen-1-yl)ethyl)amino)methyl)chroman-4-yl)-2-methylbenzoate;
Methyl 5-((2R,4S)-2-((((R)-1-(4-fluoronaphthalen-1-yl)ethyl)amino)methyl)chroman-4-yl)-2-methylbenzoate;
Methyl 3-((2R,4R)-2-((((R)-1-(4-fluoronaphthalen-1-yl)ethyl)amino)methyl)chroman-4-yl)-2-methoxybenzoate;
Methyl 3-((2R,4S)-2-((((R)-1-(4-fluoronaphthalen-1-yl)ethyl)amino)methyl)chroman-4-yl)-2-methoxybenzoate;
Methyl 4-((2R)-2-((((R)-1-(4-fluoro-3-methoxyphenyl)ethyl)amino)methyl)chroman-4-yl)-2-methylbenzoate;
Methyl 3-((2R)-2-((((R)-1-(4-fluoro-3-methoxyphenyl)ethyl)amino)methyl)chroman-4-yl)-2-methylbenzoate;
Methyl 5-((2R)-2-((((R)-1-(4-fluoro-3-methoxyphenyl)ethyl)amino)methyl)chroman-4-yl)-2-methylbenzoate;
Methyl 3-((2R)-2-((((R)-1-(4-fluoro-3-methoxyphenyl)ethyl)amino)methyl)chroman-4-yl)-5-methylbenzoate;
Methyl 3-((2R)-2-((((R)-1-(4-fluoro-3-methoxyphenyl)ethyl)amino)methyl)chroman-4-yl)-4-methylbenzoate;
Methyl 2-fluoro-5-((2S,4R)-2-(2-(((R)-1-(naphthalen-1-yl)ethyl)amino)ethyl)chroman-4-yl)benzoate;
Methyl 2-fluoro-5-((2R,4S)-2-(2-(((R)-1-(naphthalen-1-yl)ethyl)amino)ethyl)chroman-4-yl)benzoate;
Methyl 2-methyl-5-((2S,4R)-2-(2-(((R)-1-(naphthalen-1-yl)ethyl)amino)ethyl)chroman-4-yl)benzoate;
Methyl 2-methyl-5-((2R,4S)-2-(2-(((R)-1-(naphthalen-1-yl)ethyl)amino)ethyl)chroman-4-yl)benzoate;
Methyl 2-methoxy-3-((2R,4R)-2-(2-(((R)-1-(naphthalen-1-yl)ethyl)amino)ethyl)chroman-4-yl)benzoate;
Methyl 5-((2S,4R)-2-(2-(((R)-1-(4-fluoronaphthalen-1-yl)ethyl)amino)ethyl)chroman-4-yl)-2-methylbenzoate;
Methyl 5-((2R,4S)-2-(2-(((R)-1-(4-fluoronaphthalen-1-yl)ethyl)amino)ethyl)chroman-4-yl)-2-methylbenzoate;
Methyl 5-((2S,4R)-2-(2-(((R)-1-(4-fluoro-3-methoxyphenyl)ethyl)amino)ethyl)chroman-4-yl)-2-methylbenzoate;
Methyl 5-((2R,4S)-2-(2-(((R)-1-(4-fluoro-3-methoxyphenyl)ethyl)amino)ethyl)chroman-4-yl)-2-methylbenzoate;
Methyl 2-fluoro-5-((2S,4S)-2-(3-(((R)-1-(naphthalen-1-yl)ethyl)amino)propyl)chroman-4-yl)benzoate;
Methyl 2-fluoro-5-((2R,4R)-2-(3-(((R)-1-(naphthalen-1-yl)ethyl)amino)propyl)chroman-4-yl)benzoate;
Methyl 2-methyl-5-((2S,4S)-2-(3-(((R)-1-(naphthalen-1-yl)ethyl)amino)propyl)chroman-4-yl)benzoate;
Methyl 2-methyl-5-((2R,4R)-2-(3-(((R)-1-(naphthalen-1-yl)ethyl)amino)propyl)chroman-4-yl)benzoate;
Methyl 5-((2S,4S)-2-(3-(((R)-1-(4-fluoro-3-methoxyphenyl)ethyl)amino)propyl)chroman-4-yl)-2-methylbenzoate;
Methyl 4-((2S,4S)-2-(3-(((R)-1-(4-fluoronaphthalen-1-yl)ethyl)amino)propyl)chroman-4-yl)-3-methylbenzoate;
Methyl 4-((2S,4S)-2-(3-(((R)-1-(4-fluoronaphthalen-1-yl)ethyl)amino)propyl)chroman-4-yl)benzoate;
Methyl 5-((2S,4S)-2-(3-(((R)-1-(4-fluoronaphthalen-1-yl)ethyl)amino)propyl)chroman-4-yl)-2-methylbenzoate;
2,6-Dimethyl-3-((2R,4S)-2-((((R)-1-(naphthalen-1-yl)ethyl)amino)methyl)chroman-4-yl)benzoic acid hydrochloride;
2,6-Dimethyl-3-((2R,4S)-2-(2-(((R)-1-(naphthalen-1-yl)ethyl)amino)ethyl)chroman-4-yl)benzoic acid hydrochloride;
2,6-Dimethyl-3-((2R,4R)-2-(3-(((R)-1-(naphthalen-1-yl)ethyl)amino)propyl)chroman-4-yl)benzoic acid hydrochloride;
2,6-Dimethyl-3-((2S,4S)-2-(3-(((R)-1-(naphthalen-1-yl)ethyl)amino)propyl)chroman-4-yl)benzoic acid hydrochloride;
3-((2S,4S)-2-(3-(((R)-1-(4-Fluoro-3-methoxyphenyl)ethyl)amino)propyl)chroman-4-yl)-2,6-dimethylbenzoic acid hydrochloride;
2-Fluoro-5-((2R,4R)-2-((((R)-1-(naphthalen-1-yl)ethyl)amino)methyl)chroman-4-yl)benzoic acid hydrochloride;
2-Fluoro-5-((2R,4S)-2-((((R)-1-(naphthalen-1-yl)ethyl)amino)methyl)chroman-4-yl)benzoic acid hydrochloride;
3-((2R,4S)-2-((((R)-1-(Naphthalen-1-yl)ethyl)amino)methyl)chroman-4-yl)benzoic acid hydrochloride;
2-Methyl-3-((2R,4S)-2-((((R)-1-(naphthalen-1-yl)ethyl)amino)methyl)chroman-4-yl)benzoic acid hydrochloride;
3-Methyl-5-((2S,4S)-2-((((R)-1-(naphthalen-1-yl)ethyl)amino)methyl)chroman-4-yl)benzoic acid hydrochloride;
4-Methyl-3-((2S,4S)-2-((((R)-1-(naphthalen-1-yl)ethyl)amino)methyl)chroman-4-yl)benzoic acid hydrochloride;
2-Ethyl-5-((2R,4R)-2-((((R)-1-(naphthalen-1-yl)ethyl)amino)methyl)chroman-4-yl)benzoic acid hydrochloride;
2-Ethyl-5-((2R,4S)-2-((((R)-1-(naphthalen-1-yl)ethyl)amino)methyl)chroman-4-yl)benzoic acid hydrochloride;
2-Isopropyl-5-((2R,4S)-2-((((R)-1-(naphthalen-1-yl)ethyl)amino)methyl)chroman-4-yl)benzoic acid hydrochloride;
2-Cyclopropyl-5-((2R,4R)-2-((((R)-1-(naphthalen-1-yl)ethyl)amino)methyl)chroman-4-yl)benzoic acid hydrochloride;
2-Cyclopropyl-5-((2R,4S)-2-((((R)-1-(naphthalen-1-yl)ethyl)amino)methyl)chroman-4-yl)benzoic acid hydrochloride;
2,6-Difluoro-3-((2R,4R)-2-((((R)-1-(naphthalen-1-yl)ethyl)amino)methyl)chroman-4-yl)benzoic acid hydrochloride;
4-Fluoro-2-methyl-3-((2R,4S)-2-((((R)-1-(naphthalen-1-yl)ethyl)amino)methyl)chroman-4-yl)benzoic acid hydrochloride;
4-Fluoro-2-methyl-3-((2R,4R)-2-((((R)-1-(naphthalen-1-yl)ethyl)amino)methyl)chroman-4-yl)benzoic acid hydrochloride;
2,3-Dimethyl-5-((2R,4S)-2-((((R)-1-(naphthalen-1-yl)ethyl)amino)methyl)chroman-4-yl)benzoic acid hydrochloride;
5-((2R,4S)-2-((((R)-1-(Naphthalen-1-yl)ethyl)amino)methyl)chroman-4-yl)-2-(trifluoromethyl)benzoic acid hydrochloride;
2-Methyl-5-((2R,4R)-2-((((R)-1-(naphthalen-1-yl)ethyl)amino)methyl)chroman-4-yl)benzoic acid hydrochloride;
2-Methyl-5-((2R,4S)-2-((((R)-1-(naphthalen-1-yl)ethyl)amino)methyl)chroman-4-yl)benzoic acid hydrochloride;
2-Fluoro-3-((2R,4R)-2-((((R)-1-(naphthalen-1-yl)ethyl)amino)methyl)chroman-4-yl)benzoic acid hydrochloride;
3-Fluoro-5-((2R,4S)-2-((((R)-1-(naphthalen-1-yl)ethyl)amino)methyl)chroman-4-yl)benzoic acid hydrochloride;
4-Fluoro-3-((2R,4R)-2-((((R)-1-(naphthalen-1-yl)ethyl)amino)methyl)chroman-4-yl)benzoic acid hydrochloride;
2-Methoxy-5-((2R,4S)-2-((((R)-1-(naphthalen-1-yl)ethyl)amino)methyl)chroman-4-yl)benzoic acid hydrochloride;
2-Methoxy-3-((2R,4S)-2-((((R)-1-(naphthalen-1-yl)ethyl)amino)methyl)chroman-4-yl)benzoic acid hydrochloride;
2-Methoxy-3-((2R,4R)-2-((((R)-1-(naphthalen-1-yl)ethyl)amino)methyl)chroman-4-yl)benzoic acid hydrochloride;
4-Methoxy-3-((2R,4R)-2-((((R)-1-(naphthalen-1-yl)ethyl)amino)methyl)chroman-4-yl)benzoic acid hydrochloride;
2-(2-Methyl-5-((2R,4S)-2-((((R)-1-(naphthalen-1-yl)ethyl)amino)methyl)chroman-4-yl)phenoxy)acetic acid hydrochloride;
2-(3-Methyl-5-((2R,4S)-2-((((R)-1-(naphthalen-1-yl)ethyl)amino)methyl)chroman-4-yl)phenoxy)acetic acid hydrochloride;

2-(2-Fluoro-5-((2R,4R)-2-((((R)-1-(naphthalen-1-yl)ethyl)amino)methyl)chroman-4-yl)phenoxy)acetic acid hydrochloride;
2-(2-Fluoro-5-((2R,4S)-2-((((R)-1-(naphthalen-1-yl)ethyl)amino)methyl)chroman-4-yl)phenoxy)acetic acid hydrochloride;
2-(2-Fluoro-3-((2R,4R)-2-((((R)-1-(naphthalen-1-yl)ethyl)amino)methyl)chroman-4-yl)phenoxy)acetic acid hydrochloride;
2-(3-Fluoro-5-((2R,4R)-2-((((R)-1-(naphthalen-1-yl)ethyl)amino)methyl)chroman-4-yl)phenoxy)acetic acid hydrochloride;
2-(3-Fluoro-5-((2R,4S)-2-((((R)-1-(naphthalen-1-yl)ethyl)amino)methyl)chroman-4-yl)phenoxy)acetic acid hydrochloride;
2-(4-Fluoro-3-((2R,4R)-2-((((R)-1-(naphthalen-1-yl)ethyl)amino)methyl)chroman-4-yl)phenoxy)acetic acid hydrochloride;
2-Methyl-2-(3-((2R,4S)-2-((((R)-1-(naphthalen-1-yl)ethyl)amino)methyl)chroman-4-yl)phenoxy)propanoic acid hydrochloride;
4-((2R,4R)-2-((((R)-1-(Naphthalen-1-yl)ethyl)amino)methyl)chroman-4-yl)benzoic acid hydrochloride;
4-((2R,4S)-2-((((R)-1-(Naphthalen-1-yl)ethyl)amino)methyl)chroman-4-yl)benzoic acid hydrochloride;
2-Methyl-4-((2R,4R)-2-((((R)-1-(naphthalen-1-yl)ethyl)amino)methyl)chroman-4-yl)benzoic acid hydrochloride;
2-Methyl-4-((2R,4S)-2-((((R)-1-(naphthalen-1-yl)ethyl)amino)methyl)chroman-4-yl)benzoic acid hydrochloride;
4-((2R,4R)-2-((((R)-1-(Naphthalen-1-yl)ethyl)amino)methyl)chroman-4-yl)-2-(trifluoromethyl)benzoic acid hydrochloride;
4-((2R,4S)-2-((((R)-1-(Naphthalen-1-yl)ethyl)amino)methyl)chroman-4-yl)-2-(trifluoromethyl)benzoic acid hydrochloride;
2,6-Difluoro-4-((2R,4S)-2-((((R)-1-(naphthalen-1-yl)ethyl)amino)methyl)chroman-4-yl)benzoic acid hydrochloride;
3-Methoxy-4-((2R,4R)-2-((((R)-1-(naphthalen-1-yl)ethyl)amino)methyl)chroman-4-yl)benzoic acid hydrochloride;
3-Methoxy-4-((2R,4S)-2-((((R)-1-(naphthalen-1-yl)ethyl)amino)methyl)chroman-4-yl)benzoic acid hydrochloride;
3-Fluoro-4-((2R,4R)-2-((((R)-1-(naphthalen-1-yl)ethyl)amino)methyl)chroman-4-yl)benzoic acid hydrochloride;
2-Fluoro-4-((2R,4S)-2-((((R)-1-(naphthalen-1-yl)ethyl)amino)methyl)chroman-4-yl)benzoic acid hydrochloride;
2-(4-((2R,4R)-2-((((R)-1-(Naphthalen-1-yl)ethyl)amino)methyl)chroman-4-yl)phenoxy)acetic acid hydrochloride;
2-(4-((2R,4S)-2-((((R)-1-(Naphthalen-1-yl)ethyl)amino)methyl)chroman-4-yl)phenoxy)acetic acid hydrochloride;
2-(2-Fluoro-4-((2R,4R)-2-((((R)-1-(naphthalen-1-yl)ethyl)amino)methyl)chroman-4-yl)phenoxy)acetic acid hydrochloride;
2-(2-Fluoro-4-((2R,4S)-2-((((R)-1-(naphthalen-1-yl)ethyl)amino)methyl)chroman-4-yl)phenoxy)acetic acid hydrochloride;
2-(4-((2R,4R)-2-((((R)-1-(Naphthalen-1-yl)ethyl)amino)methyl)chroman-4-yl)phenyl)acetic acid hydrochloride;
2-(4-((2R,4S)-2-((((R)-1-(Naphthalen-1-yl)ethyl)amino)methyl)chroman-4-yl)phenyl)acetic acid hydrochloride;
2-Methyl-2-(4-((2R,4R)-2-((((R)-1-(naphthalen-1-yl)ethyl)amino)methyl)chroman-4-yl)phenyl)propanoic acid hydrochloride;
2-Methyl-2-(4-((2R,4S)-2-((((R)-1-(naphthalen-1-yl)ethyl)amino)methyl)chroman-4-yl)phenyl)propanoic acid hydrochloride;
3-Methyl-4-((2R,4S)-2-((((R)-1-(naphthalen-1-yl)ethyl)amino)methyl)chroman-4-yl)benzoic acid hydrochloride;
2-Fluoro-5-((2S,4R)-2-((((R)-1-(naphthalen-1-yl)ethyl)amino)methyl)chroman-4-yl)benzoic acid hydrochloride;
3-((2S,4R)-2-((((R)-1-(Naphthalen-1-yl)ethyl)amino)methyl)chroman-4-yl)benzoic acid hydrochloride;
2-Methyl-5-((2S,4R)-2-((((R)-1-(naphthalen-1-yl)ethyl)amino)methyl)chroman-4-yl)benzoic acid hydrochloride
2-Methyl-5-((2S,4S)-2-((((R)-1-(naphthalen-1-yl)ethyl)amino)methyl)chroman-4-yl)benzoic acid hydrochloride;
2-(4-((2S,4R)-2-((((R)-1-(Naphthalen-1-yl)ethyl)amino)methyl)chroman-4-yl)phenoxy)acetic acid hydrochloride;
2-(4-((2S,4S)-2-((((R)-1-(Naphthalen-1-yl)ethyl)amino)methyl)chroman-4-yl)phenoxy)acetic acid hydrochloride;
4-((2R,4S)-2-((((R)-1-(4-Fluoro-3-methoxyphenyl)ethyl)amino)methyl)chroman-4-yl)-2-methylbenzoic acid hydrochloride;
3-((2R,4S)-2-((((R)-1-(4-Fluoro-3-methoxyphenyl)ethyl)amino)methyl)chroman-4-yl)-2-methylbenzoic acid hydrochloride;
5-((2R,4S)-2-((((R)-1-(4-Fluoro-3-methoxyphenyl)ethyl)amino)methyl)chroman-4-yl)-2-methyl benzoic acid hydrochloride;
3-((2R,4S)-2-((((R)-1-(4-Fluoro-3-methoxyphenyl)ethyl)amino)methyl)chroman-4-yl)-5-methylbenzoic acid hydrochloride;
3-((2S,4S)-2-((((R)-1-(4-Fluoro-3-methoxyphenyl)ethyl)amino)methyl)chroman-4-yl)-4-methylbenzoic acid hydrochloride;
5-((2R,4R)-2-((((R)-1-(4-Fluoronaphthalen-1-yl)ethyl)amino)methyl)chroman-4-yl)-2-methyl benzoic acid hydrochloride;
5-((2R,4S)-2-((((R)-1-(4-Fluoronaphthalen-1-yl)ethyl)amino)methyl)chroman-4-yl)-2-methyl benzoic acid hydrochloride;
3-((2R,4S)-2-((((R)-1-(4-Fluoronaphthalen-1-yl)ethyl)amino)methyl)chroman-4-yl)-2-methoxybenzoic acid hydrochloride;
3-((2R,4R)-2-((((R)-1-(4-Fluoronaphthalen-1-yl)ethyl)amino)methyl)chroman-4-yl)-2-methoxybenzoic acid hydrochloride;
2-Fluoro-5-((2S,4R)-2-(2-(((R)-1-(naphthalen-1-yl)ethyl)amino)ethyl)chroman-4-yl)benzoic acid hydrochloride;
2-Fluoro-5-((2R,4S)-2-(2-(((R)-1-(naphthalen-1-yl)ethyl)amino)ethyl)chroman-4-yl)benzoic acid hydrochloride;
2-Methyl-5-((2S,4R)-2-(2-(((R)-1-(naphthalen-1-yl)ethyl)amino)ethyl)chroman-4-yl)benzoic acid hydrochloride;
2-Methyl-5-((2R,4S)-2-(2-(((R)-1-(naphthalen-1-yl)ethyl)amino)ethyl)chroman-4-yl)benzoic acid hydrochloride;
2-Methoxy-3-((2R,4R)-2-(2-(((R)-1-(naphthalen-1-yl)ethyl)amino)ethyl)chroman-4-yl)benzoic acid hydrochloride;
5-((2S,4R)-2-(2-(((R)-1-(4-Fluoronaphthalen-1-yl)ethyl)amino)ethyl)chroman-4-yl)-2-methylbenzoic acid hydrochloride;
5-((2R,4S)-2-(2-(((R)-1-(4-Fluoronaphthalen-1-yl)ethyl)amino)ethyl)chroman-4-yl)-2-methylbenzoic acid hydrochloride;
5-((2S,4R)-2-(2-(((R)-1-(4-Fluoro-3-methoxy phenyl)ethyl)amino)ethyl)chroman-4-yl)-2-methylbenzoic acid hydrochloride;
5-((2R,4S)-2-(2-(((R)-1-(4-Fluoro-3-methoxy phenyl)ethyl)amino)ethyl)chroman-4-yl)-2-methylbenzoic acid hydrochloride;
2-Fluoro-5-((2S,4S)-2-(3-(((R)-1-(naphthalen-1-yl)ethyl)amino)propyl)chroman-4-yl)benzoic acid hydrochloride;
2-Fluoro-5-((2R,4R)-2-(3-(((R)-1-(naphthalen-1-yl)ethyl)amino)propyl)chroman-4-yl)benzoic acid hydrochloride;

2-Methyl-5-((2S,4S)-2-(3-(((R)-1-(naphthalen-1-yl)ethyl) amino)propyl)chroman-4-yl)benzoic acid hydrochloride;
2-Methyl-5-((2R,4R)-2-(3-(((R)-1-(naphthalen-1-yl)ethyl) amino)propyl)chroman-4-yl)benzoic acid hydrochloride;
5-((2S,4S)-2-(3-(((R)-1-(4-Fluoro-3-methoxyphenyl)ethyl) amino)propyl)chroman-4-yl)-2-methylbenzoic acid hydrochloride;
4-((2S,4S)-2-(3-(((R)-1-(4-Fluoronaphthalen-1-yl)ethyl) amino)propyl)chroman-4-yl)-3-methylbenzoic acid hydrochloride;
4-((2S,4S)-2-(3-(((R)-1-(4-Fluoronaphthalen-1-yl)ethyl) amino)propyl)chroman-4-yl)benzoic acid hydrochloride;
5-((2S,4S)-2-(3-(((R)-1-(4-Fluoronaphthalen-1-yl)ethyl) amino)propyl)chroman-4-yl)-2-methylbenzoic acid hydrochloride;
Methyl 2-(3-((2R,4S)-2-((((R)-1-(naphthalen-1-yl)ethyl) amino)methyl)chroman-4-yl)benzamido)acetate;
Methyl 2-(2-methyl-5-((2R,4S)-2-((((R)-1-(naphthalen-1-yl)ethyl)amino)methyl)chroman-4-yl)benzamido)acetate;
2-(3-((2R,4S)-2-((((R)-1-(Naphthalen-1-yl)ethyl)amino) methyl)chroman-4-yl)benzamido) acetic acid hydrochloride;
2-(2-Methyl-5-((2R,4S)-2-((((R)-1-(naphthalen-1-yl)ethyl) amino)methyl)chroman-4-yl)benzamido) acetic acid hydrochloride;
N,2-Dimethyl-5-((2R,4S)-2-((((R)-1-(naphthalen-1-yl) ethyl)amino)methyl)chroman-4-yl)benzamide hydrochloride;
N,N,2-Trimethyl-5-((2R,4S)-2-((((R)-1-(naphthalen-1-yl) ethyl)amino)methyl)chroman-4-yl)benzamide hydrochloride;
2-Methyl-5-((2R,4S)-2-((((R)-1-(naphthalen-1-yl)ethyl) amino)methyl)chroman-4-yl)benzamide hydrochloride;
N-Ethyl-N,2-dimethyl-5-((2R,4S)-2-((((R)-1-(naphthalen-1-yl)ethyl)amino)methyl)chroman-4-yl)benzamide hydrochloride;
N,N-Diethyl-2-methyl-5-((2R,4S)-2-((((R)-1-(naphthalen-1-yl)ethyl)amino)methyl)chroman-4-yl)benzamide hydrochloride;
(2-Methyl-5-((2R,4S)-2-((((R)-1-(naphthalen-1-yl)ethyl) amino)methyl)chroman-4-yl)phenyl)(pyrrolidin-1-yl) methanone hydrochloride;
2-(2-Methyl-4-(2-((((R)-1-(naphthalen-1-yl)ethyl)amino) methyl)chroman-4-yl)phenoxy)acetic acid hydrochloride;
3-(3-(2-((((R)-1-(Naphthalen-1-yl)ethyl)amino)methyl) chroman-4-yl)phenyl)propanoic acid hydrochloride;
2-(3-(2-((((R)-1-(Naphthalen-1-yl)ethyl)amino)methyl) chroman-4-yl)phenoxy)acetic acid hydrochloride;
3-(2-Fluoro-5-(2-((((R)-1-(naphthalen-1-yl)ethyl)amino) methyl)chroman-4-yl)phenyl)propanoic acid hydrochloride;
3-(2-(2-(((R)-1-(Naphthalen-1-yl)ethyl)amino)ethyl)chroman-4-yl)benzoic acid hydrochloride;
3-(3-(2-(2-(((R)-1-(Naphthalen-1-yl)ethyl)amino)ethyl) chroman-4-yl)phenyl)propanoic acid hydrochloride;
2-(2-Methyl-5-(2-(2-(((R)-1-(naphthalen-1-yl)ethyl)amino) ethyl)chroman-4-yl)phenoxy)acetic acid hydrochloride;
2-(4-(2-(2-(((R)-1-(Naphthalen-1-yl)ethyl)amino)ethyl) chroman-4-yl)phenoxy)acetic acid hydrochloride;
3-(2-(2-(((R)-1-(4-Fluoronaphthalen-1-yl)ethyl)amino) ethyl)chroman-4-yl)benzoic acid hydrochloride;
4-(2-(3-(((R)-1-(Naphthalen-1-yl)ethyl)amino)propyl)chroman-4-yl)benzoic acid hydrochloride;
3-(2-(3-(((R)-1-(Naphthalen-1-yl)ethyl)amino)propyl)chroman-4-yl)benzoic acid hydrochloride;
2-Methyl-4-(2-(3-(((R)-1-(naphthalen-1-yl)ethyl)amino) propyl)chroman-4-yl)benzoic acid hydrochloride;

3-(2-(3-(((R)-1-(4-Fluoronaphthalen-1-yl)ethyl)amino)propyl)chroman-4-yl)benzoic acid hydrochloride;
3-(2-((((R)-1-(4-Fluoro-3-methoxyphenyl)ethyl)amino)methyl)chroman-4-yl)-2,6-dimethylbenzoic acid hydrochloride;
2-Fluoro-3-(2-((((R)-1-(4-fluoro-3-methoxyphenyl)ethyl) amino)methyl)chroman-4-yl)-6-methylbenzoic acid hydrochloride;
2,6-Difluoro-3-(2-((((R)-1-(4-fluoro-3-methoxyphenyl) ethyl)amino)methyl)chroman-4-yl)benzoic acid hydrochloride;
2-Fluoro-5-(2-((((R)-1-(4-fluoro-3-methoxyphenyl)ethyl) amino)methyl)chroman-4-yl)benzoic acid hydrochloride; and
2-(2-Fluoro-5-(2-((((R)-1-(4-fluoro-3-methoxyphenyl) ethyl)amino)methyl)chroman-4-yl)phenoxy)acetic acid hydrochloride;

or its pharmaceutically acceptable salt thereof.

In another aspect of the invention, there is provided a compound of Formula (I) useful in treating, preventing, managing and/or lessening the severity of diseases, disorders, syndromes or conditions associated with calcium sensing receptor (CaSR) modulators.

In another aspect, the invention provides a pharmaceutical composition comprising at least one compound of Formula (I) and at least one pharmaceutically acceptable excipient.

In another aspect, the invention provides a pharmaceutical composition of compound of formula (I) useful in treating, preventing, managing and/or lessening the severity of the diseases disorders, syndromes or conditions associated with calcium sensing receptor (CaSR) modulators in a subject, in need thereof by administering to the subject, one or more compounds described herein in a therapeutically effective amount to cause modulation of such receptor.

In another aspect, the invention provides a pharmaceutical composition comprising a compound of formula (I) or a pharmaceutically acceptable salt thereof together with a pharmaceutically acceptable excipient.

In another aspect, there are provided processes for the preparation compounds of Formula (Ib):

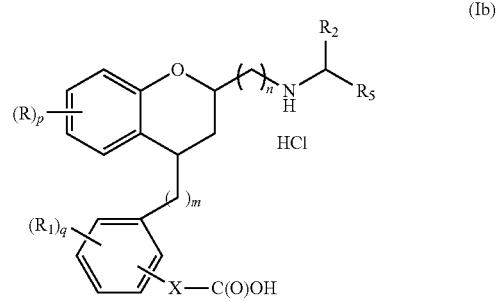

where X, R, $R_1$, $R_2$, $R_5$ 'm', 'n', 'p' and 'q' are as described herein above, the process comprising the steps:

a) oxidizing a compound of Formula (15) by using suitable oxidation agents to give compound of Formula (16) in suitable solvent(s);

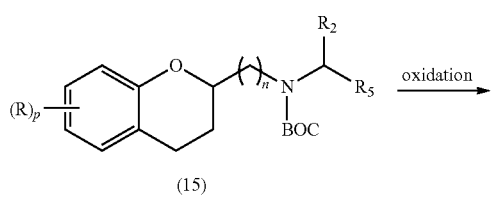

(15)

→ oxidation

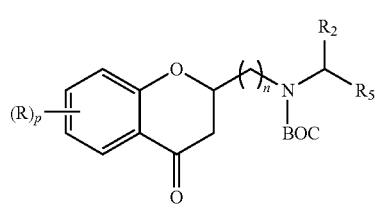

(16)

b) converting a compound of Formula (16) to compound of Formula (17) using PhNTf$_2$ (N-phenylbis(trifluoromethanesulfonimide) in presence of KHMDS (potassium hexamethyldisilazide);

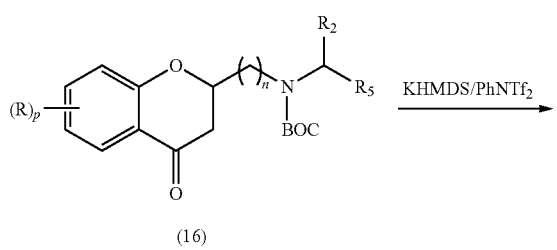

(16) → KHMDS/PhNTf$_2$ → (17)

c) coupling of compound of Formula (17) with suitable aryl boronic acid or aryl boronic ester by following Suzuki coupling reaction to give compound of Formula (18) where Z is —OR$_6$ and R$_6$ is alkyl or benzyl;

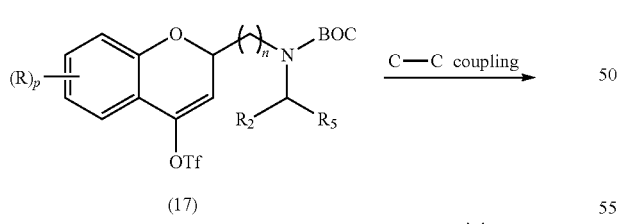

(17) → C—C coupling → (18)

d) when Z is O-alkyl, then reducing the compound of Formula (18) with hydrogen over Palladium-Carbon to give ester compound of Formula (19) where Z is —O-alkyl;

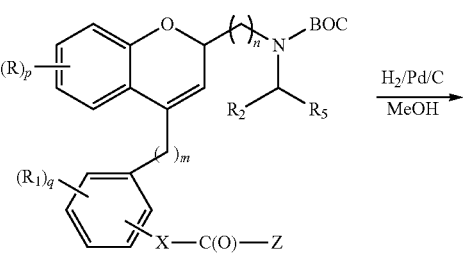

(18) → H$_2$/Pd/C / MeOH → (19)

e) converting the compound of Formula (19) obtained in step d) to the compound of Formula (Ia);

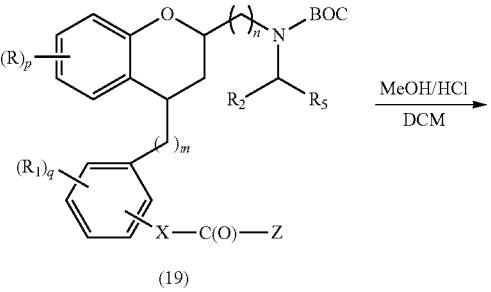

(19) → MeOH/HCl / DCM →

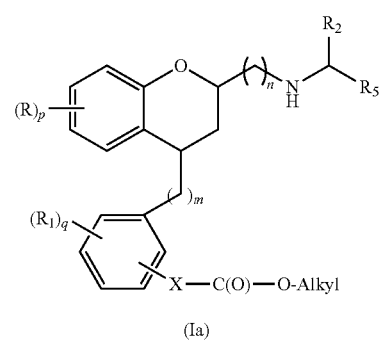

(Ia)

f) hydrolyzing the ester group in compound of Formula (Ia) to corresponding acid compound using suitable base and in suitable solvents;

g) converting the compound obtained in step f) to its hydrochloride salt having Formula (Ib);

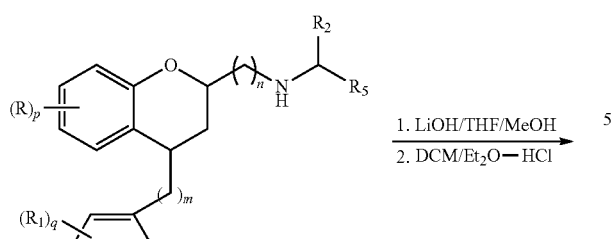

(Ia)

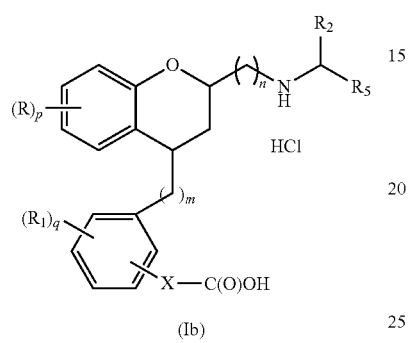

(Ib)

h) when Z is O-benzyl in compound of Formula (18), then reducing the compound of Formula (18) with hydrogen over Palladium-Carbon to give acid compound of Formula (19) where Z is OH;

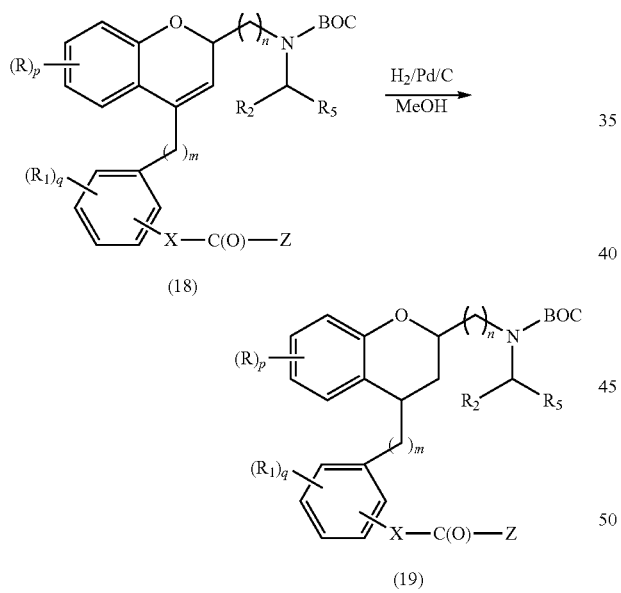

i) converting the compound of Formula (19) obtained in step h) to the compound of Formula (Ib);

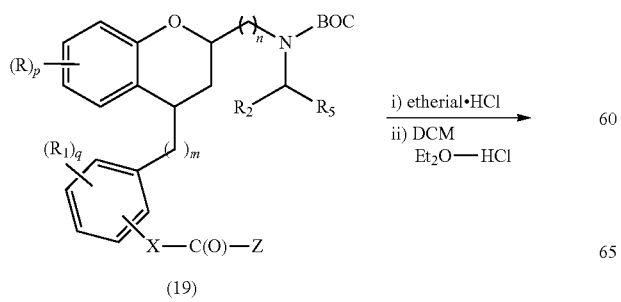

-continued

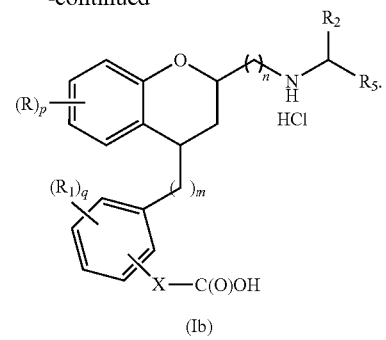

(Ib)

In another aspect, there are provided processes for the preparation compounds of Formula (Id):

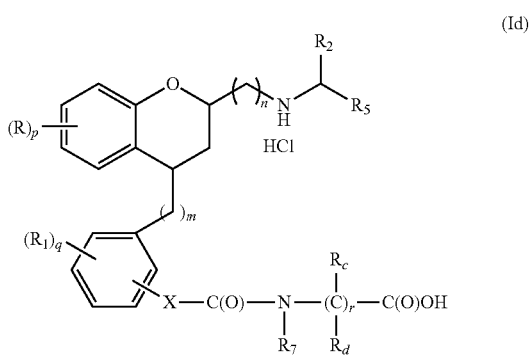

(Id)

wherein X, R, $R_1$, $R_2$, $R_5$, $R_7$, $R_c$, $R_d$ 'm', 'n', 'p', 'q' and 'r' are as described in claim 1, the process comprising the steps of:

a) coupling of acid compound of Formula (Ib) with suitable amines using suitable amide coupling reagents to give compound of Formula (Ic)

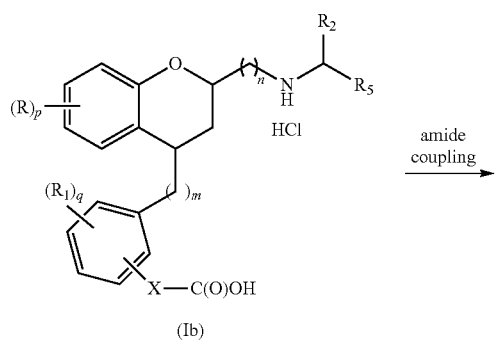

(Ib)

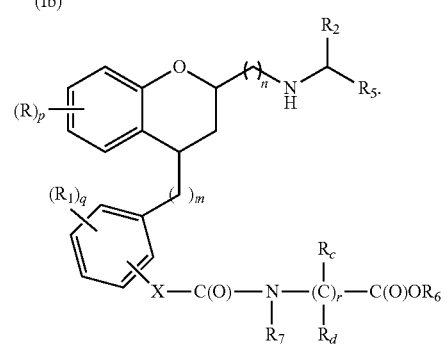

(Ic)
when $R_6$ is alkyl/benzyl etc., b) hydrolyzing the amido ester group, if the compound of Formula (Ic) is an ester, to corresponding acid compound of Formula (Id) using suitable reagent and solvents.

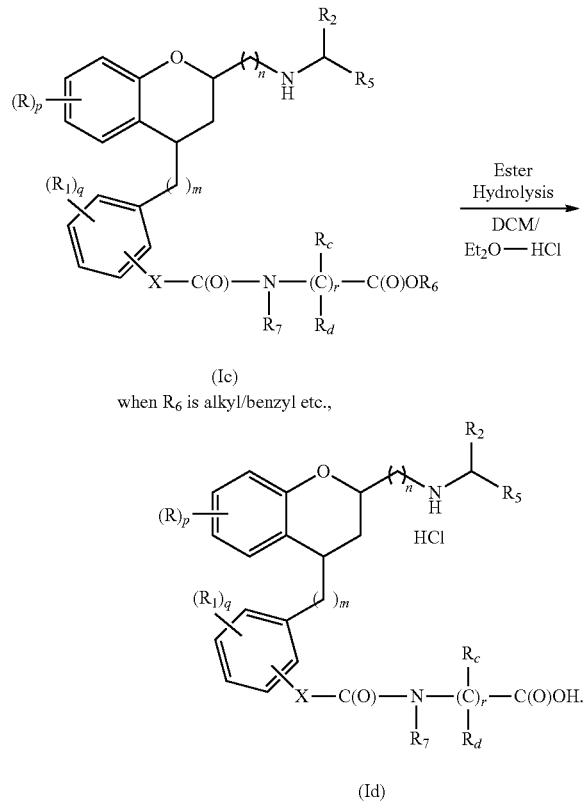

(Ic)
when R$_6$ is alkyl/benzyl etc.,

DETAILED DESCRIPTION OF THE INVENTION

Definitions and Abbreviations

Unless otherwise stated, the following terms used in the specification and claims have the meanings given below.

For purposes of interpreting the specification and claims, the following definitions will apply and whenever appropriate, terms used in the singular will also include the plural and vice versa.

The terms "halogen" or "halo" means fluorine, chlorine, bromine, or iodine.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting examples of such groups are methoxy, ethoxy and propoxy and the like. Unless set forth or recited to the contrary, all alkoxy groups described or claimed herein may be straight chain or branched, substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched, substituted or unsubstituted.

The term "haloalkoxy" refers to a haloalkyl, defined herein, group attached via an oxygen linkage. Preferably, the haloalkoxy may be monohaloalkoxy, dihaloalkoxy or polyhaloalkoxy including perhaloalkoxy. Non-limiting examples of a haloalkoxy include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy, dichloropropoxy, dichlor-oisopropoxy and the like. Unless set forth or recited to the contrary, all haloalkoxy group described or claimed herein may be straight chain or branched, substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapthyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkylene" refers to a saturated divalent cyclic hydrocarbon radical that includes solely carbon and hydrogen atoms in the backbone. In particular, "$C_3$-$C_7$ cycloalkylene" means a saturated divalent cyclic hydrocarbon radical with 3 to 7 carbon atoms e.g. cyclopropylene, cyclobutylene, cyclopentylene, cyclohexylene and the like. Unless set forth or recited to the contrary, all cycloalkylene groups described or claimed herein may be substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

A "carbocyclic ring" or "carbocycle" as used herein refers to a 3- to 10-membered saturated or unsaturated, monocyclic, fused bicyclic, spirocyclic or bridged polycyclic ring containing carbon atoms, which may optionally be substituted, for example, carbocyclic rings include but are not limited to cyclopropyl, cyclobutyl, cyclopentyl, cyclohexyl, cyclopropylene, cyclohexanone, aryl, naphthyl, adamentyl etc. Unless set forth or recited to the contrary, all carbocyclic groups or rings described or claimed herein may be aromatic or non aromatic.

A "3-12 membered cyclic ring" as used herein refers to a monocyclic, bicyclic, polycyclic heteroaryl or heterocyclic ring systems.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —$CF_2$—, —C(O)—, —S(O)—, S(O)$_2$, —C(=N-alkyl)-, or —C(=N-cycloalkyl), etc. In addition heterocyclic ring may also be fused with aromatic ring. Non-limiting examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached by any atom of the heterocyclic ring that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached by any atom of the heteroaryl ring that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR", —C(O)R$^x$, —C(S)R", —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O) R$^y$, —NR$^x$C(S)R$^y$, —NR$^x$C(S)NR$^y$R$^z$, —S(O)$_2$NR$^x$R$^y$, —OR", —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, and —S(O)$_2$R$^x$; wherein each occurrence of R$^x$, R$^y$ and R$^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl. The aforementioned "substituted" groups cannot be further substituted. For example, when the substituent on "substituted alkyl" is "aryl" or "alkenyl", the aryl or alkenyl cannot be substituted aryl or substituted alkenyl, respectively.

The compounds of the present invention may have one or more chiral centers. The absolute stereochemistry at each chiral centre may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the severity of a disease disorder or condition or at least one of its clinical or subclinical symptoms or (d) relieving the disease, i.e., causing regression of the state, disorder or condition or at least one of its clinical or subclinical symptoms.

The term "modulate" or "modulating" or "modulation" or "modulator" refers to an increase in the amount, quality, or effect of a particular activity or function of the receptor. By way of illustration and not limitation, it includes agonists, partial agonists, allosteric modulators of calcium sensing receptor (CaSR) of the present invention. Such modulation may be contingent on the occurrence of a specific event, such as activation of a signal transduction pathway.

The term "allosteric modulators of calcium-sensing receptor", refers to the ability of a compound that binds to calcium sensing receptors and induces a conformational change that reduces the threshold for calcium sensing receptor activation by the endogenous ligand $Ca^{2+}$ depending on the concentration of the compound exposed to the calcium-sensing receptor.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting examples of pharmaceutically acceptable salts are inorganic, organic acid addition salts formed by addition of acids including hydrochloride salts. Non-limiting examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting a sufficiently basic compound such as an amine with a suitable acid affording a physiologically acceptable anion.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereo specific or asymmetric synthesis or chiral HPLC (high performance liquid chromatography. Tautomeric forms and mixtures of compounds described herein are also contemplated.

Screening of compounds of invention for calcium sensing receptor (CaSR) modulation activity can be achieved by using various in vitro and in vivo protocols mentioned herein below or methods known in the art.

Pharmaceutical Compositions

The invention relates to pharmaceutical compositions containing the compounds of the Formula (I) disclosed herein. In particular, pharmaceutical compositions containing a therapeutically effective amount of at least one compound of Formula (I) described herein and at least one pharmaceutically acceptable excipient (such as a carrier or diluent). Preferably, the contemplated pharmaceutical compositions include the compound(s) described herein in an amount sufficient to modulate calcium sensing receptor (CaSR) mediated diseases described herein when administered to a subject.

The subjects contemplated include, for example, a living cell and a mammal, including human mammal. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, caplets, orally disintegrating tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg according to the potency of the active component or mode of administration.

Suitable doses of the compounds for use in treating the diseases and disorders described herein can be determined by those skilled in the relevant art. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the CaSR modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Methods of Treatment

In another aspect, the invention provides compounds and pharmaceutical compositions thereof that are useful in treating, managing and/or lessening the severity of diseases, disorders, syndromes or conditions modulated by calcium sensing receptor (CaSR). The invention further provides method of treating diseases, disorders, syndromes or conditions modulated by CaSR in a subject in need thereof by administering to the subject a therapeutically effective amount of a compound or a pharmaceutical composition of the invention.

In another aspect of the invention, the methods provided are also useful for diagnosis of conditions that can be treated by modulating CaSR for determining if a patient will be responsible to therapeutic agents.

In another aspect, the invention provides a method for the treatment of diseases, disorders or conditions through modulating CaSR. In this method, a subject in need of such treatment is administered a therapeutically effective amount of a compound of Formula (I) described herein.

The compound and pharmaceutical composition of the present invention is useful to a subject in need of the treatment having a disease, disorder, syndrome or condition characterized by one or more of the following: (a) abnormal calcium ion homeostasis, (b) an abnormal level of a messenger whose production or secretion is affected by the calcium sensing receptor (CaSR) activity or (c) an abnormal level of activity of a messenger whose function is affected by the calcium sensing receptor activity. In one aspect, the patient has a disease, disorder, syndrome or condition characterized by an abnormal level of one or more calcium sensing receptor-regulated components and the compound is active on a CaSR of a cell including parathyroid cell, bone cells (pre-osteoclast, osteoclast, pre-osteoblast, osteoblast), juxtaglomerular kidney cell, kidney messengial cell, glomerular kidney cell, proximal tubule kidney cell, distal tubule kidney cell, cell of the thick ascending limb of Henle's loop and/or collecting duct, parafollicular cell in the thyroid (C-cell), intestinal cell, platelet, vascular smooth muscle cell, gastrointestinal tract cell, pituitary cell or hypothalamic cell. The messenger of the calcium sensing receptor is Calcium.

The compound of Formula (I), being modulators of CaSR, is potentially useful in treating, managing and/or lessening the severity, morbidity/mortality or complications of diseases, disorders, syndromes or conditions include but are not limited to primary hyperparathyroidism, secondary hyperparathyroidism, tertiary hyperparathyroidism, chronic renal failure (with or without dialysis), chronic kidney disease (with or without dialysis) parathyroid adenoma, parathyroid hyperplasia, parathyroid carcinoma, vascular & valvular calcification, abnormal calcium homeostasis such as hypercalcemia, abnormal phosphorous homeostasis such as hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which $(Ca^{2+})_e$ ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastro-intestinal tract by augmenting gastric acidity.

Primary hyperparathyroidism, is a disorder of one or more of the parathyroid glands, resulting from a hyper function of the parathyroid glands themselves (acquired sporadically or familial) resulting in PTH over secretion which could be due to single or double adenoma, hyperplasia, multigland disease or rarely, carcinoma of the parathyroid glands. As a result, the blood calcium rises to a level that is higher than normal (called hypercalcemia). This elevated calcium level can cause many short-term and long-term complications.

Secondary hyperparathyroidism occurs when a decrease in circulating levels of $Ca^{2+}$ level stimulates PTH secretion. One cause of secondary hyperparathyroidism is chronic renal insufficiency (also referred to as chronic kidney disease or CKD), such as that in renal polycystic disease or chronic pyelonephritis, or chronic renal failure, such as that in hemodialysis patients (also referred to as end stage renal disease or ESRD). Excess PTH may be produced in response to hypocalcemia resulting from low calcium intake, GI disorders, renal insufficiency, vitamin D deficiency, magnesium deficiency and renal hypercalciuria. Tertiary hyperparathyroidism may occur after a long period of secondary hyperparathyroidism and hypercalcemia.

In one aspect, the compound and composition of the present invention can be used in treating, managing and/or lessening the vascular or valvular calcification in a subject. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits. In one aspect, the compounds of the invention may also be used to prevent or treat atherosclerotic calcification and medial calcification and other conditions characterized by vascular calcification. In one aspect, vascular calcification may be associated with chronic renal insufficiency or end-stage renal disease or excess calcium or PTH itself. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

Abnormal calcium homeostasis such as hyperparathyroidism related diseases can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hyperparathyroidism.

Abnormal phosphorous homeostasis such as hypophosphatemia can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hypophosphatemia.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intraglomerular pressure; (v) synthesis and maintenance of the glomerular basement membrane (GMB); (vi) production and secretion of vascular endothelial growth factor (VEGF) required for the glomerular endothelial cell (GEN) integrity. Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgestic or anticancer agent), an organ failure, an organ transplantation, or uropathy. In one aspect, ischemia can be sickle-cell anemia, thrombosis, transplantation, obstruction, shock or blood loss. In one aspect, the genetic disorders may include congenital nephritic syndrome of the Finnish type, the fetal membranous nephropathy or mutations in podocyte-specific proteins.

In one aspect, the compounds of the invention can be used for treating abnormal intestinal motilities disorders such as diarrhea. The methods of the invention comprise administering to the subject a therapeutically effective amount of the compounds of Formula I. In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with gastrointestinal or abdominal surgery, chemotherapy, radiation treatment, inflammation or toxic traumatic injury. In another aspect, diarrhea can be secretary, means that there is an increase in the active secretion, or there is an inhibition of absorption. There is little to no structural damage. The most common cause of this type of diarrhea is cholera. In another aspect, diarrhea can be due to acceleration of intestinal transit (rapid transit diarrhea). Such condition may occur because the rapid flow-through impairs the ability of the gut to absorb water.

The compound and composition of the present invention can be used, in particular, to participate in an augmenting gastrin or gastric acid secretion to directly or indirectly benefit certain medical conditions such as but not limited to atrophic gastritis or to improve absorption of pharmacological compounds, drugs or supplements from gastro-intestinal tract by augmenting gastric acidity.

All of the patent, patent application and non-patent publications referred to in this specification are incorporated herein by reference in their entireties.

General Methods of Preparation

The compounds described herein may be prepared by techniques known in the art. In addition, the compounds described herein may be prepared by following the reaction sequence as depicted in Scheme-1 to Scheme-2. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art, are also within the scope of the present invention. All the isomers of the compounds described in these schemes, unless otherwise specified, are also encompassed within the scope of this invention.

Scheme-1
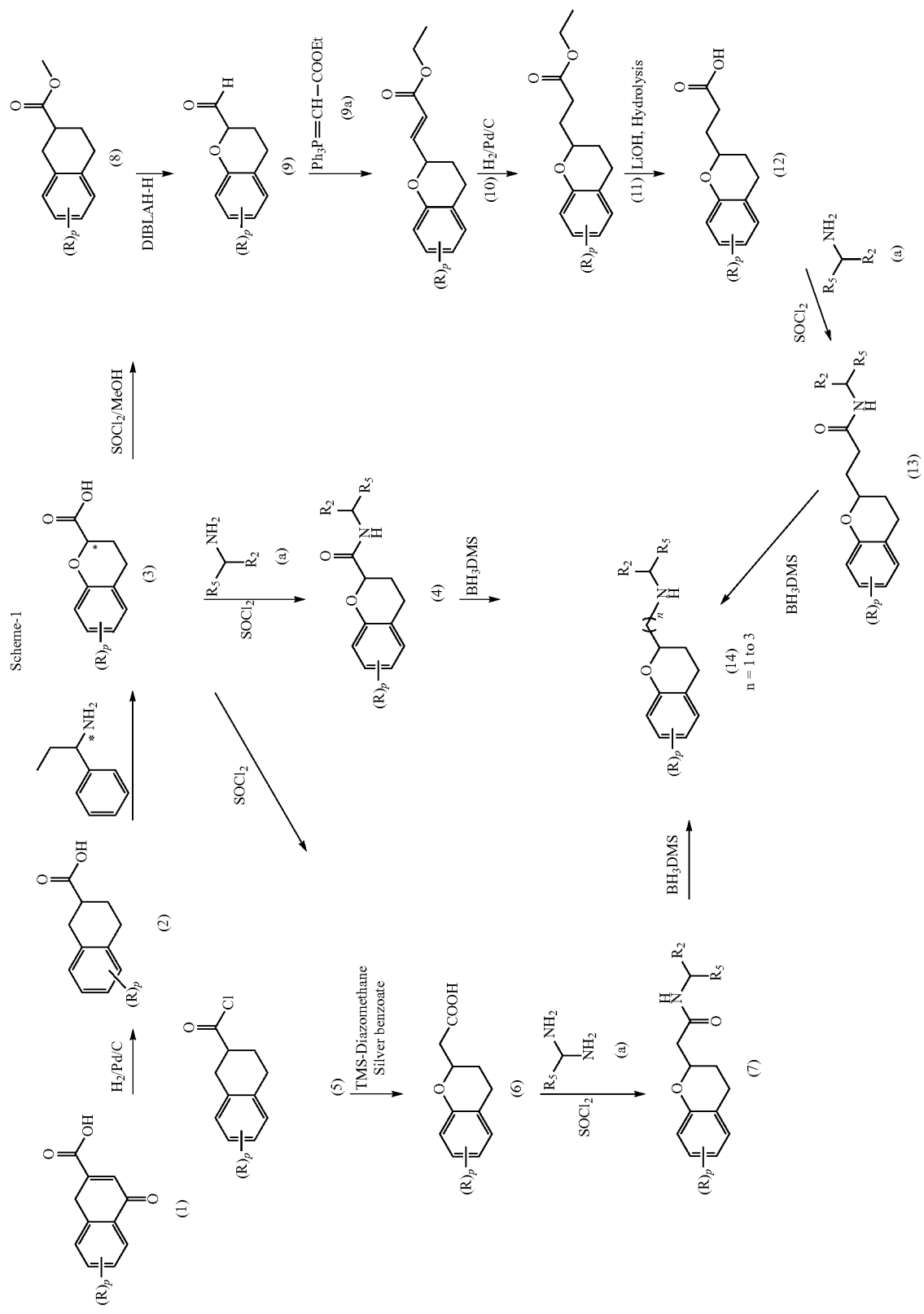

The compound of Formula (14) where n is 1, is prepared by following the procedure as depicted in Scheme-1, thus starting from commercially available chromone-2-carboxylic acid is reduced to give compound of Formula (2) with hydrogen over Palladium-Carbon. Compound of Formula (2) can be resolved by using R-(+)-1-phenylpropyl amine or (S)-(+)-1-phenylpropyl amine (WO2007/123941) which gives corresponding resolved acid of Formula (3). The compound of Formula (3) is reacted with amine of Formula (a) in presence suitable reagents such as $SOCl_2$ to give compound of Formula (4). The compound of Formula (4) undergoes reduction using suitable reducing agents to give compound of Formula (14).

The compound of Formula (14) where n is 2, is prepared from compound of Formula (3) thus, acid compound of Formula (3) is reacted with $SOCl_2$ to give corresponding acid chloride of Formula (5). Further this Formula (5) undergoes one-carbon homologation (Arndt-Eistert Synthesis) by using trimethylsilyl diazomethane followed by silver benzoate to give compound of Formula (6). The compound of Formula (6) reacting with amine of Formula (a) using suitable reagents such as $SOCl_2$ to give compound of Formula (7). The compound of Formula (7) undergoes reduction using suitable reducing agents to give compound of Formula (14).

Similarly, the compound of Formula (14) where n is 3, is prepared from Formula (3) by reacting compound of Formula (3) with $SOCl_2$ in presence of alcohol to give corresponding ester. Compound of Formula (8) is reduced to give aldehyde of Formula (9). This compound of Formula (9) undergoes Wittig reaction to give corresponding alkenes of Formula (10). Compound of Formula (10) is reduced to give compound of Formula (11). Further, this ester compound of Formula (11) can be hydrolyzed to give corresponding acid of Formula (12) using suitable base such as NaOH, LiOH, etc. The compound of Formula (12) is reacted with amine of Formula (a) using suitable reagents for example $SOCl_2$ to give compound of Formula (13). The compound of Formula (13) undergoes reduction using suitable reducing agents to give compound of Formula (14).

Scheme-2

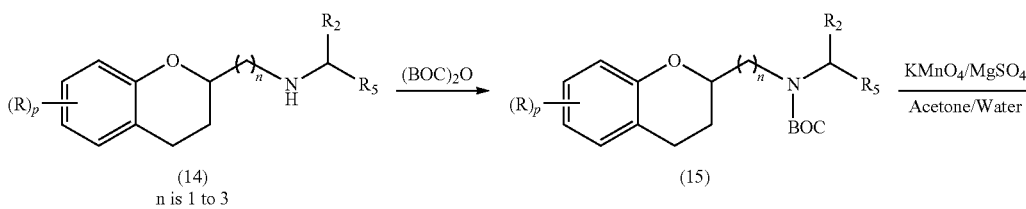

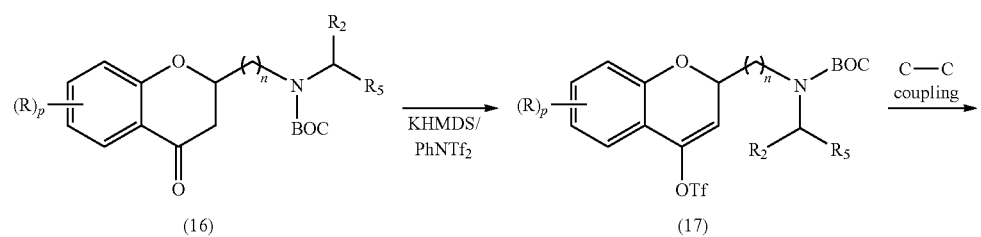

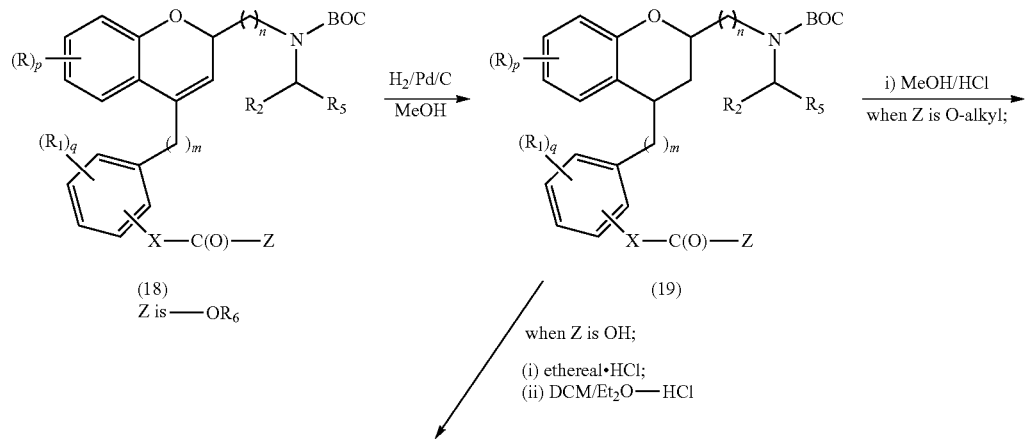

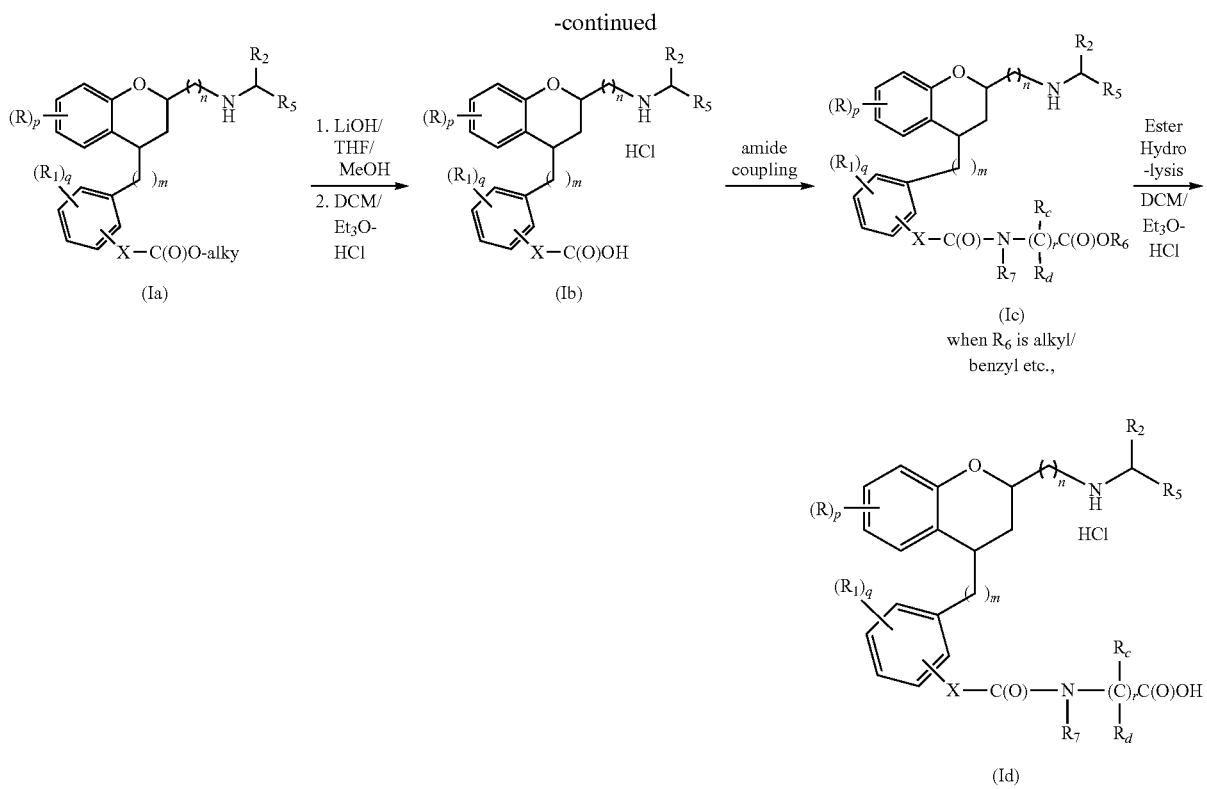

The compound of Formula (Ia), (Ib), (Ic) or (Id) where X, R, $R_1$, $R_2$, $R_5$, $R_7$, $R_c$, $R_d$, 'm', 'n', 'p', 'q' and 'r' are as defined herein above, can be prepared by following the procedure as depicted in Scheme-2 starting from Formula (14), which is protected with BOC-anhydride in acetonitrile to give N—BOC protected compound of Formula (15). The compound of Formula (15) is oxidized with suitable oxidizing agent to give compound of Formula (16) (Chem. Eur. J. 2009, 15, 3403-3410). Compound of Formula (16) is converted to trifluoromethanesulfonate of Formula (17) using $PhNTf_2$ (N-phenylbis(trifluoromethanesulfonimide) in presence of KHMDS (potassium hexamethyldisilazide), which further undergoes carbon-carbon (C—C) coupling reaction with corresponding boronic acid/boronic ester by following the methods known in the art for example Suzuki coupling reaction to give compound of Formula (18) where Z is —$OR_6$ and $R_6$ is alkyl or benzyl etc.

The double bond in compound of Formula (18) is reduced by using hydrogen over Palladium-Carbon to give ester compound of Formula (19). But compound of Formula (18) when Z is —$OR_6$ where $R_6$ is benzyl, is converted to give acid compound of Formula (19) where Z is OH, by carried-out the reduction and benzyl ester hydrolysis in single step using hydrogen over Palladium-Carbon in suitable solvent. This ester compound of Formula (19) where Z is OH, undergoes Boc deprotection using ethereal HCl followed by salt preparation with hydrochloric acid in suitable solvent to give corresponding acid of Formula (Ib).

Also, compound of Formula (19) is further deprotected the BOC group using methanolic hydrochloric acid to afford compound of Formula (Ia). This compound of Formula (19) is obtained in diastereomeric mixture either in equal ratios (50:50) or obtained in different diastereomeric ratio(s). Optionally, these diastereomeric mixture can be further separated by known methods in the art for example chiral chromatography, crystallization technique etc., either at this step or in any of the subsequent steps. Further, ester group in Formula (Ia) can be hydrolyzed to give corresponding acid using suitable base such as NaOH, LiOH, KOH etc., followed by salt preparation with hydrochloric acid in suitable solvent to give corresponding acid of Formula (Ib). This acid compound of Formula (Ib) is coupled with suitable amines using suitable amide coupling agents by following the general amide coupling procedure as described in the art. Further, if the compound of Formula (Ic) is an ester then it can be further hydrolyzed to give corresponding acid compound Formula (Id) using suitable base such as NaOH, LiOH, KOH etc., followed by salt preparation with hydrochloric acid in suitable solvent.

Experimental

The invention is further illustrated by the following examples which are provided merely to be exemplary of the invention and do not limit the scope of the invention. The examples set forth below demonstrate the synthetic procedures for the preparation of the representative compounds. Certain modifications and equivalents will be apparent to those skilled in the art and are intended to be included within the scope of the invention. The aforementioned patents and patent applications are incorporated herein by reference.

Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase.

INTERMEDIATES

Intermediate-1

Chromane-2-carboxylic Acid

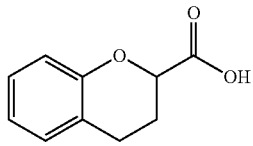 [SMILES: O=C(O)C1CCc2ccccc2O1]

To a suspension of commercially available chromone-2-carboxylic acid (50 g, 281 mmol) in methanol (500 mL), slurry of (10% Pd/C wet, 5 g) in water (10 mL) was added under nitrogen atmosphere. The mixture was hydrogenated at 60 psi at room temperature (RT) and further maintained hydrogen reservoir up to 60 psi for 2 h. The progress of reaction was monitored by TLC. Reaction mixture was filtered through celite and the filtrate was concentrated under reduced pressure to yield chromane-2-carboxylic acid as off-white solid (44.7 g, 95%). m/z-178.02.

Intermediate-2

(R)-(−)-Chromane-2-carboxylic Acid

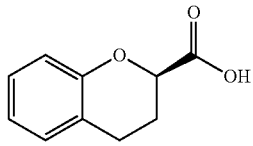 [SMILES: O=C(O)[C@H]1CCc2ccccc2O1]

To a solution of Intermediate-1 (18.6 g, 104 mmol) in acetonitrile (91 mL), (R)-(+)-1-phenylpropylamine (9.14 g, 67.9 mmol) in methyl tert butyl ether (MTBE) (12 mL) solution was added in dropwise manner. After about half of the total amount of the (R)-(+)-1-phenylpropylamine solution was added. The reaction mixture was seeded with few crystals of ((R)-(+)-1-phenyl propyl ammonium (R)-(−)-chromane-2-carboxylate). The resultant thick slurry was diluted with MTBE (80 mL) and the mixture was further stirred for 6 h at RT. The salt was filtered, washed with MTBE and dried. The salt (13.7 g) was suspended in MTBE (80 mL) further aqueous HCl solution (1:1) (88 mL) was added and the mixture was stirred in cooling to 0° C. The aqueous layer was extracted with methyl tert-butyl ether (70 mL×2). The extracts were combined with organic layer and the solution was washed with 1:1 HCl solution (40 mL). The organic layer was dried over $Na_2SO_4$ and evaporated under reduced pressure to afford the title compound as a white crystalline solid (6.5 g); m/z-178.02.

C $[α]^{20}_D$=−6.8.degree (c=1% in methanol) observed.

C $[α]^{20}_D$=−6.7.degree. (c=1% in methanol) reported in U.S. Pat. No. 6,133,277 A1, 2000.

Intermediate-3

(R)—N—((R)-1-(Naphthalen-1-yl)ethyl)chroman-2-carboxamide

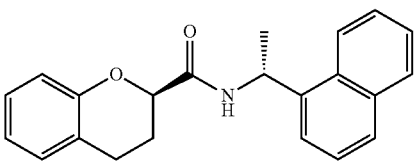 [SMILES: C[C@@H](NC(=O)[C@H]1CCc2ccccc2O1)c1cccc2ccccc12]

Thionyl chloride (11.4 mL, 156 mmol) was added in dropwise manner to a cooled 0° C. solution of Intermediate-2 (15.9 g, 89 mmol) in ethylene dichloride (160 mL). The reaction mixture was allowed to RT then heated to reflux and further maintained for 1 h then dimethyl formamide (5 drop) was added carefully. The progress of reaction was monitored by TLC. After reaction completion the reaction mixture was concentrated under vacuum to get oily mass. The solution of acid chloride in dichloromethane (DCM) (30 mL) was added to a solution of (R)-1-(naphthalen-1-yl)ethanamine (15.3 g, 89 mmol) and triethylamine (15.5 mL, 112 mmol) in DCM (130 mL) at 0° C. The reaction was further stirred for 1 h at 0° C. The progress of reaction was monitored by TLC. The reaction mixture was diluted with water (25 mL) and extracted with DCM (50 mL×3). The combined organic phase was dried over $Na_2SO_4$ and concentrated under reduced pressure to afford the title compound (29 g, 98%). m/z-331.9.

Intermediate-4

(R)—N—((R)-Chroman-2-ylmethyl)-1-(naphthalen-1-yl)ethanamine

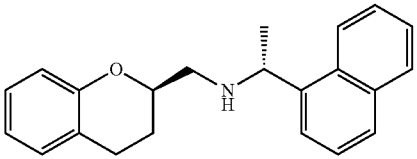 [SMILES: C[C@@H](NC[C@H]1CCc2ccccc2O1)c1cccc2ccccc12]

To a solution of Intermediate-3 (11.8 g, 35.6 mmol) in tetrahydrofuran (THF) (90 mL), borane-dimethyl sulphide complex (8.9 mL, 89 mmol, 10M) was added at 0° C. The reaction was allowed to RT then heated to 70° C. and further maintained for 2 h. The progress of reaction was monitored by TLC. The reaction mixture was cooled to 0° C. and 1:1 HCl solution was added very slowly (15 mL). After quenching, the reaction was heated to 90° C. and further maintained for 1 h. THF was distilled off under vacuum and the resultant residue was cooled to 0° C. and basified with 2M NaOH solution. Product was extracted with ethyl acetate (50 mL×3) and washed with water (25 mL×2) and a brine solution (25 mL). The combined organic layer was dried over $Na_2SO_4$ and evaporated under reduced pressure to afford the title compound as an oily mass (11 g, 97%). m/z-318.1.

Intermediate-5 tert-Butyl((R)-chroman-2-ylmethyl) ((R)-1-(naphthalen-1-yl)ethyl)carbamate

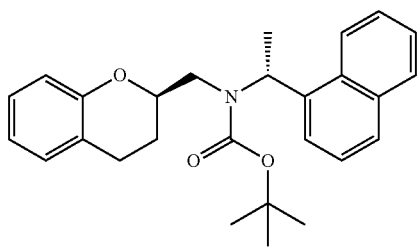 [SMILES: C[C@H](c1cccc2ccccc12)N(C[C@H]1CCc2ccccc2O1)C(=O)OC(C)(C)C]

To a solution of Intermediate-4 (11 g, 34.7 mmol) in acetonitrile (90 mL), di-tert-butyl dicarbonate (9.7 mL, 41.6 mmol) was added and the solution was heated to 50° C. and maintained for overnight. The progress of reaction was monitored by TLC. The reaction was cooled to RT and the organic solvent was evaporated under reduced pressure. The residue was dissolved in ethyl acetate (50 mL×2) and washed with water (25 mL) subsequently with brine solution (20 mL). The organic layer was separated and dried over $Na_2SO_4$ and concentrated under reduced pressure to afford the title compound as an oily mass (13.9 g, 96%). m/z-417.3.

Intermediate-6 tert-Butyl((R)-1-(naphthalen-1-yl)ethyl)(((R)-4-oxochroman-2-yl)methyl)carbamate

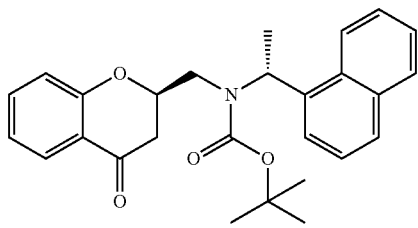 [SMILES: C[C@H](c1cccc2ccccc12)N(C[C@H]1CC(=O)c2ccccc2O1)C(=O)OC(C)(C)C]

The mixture of Intermediate-5 (13.7 g, 32.8 mmol), magnesium sulphate (9.5 g, 79 mmol) in acetone (160 mL) and water (80 mL) was cooled to 0° C. To this, $KMnO_4$ (28.5 g, 180 mmol) was added in portions wise for 1 h at 0 to 5° C. The reaction mixture was then allowed to RT and further stirred for 16 h. The progress of reaction was monitored by TLC. The reaction mass was filtered and filtrate was extracted in ethyl acetate (100 mL×2). Combined organic layer was washed with saturated sodium sulphite (30 mL) solution followed by water (50 mL) and brine solution (40 mL). The organic layer was separated and dried over $Na_2SO_4$ and concentrated. This was further purified by flash chromatography using a mixture of 5% ethyl acetate in hexane as eluent to give title compound (9.6 g, 68%). m/z-454.1 as Na+1.

Intermediate-7

(2R)-2-(((tert-Butoxycarbonyl)((R)-1-(naphthalen-1-yl)ethyl)amino)methyl)-4-a,8a-dihydro-2H-chromen-4-yl trifluoromethanesulfonate

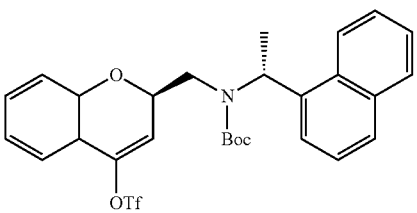 [SMILES: C[C@H](c1cccc2ccccc12)N(C[C@H]1C=C(OS(=O)(=O)C(F)(F)F)C2C=CC=CC2O1)C(=O)OC(C)(C)C]

To a solution of Intermediate-6 (0.9 g, 2.09 mmol) in THF (5 mL), potassium bis(trimethylsilyl) amide (0.6 g, 3.13 mmol) was added at −78° C. and stirred for 1 h at the same temperature. 1,1,1-trifluoro-N-phenyl-N-((trifluoromethyl)sulfonyl)methane sulfonamide (0.89 g, 2.5 mmol) was added at −78° C. under nitrogen atmosphere. The progress of reaction was monitored by TLC. To this reaction mixture water (3 mL) was added at −78° C. then allowed to RT. The reaction mass extracted with diethyl ether (25 mL×2), washed with water (25 mL×2) followed by brine (10 mL), dried over $Na_2SO_4$ and concentrated under reduced pressure to get the crude product. It was purified by flash chromatography by using 5% ethyl acetate in hexane to get the title compound (0.9 g, 77% yield). m/z-586.1 as Na+1.

Intermediate-8

(S)-Chroman-2-carboxylic Acid

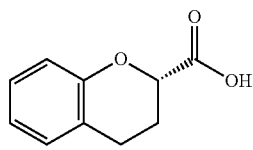 [SMILES: O=C(O)[C@@H]1CCc2ccccc2O1]

The title compound was resolved by following the similar procedure as described in Intermediate-2 by taking Intermediate-1 and (S)-(+)-1-phenyl propyl amine as resolving agent. m/z-178.

Intermediate-9

(S)-2-(((tert-Butoxycarbonyl)((R)-1-(naphthalen-1-yl)ethyl)amino)methyl)-2H-chromen-4-yl trifluoromethanesulfonate

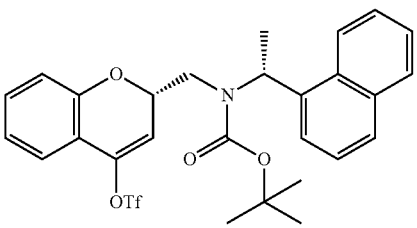 [SMILES: C[C@H](c1cccc2ccccc12)N(C[C@@H]1C=C(OS(=O)(=O)C(F)(F)F)c2ccccc2O1)C(=O)OC(C)(C)C]

The title compound was prepared in five steps:
Step: 1-Intermediate-8 was reacted with (R)-1-(naphthalen-1-yl)ethanamine by following the similar procedure as described in Intermediate-3;

Step: 2—Reduction of Step-1 Intermediate using borane dimethyl sulphide complex by following the similar procedure as described in Intermediate-4;

Step: 3—BOC protection of Step-2 Intermediate using BOC anhydride in presence of acetonitrile by following the similar procedure as described in Intermediate-5;

Step: 4—Oxidation of Step-3 Intermediate using KMnO$_4$ by following the similar procedure as described in Intermediate-6;

Step: 5—Intermediate Step-4 treating with 1,1,1-trifluoro-N-phenyl-N-((trifluoro methyl) sulfonyl)methane sulfonamide in presence of KHMDS by following the similar procedure as described in Intermediate-7; m/z-586.1 as Na+1.

Intermediate-10

(R)-2-(((tert-Butoxycarbonyl)((R)-1-(4-fluoro-3-methoxyphenyl)ethyl)amino)methyl)-2H-chromen-4-yl trifluoromethanesulfonate

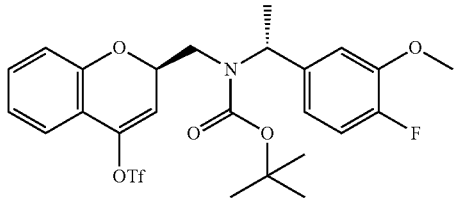 [SMILES: COc1cc([C@@H](C)N(C[C@H]2C=C(OS(=O)(=O)C(F)(F)F)c3ccccc3O2)C(=O)OC(C)(C)C)ccc1F]

The title compound was prepared in following five steps:

Step 1: By taking Intermediate-2 and corresponding (R)-1-(4-fluoro-3-methoxyphenyl)ethanamine hydrochloride by following the similar procedure as described in Intermediate-3.

Step 2: Reduction of Step-1 Intermediate using borane dimethyl sulphide complex by following the similar procedure as described in Intermediate-4.

Step 3: Step-2 Intermediate was protected with BOC by reacting with BOC anhydride in presence of acetonitrile by following the similar procedure as described in Intermediate-5.

Step: 4—Oxidation of Step-3 Intermediate using KMnO$_4$ by following the similar procedure as described in Intermediate-6.

Step 5: The title compound was prepared by reacting Step-4 Intermediate with 1,1,1-trifluoro-N-phenyl-N-((trifluoromethyl) sulfonyl)methane sulfonamide in presence of KHMDS by following the similar procedure as described in Intermediate-7; m/z-584.1 as Na+1.

Intermediate-11

(R)-2-(((tert-Butoxycarbonyl) ((R)-1-(4-fluoronaphthalen-1-yl)ethyl)amino)methyl)-2H-chromen-4-yl trifluoromethanesulfonate

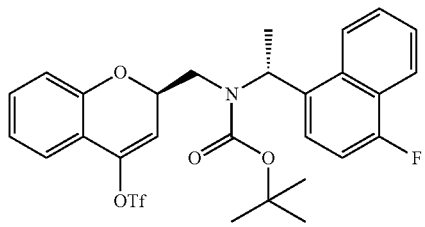 [SMILES: C[C@H](c1ccc(F)c2ccccc12)N(C[C@H]1C=C(OS(=O)(=O)C(F)(F)F)c2ccccc2O1)C(=O)OC(C)(C)C]

The title compound was prepared in five steps:

Step 1: Intermediate-2 was reacted with corresponding (R)-1-(4-fluoronaphthalen-1-yl)ethanamine hydrochloride by following the similar procedure as described in Intermediate-3.

Step 2: Step-1 Intermediate was undergone reduction reaction using borane dimethyl sulphide complex by following the similar procedure as described in Intermediate-4.

Step 3: The Step-2 Intermediate was protected with BOC by reacting with BOC anhydride in acetonitrile by following the similar procedure as described in Intermediate-5.

Step 4: Step-3 Intermediate was undergone oxidation reaction using KMnO$_4$ by following the similar procedure as described in Intermediate-6.

Step: 5: Step-4 Intermediate was reacted with 1,1,1-trifluoro-N-phenyl-N-((trifluoro methyl)sulfonyl)methane sulfonamide in presence of KHMDS by following the similar procedure as described in Intermediate-7; m/z-481.7 (m-100).

Intermediate-12

(S)-2-(Chroman-2-yl)acetic Acid

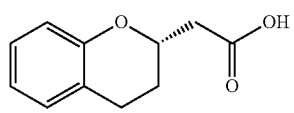 [SMILES: O=C(O)C[C@@H]1CCc2ccccc2O1]

To a solution of Intermediate-8 (0.5 g, 2.81 mmol) in ethylene dichloride (10 mL), thionyl chloride (0.35 mL, 4.77 mmol) was added in dropwise manner at 0° C. The mixture was heated to reflux and maintained for 1 h. The progress of reaction was monitored by TLC. The reaction mixture was concentrated under vacuum to get oily mass (0.55 g).

To a solution of (S)-chroman-2-carbonyl chloride (0.2 g, 1.02 mmol) in dry THF (5 mL), triethylamine (0.28 mL, 2.03 mmol) was slowly added at 0° C. After 10 minutes trimethylsilyldiazomethane (1 mL, 2.03 mmol, 2M) was added. The reaction was monitored by TLC, after completion of reaction the reaction mixture was diluted with water (5 mL) and extracted with ethyl acetate (10 mL×3). The combined organic phase was dried over Na$_2$SO$_4$, concentrated under vacuum to get crude (S)-2-(chroman-2-yl)-2-oxoethanediazonium (0.16 g, 77% yield).

To a solution of silver benzoate (0.047 g, 0.20 mmol) in 1,4-dioxane (5 mL) and water (1 mL), triethylamine (0.28 mL, 2.03 mmol) was added at 0° C. After 10 minutes (S)-2-(chroman-2-yl)-2-oxoethanediazonium (0.16 g, 0.79 mmol) was slowly added at 0° C. The reaction mixture was allowed to RT and maintained overnight. The reaction was monitored by TLC after completion of the reaction and mixture diluted with water (5 mL) and acidified with 1:1 HCl, extracted with ethyl acetate (10 mL×3). The combined organic phase was dried over Na$_2$SO$_4$, concentrated under vacuum to get crude product. Further purification was carried out by using flash chromatography (20% ethyl acetate in n-Hexane) to get title compound (60 mg, 30.7% yield). m/z-192.13.

Intermediate-13

(R)-2-(2-((tert-Butoxycarbonyl) ((R)-1-(naphthalen-1-yl)ethyl)amino)ethyl)-2H-chromen-4-yl trifluoromethanesulfonate

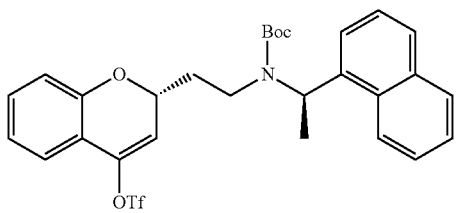 [SMILES: C[C@H](c1cccc2ccccc12)N(CC[C@@H]1C=C(OS(=O)(=O)C(F)(F)F)c2ccccc2O1)C(=O)OC(C)(C)C]

The title compound was prepared in five steps:

Step 1: Intermediate-12 was coupled with (R)-1-(naphthalen-1-yl)ethanamine by following the similar procedure as described in Intermediate-3;

Step 2: The above Step-1 Intermediate was undergone reduction reaction using borane dimethyl sulphide complex by following the similar procedure as described in Intermediate-4;

Step 3: The above Step-2 Intermediate undergone BOC protection using BOC anhydride in acetonitrile by following the similar procedure as described in Intermediate-5;

Step 4: Step-3 Intermediate was oxidized using KMnO₄ by following the similar procedure as described in Intermediate-6;

Step 5: Finally, the above Step-4 Intermediate was reacted with 1,1,1-trifluoro-N-phenyl-N-((trifluoro methyl) sulfonyl) methane sulfonamide in presence of KHMDS by following the similar procedure as described in Intermediate-7; m/z: 478.0 (m-100).

Intermediate-14

(R)-2-(Chroman-2-yl)acetic Acid

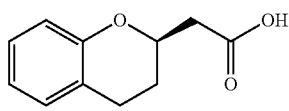 [SMILES: O=C(O)C[C@H]1CCc2ccccc2O1]

The title compound was prepared by following the similar procedure as described in Intermediate-12 by taking Intermediate-2; m/z-192.13.

Intermediate-15

(S)-2-(2-((tert-Butoxycarbonyl) ((R)-1-(naphthalen-1-yl)ethyl)amino)ethyl)-2H-chromen-4-yl trifluoromethanesulfonate

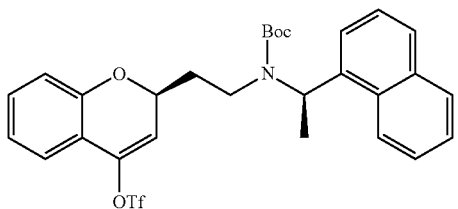 [SMILES: C[C@H](c1cccc2ccccc12)N(CC[C@H]1C=C(OS(=O)(=O)C(F)(F)F)c2ccccc2O1)C(=O)OC(C)(C)C]

The title compound was prepared in five steps:

Step 1: Intermediate-14 was coupled with (R)-1-(naphthalen-1-yl)ethanamine by following the similar procedure as described in Intermediate-3;

Step 2: The above Step-1 Intermediate was undergone reduction reaction using borane dimethyl sulphide complex by following the similar procedure as described in Intermediate-4;

Step 3: The above Step-2 Intermediate was undergone BOC protection using BOC anhydride in acetonitrile by following the similar procedure as described in Intermediate-5;

Step 4: Step-3 Intermediate was oxidized using KMnO₄ by following the similar procedure as described in Intermediate-6;

Step 5: Finally, The above Step-4 Intermediate was reacted with 1,1,1-trifluoro-N-phenyl-N-((trifluoro methyl) sulfonyl) methane sulfonamide in presence of KHMDS by following the similar procedure as described in Intermediate-7; m/z: 478 (m-100).

Intermediate-16

(R)-Methyl chroman-2-carboxylate

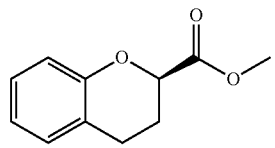

To a solution of Intermediate-2 (15 g, 84 mmol) in methanol (140 mL) was added thionyl chloride (15.36 mL, 210 mmol) at 0° C. and the mixture was heated to 65° C. and maintained for 1 h. The progress of reaction was monitored by TLC. The reaction mixture was evaporated and quenched with saturated sodium bicarbonate solution. The aqueous layer was extracted with ethyl acetate (50 mL×2). Combined organic layer was washed with water (50 mL) followed by brine solution (25 mL). The organic layer was dried over Na₂SO₄ and evaporated under reduced pressure to give colorless oily mass (15.6 g, 96%); m/z-192.8.

Intermediate-17

(R)-Chroman-2-carbaldehyde

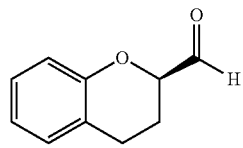 [SMILES: O=C[C@H]1CCc2ccccc2O1]

To a solution of Intermediate-16 (15.6 g, 81 mmol) in a mixture of dry toluene (120 mL) and DCM (30 mL), DIBAL-H (85 mL, 85 mmol, 1M) was added in dropwise manner at −65° C. and further stirred for 2 h at the same temperature. The progress of reaction was monitored by TLC. Reaction mixture was quenched with methanol (15 mL) at −65° C. and allowed to RT, filtered through celite, diluted with water (50 mL). It was extracted with ethyl acetate (50 mL×2) washed with water (25 mL) and brine solution (25 mL), dried over Na₂SO₄ and concentrated under reduced pressure to get the crude product. This crude product was further purified by flash chromatography (20% ethyl acetate in Hexane) to give the title compound (12.5 g, 95%); m/z-162.94.

Intermediate-18

(R,E)-Ethyl 3-(chroman-2-yl)acrylate

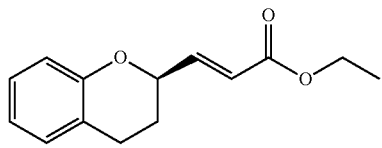 [SMILES: CCOC(=O)/C=C/[C@H]1CCc2ccccc2O1]

To solution of Intermediate-17 (11.2 g, 69 mmol) and ethyl 2-(triphenyl phosphoranylidene) acetate (26.5 g, 76 mmol) in toluene (115 mL) was heated to 110° C. and maintained for 3 h. The progress of reaction was monitored by TLC. Reaction mixture was allowed to RT then diluted with water (50 mL) and extracted with ethyl acetate (50 mL×3). The combined organic layer was washed with water (50 mL) followed by brine solution (50 mL), dried over $Na_2SO_4$ and concentrated to give crude product. The crude product was further purified by flash chromatography (10% ethyl acetate in hexane) to give title compound as colorless oily mass (11.1 g, 69.2%); m/z-232.11.

Intermediate-19

(R)-Ethyl 3-(chroman-2-yl) propanoate

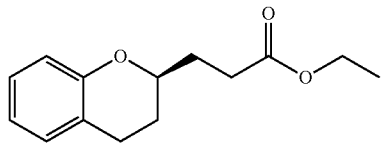 [SMILES: CCOC(=O)CC[C@H]1CCc2ccccc2O1]

To a suspension of 10% palladium on carbon (2.1 g, 50% wet) in ethanol (10 mL), Intermediate-18 (11.1 g, 47.8 mmol) in ethanol (100 mL) was carefully added and the mixture was stirred overnight under a pressure of balloon of hydrogen. The progress of reaction was monitored by TLC. Reaction mixture was filtered through celite and the filtrate was concentrated to get the crude product as colorless oily mass (11.1 g, 99%); m/z-234.4.

Intermediate-20

(R)-3-(Chroman-2-yl)propanoic Acid

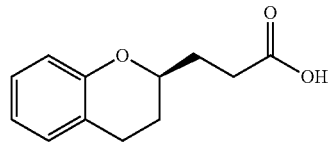 [SMILES: O=C(O)CC[C@H]1CCc2ccccc2O1]

To a solution of Intermediate-19 (11.1 g, 47.4 mmol) in THF (100 mL), methanol (100 mL) and water (10 mL) lithium hydroxide hydrate (2.98 g, 71.1 mmol) was added. The reaction mixture was stirred for 2 h at RT. The progress of reaction was monitored by TLC. The reaction mixture was concentrated under vacuum then cooled to 0° C. and acidified with dilute HCl solution. The mixture was extracted with ethyl acetate (50 mL×2), washed with water (50 mL×2) followed by brine solution (50 mL), dried over $Na_2SO_4$ and concentrated under vacuum to get white solid (9.2 g, 94%); m/z-206.17.

Intermediate-21

(S)-2-(3-(((tert-Butoxycarbonyl)((R)-1-(naphthalen-1-yl)ethyl)amino)propyl)-2H-chromen-4-yl trifluoromethanesulfonate

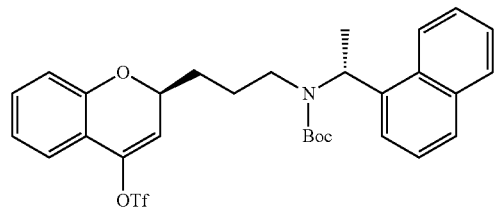 [SMILES: C[C@H](c1cccc2ccccc12)N(CCC[C@H]1C=C(OS(=O)(=O)C(F)(F)F)c2ccccc2O1)C(=O)OC(C)(C)C]

The title compound was prepared in following five steps:
Step 1: Intermediate-20 was coupled with (R)-1-(naphthalen-1-yl)ethanamine by following the similar procedure as described in Intermediate-3;
Step 2: The above Step-1 Intermediate was undergone reduction reaction using borane dimethyl sulphide complex by following the similar procedure as described in Intermediate-4;
Step 3: The above Step-2 Intermediate was undergone BOC protection using BOC anhydride in acetonitrile by following the similar procedure as described in Intermediate-5;
Step 4: Step-3 Intermediate was oxidized using $KMnO_4$ by following the similar procedure as described in Intermediate-6;
Step 5: Finally, the above Step-4 Intermediate was reacted with 1,1,1-trifluoro-N-phenyl-N-((trifluoro methyl) sulfonyl) methane sulfonamide in presence of KHMDS by following the similar procedure as described in Intermediate-7; m/z: 491.4 (M-100).

Intermediate-22

(S)-Methyl chroman-2-carboxylate

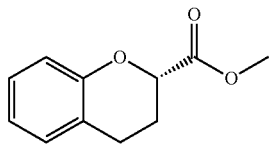

The title compound was prepared by following the similar procedure as described in Intermediate-16 by taking Intermediate-8; m/z-192.2.

Intermediate-23

(S)-Chroman-2-carbaldehyde

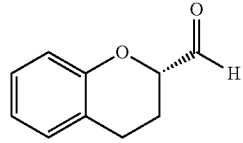 [SMILES: O=C[C@@H]1CCc2ccccc2O1]

The title compound was prepared by following the similar procedure as described in Intermediate-17 by taking Intermediate-22; m/z-163.

Intermediate-24

(R)-2-(3-((tert-Butoxycarbonyl) ((R)-1-(naphthalen-1-yl)ethyl)amino)propyl)-2H-chromen-4-yl trifluoromethanesulfonate

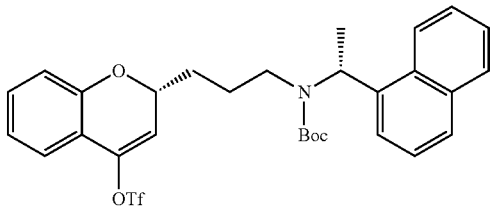 [SMILES: C[C@H](c1cccc2ccccc12)N(CCC[C@@H]1C=C(OS(=O)(=O)C(F)(F)F)c2ccccc2O1)C(=O)OC(C)(C)C]

The title compound was prepared in following eight steps:
Step 1: Intermediate-23 was reacted with ethyl 2-(triphenyl phosphoranylidene)acetate by following the similar procedure as described in Intermediate-18;
Step 2: The above Step-1 Intermediate undergone hydrogenation with 10% palladium by following the similar procedure as described in Intermediate-19;
Step 3: The above Step-2 Intermediate was hydrolyzed in presence of lithium hydroxide by following the similar procedure as described in Intermediate-20;
Step 4: Step-3 Intermediate was condensed with (R)-1-(naphthalen-1-yl)ethanamine by following the similar procedure as described in Intermediate-3;
Step 5: The above Step-4 Intermediate undergone reduction reaction using borane dimethyl sulphide complex by following the similar procedure as described in Intermediate-4;
Step 6: The above Step-5 Intermediate was protected with BOC by reacting with BOC anhydride in acetonitrile by following the similar procedure as described in Intermediate-5;
Step 7: Step-6 Intermediate was undergone oxidation reaction using KMnO$_4$ by following the similar procedure as described in Intermediate-6.
Step 8: Step-7 Intermediate was reacted with 1,1,1-trifluoro-N-phenyl-N-((trifluoro methyl) sulfonyl)methane sulfonamide in presence of KHMDS by following the similar procedure as described in Intermediate-7: m/z: 491.4 (M-100).

Intermediate-25

(S)-2-(2-((tert-Butoxycarbonyl) ((R)-1-(4-fluoronaphthalen-1-yl)ethyl)amino)ethyl)-2H-chromen-4-yl trifluoromethanesulfonate

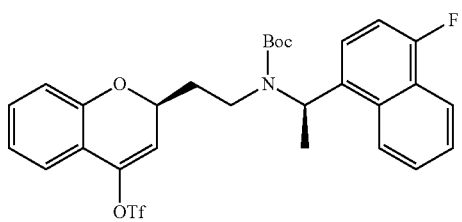 [SMILES: C[C@H](c1ccc(F)c2ccccc12)N(CC[C@H]1C=C(OS(=O)(=O)C(F)(F)F)c2ccccc2O1)C(=O)OC(C)(C)C]

The title compound was prepared in five steps:
Step 1: Intermediate-14 was coupled with (R)-1-(4-fluoronaphthalen-1-yl)ethanamine hydrochloride by following the similar procedure as described in Intermediate-3;
Step 2: The above Step-1 Intermediate was undergone reduction reaction using borane dimethyl sulphide complex by following the similar procedure as described in Intermediate-4;
Step 3: The above Step-2 Intermediate was undergone BOC protection using BOC anhydride in acetonitrile by following the similar procedure as described in Intermediate-5;
Step 4: Step-3 Intermediate was oxidized using KMnO$_4$ by following the similar procedure as described in Intermediate-6;
Step 5: Finally, the above Step-4 Intermediate was reacted with 1,1,1-trifluoro-N-phenyl-N-((trifluoro methyl) sulfonyl) methane sulfonamide in presence of KHMDS by following the similar procedure as described in Intermediate-7; m/z: 617.8 as Na+1.

Intermediate-26

(R)-2-(2-((tert-Butoxycarbonyl) ((R)-1-(4-fluoronaphthalen-1-yl)ethyl)amino)ethyl)-2H-chromen-4-yl trifluoromethanesulfonate

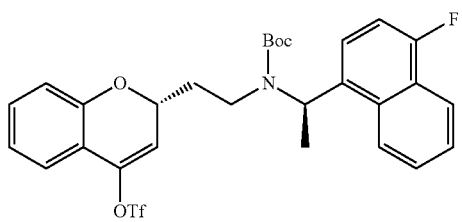 [SMILES: C[C@H](c1ccc(F)c2ccccc12)N(CC[C@@H]1C=C(OS(=O)(=O)C(F)(F)F)c2ccccc2O1)C(=O)OC(C)(C)C]

The title compound was prepared in five steps:
Step 1: Intermediate-12 was coupled with (R)-1-(4-fluoronaphthalen-1-yl)ethanamine hydrochloride by following the similar procedure as described in Intermediate-3;
Step 2: The above Step-1 Intermediate was undergone reduction reaction using borane dimethyl sulphide complex by following the similar procedure as described in Intermediate-4;
Step 3: The above Step-2 Intermediate was undergone BOC protection using BOC anhydride in acetonitrile by following the similar procedure as described in Intermediate-5;
Step 4: Step-3 Intermediate was oxidized using KMnO$_4$ by following the similar procedure as described in Intermediate-6;
Step 5: Finally, The above Step-4 Intermediate was reacted with 1,1,1-trifluoro-N-phenyl-N-((trifluoro methyl) sulfonyl) methane sulfonamide in presence of KHMDS by following the similar procedure as described in Intermediate-7; m/z: 617.8 as Na+1.

Intermediate-27

(S)-2-(2-((tert-Butoxycarbonyl) ((R)-1-(4-fluoro-3-methoxyphenyl)ethyl)amino)ethyl)-2H-chromen-4-yl trifluoromethanesulfonate

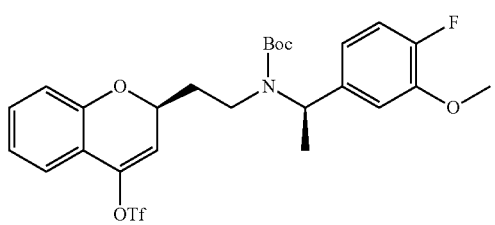 [SMILES: COc1cc([C@@H](C)N(CC[C@H]2C=C(OS(=O)(=O)C(F)(F)F)c3ccccc3O2)C(=O)OC(C)(C)C)ccc1F]

The title compound was prepared in five steps:

Step 1: Intermediate-14 was coupled with (R)-1-(4-fluoro-3-methoxyphenyl)ethanamine hydrochloride by following the similar procedure as described in Intermediate-3;

Step 2: The above Step-1 Intermediate was undergone reduction reaction using borane dimethyl sulphide complex by following the similar procedure as described in Intermediate-4;

Step 3: The above Step-2 Intermediate was undergone BOC protection using BOC anhydride in acetonitrile by following the similar procedure as described in Intermediate-5;

Step 4: Step-3 Intermediate was oxidized using KMnO$_4$ by following the similar procedure as described in Intermediate-6;

Step 5: Finally, The above Step-4 Intermediate was reacted with 1,1,1-trifluoro-N-phenyl-N-((trifluoro methyl) sulfonyl) methane sulfonamide in presence of KHMDS by following the similar procedure as described in Intermediate-7; m/z: 576.

Intermediate-28

(R)-2-(2-((tert-Butoxycarbonyl) ((R)-1-(4-fluoro-3-methoxyphenyl)ethyl)amino)ethyl)-2H-chromen-4-yl trifluoromethanesulfonate

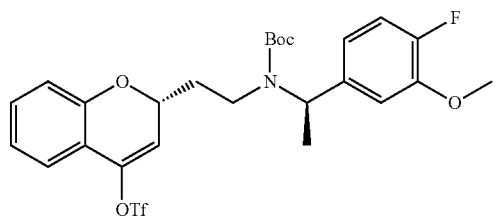 [SMILES: COc1cc([C@@H](C)N(CC[C@@H]2C=C(OS(=O)(=O)C(F)(F)F)c3ccccc3O2)C(=O)OC(C)(C)C)ccc1F]

The title compound was prepared in five steps:

Step 1: Intermediate-12 was coupled with (R)-1-(4-fluoro-3-methoxyphenyl)ethanamine hydrochloride by following the similar procedure as described in Intermediate-3;

Step 2: The above Step-1 Intermediate was undergone reduction reaction using borane dimethyl sulphide complex by following the similar procedure as described in Intermediate-4;

Step 3: The above Step-2 Intermediate was undergone BOC protection using BOC anhydride in acetonitrile by following the similar procedure as described in Intermediate-5;

Step 4: Step-3 Intermediate was oxidized using KMnO$_4$ by following the similar procedure as described in Intermediate-6;

Step 5: Finally, the above Step-4 Intermediate was reacted with 1,1,1-trifluoro-N-phenyl-N-((trifluoro methyl) sulfonyl) methane sulfonamide in presence of KHMDS by following the similar procedure as described in Intermediate-7; m/z: 576.

Intermediate-29

(S)-2-(3-((tert-Butoxycarbonyl) ((R)-1-(4-fluoronaphthalen-1-yl)ethyl)amino)propyl)-2H-chromen-4-yl trifluoromethanesulfonate

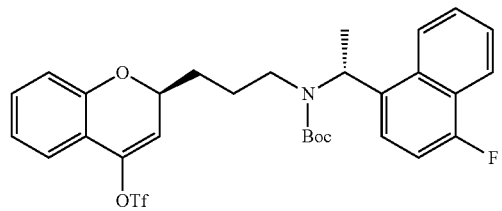 [SMILES: C[C@H](c1ccc(F)c2ccccc12)N(CCC[C@H]1C=C(OS(=O)(=O)C(F)(F)F)c2ccccc2O1)C(=O)OC(C)(C)C]

The title compound was prepared in following five steps:

Step 1: Intermediate-20 was condensed (R)-1-(4-fluoronaphthalen-1-yl)ethanamine hydrochloride by following the similar procedure as described in Intermediate-3;

Step 2: The above Step-1 Intermediate undergone reduction reaction using borane dimethyl sulphide complex by following the similar procedure as described in Intermediate-4;

Step 3: The above Step-2 Intermediate was protected with BOC by reacting with BOC anhydride in acetonitrile by following the similar procedure as described in Intermediate-5.

Step 4: Step-3 Intermediate was undergone oxidation reaction using KMnO$_4$ by following the similar procedure as described in Intermediate-6.

Step 5: Step-4 Intermediate was reacted with 1,1,1-trifluoro-N-phenyl-N-((trifluoro methyl) sulfonyl)methane sulfonamide in presence of KHMDS by following the similar procedure as described in Intermediate-7: m/z: 509.6 (M-100).

Intermediate-30

(S)-2-(3-((tert-Butoxycarbonyl) ((R)-1-(4-fluoro-3-methoxyphenyl)ethyl)amino)propyl)-2H-chromen-4-yl trifluoromethanesulfonate

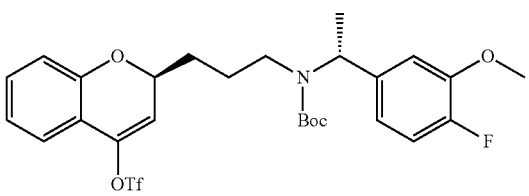 [SMILES: COc1cc([C@@H](C)N(CCC[C@H]2C=C(OS(=O)(=O)C(F)(F)F)c3ccccc3O2)C(=O)OC(C)(C)C)ccc1F]

The title compound was prepared in following five steps:

Step 1: Intermediate-20 was condensed with (R)-1-(4-fluoro-3-methoxyphenyl)ethanamine hydrochloride by following the similar procedure as described in Intermediate-3;

Step 2: The above Step-1 Intermediate undergone reduction reaction using borane dimethyl sulphide complex by following the similar procedure as described in Intermediate-4;

Step 3: The above Step-2 Intermediate was protected with BOC by reacting with BOC anhydride in acetonitrile by following the similar procedure as described in Intermediate-5.

Step 4: Step-3 Intermediate was undergone oxidation reaction using KMnO$_4$ by following the similar procedure as described in Intermediate-6.

Step 5: Step-4 Intermediate was reacted with 1,1,1-trifluoro-N-phenyl-N-((trifluoro methyl) sulfonyl)methane sulfonamide in presence of KHMDS by following the similar procedure as described in Intermediate-7: m/z: 489.8 (M-100).

Intermediate-31

Methyl 5-((2R)-2-(((tert-Butoxycarbonyl)((R)-1-(naphthalen-1-yl)ethyl)amino)methyl)chroman-4-yl)-2-fluorobenzoate

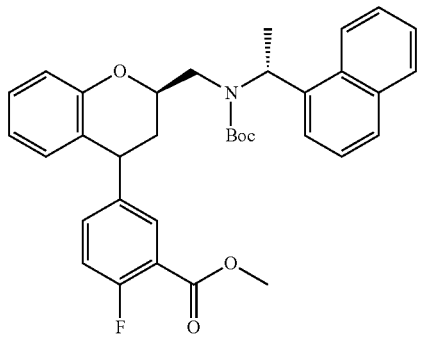 [SMILES: COC(=O)c1cc(C2C[C@H](CN(C(=O)OC(C)(C)C)[C@H](C)c3cccc4ccccc34)Oc3ccccc32)ccc1F]

Step-1: Methyl 5-((R)-2-(((tert-butoxycarbonyl) ((R)-1-(naphthalen-1-yl)ethyl)amino)methyl)-2H-chromen-4-yl)-2-fluorobenzoate Intermediate-7 (0.850 g, 1.503 mmol) was dissolved in toluene (5 mL), ethanol (5 mL) and water (0.5 mL) then (4-fluoro-3-(methoxycarbonyl)phenyl)boronic acid (0.45 g, 2.254 mmol) and Na$_2$CO$_3$ (0.478 g, 4.51 mmol) were added under nitrogen atmosphere. After 20 minutes Tetrakis(triphenylphosphane)palladium(0) (Pd(Ph$_3$P)$_4$) (0.087 g, 0.075 mmol) was added under Nitrogen purging. The reaction mixture was heated to 65° C. and further maintained for 1 h. The progress of reaction was monitored by TLC. The separated out solid in reaction mass was filtered through Celite. The filtrate was extracted with ethyl acetate (25 mL×2) and washed with water (15 mL) and brine solution (15 mL). The organic layer was dried over Na$_2$SO$_4$ and concentrated under reduced pressure to get crude product. The crude compound was purified by flash chromatography (5% ethyl acetate in Hexane) to give title compound as solid (0.72 g, 85% yield); m/z-467.1.

Step-2:—Methyl 5-((2R)-2-(((tert-butoxycarbonyl) ((R)-1-(naphthalen-1-yl)ethyl)amino)methyl)chroman-4-yl)-2-fluorobenzoate To a stirred solution of Step-1 Intermediate (0.7 g, 1.242 mmol) in methanol (10 mL), 10% palladium on carbon (150 mg) in methanol (5 mL) was carefully added and the mixture was stirred overnight under a pressure of balloon of hydrogen. The progress of reaction was monitored by TLC. Reaction mixture was filtered through celite bed and the filtrate concentrated to get the crude product (0.7 g, 100% yield). The title compound was obtained as diastereomeric mixture having different diastereomeric ratio(s); m/z-469.2 (M-100).

The below Intermediates 32 to 96 given in Table-1 were prepared in two steps:

Step-1: Synthesis of Chromene Intermediate (C—C Coupling)

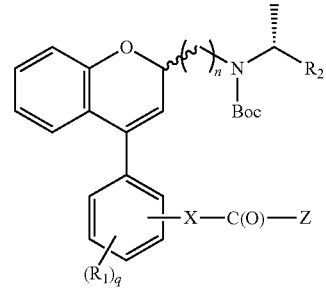

where R$_2$ is substituted or unsubstituted aryl; X, Z, R$_1$, 'n' and 'q' are as defined herein above;

The chromene intermediate was prepared by following procedure.

Triflate intermediate for example any one of Intermediate-7, Intermediate-9 to 11, Intermediate-13, Intermediate-15, Intermediate-21, or Intermediate-24 to 30 was dissolved in mixture of toluene, ethanol and water. Then optionally substituted phenyl boronic acid and Na$_2$CO$_3$ were added under nitrogen atmosphere and stirred for 30 minutes. To this reaction mixture Pd (Ph$_3$P)$_4$ was added under Nitrogen purging then heated to 65° C. and further maintained for 1 h. The progress of reaction was monitored by TLC. The reaction mixture was cooled to RT and filtered through Celite bed. The filtrate was extracted with ethylacetate and washed with water then with brine solution. The organic layer was dried over Na$_2$SO$_4$ and concentrated under reduced pressure to get crude product. This crude compound was further purified by flash chromatography to give title compound.

Step-2: Synthesis of Chromane Intermediate (Double Bond Reduction)

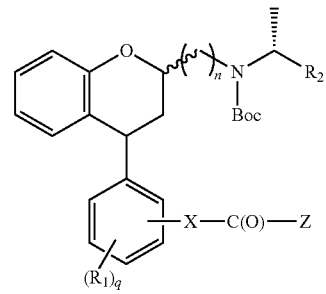

where R$_2$ is substituted or unsubstituted aryl; X, Z, R$_1$, 'n' and 'q' are as defined herein above;

The chromane intermediate was prepared by following procedure.

To a stirred solution of above Step-1 Intermediate in methanol, 10% palladium on carbon in methanol was carefully added and the mixture was stirred overnight under a pressure of balloon of hydrogen. The progress of reaction was monitored by TLC. The reaction mixture was filtered through celite bed and the filtrate was concentrated to get the crude product. In this stage the title compounds of diastereomers were obtained in different diastereomeric ratio(s).

The intermediates of 32 to 96 as mentioned in below Table-1 were obtained as diastereomeric mixture having different diastereomeric ratio(s) by following the procedure as described in Step-1 and then Step-2;

TABLE 1

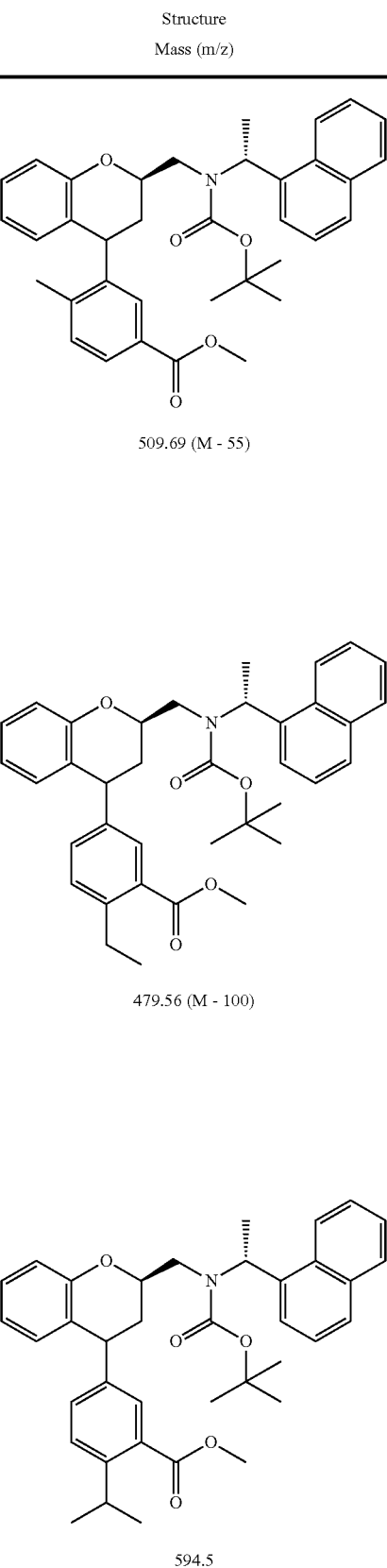

| Intermediate | Structure Mass (m/z) |
|---|---|
| 32 | 452.2 (M − 100) |
| 33 | 509.69 (M − 55) |
| 34 | 509.69 (M − 55) |
| 35 | 509.69 (M − 55) |
| 36 | 479.56 (M − 100) |
| 37 | 594.5 |

TABLE 1-continued

| Intermediate | Structure Mass (m/z) |
|---|---|
| 38 | 591.95 |
| 39 | 488.1 (M - 100) |
| 40 | 484.2 (M - 100) |
| 41 | 480.1 (M - 100) |
| 42 | 620 |
| 43 | 463.4 (M - 100) |
| 44 | 470.2 (M - 100) |
| 45 | 470.2 (M - 100) |

TABLE 1-continued

| Intermediate | Structure Mass (m/z) |
|---|---|
| 46 | 470.2 (M − 100) |
| 47 | 480.68 (M − 100) |
| 48 | 480.68 (M − 100) |
| 49 | 480.68 (M − 100) |
| 50 | 496 (M − 100) |
| 51 | 496.1 (M − 100) |
| 52 | 500 (M − 100) |
| 53 | 500 (M − 100) |

TABLE 1-continued
| Intermediate | Structure Mass (m/z) |
|---|---|
| 54 | 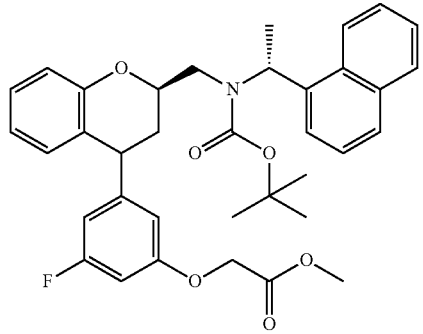 [SMILES: COC(=O)COc1cc(F)cc(C2C[C@H](CN(C(=O)OC(C)(C)C)[C@H](C)c3cccc4ccccc34)Oc3ccccc32)c1]<br>500 (M − 100) |
| 55 | 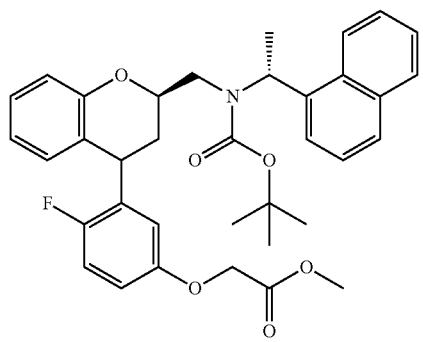 [SMILES: COC(=O)COc1ccc(F)c(C2C[C@H](CN(C(=O)OC(C)(C)C)[C@H](C)c3cccc4ccccc34)Oc3ccccc32)c1]<br>500 (M − 100) |
| 56 | 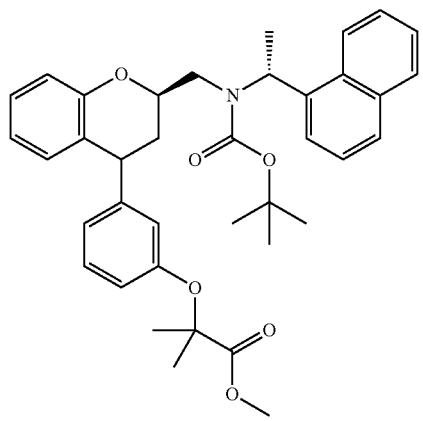 [SMILES: COC(=O)C(C)(C)Oc1cccc(C2C[C@H](CN(C(=O)OC(C)(C)C)[C@H](C)c3cccc4ccccc34)Oc3ccccc32)c1]<br>555.2 (M − 55) |long
TABLE 1-continued
| Intermediate | Structure Mass (m/z) |
|---|---|
| 57 | 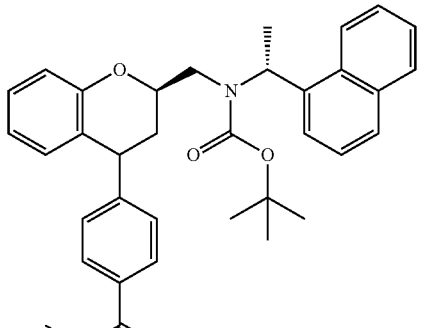<br>511.9 (M − 39) |
| 58 | 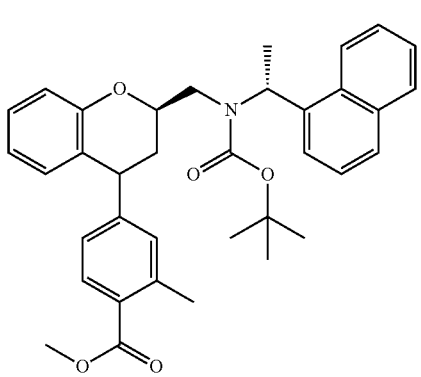<br>466.2 (M − 100) |
| 59 | 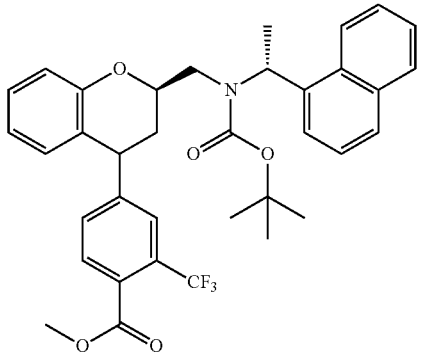<br>620.1 |

TABLE 1-continued
| Intermediate | Structure Mass (m/z) |
|---|---|
| 60 | 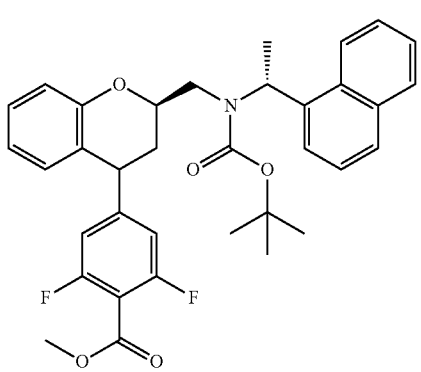 [SMILES: COC(=O)c1c(F)cc(C2C[C@H](CN(C(=O)OC(C)(C)C)[C@H](C)c3cccc4ccccc34)Oc3ccccc32)cc1F]<br>488.1 (M − 100) |
| 61 | 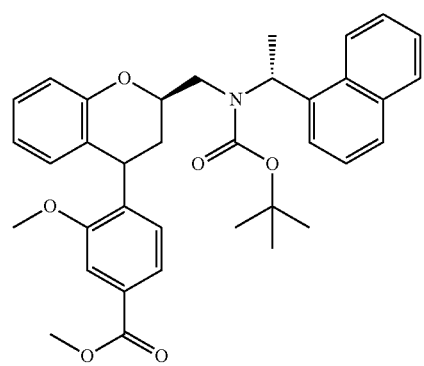 [SMILES: COC(=O)c1ccc(C2C[C@H](CN(C(=O)OC(C)(C)C)[C@H](C)c3cccc4ccccc34)Oc3ccccc32)c(OC)c1]<br>581.33 |
| 62 | 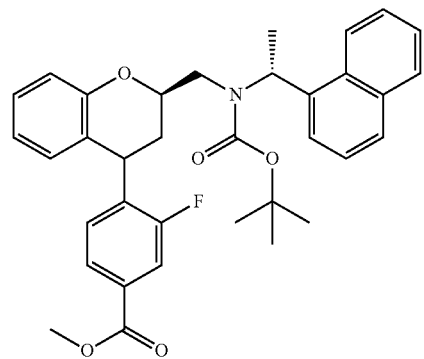 [SMILES: COC(=O)c1ccc(C2C[C@H](CN(C(=O)OC(C)(C)C)[C@H](C)c3cccc4ccccc34)Oc3ccccc32)c(F)c1]<br>469.3 (M − 100) |
| 63 | 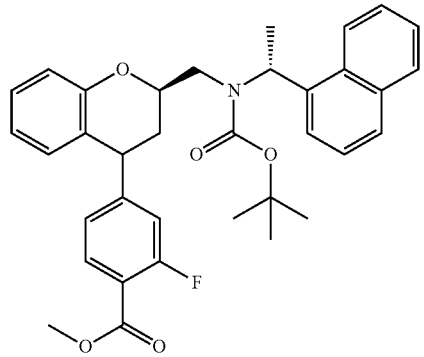 [SMILES: COC(=O)c1ccc(C2C[C@H](CN(C(=O)OC(C)(C)C)[C@H](C)c3cccc4ccccc34)Oc3ccccc32)cc1F]<br>569.32 |
| 64 | 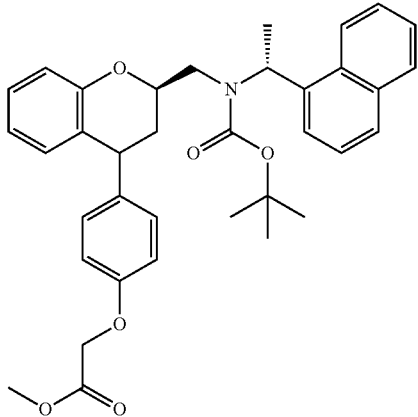 [SMILES: COC(=O)COc1ccc(C2C[C@H](CN(C(=O)OC(C)(C)C)[C@H](C)c3cccc4ccccc34)Oc3ccccc32)cc1]<br>526 (M − 69) |
| 65 | 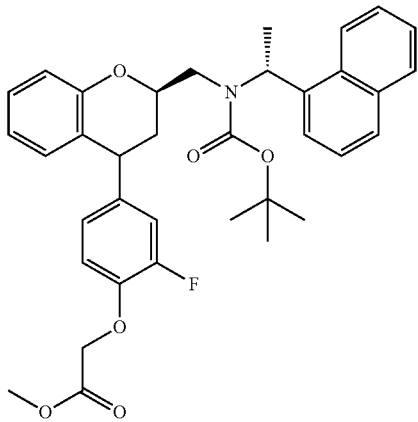 [SMILES: COC(=O)COc1ccc(C2C[C@H](CN(C(=O)OC(C)(C)C)[C@H](C)c3cccc4ccccc34)Oc3ccccc32)cc1F]<br>500 (M − 100) |

TABLE 1-continued
| Intermediate | Structure Mass (m/z) |
|---|---|
| 66 | 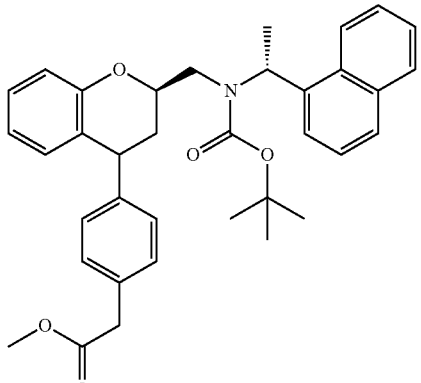<br>466.1 (M − 100) |
| 67 | 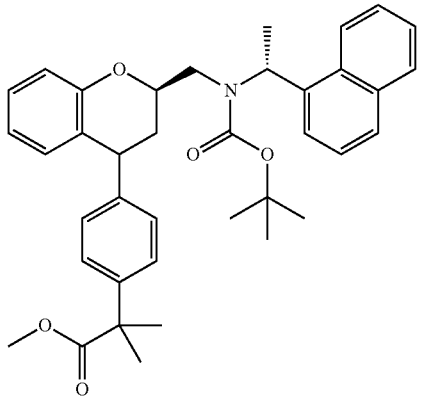 [SMILES: COC(=O)C(C)(C)c1ccc(C2C[C@H](CN(C(=O)OC(C)(C)C)[C@H](C)c3cccc4ccccc34)Oc3ccccc32)cc1]<br>494.1 (M − 100) |
| 68 | 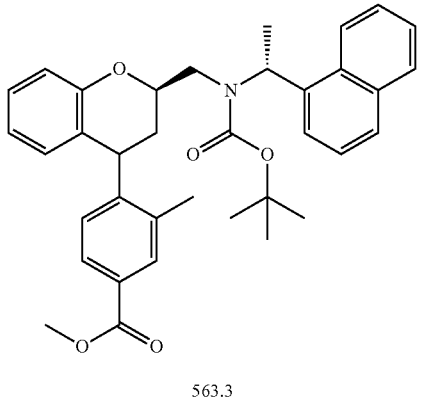<br>563.3 |
| 69 | 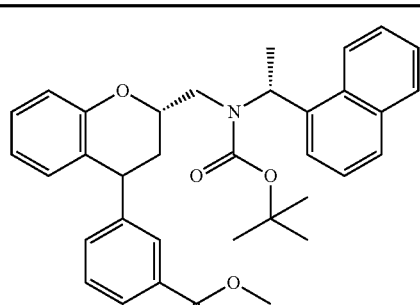<br>469.2 (M − 100) |
| 70 | 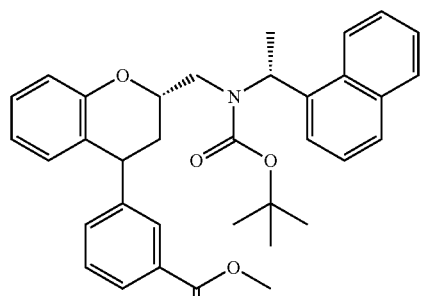<br>451.7 (M − 100) |
| 71 | 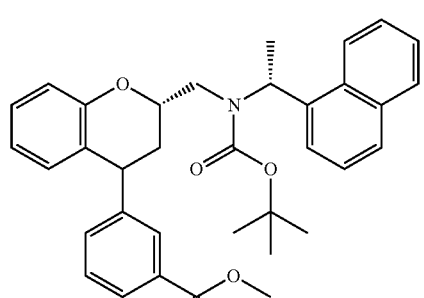<br>463.1 (M − 100) |

TABLE 1-continued

| Intermediate | Structure Mass (m/z) |
|---|---|
| 72 | 526 (M-69) |
| 73 | 463.6 (M - 100) |
| 74 | 463.6 (M - 100) |
| 75 | 463.6 (M - 100) |
| 76 | 463.6 (M - 100) |
| 77 | 463.6 (M - 100) |
| 78 | 484.29 (M - 100) |

TABLE 1-continued
| Intermediate | Structure Mass (m/z) |
|---|---|
| 79 | 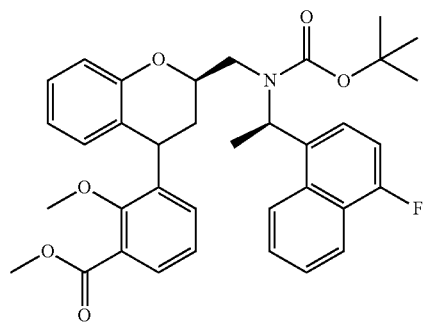 [SMILES: COC(=O)c1cccc(C2C[C@H](CN(C(=O)OC(C)(C)C)[C@H](C)c3ccc(F)c4ccccc34)Oc3ccccc32)c1OC]<br>500 (M − 100) |
| 80 | 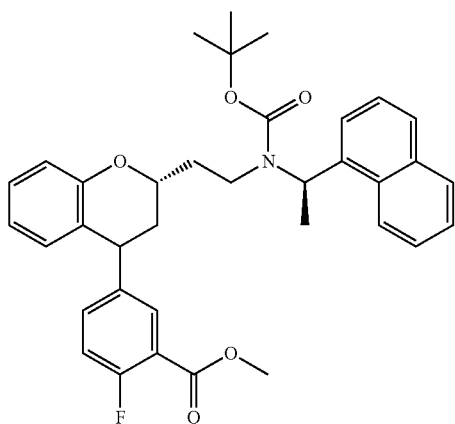 [SMILES: COC(=O)c1cc(C2C[C@@H](CCN(C(=O)OC(C)(C)C)[C@H](C)c3cccc4ccccc34)Oc3ccccc32)ccc1F]<br>484.1 (M − 100) |
| 81 | 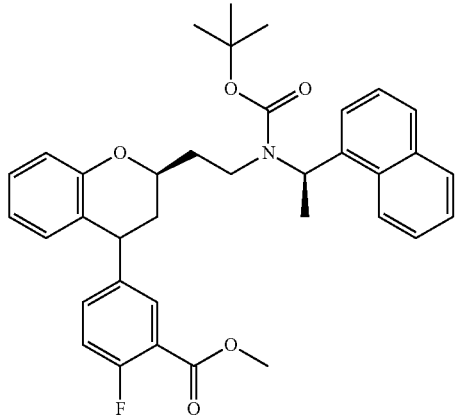 [SMILES: COC(=O)c1cc(C2C[C@H](CCN(C(=O)OC(C)(C)C)[C@H](C)c3cccc4ccccc34)Oc3ccccc32)ccc1F]<br>484.1 (M − 100) |
| 82 | 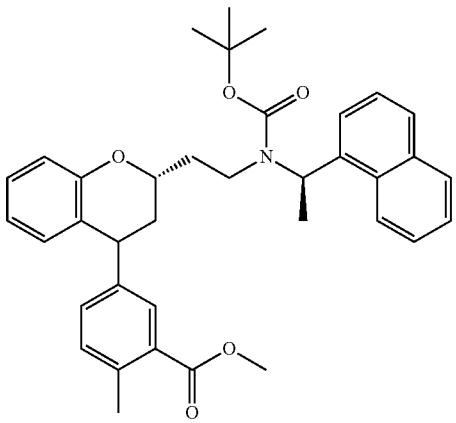 [SMILES: COC(=O)c1cc(C2C[C@@H](CCN(C(=O)OC(C)(C)C)[C@H](C)c3cccc4ccccc34)Oc3ccccc32)ccc1C]<br>480.1 (M − 100) |
| 83 | 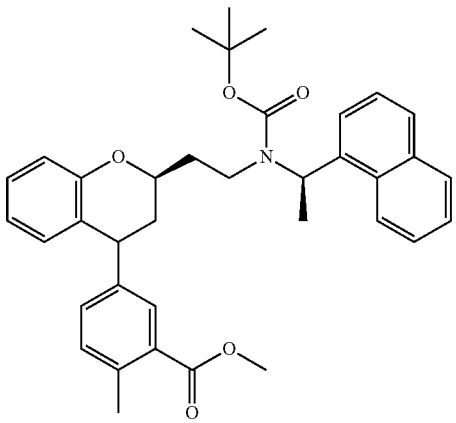 [SMILES: COC(=O)c1cc(C2C[C@H](CCN(C(=O)OC(C)(C)C)[C@H](C)c3cccc4ccccc34)Oc3ccccc32)ccc1C]<br>480.1 (M − 100) |
| 84 | 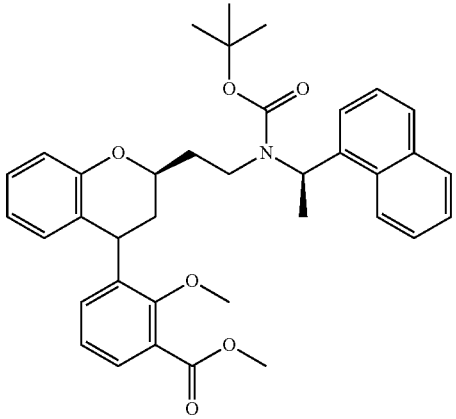 [SMILES: COC(=O)c1cccc(C2C[C@H](CCN(C(=O)OC(C)(C)C)[C@H](C)c3cccc4ccccc34)Oc3ccccc32)c1OC]<br>495 |

TABLE 1-continued
| Intermediate | Structure Mass (m/z) |
|---|---|
| 85 | 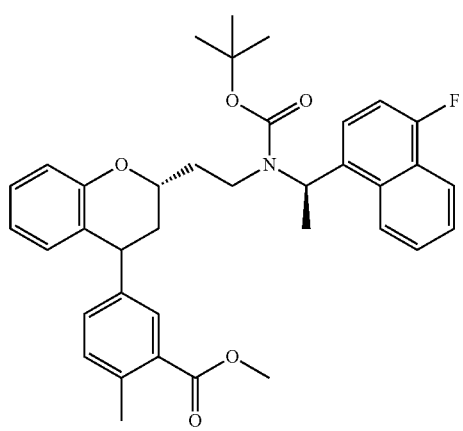 [SMILES: COC(=O)c1cc(C2C[C@@H](CCN(C(=O)OC(C)(C)C)[C@H](C)c3ccc(F)c4ccccc34)Oc3ccccc32)ccc1C] 497.7 (M − 100) |
| 86 | 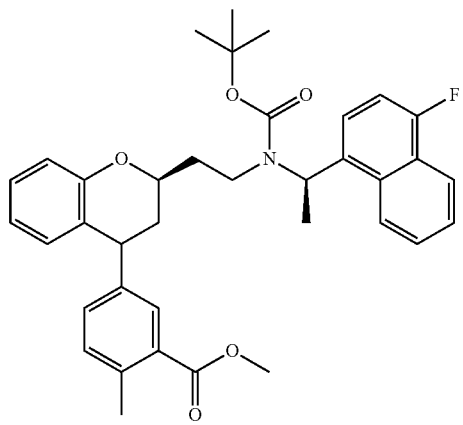 [SMILES: COC(=O)c1cc(C2C[C@H](CCN(C(=O)OC(C)(C)C)[C@H](C)c3ccc(F)c4ccccc34)Oc3ccccc32)ccc1C] 497.7 (M − 100) |
| 87 | 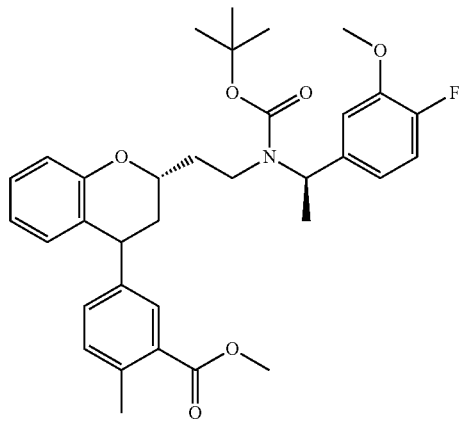 [SMILES: COC(=O)c1cc(C2C[C@@H](CCN(C(=O)OC(C)(C)C)[C@H](C)c3ccc(F)c(OC)c3)Oc3ccccc32)ccc1C] 600 (Na + 1) |
| 88 | 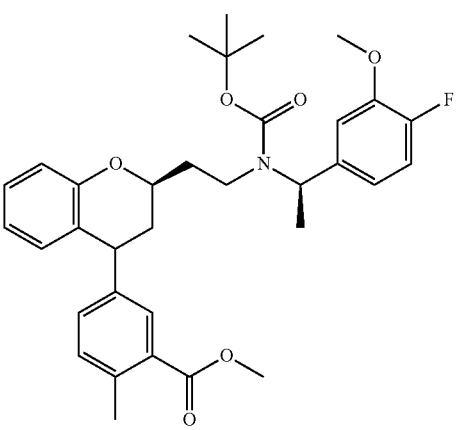 [SMILES: COC(=O)c1cc(C2C[C@H](CCN(C(=O)OC(C)(C)C)[C@H](C)c3ccc(F)c(OC)c3)Oc3ccccc32)ccc1C] 600 (Na + 1) |
| 89 | 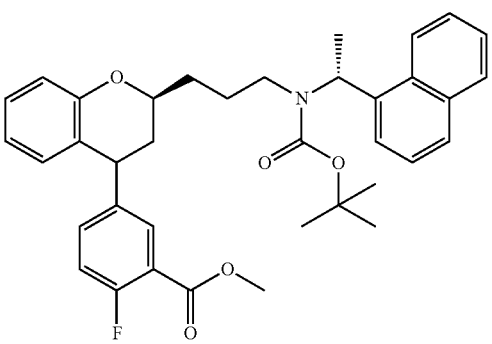 [SMILES: COC(=O)c1cc(C2C[C@H](CCCN(C(=O)OC(C)(C)C)[C@H](C)c3cccc4ccccc34)Oc3ccccc32)ccc1C] 498.56 (M − 100) |
| 90 | 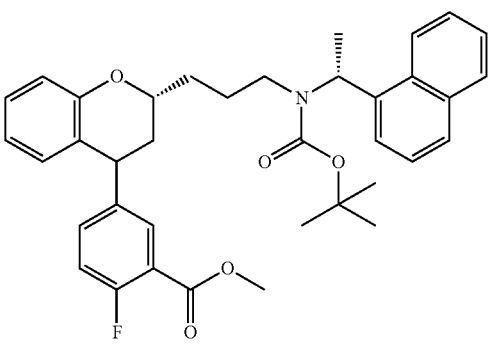 [SMILES: COC(=O)c1cc(C2C[C@@H](CCCN(C(=O)OC(C)(C)C)[C@H](C)c3cccc4ccccc34)Oc3ccccc32)ccc1C] 498.56 (M − 100) |

TABLE 1-continued

| Intermediate | Structure Mass (m/z) |
|---|---|
| 91 | 493.2 (M −100) |
| 92 | 493.2 (M −100) |
| 93 | 492.56 (M −100) |
| 94 | 511.8 (M −100) |
| 95 | 497.7 (M −100) |
| 96 | 511 (M −100) |

Intermediate-97

3-((2R,4S)-2-(((tert-Butoxycarbonyl)((R)-1-(naphthalen-1-yl)ethyl)amino)methyl)chroman-4-yl)-2,6-dimethylbenzoic Acid Step-1: 3-(((R)-2-(((tert-Butoxycarbonyl)((R)-1-(naphthalen-1-yl)ethyl)amino)methyl)-2H-chromen-4-yl)-2,6-dimethylbenzoic Acid Intermediate-7 (0.32 g, 0.57 mmol) was dissolved in toluene (5 mL), ethanol (5 mL) and water (0.5 mL) then (3-((benzyloxy)carbonyl)-2,4-dimethylphenyl)boronic acid (0.2 g, 0.57 mmol) and Na₂CO₃ (0.18 g, 1.7 mmol) were added under nitrogen atmosphere. The reaction mixture was stirred for 30 minutes then added Pd (Ph₃P)₄ (0.03 g, 0.028 mmol) under nitrogen purging. The reaction mixture was heated to 65° C. and further maintained for 1 h. The progress of reaction was monitored by TLC. The reaction mixture was cooled to RT and filtered through Celite. The filtrate was extracted with ethyl acetate (25 mL×2) and washed with water (15 mL) and brine solution (15 mL). The organic layer was dried over Na₂SO₄ and concentrated under reduced pressure to get crude product. The crude compound was purified by flash chromatography (5% ethyl acetate in Hexane) to give title compound as solid (0.25 g, 67.3% yield); m/z-654.7.

Step-2: 3-((2R,4S)-2-(((tert-Butoxycarbonyl)((R)-1-(naphthalen-1-yl)ethyl)amino)methyl)chroman-4-yl)-2,6-dimethylbenzoic Acid To a stirred solution of above Step-1 Intermediate (0.25 g, 0.38 mmol) in methanol (5 mL), 10% palladium on carbon (40 mg) in methanol (5 mL) was carefully added and the mixture was stirred overnight under a pressure of balloon of hydrogen. The progress of reaction was monitored by TLC. Reaction mixture was filtered through celite bed and the filtrate concentrated to get the crude product (0.15 g, 69.6% yield) m/z-465.9 (M-100)

The two diastereomers were separated by using following chiral preparative HPLC method. Separation Method: LUX AMYLOSE-2, 250×4.6 5u; Mobile Phase: A: Hexane/IPA (9:1, 0.1% TFA), A=100% v/v.

The below intermediates-98 to 101 as mentioned in Table-2 were prepared by following the similar procedure as described in Step-1 and then step-2 of Intermediate-97 in two steps, thus the first step of C—C coupling reaction was carried out by following the similar procedure as described in Step-1 of intermediate-97 by taking intermediate-15, intermediate-21, intermediate-24 or intermediate-27 and (3-((benzyloxy)carbonyl)-2,4-dimethyl phenyl) boronic acid. In this stage the title compounds of diastereomers were obtained in different diastereomeric ratio(s).

Further, the two diastereomers of intermediate-98 were separated by using chiral preparative HPLC.
Separation Method: CHIRAL PAK IC, 250×4.6 5u; Mobile Phase: A=Hexane/IPA (90:10, % v/v, 0.1% DEA), B=EtOH A: B 80/20% v/v.

Similarly, the two diastereomers of intermediate-99 to intermediate-101 were separated by using chiral preparative HPLC.
Separation Method: CELLULOSE-1 250×4.6 5u; Mobile Phase: A: Hexane/IPA (9:1, 0.1% TFA) B=IPA A=100% v/v.

TABLE 2

| Intermediate | Structure Mass (m/z) |
|---|---|
| 98 | 479.7 (M - 100) |
| 99 | 493.5 (M - 100) |
| 100 | 493.5 (M - 100) |
| 101 | 492.56 (M - 100) |

EXAMPLES

Example-1a, 1b

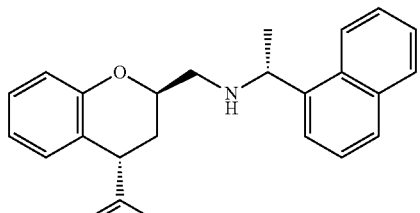

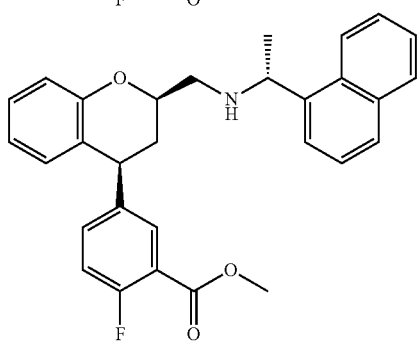

Intermediate-31 (0.35 g, 0.614 mmol) was dissolved in dichloromethane (DCM) (5 mL) and methanolic HCl (10 mL, 3N) was added. The reaction mixture was stirred at RT overnight. The progress of reaction was monitored by TLC. The reaction was evaporated under reduced pressure then added saturated $Na_2CO_3$ solution (10 mL). The mixture was extracted with ethyl acetate (10 mL×2) and washed with water (5 mL×2) followed by brine solution (5 mL), dried over $Na_2SO_4$ and concentrated under reduced pressure. This was further purified by flash chromatography (15% ethyl acetate in Hexane) to give diastereomers. Further these diastereomers were separated by chiral preparative HPLC to give Example-1a 30 mg (at RT 4.79 mins) and Example-1b 100 mg (at RT 9.65 mins); m/z-470.1.

Separation Method: CHIRAL IA 250×4.6 5u; Mobile Phase: A=(n-Hexane/IPA, 90/10, 0.1% DEA), B=IPA, A:B=70/30% V/V.

The below Examples-2 to 44 given in Table-3 were prepared by following the similar deprotection procedure as described in Example-1a, 1b by taking from corresponding Intermediate-32 to 72, Intermediate-78 or Intermediate-79 using methanolic HCl.

The two diastereomers of Example-2 to 44 were separated by using similar chiral preparative HPLC method as mentioned in Example-1a, 1b.

TABLE 3

| Ex. No. | Intermediate No. | Structure | Mass (m/z) |
|---|---|---|---|
| 2 | 32 | 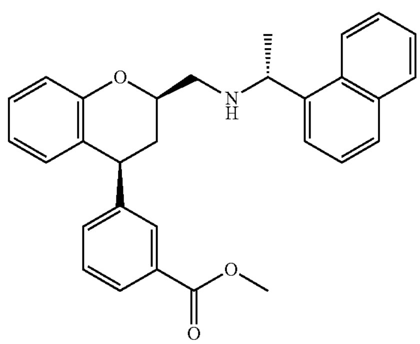 [SMILES: COC(=O)c1cccc([C@@H]2C[C@H](CN[C@H](C)c3cccc4ccccc34)Oc3ccccc32)c1] | 452.2 |
| 3 | 33 | 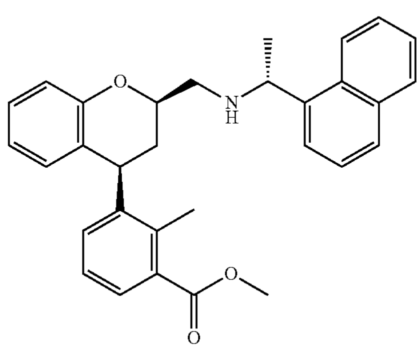 [SMILES: COC(=O)c1cccc([C@@H]2C[C@H](CN[C@H](C)c3cccc4ccccc34)Oc3ccccc32)c1C] | 465.61 |

TABLE 3-continued

| Ex. No. | Intermediate No. | Structure | Mass (m/z) |
|---|---|---|---|
| 4 | 34 | 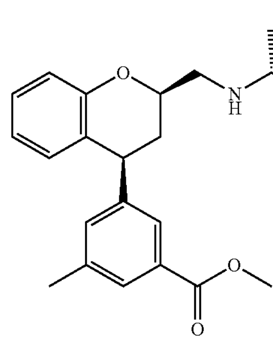 | 465.6 |
| 5 | 35 | 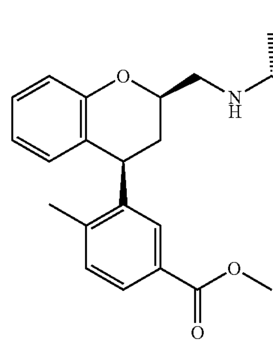 | 465.61 |
| 6a, 6b | 36 | | 480.1 |
| 7 | 37 | | 494.5 |

TABLE 3-continued

| Ex. No. | Intermediate No. | Structure | Mass (m/z) |
|---|---|---|---|
| 8a, 8b | 38 | | 491.9 |
| 9 | 39 | 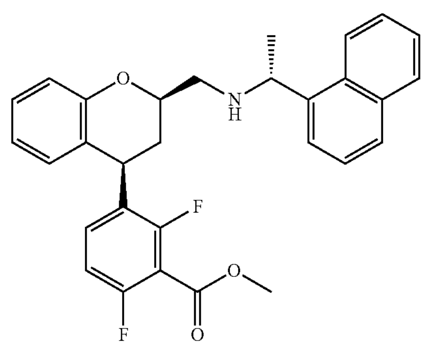 [SMILES: COC(=O)c1c(F)ccc([C@@H]2C[C@H](CN[C@H](C)c3cccc4ccccc34)Oc3ccccc32)c1F] | 487.73 |
| 10a, 10b | 40 | | 484.1 |
| 11 | 41 | 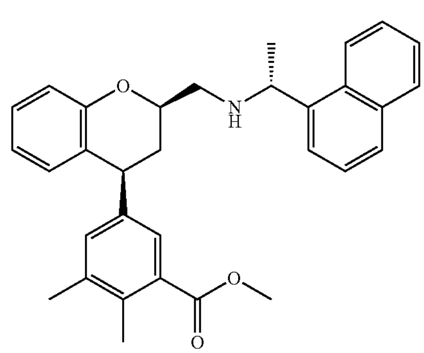 [SMILES: COC(=O)c1cc([C@@H]2C[C@H](CN[C@H](C)c3cccc4ccccc34)Oc3ccccc32)cc(C)c1C] | 480.1 |

TABLE 3-continued

| Ex. No. | Intermediate No. | Structure | Mass (m/z) |
|---|---|---|---|
| 12 | 42 | 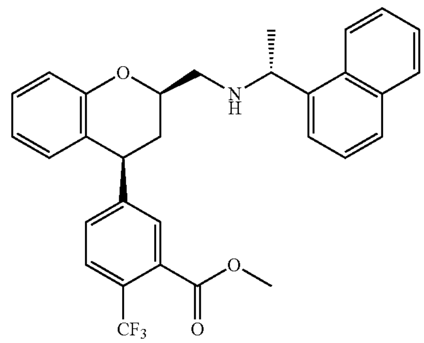 [SMILES: COC(=O)c1cc([C@@H]2C[C@H](CN[C@H](C)c3cccc4ccccc34)Oc3ccccc32)ccc1C(F)(F)F] | 520.1 |
| 13a, 13b | 43 | | 465.61 |
| 14 | 44 | 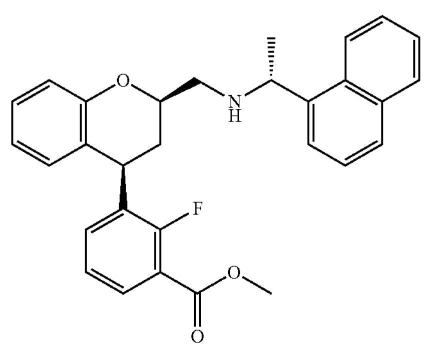 | 470.1 |
| 15 | 45 | 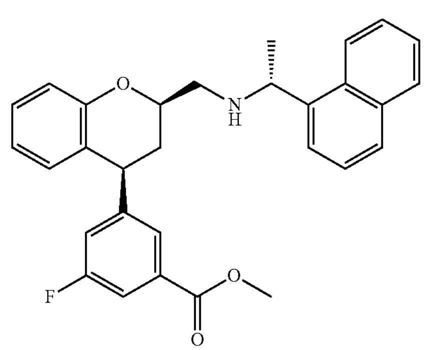 | 470.36 |

TABLE 3-continued

| Ex. No. | Intermediate No. | Structure | Mass (m/z) |
|---|---|---|---|
| 16 | 46 | 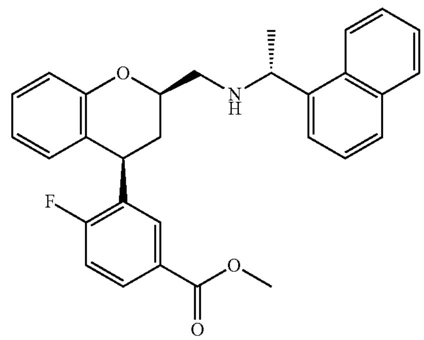 [SMILES: COC(=O)c1ccc(F)c([C@@H]2C[C@H](CN[C@H](C)c3cccc4ccccc34)Oc3ccccc32)c1] | 470.1 |
| 17 | 47 | 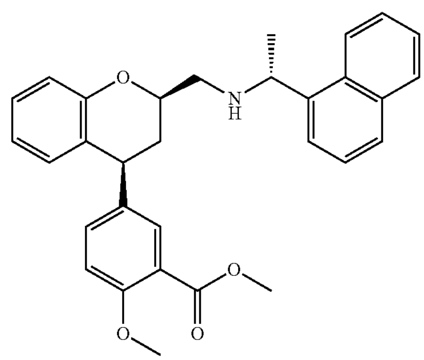 [SMILES: COC(=O)c1cc([C@@H]2C[C@H](CN[C@H](C)c3cccc4ccccc34)Oc3ccccc32)ccc1OC] | 482.1 |
| 18a, 18b | 48 | | 482 |
| 19 | 49 | 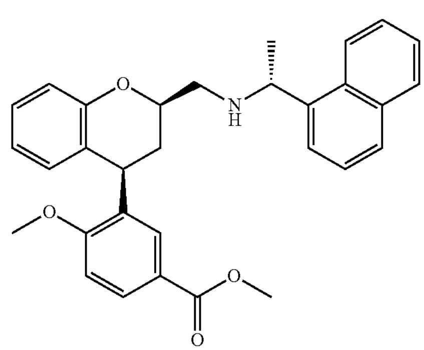 [SMILES: COC(=O)c1ccc(OC)c([C@@H]2C[C@H](CN[C@H](C)c3cccc4ccccc34)Oc3ccccc32)c1] | 482.1 |

TABLE 3-continued

| Ex. No. | Intermediate No. | Structure | Mass (m/z) |
|---|---|---|---|
| 20 | 50 | 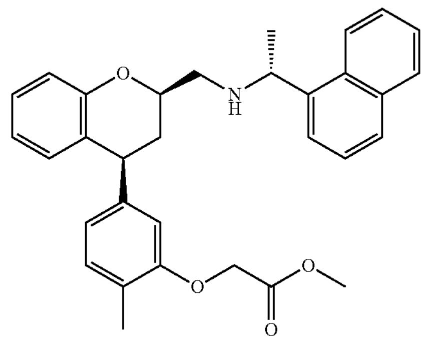 [SMILES: COC(=O)COc1cc([C@@H]2C[C@H](CN[C@H](C)c3cccc4ccccc34)Oc3ccccc32)ccc1C] | 496.1 |
| 21 | 51 | 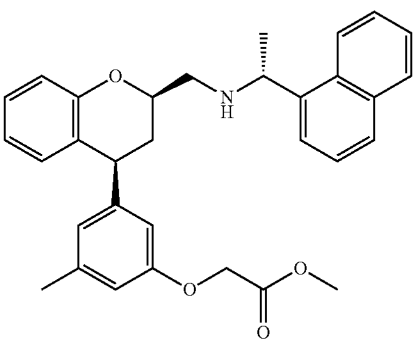 [SMILES: COC(=O)COc1cc(C)cc([C@@H]2C[C@H](CN[C@H](C)c3cccc4ccccc34)Oc3ccccc32)c1] | 496 |
| 22a, 22b | 52 | | 500 |
| 23 | 53 | 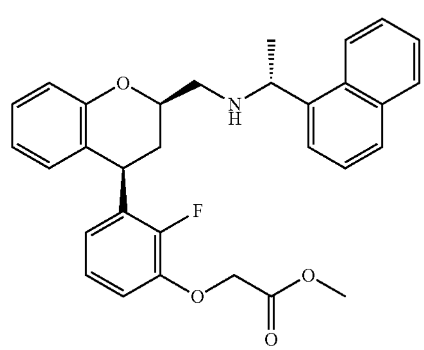 [SMILES: COC(=O)COc1cccc([C@@H]2C[C@H](CN[C@H](C)c3cccc4ccccc34)Oc3ccccc32)c1F] | 500.1 |

TABLE 3-continued

| Ex. No. | Intermediate No. | Structure | Mass (m/z) |
|---|---|---|---|
| 24a, 24b | 54 | | 500 |
| 25 | 55 | 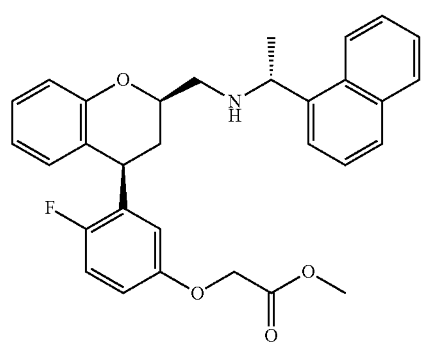 [SMILES: COC(=O)COc1ccc(F)c([C@@H]2C[C@H](CN[C@H](C)c3cccc4ccccc34)Oc3ccccc32)c1] | 500 |
| 26 | 56 | 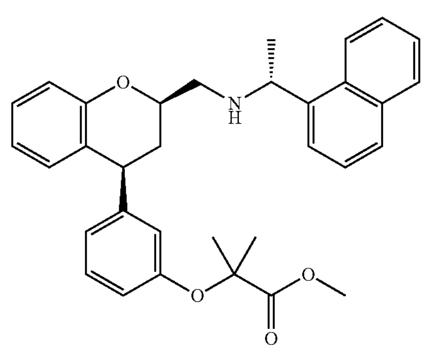 [SMILES: COC(=O)C(C)(C)Oc1cccc([C@@H]2C[C@H](CN[C@H](C)c3cccc4ccccc34)Oc3ccccc32)c1] | 524.57 |
| 27a, 27b | 57 | | 451.6 |

TABLE 3-continued

| Ex. No. | Intermediate No. | Structure | Mass (m/z) |
|---|---|---|---|
| 28a, 28b | 58 | | 465.61 |
| 29a, 29b | 59 | | 520.44 |
| 30 | 60 | 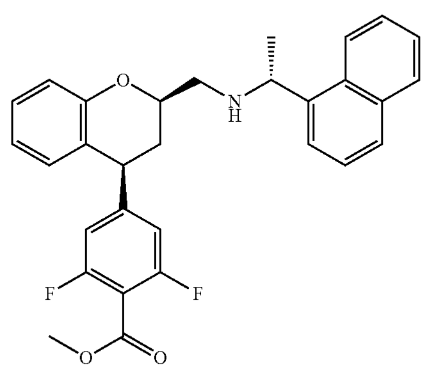 [SMILES: COC(=O)c1c(F)cc([C@@H]2C[C@H](CN[C@H](C)c3cccc4ccccc34)Oc3ccccc32)cc1F] | 488.1 |
| 31a, 31b | 61 | | 481.86 |

TABLE 3-continued

| Ex. No. | Intermediate No. | Structure | Mass (m/z) |
|---|---|---|---|
| 32 | 62 | 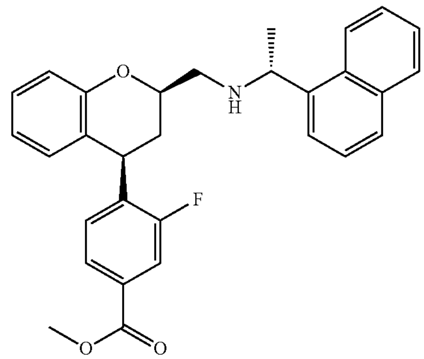 [SMILES: COC(=O)c1ccc([C@@H]2C[C@H](CN[C@H](C)c3cccc4ccccc34)Oc3ccccc32)c(F)c1] | 469.9 |
| 33 | 63 | 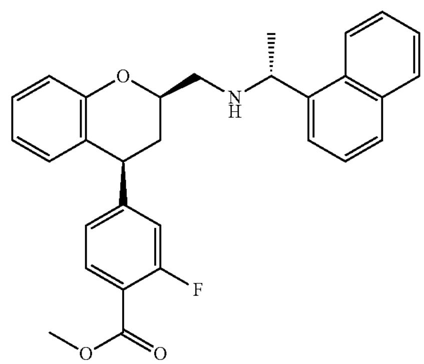 [SMILES: COC(=O)c1ccc([C@@H]2C[C@H](CN[C@H](C)c3cccc4ccccc34)Oc3ccccc32)cc1F] | 470 |
| 34a, 34b | 64 | | 482.2 |
| 35a, 35b | 65 | | 500 |

TABLE 3-continued

| Ex. No. | Intermediate No. | Structure | Mass (m/z) |
|---|---|---|---|
| 36a, 36b | 66 | | 466.1 |
| 37a, 37b | 67 | | 494.1 |
| 38 | 68 | 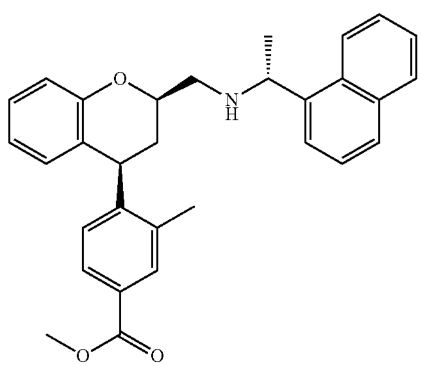 [SMILES: COC(=O)c1ccc([C@@H]2C[C@H](CN[C@H](C)c3cccc4ccccc34)Oc3ccccc32)c(C)c1] | 465.6 |
| 39 | 69 | 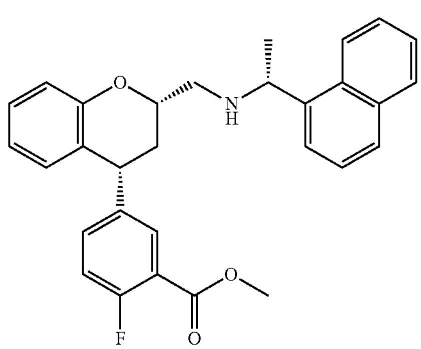 [SMILES: COC(=O)c1cc([C@H]2C[C@@H](CN[C@H](C)c3cccc4ccccc34)Oc3ccccc32)ccc1F] | 470.1 |

TABLE 3-continued

| Ex. No. | Intermediate No. | Structure | Mass (m/z) |
|---|---|---|---|
| 40 | 70 | 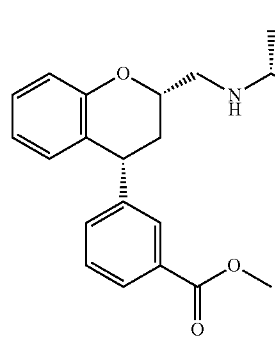 | 452.2 |
| 41a, 41b | 71 | 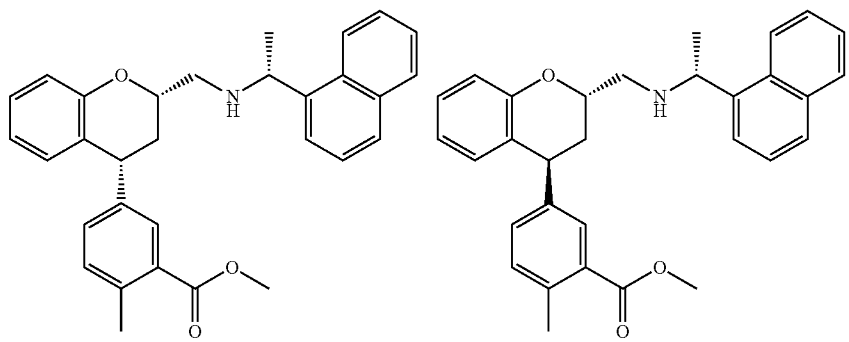 | 465.61 |
| 42a, 42b | 72 | 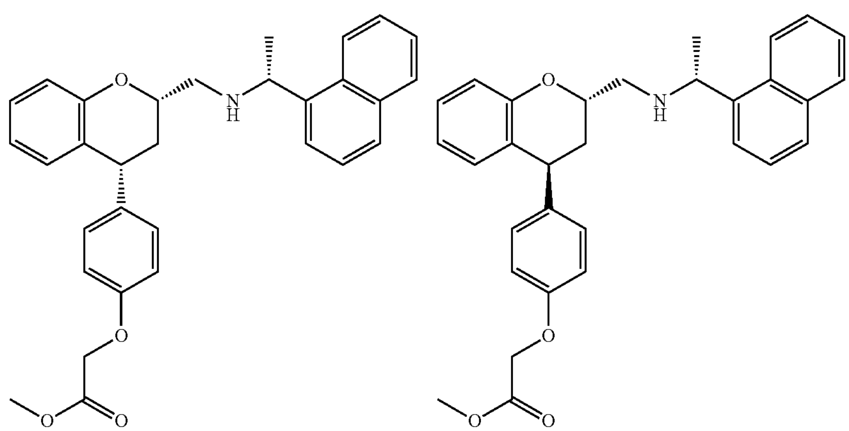 | 482.2 |
| 43a, 43b | 78 | 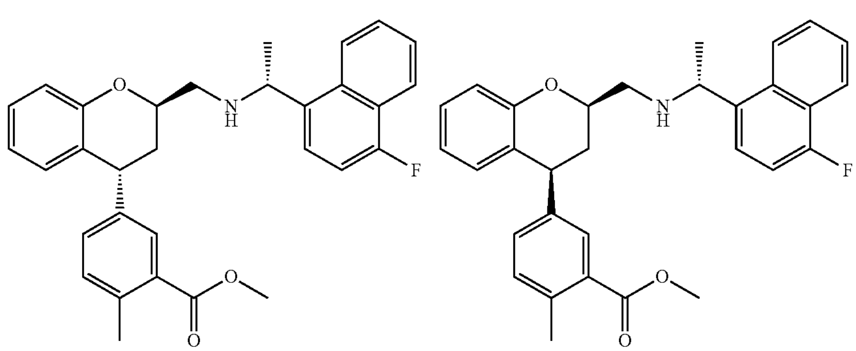 | 484.3 |

TABLE 3-continued

| Ex. No. | Intermediate No. | Structure | Mass (m/z) |
|---|---|---|---|
| 44a, 44b | 79 | 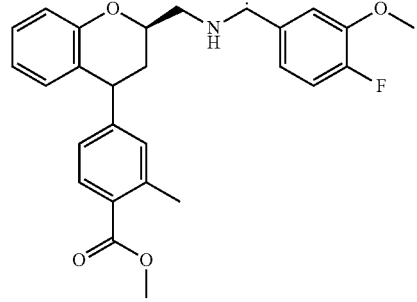 | 500.43 |

The below Examples-45 to 49 given in Table-4 were prepared by following the similar deprotection procedure as described in Example-1a, 1b by taking corresponding Intermediate-73 to 77 using methanolic HCl. These examples were obtained with more than 90% enantiomeric purity and they were directly used for ester hydrolysis without separation by chiral HPLC.

TABLE 4

| Ex. No. | Intermediate No | Structure | Mass (m/z) |
|---|---|---|---|
| 45 | 73 | 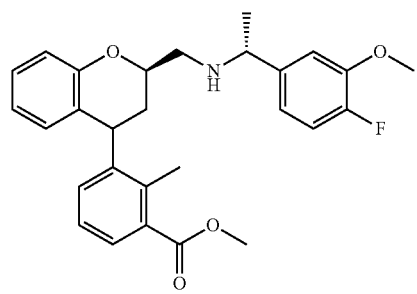 [SMILES: COC(=O)c1cccc(C2C[C@H](CN[C@H](C)c3ccc(F)c(OC)c3)Oc3ccccc32)c1C] | 463.5 |
| 46 | 74 | 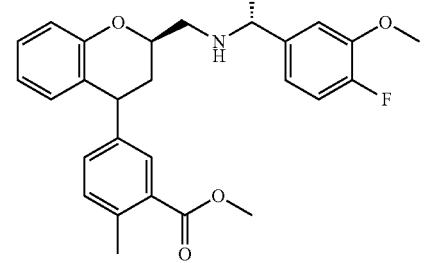 | 463.5 |
| 47 | 75 | 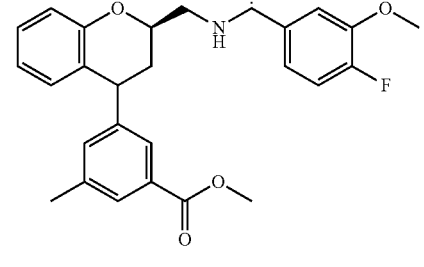 | 463.5 |
| 48 | 76 | 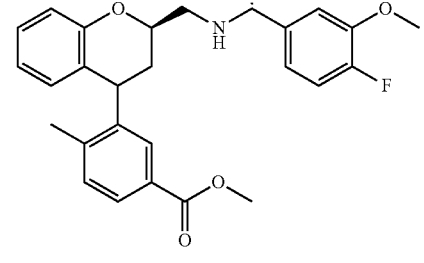 | 463.5 |
| 49 | 77 | 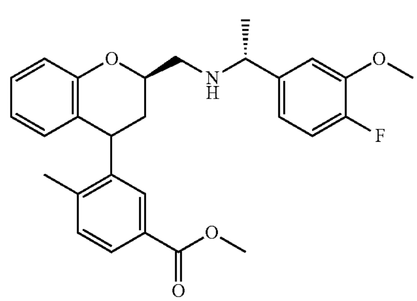 [SMILES: COC(=O)c1ccc(C)c(C2C[C@H](CN[C@H](C)c3ccc(F)c(OC)c3)Oc3ccccc32)c1] | 463.5 |

Example-50

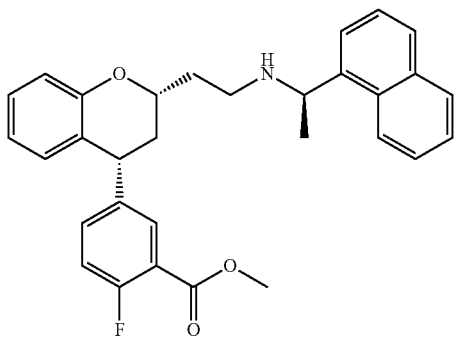 [SMILES: COC(=O)c1cc([C@H]2C[C@@H](CCN[C@H](C)c3cccc4ccccc34)Oc3ccccc32)ccc1F]

Intermediate-80 (0.3 g, 0.514 mmol) was dissolved in DCM (10 mL) and methanol/HCl (3 mL, 3N). The reaction mixture was stirred at 40° C. overnight. The progress of reaction was monitored by TLC. The reaction was evaporated under reduced pressure then added saturated $Na_2CO_3$ solution (5 mL). The mixture was extracted with ethyl acetate (10 mL×2) and washed with water (5 mL×2) followed by brine solution (5 mL), dried over $Na_2SO_4$ and concentrated under reduced pressure. This was further purified by flash chromatography (15% Ethyl acetate in Hexane) to give diastereomers of the title compound (190 mg, 76%). m/z-498. Further, these diastereomers were separated by similar chiral preparative HPLC method as mentioned in Example 1a, 1b to give Example-50 (80 mg); m/z: 484.3.

The below examples 51 to 66 given in Table-5 were prepared by following the similar deprotection procedure as described in Example-50 by taking any one of Intermediate-81 to 96 using methanolic HCl. Further, the diastereomers of Example-51 to 53 and 59 to 66 were separated by chiral preparative HPLC.

Method: CHIRAL IA 250×4.6, 5u; Mobile Phase: A=(n-Hexane/IPA, 90/10, 0.1% DEA) B=IPA, A: B=70/30% V/V.

The diastereomers of Example-54 to 58 were also separated by chiral preparative HPLC method. Method: CHIRAL PAK ID: 250 mm×4.6, 5µ; Mobile Phase: A=n-hexane IPA (90/10% v/v, 0.1% DEA) B=IPA, A: B=95/5% v/v.

TABLE 5

| Ex. No. | Intermediate-No | Structure | Mass (m/z) |
|---|---|---|---|
| 51 | 81 | 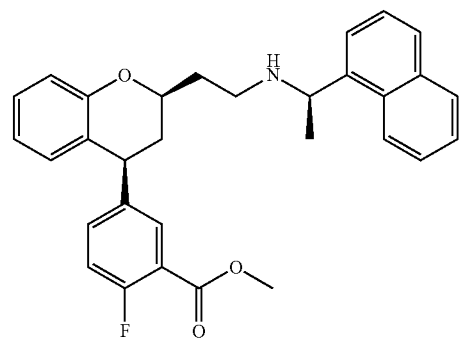 [SMILES: COC(=O)c1cc([C@@H]2C[C@H](CCN[C@H](C)c3cccc4ccccc34)Oc3ccccc32)ccc1C] | 484.3 |
| 52 | 82 | 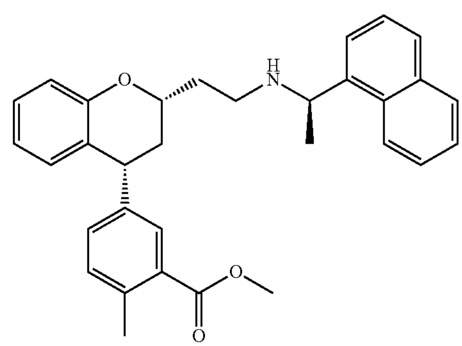 | 480.05 |
| 53 | 83 | 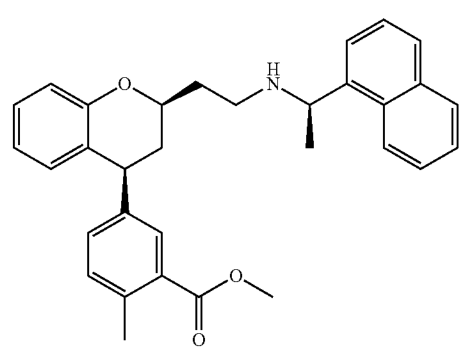 | 480 |

TABLE 5-continued

| Ex. No. | Intermediate-No | Structure | Mass (m/z) |
|---|---|---|---|
| 54 | 84 | 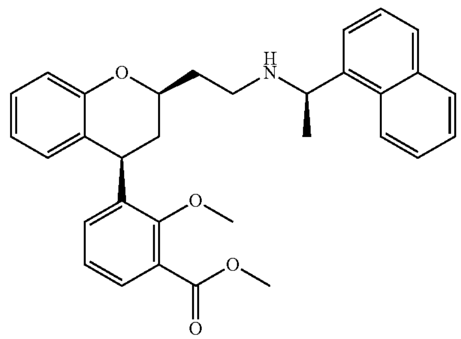 [SMILES: COC(=O)c1cccc([C@@H]2C[C@H](CCN[C@H](C)c3cccc4ccccc34)Oc3ccccc32)c1OC] | 481.51 |
| 55 | 85 | 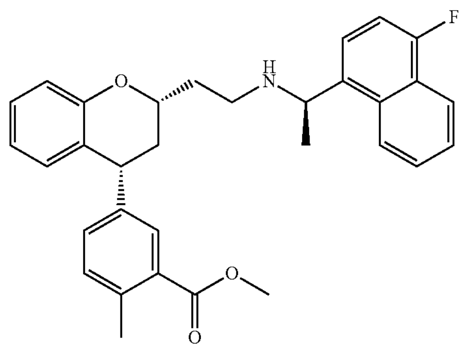 [SMILES: COC(=O)c1cc([C@H]2C[C@@H](CCN[C@H](C)c3ccc(F)c4ccccc34)Oc3ccccc32)ccc1C] | 497.8 |
| 56 | 86 | 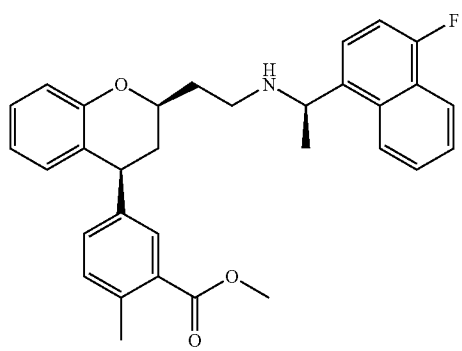 [SMILES: COC(=O)c1cc([C@@H]2C[C@H](CCN[C@H](C)c3ccc(F)c4ccccc34)Oc3ccccc32)ccc1C] | 497.8 |
| 57 | 87 | 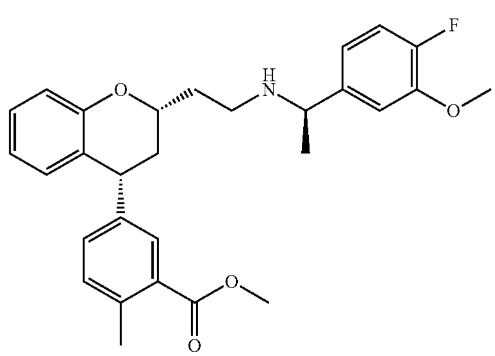 [SMILES: COC(=O)c1cc([C@H]2C[C@@H](CCN[C@H](C)c3ccc(F)c(OC)c3)Oc3ccccc32)ccc1C] | 478.48 |

TABLE 5-continued

| Ex. No. | Intermediate-No | Structure | Mass (m/z) |
|---|---|---|---|
| 58 | 88 | 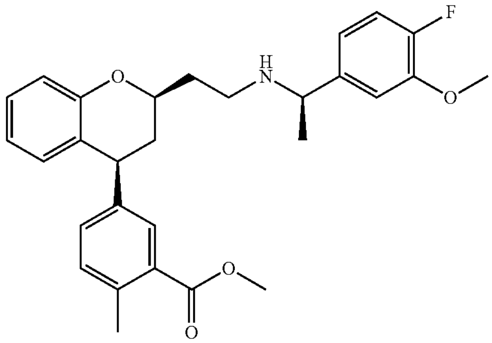 [SMILES: COC(=O)c1cc([C@@H]2C[C@H](CCN[C@H](C)c3ccc(F)c(OC)c3)Oc3ccccc32)ccc1C] | 478.48 |
| 59 | 89 | 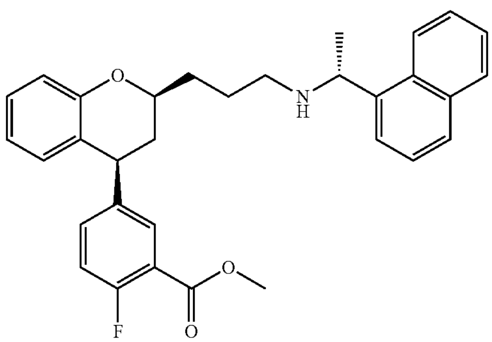 [SMILES: COC(=O)c1cc([C@@H]2C[C@H](CCCN[C@H](C)c3cccc4ccccc34)Oc3ccccc32)ccc1F] | 498.49 |
| 60 | 90 | 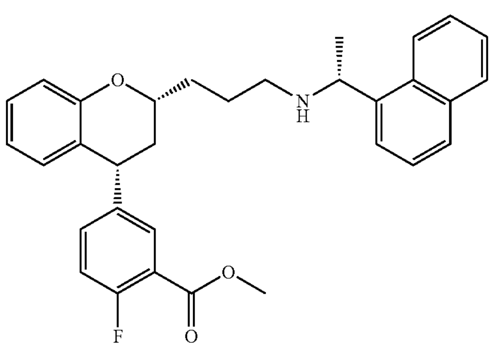 [SMILES: COC(=O)c1cc([C@H]2C[C@@H](CCCN[C@H](C)c3cccc4ccccc34)Oc3ccccc32)ccc1F] | 498.49 |
| 61 | 91 | 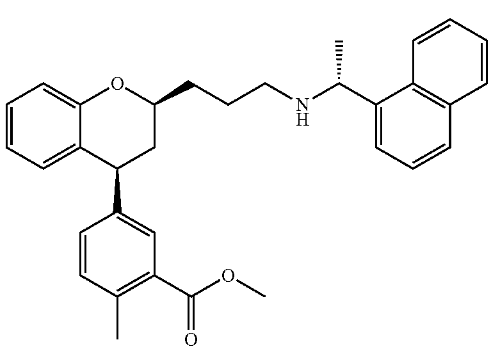 [SMILES: COC(=O)c1cc([C@@H]2C[C@H](CCCN[C@H](C)c3cccc4ccccc34)Oc3ccccc32)ccc1C] | 494 |

TABLE 5-continued

| Ex. No. | Intermediate-No | Structure | Mass (m/z) |
|---|---|---|---|
| 62 | 92 | 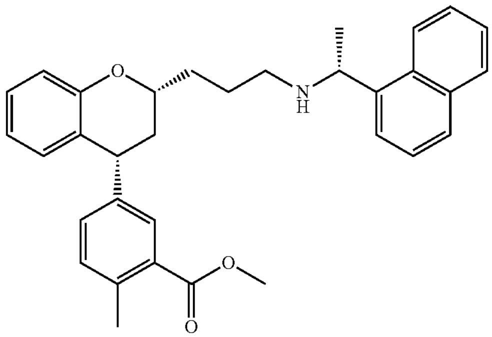 [SMILES: COC(=O)c1cc([C@H]2C[C@@H](CCCN[C@H](C)c3cccc4ccccc34)Oc3ccccc32)ccc1C] | 494 |
| 63 | 93 | 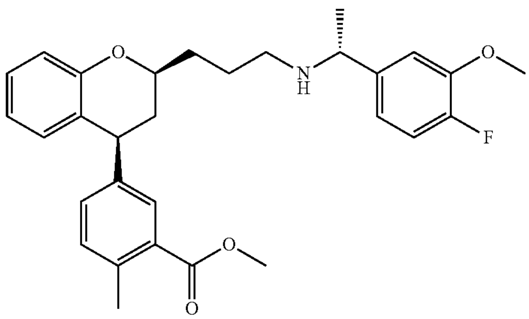 [SMILES: COC(=O)c1cc([C@@H]2C[C@H](CCCN[C@H](C)c3ccc(F)c(OC)c3)Oc3ccccc32)ccc1C] | 492.49 |
| 64 | 94 | 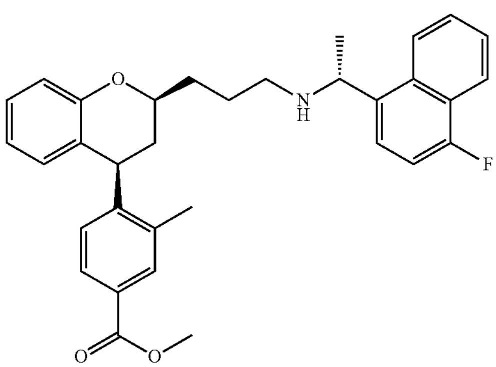 [SMILES: COC(=O)c1ccc([C@@H]2C[C@H](CCCN[C@H](C)c3ccc(F)c4ccccc34)Oc3ccccc32)c(C)c1] | 512.56 |
| 65 | 95 | 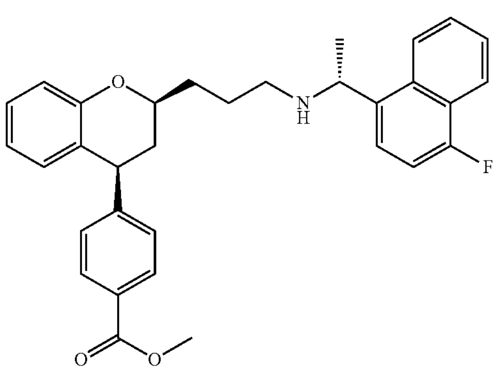 [SMILES: COC(=O)c1ccc([C@@H]2C[C@H](CCCN[C@H](C)c3ccc(F)c4ccccc34)Oc3ccccc32)cc1] | 498 |

TABLE 5-continued

| Ex. No. | Intermediate-No | Structure | Mass (m/z) |
|---|---|---|---|
| 66 | 96 | 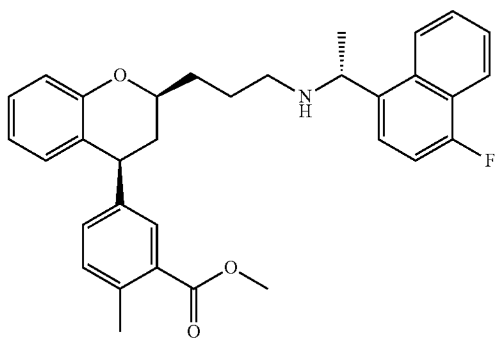 [SMILES: COC(=O)c1cc([C@@H]2C[C@H](CCCN[C@H](C)c3ccc(F)c4ccccc34)Oc3ccccc32)ccc1C] | 512 |

Example-67

2,6-Dimethyl-3-((2R,4S)-2-((((R)-1-(naphthalen-1-yl)ethyl)amino)methyl)chroman-4-yl)benzoic Acid Hydrochloride

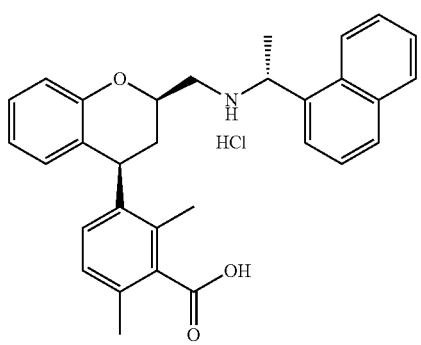 [SMILES: Cc1ccc([C@@H]2C[C@H](CN[C@H](C)c3cccc4ccccc34)Oc3ccccc32)c(C)c1C(=O)O ; Cl]

Intermediate-97 (0.45 g, 0.795 mmol) was dissolved in DCM (10 mL) and ethereal HCl (10 mL) was added. The reaction mixture was stirred at RT overnight. The progress of reaction was monitored by TLC. The reaction was evaporated under reduced pressure.

The resultant solid was washed with diethyl ether (2 mL) followed by n-pentane (2 mL), dried to get the corresponding hydrochloride salt (0.32 g, 85% yield).

m/z: 466.1; $^1$HNMR (400 MHz, DMSO-$d_6$): δ 13.21 (bs, 1H), 9.80 (bs, 1H), 9.48 (bs, 1H), 8.30 (d, J=8.0 Hz, 1H), 8.05 (m, 3H), 7.68-7.60 (m, 3H), 7.15 (t, J=7.6 Hz, 1H), 7.02 (d, J=7.2 Hz, 1H), 6.89 (d, J=7.2 Hz, 1H), 6.82-6.78 (t, J=7.6 Hz, 2H), 6.54 (m, 1H), 5.47-5.46 (m, 1H) 4.66 (m, 1H), 4.51 (m, 1H), 3.34 (m, 1H), 3.16 (m, 1H), 2.45 (s, 3H), 2.22 (m, 1H), 2.20 (s, 3H), 1.85 (m, 1H), 1.75 (d, J=6.8 Hz, 3H).

The below Examples-68 to 71 given in Table-6 were prepared by following the similar deprotection procedure as described in Example-67 by taking corresponding Intermediate-98 to 101 using ethereal HCl.

TABLE 6

| Ex. No. | Intermediate-No | Structure | Mass (m/z) |
|---|---|---|---|
| 68 | 98 | 2,6-Dimethyl-3-((2R,4S)-2-(2-(((R)-1-(naphthalen-1-yl)ethyl)amino)ethyl)chroman-4-yl)benzoic acid hydrochloride | 480.1 |

$^1$H NMR (400 MHz, DMSO-d6): δ 13.2 (bs, 1H), 9.60 (bs, 1H), 9.20 (bs, 1H), 8.27-8.25 (d, J = 8.4 Hz, 1H), 8.03-8.00 (m, 2H), 7.83-7.81 (d, J = 7.6 Hz, 1H), 7.66-7.58 (m, 3H), 7.07-7.00 (m, 2H), 6.76-6.69 (m, 3H), 6.60-6.50 (m, 1H) 5.43-5.40 (m, 1H), 4.50-4.10 (m, 1H), 4.31-4.26 (m, 1H), 3.32-3.20 (m, 2H), 2.33 (s, 3H), 2.22 (s, 3H), 2.09-2.07 (m, 3H), 1.80-1.68 (m, 4H).

TABLE 6-continued

| Ex. No. | Intermediate-No | Structure | Mass (m/z) |
|---|---|---|---|
| 69 | 99 | 2,6-Dimethyl-3-((2R,4R)-2-(3-(((R)-1-(naphthalen-1-yl)ethyl)amino)propyl)chroman-4-yl)benzoic acid hydrochloride | 494.1 |

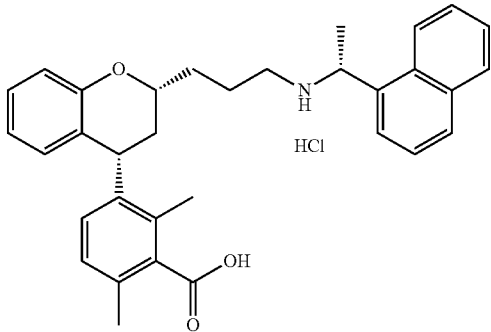

$^1$H NMR (400 MHz, DMSO-d$_6$): δ 13.20 (bs, 1H), 9.82 (bs, 1H), 9.25 (bs, 1H), 8.28 (d, J = 8.4 Hz, 1H), 8.03-7.98 (m, 3H), 7.65-7.58 (m, 3H), 7.05-6.98 (m, 2H), 6.77-6.70 (m, 2H), 6.54-6.38 (m, 2H), 5.33 (m, 1H), 4.46 (m, 1H), 4.13 (m, 1H), 3.04 (m, 1H), 2.85 (m, 1H), 2.32 (s, 3H), 2.22 (s, 3H), 2.05 (m, 1H), 1.89 (m, 2H), 1.74-1.64 (m, 6H).

| Ex. No. | Intermediate-No | Structure | Mass (m/z) |
|---|---|---|---|
| 70 | 100 | 2,6-Dimethyl-3-((2S,4S)-2-(3-(((R)-1-(naphthalen-1-yl)ethyl)amino)propyl)chroman-4-yl)benzoic acid hydrochloride | 494.1 |

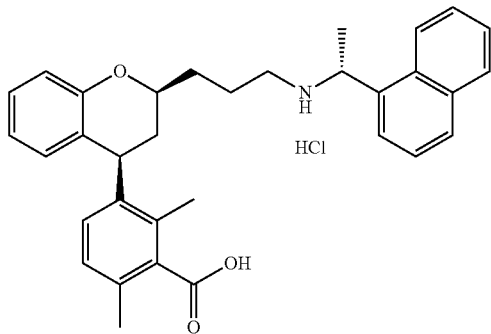

$^1$H NMR (400 MHz, DMSO-d$_6$): δ 13.20 (bs, 1H), 9.58 (bs, 1H), 9.13 (bs, 1H), 8.28 (d, J = 8.4 Hz, 1H), 8.00 (t, J = 8.4 Hz, 2H), 7.93 (d, J = 7.2 Hz, 1H), 7.65-7.58 (m, 3H), 7.07-6.99 (m, 2H), 6.78-6.66 (m, 3H), 6.55-6.49 (m, 1H), 5.34 (m, 1H), 4.47 (m, 1H), 4.17 (m, 1H), 3.04 (m, 1H), 2.85 (m, 1H), 2.33 (s, 3H), 2.22 (s, 3H), 2.05 (m, 1H), 1.92 (m, 2H), 1.73-1.68 (m, 6H).

TABLE 6-continued

| Ex. No. | Intermediate-No | Structure | Mass (m/z) |
|---|---|---|---|
| 71 | 101 | 3-((2S,4S)-2-(3-(((R)-1-(4-Fluoro-3-methoxyphenyl)ethyl)amino)propyl)chroman-4-yl)-2,6-dimethylbenzoic acid hydrochloride 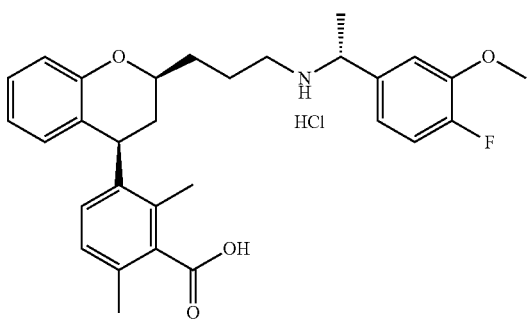 | 492.42 |

$^1$H NMR (400 MHz, DMSO-d$_6$): 13.39 (bs, 1H), 9.40 (bs, 1H), 9.18 (bs, 1H), 7.53 (dd, J = 8.4 Hz & J = 1.6 Hz 1H), 7.30-7.25 (dd, J = 11.2 Hz & J = 8.4 Hz, 1H), 7.12-6.99 (m, 3H), 6.80-6.71 (m, 3H), 6.50-6.48 (m, 1H), 4.47 (m, 1H), 4.36 (q, J = 6.4 Hz, 1H), 4.16 (m, 1H), 3.84 (s, 3H), 2.94-2.87 (m, 1H), 2.71-2.66 (m, 1H), 2.32 (s, 3H), 2.20 (s, 3H), 2.07 (m, 1H), 1.85 (m, 1H), 1.72-1.67 (m, 4H), 1.55 (d J = 6.8 Hz, 3H).

Example-72a, 72b

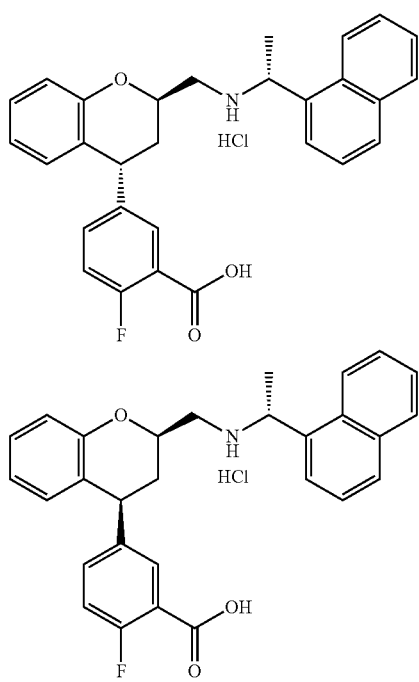

To a solution of Example-1a (0.1 g, 0.21 mmol) in methanol (5 mL), THF (5 mL) and water (0.5 mL), lithium hydroxide hydrate (0.025 g, 1.07 mmol) was added. The reaction mixture was heated to 80° C. and further maintained for 2 h. The progress of reaction was monitored by TLC. The reaction mixture was concentrated under vacuum then cooled to 0° C. and acidified with dilute HCl solution [pH=3 to 4]. Extract the product with ethyl acetate (10 mL×2) washed with water (5 mL×2) followed by brine solution (5 mL), dried over Na$_2$SO$_4$ and concentrated under vacuum to get the solid.

Preparation of Hydrochloride Salt:

To the above compound ethereal HCl (2 mL) was added and stirred for 10 minutes. Then the solvent was removed and the resultant solid was washed with diethyl ether (2 mL) followed by n-pentane (2 mL), dried to get the corresponding hydrochloride salt (0.08 g, 82% yield).

m/z-456.1; $^1$H NMR (400 MHz, DMSO-d$_6$): δ13.30 (bs, 1H), 9.65 (bs, 1H), 9.20 (bs, 1H), 8.21 (d, J=8.0 Hz, 1H), 8.02-7.98 (m, 2H), 7.90 (d, J=7.2 Hz, 1H), 7.65-7.59 (m, 3H), 7.46-7.44 (m, 1H), 7.34-7.22 (m, 3H), 6.99-6.89 (m, 3H), 5.40 (m, 1H), 4.37 (m, 1H), 4.24-4.22 (m, 1H), 3.40-3.30 (m, 1H), 3.06-3.04 (m, 1H), 2.12-2.04 (m, 1H), 2.00-1.96 (m, 1H), 1.68 (d, J=6.8 Hz, 3H).

Similarly, Example-72b was prepared from Example-1b by using the above procedure.

m/z-456.1; $^1$H NMR (400 MHz, DMSO-d$_6$): δ 13.30 (bs, 1H), 9.76 (bs, 1H), 9.36 (bs, 1H), 8.30 (d, J=8.4 Hz, 1H), 8.05 (t, J=8.0 Hz, 2H), 7.97 (d, J=7.2 Hz, 1H), 7.68-7.61 (m, 4H), 7.46-7.44 (m, 1H), 7.31-7.27 (m, 1H), 7.17 (t, J=7.2 Hz, 1H), 6.89 (d, J=8.0 Hz, 1H), 6.83 (t, J=8.0 Hz, 1H), 6.58 (d, J=7.8 Hz, 1H), 5.47 (m, 1H), 4.64-4.62 (m, 1H), 4.39-4.35 (m, 1H), 3.30-3.24 (m, 2H), 2.25-2.20 (m, 1H), 2.08-1.89 (m, 1H), 1.75 (d, J=6.8 Hz, 3H)

The below Examples 73 to 120 given Table-5 were prepared by following the similar ester hydrolysis procedures as described in Example-72a, 72b by taking appropriate ester compound of Example-2 to 49;

Further, HCl salt of these amino compounds were prepared by following the similar hydrochloride salt procedure as described in Example-72a, 72b;

Example-114 to 118 diastereomers formed in more than 90% isomers were purified by recrystallization method.

TABLE 7

| Ex. No. | Ester Ex. No. | Structure | Mass (m/z) |
|---|---|---|---|
| 73 | 2 | 3-((2R,4S)-2-((((R)-1-(Naphthalen-1-yl)ethyl)amino)methyl)chroman-4-yl)benzoic acid hydrochloride | 437.73 |

¹HNMR (400 MHz, DMSO-d₆): δ 12.99 (bs, 1H), 9.77 (bs, 1H), 9.38 (bs, 1H), 8.27 (d, J = 8.4 Hz, 1H), 8.05-7.96 (m, 3H), 7.85-7.83 (m, 1H), 7.74-7.61 (m, 4H), 7.48-7.46 (m, 2H), 7.15 (t, J = 8.0 Hz, 1H), 6.90 (d, J = 8.4 Hz, 1H), 6.82 (t, J = 7.6 Hz, 1H), 6.56 (d, J = 7.6 Hz, 1H), 5.48-5.46 (m, 1H), 4.66-4.62 (m, 1H), 4.39-4.35 (m, 1H), 3.40-3.24 (m, 2H), 2.27-2.22 (m, 1H), 2.00-1.91 (m, 1H), 1.75 (d, J = 6.8 Hz, 3H).

| Ex. No. | Ester Ex. No. | Structure | Mass (m/z) |
|---|---|---|---|
| 74 | 3 | 2-Methyl-3-((2R,4S)-2-((((R)-1-(naphthalen-1-yl)ethyl)amino)methyl)chroman-4-yl)benzoic acid hydrochloride | 451.6 |

¹HNMR (400 MHz, DMSO-d₆): δ 12.89 (bs, 1H), 9.87 (bs, 1H), 9.54 (bs, 1H), 8.30 (d, J = 8.4 Hz, 1H), 8.04-8.00 (m, 3H), 7.70-7.48 (m, 4H), 7.18-7.12 (m, 2H), 7.00 (m, 1H), 6.90 (d, J = 8.0 Hz, 1H), 6.82 (t, J = 7.2 Hz, 1H), 6.53 (m, 1H), 5.46-5.44 (m, 1H), 4.69-4.66 (m, 2H), 3.40-3.37 (m, 1H), 3.29-3.22 (m, 1H), 2.56 (S, 3H), 2.26-2.19 (m, 1H), 1.95-1.93 (m, 1H), 1.75 (d, J = 6.4 Hz, 3H).

TABLE 7-continued

| Ex. No. | Ester Ex. No. | Structure | Mass (m/z) |
|---|---|---|---|
| 75 | 4 | 3-Methyl-5-((2R,4S)-2-((((R)-1-(naphthalen-1-yl)ethyl)amino)methyl)chroman-4-yl)benzoic acid hydrochloride | 452.1 |

¹H NMR (400 MHz, DMSO-d₆): δ 12.91 (bs, 1H), 9.96 (bs, 1H), 9.53 (bs, 1H), 8.30 (d, J = 8.4 Hz, 1H), 8.02 (t, J = 7.2 Hz, 3H), 7.68-7.59 (m, 4H), 7.54 (s, 1H), 7.27 (s, 1H), 7.14 (t, J = 7.6 Hz, 1H), 6.88 (d, J = 7.6 Hz, 1H), 6.79 (t, J = 7.6 Hz, 1H), 6.57 (d, J = 7.6 Hz, 1H), 5.50-5.45 (m, 1H), 4.68-4.63 (m, 1H), 4.33-4.28 (m, 1H), 3.40 (m, 1H), 3.22-3.16 (m, 1H), 2.33 (s, 3H), 2.26-2.22 (m, 1H), 1.95-1.92 (m, 1H), 1.76 (d, J = 6.8 Hz, 3H).

| Ex. No. | Ester Ex. No. | Structure | Mass (m/z) |
|---|---|---|---|
| 76 | 5 | 4-Methyl-3-((2R,4S)-2-((((R)-1-(naphthalen-1-yl)ethyl)amino)methyl)chroman-4-yl)benzoic acid hydrochloride | 451.6 |

¹HNMR (400 MHz, DMSO-d₆): δ 12.80 (bs, 1H), 9.90 (bs, 1H), 9.48 (bs, 1H), 8.27 (d, J = 8.4 Hz, 1H), 8.04-8.01 (m, 3H), 7.72-7.59 (m, 4H), 7.49-7.39 (m, 2H), 7.15 (t, J = 8.0 Hz, 1H), 6.91 (d, J = 8.4 Hz, 1H), 6.80 (t, J = 8.0 Hz, 1H), 6.53 (d, J = 7.2 Hz, 1H), 5.48-5.44 (m, 1H), 4.68 (m, 1H), 4.58-4.54 (m, 1H), 3.40 (m, 1H), 3.21-3.17 (m, 1H), 2.50 (s, 3H), 2.26 (m, 1H), 1.98-1.88 (m, 1H), 1.77 (d, J = 6.8 Hz, 3H).

TABLE 7-continued

| Ex. No. | Ester Ex. No. | Structure | Mass (m/z) |
|---|---|---|---|
| 77a, | 6a | 2-Ethyl-5-((2R,4R)-2-((((R)-1-(naphthalen-1-yl)ethyl)amino)methyl)chroman-4-yl)benzoic acid hydrochloride | 466.1 |

¹H NMR (400 MHz, DMSO-d6): δ 12.85 (bs, 1H), 9.47 (bs, 1H), 9.26 (bs, 1H), 8.23-8.21 (d, J = 8.4 Hz, 1H), 7.99-7.90 (m, 2H), 7.88-7.86 (d, J = 6.8 Hz, 1H), 7.70-7.59 (m, 3H), 7.39-7.38 (d, J = 2 Hz, 1H), 7.27-7.20 (m, 2H), 7.12-7.10 (m, 1H), 6.97-6.87 (m, 3H), 5.46-5.38 (m, 1H), 4.32-4.31 (m, 1H), 4.14-4.12 (m, 1H), 3.38-3.34 (m, 1H), 3.20-3.19 (m, 1H), 2.87-2.64 (q, 2H), 2.08-1.90 (m, 2H), 1.69-1.67 (d, J = 6.8 Hz, 3H), 1.16-1.13 (t, 3H).

| Ex. No. | Ester Ex. No. | Structure | Mass (m/z) |
|---|---|---|---|
| 77b | 6b | 2-Ethyl-5-((2R,4S)-2-((((R)-1-(naphthalen-1-yl)ethyl)amino)methyl)chroman-4-yl)benzoic acid hydrochloride | |

¹HNMR (400 MHz, DMSO-d6): δ 12.80 (bs, 1H), 9.64 (bs, 1H), 9.28 (bs, 1H), 8.29-8.27 (d, J = 8.4 Hz, 1H), 8.05-8.01 (t, J = 7.2 Hz, 2H), 7.95-7.93 (d, J = 7.2 Hz, 1H), 7.70-7.58 (m, 4H), 7.29 (s, 2H), 7.16-7.13 (t, J = 7.6 Hz, 1H), 6.89-6.87 (d, J = 7.6 Hz, 1H), 6.83-6.79 (t, J = 7.6 Hz, 1H), 6.59-6.57 (d, J = 7.6 Hz, 1H), 5.48-5.47 (m, 1H), 4.63-4.61 (m, 1H), 4.32-4.28 (m, 1H), 3.30-3.28 (m, 2H), 2.92-2.87 (q, 2H), 2.23-2.25 (m, 1H), 1.98-1.90 (m, 1H), 1.74-1.72 (d, J = 6.8 Hz, 3H), 1.17-1.13 (t, 3H).

| Ex. No. | Ester Ex. No. | Structure | Mass (m/z) |
|---|---|---|---|
| 78 | 7 | 2-Isopropyl-5-(2R,4S)-2-((((R)-1-(naphthalen-1-yl)ethyl)amino)methyl)chroman-4-yl)benzoic acid hydrochloride | 480.1 |

¹HNMR (400 MHz, DMSO-d6): δ 13.0 (bs, 1H), 9.76 (bs, 1H), 9.36 (bs, 1H), 8.24-8.22 (d, J = 8 Hz, 1H), 8.05-7.96 (m, 3H), 7.68-7.61 (m, 3H), 7.42-7.40 (d, J = 7.6 Hz, 2H), 7.36-7.29 (dd, J = 8 Hz, 1H), 7.16-7.12 (t, J = 7.6 Hz, 1H), 6.88-6.86 (d, J = 7.2 Hz, 1H), 6.83-6.79 (t, J = 7.6 Hz, 1H) 6.59-6.57 (d, J = 7.6 Hz, 1H), 5.48-5.46 (m, 1H), 4.63-4.55 (m, 1H), 4.31-4.27 (m, 1H), 3.78-3.66 (m, 1H), 3.39-3.34 (m, 1H), 3.25-3.23 (m, 1H), 2.23-2.19 (m, 1H), 1.97-1.88 (m, 1H), 1.75-1.73 (d, J = 6.4 Hz, 3H), 1.14-1.12 (m, 6H).

| Ex. No. | Ester Ex. No. | Structure | Mass (m/z) |
|---|---|---|---|
| 79a, | 8a | 2-Cyclopropyl-5-((2R,4R)-2-((((R)-1-(naphthalen-1-yl)ethyl)amino)methyl)chroman-4-yl)benzoic acid hydrochloride | 478.1 |

¹HNMR (400 MHz, DMSO-d6): δ 12.90 (bs, 1H), 9.60 (bs, 1H), 9.30 (bs, 1H), 8.23-8.21 (d, J = 8 Hz, 1H), 8.02-7.97 (m, 2H), 7.86-7.84 (d, J = 6.8 Hz, 1H), 7.65-7.57 (m, 3H), 7.31-7.30 (d, J = 2 Hz, 1H), 7.24-7.20 (t, J = 8.4 Hz, 1H), 7.06-7.04 (d, J = 8.4 Hz, 1H), 6.97-6.87 (m, 4H), 5.40-5.35 (m, 1H), 4.35-4.15 (m, 2H), 3.25-3.10 (m, 2H), 2.65-2.55 (m, 1H), 2.10-1.95 (m, 2H), 1.69-1.67 (d, J = 6.4 Hz, 3H), 0.93-0.83 (m, 2H), 0.69-0.67 (m, 2H).

TABLE 7-continued

| Ex. No. | Ester Ex. No. | Structure | Mass (m/z) |
|---|---|---|---|
| 79b | 8b | 2-Cyclopropyl-5-((2R,4S)-2-((((R)-1-(naphthalen-1-yl)ethyl)amino)methyl)chroman-4-yl)benzoic acid hydrochloride | 478.1 |

$^1$HNMR (400 MHz, DMSO-d6): δ 12.90 (bs, 1H), 9.70 (bs, 1H), 9.20 (bs, 1H), 8.29-8.27 (d, J = 8.8 Hz, 1H), 8.05-8.02 (t, J = 7.6 Hz, 2H), 7.94-7.92 (d, J = 6.8 Hz, 1H), 7.69-7.64 (m, 3H), 7.52-7.51 (d, J = 2 Hz, 1H), 7.25-7.22 (dd, J = 8.4 & 2, 1H), 7.14-7.12 (t, J = 7.6 Hz, 1H), 6.96-6.94 (d, J = 8.4 Hz, 1H), 6.88-6.86 (d, J = 7.2 Hz, 1H), 6.82-6.78 (t, J = 8.4 Hz, 1H), 6.59-6.57 (d, J = 7.6 Hz, 1H), 5.50-5.40 (m, 1H), 4.65-4.55 (m, 1H), 4.32-4.20 (m, 1H), 3.40-3.20 (m, 2H), 2.70-2.60 (m, 1H), 2.25-2.10 (m, 1H), 2.00-1.90 (m, 1H), 1.76-1.73 (d, J = 6.4 Hz, 3H), 0.97-0.94 (m, 2H), 0.69-0.65 (m, 2H).

| Ex. No. | Ester Ex. No. | Structure | Mass (m/z) |
|---|---|---|---|
| 80 | 9 | 2,6-Difluoro-3-((2R,4R)-2-((((R)-1-(naphthalen-1-yl)ethyl)amino)methyl)chroman-4-yl)benzoic acid hydrochloride | 474.1 |

$^1$H NMR (400 MHz, DMSO-d$_6$): δ 13.98 (bs, 1H), 9.82 (bs, 1H), 9.48 (bs, 1H), 8.27 (d, J = 8.4 Hz, 1H), 8.05-7.98 (m, 3H), 7.67-7.60 (m, 3H), 7.37 (s, 1H), 7.21-7.14 (m, 2H), 6.90-6.82 (d, J = 7.6 Hz, 1H), 6.86 (t, J = 8 Hz, 1H), 6.63 (d, J = 8 Hz, 1H), 5.47 (m, 1H), 4.69-4.53 (m, 1H), 4.57-4.55 (m, 1H), 3.40-3.22 (m, 2H), 2.33-2.22 (m, 1H), 2.02-1.96 (m, 1H), 1.76 (d, J = 6.4 Hz, 3H).

| Ex. No. | Ester Ex. No. | Structure | Mass (m/z) |
|---|---|---|---|
| 81a | 10a | 4-Fluoro-2-methyl-3-((2R,4S)-2-((((R)-1-(naphthalen-1-yl)ethyl)amino)methyl)chroman-4-yl)benzoic acid hydrochloride | 470.42 |

$^1$HNMR (400 MHz, DMSO-d6): δ 12.81 (bs, 1H), 9.52 (bs, 1H), 9.34 (bs, 1H), 8.24-8.22 (d, J = 8 Hz, 1H), 8.05-7.99 (m, 2H), 7.90-7.88 (d, J = 7.2 Hz, 1H), 7.70-7.57 (m, 3H), 7.26-7.14 (m, 3H), 6.99-6.86 (m, 3H), 5.39-5.38 (m, 1H), 4.49-4.48 (m, 1H), 4.22-4.10 (m, 1H), 3.30-3.18 (m, 2H), 2.49 (s, 3H), 2.15-1.90 (m, 2H), 1.64-1.62 (d, J = 6.4 Hz, 3H).

| Ex. No. | Ester Ex. No. | Structure | Mass (m/z) |
|---|---|---|---|
| 81b | 10b | 4-Fluoro-2-methyl-3-((2R,4R)-2-((((R)-1-(naphthalen-1-yl)ethyl)amino)methyl)chroman-4-yl)benzoic acid hydrochloride | 470.42 |

$^1$HNMR (400 MHz, DMSO-d6): δ 12.93 (bs, 1H), 9.68 (bs, 1H), 9.29 (bs, 1H), 8.29-8.27 (d, J = 8.4 Hz, 1H), 8.05-8.01 (m, 2H), 7.95-7.93 (d, J = 7.2 Hz, 1H), 7.69-7.60 (m, 4H), 7.22-7.14 (m, 2H), 6.90-6.88 (d, J = 7.6 Hz, 1H), 6.84-6.80 (t, J = 7.6 Hz, 1H), 6.62-6.18 (d, J = 7.6 Hz, 1H), 5.48-5.46 (m, 1H), 4.66-4.57 (m, 1H), 4.56-4.55 (m, 1H), 3.24-3.21 (m, 2H), 2.49 (s, 3H), 2.23-2.15 (m, 1H), 2.10-1.95 (m, 1H), 1.75-1.73 (d, J = 6.8 Hz, 3H).

TABLE 7-continued

| Ex. No. | Ester Ex. No. | Structure | Mass (m/z) |
|---|---|---|---|
| 82 | 11 | 2,3-Dimethyl-5-((2R,4S)-2-((((R)-1-(naphthalen-1-yl)ethyl)amino)methyl)chroman-4-yl)benzoic acid hydrochloride 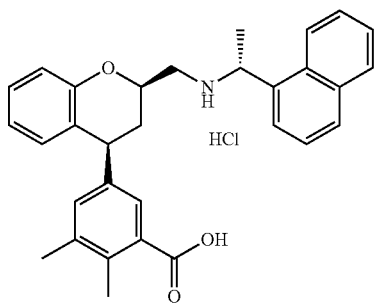 ¹HNMR (400 MHz, DMSO-d₆): δ 12.83 (bs, 1H), 9.81 (bs, 1H), 9.41 (bs, 1H), 8.30 (d, J = 8.4 Hz, 1H), 8.05-7.98 (m, 3H), 7.68-7.60 (m, 3H), 7.36 (S, 1H), 7.15-7.11 (m, 2H), 6.87 (d, J = 8 Hz, 1H), 6.81 (t, J = 7.6 Hz, 1H), 6.59 (d, J = 7.6 Hz, 1H), 5.48-5.47 (m, 1H), 4.65-4.61 (m, 1H), 4.25-4.20 (m, 1H), 3.40-3.24 (m, 2H), 2.35 (s, 3H), 2.24 (s, 3H), 2.22-2.17 (m, 1H), 1.96-1.93 (m, 1H), 1.75 (d, J = 6.4 Hz, 3H). | 466.1 |
| 83 | 12 | 5-((2R,4S)-2-((((R)-1-(Naphthalen-1-yl)ethyl)amino)methyl)chroman-4-yl)-2-(trifluoromethyl)benzoic acid hydrochloride 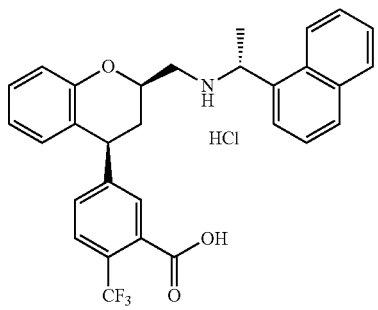 ¹H NMR (400 MHz, DMSO-d₆): δ 12.9 (bs, 1H), 9.82 (bs, 1H), 9.43 (bs, 1H), 8.30 (d, J = 8 Hz, 1H), 8.04-7.98 (m, 3H), 7.82 (d, J = 8 Hz, 1H), 7.68-7.60 (m, 4H), 7.55 (d, J = 7.6 Hz, 1H), 7.19-7.12 (m, 1H), 6.91 (d, J = 8 Hz, 1H), 6.84 (m, 1H), 6.57 (d, J = 7.6 Hz, 1H), 5.47 (m, 1H), 4.63 (m, 1H), 4.50-4.45 (m, 1H), 3.24 (m, 2H), 2.28-2.25 (m, 1H), 1.98-1.95 (m, 1H), 1.75 (d, J = 6.4 Hz, 3H). | 505.5 |
| 84a | 13a | 2-Methyl-5-((2R,4R)-2-((((R)-1-(naphthalen-1-yl)ethyl)amino)methyl)chroman-4-yl)benzoic acid hydrochloride 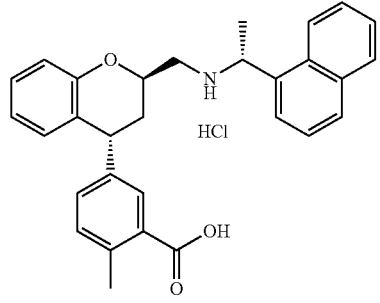 ¹HNMR (400 MHz, DMSO-d₆): δ 12.79 (bs, 1H), 9.49 (bs, 1H), 9.28 (bs, 1H), 8.24 (d, J = 8 Hz, 1H), 8.02 (t, J = 8.4 Hz, 2H), 7.89 (d, J = 7.2 Hz, 1H), 7.64-7.58 (m, 3H), 7.44 (d, J = 2 Hz, 1H), 7.24-7.20 (m, 2H), 7.11 (dd, J = 8 Hz & J = 2 Hz, 1H), 6.97-6.88 (m, 3H), 5.40-5.38 (m, 1H), 4.33 (m, 1H), 4.25-4.20 (m, 1H), 3.20 (m, 2H), 2.46 (s, 3H), 2.09-2.05 (m, 1H), 1.99-1.95 (m, 1H), 1.69 (d, J = 6.4 Hz, 3H). | 451.92 |
| 84b | 13b | 2-Methyl-5-((2R,4S)-2-((((R)-1-(naphthalen-1-yl)ethyl)amino)methyl)chroman-4-yl)benzoic acid hydrochloride 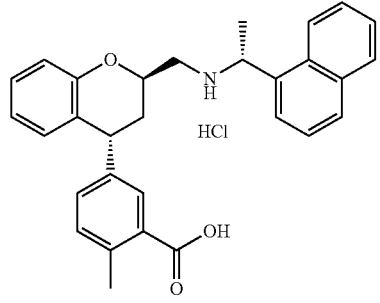 ¹HNMR (400 MHz, DMSO-d₆): δ 12.88 (bs, 1H), 10.37 (bs, 1H), 9.93 (bs, 1H), 8.30 (d, J = 8.8 Hz, 1H), 8.19 (t, J = 8.4 Hz, 1H), 8.02 (t, J = 7.2 Hz, 2H), 7.66-7.57 (m, 4H), 7.23 (s, 2H), 7.13 (t, J = 7.6 Hz, 1H), 6.86 (dd, J = 8 Hz & 0.8 Hz, 1H), 6.77 (t, J = 8 Hz, 1H), 6.55 (d, J = 7.6 Hz, 1H), 5.51-5.49 (m, 1H), 4.76-4.74 (m, 1H), 4.28-4.24 (m, 1H), 3.29-3.27 (m, 1H), 3.19-3.17 (m, 1H), 2.48 (s, 3H), 2.27-2.23 (m, 1H), 1.93-1.87 (m, 1H), 1.78 (d, J = 6.4 Hz, 3H). | 451.92 |

TABLE 7-continued

| Ex. No. | Ester Ex. No. | Structure | Mass (m/z) |
|---|---|---|---|
| 85 | 14 | 2-Fluoro-3-((2R,4R)-2-((((R)-1-(naphthalen-1-yl)ethyl)amino)methyl)chroman-4-yl)benzoic acid hydrochloride 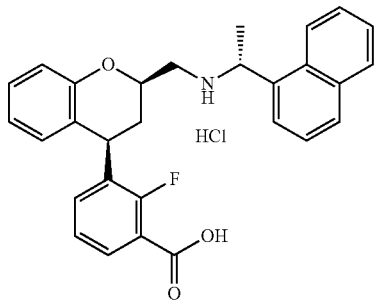 ¹HNMR (400 MHz, DMSO-d₆): δ 13.24 (bs, 1H), 9.89 (bs, 1H), 9.52 (bs, 1H), 8.30 (d, J = 8.0 Hz, 1H), 8.04-8.00 (m, 3H), 7.79-7.75 (m, 1H), 7.67-7.59 (m, 3H), 7.42 (m, 1H), 7.26 (t, J = 7.6 Hz, 1H), 7.15 (t, J = 7.6 Hz, 1H), 6.89 (d, J = 8 Hz, 1H), 6.82 (t, J = 7.4 Hz, 1H), 6.61 (d, J = 7.6 Hz, 1H), 5.48-5.46 (m, 1H), 4.72-4.68 (m, 1H), 4.59-4.58 (m, 1H), 3.38-3.24 (m, 2H), 2.25-2.24 (m, 1H), 2.00-1.97 (m, 1H), 1.76 (d, J = 6.4 Hz, 3H). | 456.1 |
| 86 | 15 | 3-Fluoro-5-((2R,4S)-2-((((R)-1-(naphthalen-1-yl)ethyl)amino)methyl)chroman-4-yl)benzoic acid hydrochloride 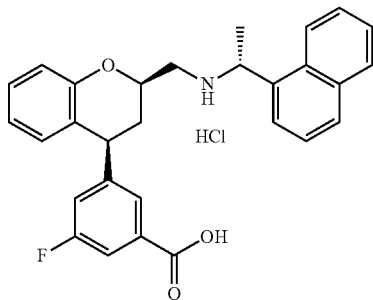 ¹HNMR (400 MHz, DMSO-d₆): δ 13.34 (bs, 1H), 10.07 (bs, 1H), 10.00 (bs, 1H), 8.30 (d, J = 8.4 Hz, 1H), 8.04 (m, 3H), 7.67-7.54 (m, 5H), 7.37 (d, J = 8.4 Hz, 1H), 7.18-7.14 (t, J = 7.6 Hz, 1H), 6.89 (d, J = 7.2 Hz, 1H), 6.83 (t, J = 7.6 Hz, 1H), 6.59 (d, J = 8 Hz, 1H), 5.49 (m, 1H), 4.67-4.63 (m, 1H), 4.44-4.39 (m, 1H), 3.40-3.22 (m, 2H), 2.29-2.24 (m, 1H), 2.01-1.92 (m, 1H), 1.76 (d, J = 6.8 Hz, 3H). | 456.42 |
| 87 | 16 | 4-Fluoro-3-((2R,4R)-2-((((R)-1-(naphthalen-1-yl)ethyl)amino)methyl)chroman-4-yl)benzoic acid hydrochloride 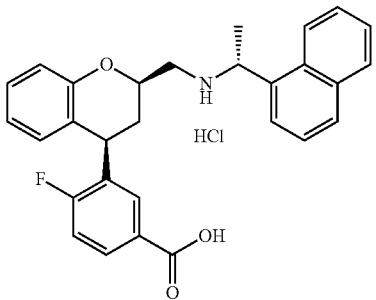 ¹HNMR (400 MHz, DMSO-d₆): δ 13.08 (bs, 1H), 9.80 (bs, 1H), 9.4 (bs, 1H), 8.29 (d, J = 8.4 Hz, 1H), 8.05-7.97 (m, 3H), 7.93-7.89 (m, 1H), 7.79-7.60 (m, 4H), 7.35 (t, J = 8.0 Hz, 1H), 7.17 (t, J = 8.0 Hz, 1H), 6.90 (d, J = 8.0 Hz, 1H), 6.84 (t, J = 7 Hz, 1H), 6.62 (d, J = 7.6 Hz, 1H), 5.47-5.46 (m, 1H), 4.68-4.59 (m, 2H), 3.40-3.25 (m, 2H), 2.33-2.25 (m, 1H), 2.03-1.99 (m, 1H), 1.75 (d, J = 6.4 Hz, 3H). | 456.1 |
| 88 | 17 | 2-Methoxy-5-((2R,4S)-2-((((R)-1-(naphthalen-1-yl)ethyl)amino)methyl)chroman-4-yl)benzoic acid hydrochloride 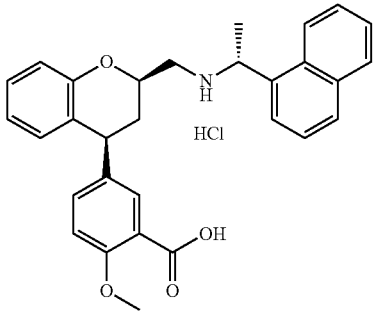 ¹HNMR (400 MHz, DMSO-d₆): δ 12.62 (bs, 1H), 9.95 (bs, 1H), 9.54 (bs, 1H), 8.29 (d, J = 8.4 Hz, 1H), 8.04-8.00 (m, 3H), 7.67-7.61 (m, 3H), 7.43 (d, J = 2.4 Hz, 1H), 7.32 (dd, J = 8.8 Hz & 2.4 Hz, 1H), 7.13-7.08 (m, 2H), 6.85 (d, J = 7.6 Hz, 1H), 6.79 (t, J = 7.2 Hz, 1H), 6.57 (d, J = 7.6 Hz, 1H), 5.50-5.45 (m, 1H), 4.67-4.63 (m, 1H), 4.27-4.22 (m, 1H), 3.80 (s, 3H), 3.32-3.21 (m, 2H), 2.23-2.18 (m, 1H), 1.96-1.87 (m, 1H), 1.75 (d, J = 6.4 Hz, 3H). | 466.86 |

TABLE 7-continued

| Ex. No. | Ester Ex. No. | Structure | Mass (m/z) |
|---|---|---|---|
| 89a | 18a | 2-Methoxy-3-((2R,4S)-2-((((R)-1-(naphthalen-1-yl)ethyl)amino)methyl)chroman-4-yl)benzoic acid hydrochloride 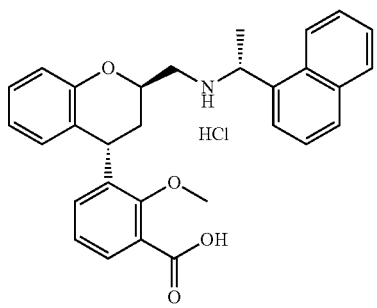 ¹HNMR (400 MHz, DMSO-d₆): δ 13.01 (bs, 1H), 9.70 (bs, 1H), 9.42 (bs, 1H), 8.23 (d, J = 8.4 Hz, 1H), 8.04-7.94 (m, 3H), 7.64-7.54 (m, 4H), 7.20 (t, J = 6.8 Hz, 1H), 7.02 (t, J = 7.6 Hz, 1H), 6.95-6.88 (m, 3H), 6.69 (d, J = 6.4 Hz, 1H), 5.50-5.45 (m, 1H), 4.52-4.51 (m, 1H), 4.30-4.26 (m, 1H), 3.84 (s, 3H), 3.33-3.16 (m, 2H), 2.12-2.05 (m, 1H), 1.96-1.93 (m, 1H), 1.69 (d, J = 6.4 Hz, 3H). | 468.48 |
| 89b | 18b | 2-Methoxy-3-((2R,4R)-2-((((R)-1-(naphthalen-1-yl)ethyl)amino)methyl)chroman-4-yl)benzoic acid hydrochloride 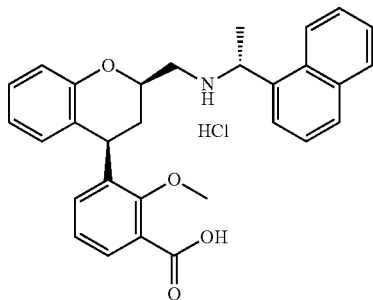 ¹HNMR (400 MHz, DMSO-d₆): δ 12.98 (bs, 1H), 9.95 (bs, 1H), 9.57 (bs, 1H), 8.29 (d, J = 8.4 Hz, 1H), 8.02 (t, J = 7.6 Hz, 3H), 7.67-7.59 (m, 4H), 7.13 (t, J = 7.6 Hz, 3H), 6.87 (d, J = 8 Hz, 1H), 6.80 (t, J = 8 Hz, 1H), 6.57 (d, J = 7.6 Hz, 1H), 5.49-5.48 (m, 1H), 4.72 (m, 2H), 3.79 (s, 3H), 3.37 (m, 1H), 3.24 (m, 1H), 2.23 (m, 1H), 1.93, (m, 1H), 1.77 (d, J = 6.4 Hz, 3H). | 468.48 |
| 90 | 19 | 4-Methoxy-3-((2R,4R)-2-((((R)-1-(naphthalen-1-yl)ethyl)amino)methyl)chroman-4-yl)benzoic acid hydrochloride 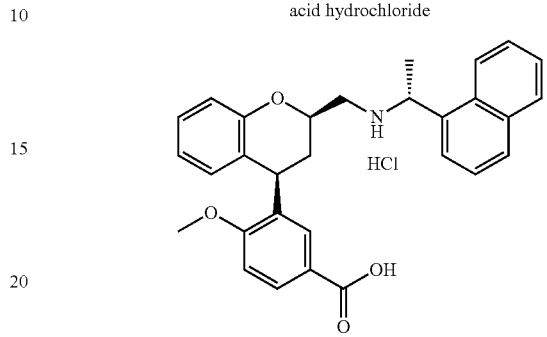 ¹HNMR (400 MHz, DMSO-d₆): δ 12.62 (bs, 1H), 9.96 (bs, 1H), 9.54 (bs, 1H), 8.29 (d, J = 8.4 Hz, 1H), 8.02 (t, J = 7.6 Hz, 3H), 7.67-7.61 (m, 3H), 7.43 (d, J = 2.4 Hz, 1H), 7.33 (dd, J = 6 Hz & 2.4 Hz, 1H), 7.14-7.08 (m, 2H), 6.85 (d, J = 7.6 Hz, 1H), 6.79 (t, J = 7.2 Hz, 1H), 6.57 (d, J = 7.6 Hz, 1H), 5.50-5.45 (m, 1H), 4.67-4.63 (m, 1H), 4.27-4.22 (m, 1H), 3.80 (s, 3H), 3.27-3.22 (m, 2H), 2.23-2.18 (m, 1H), 1.96-1.87 (m, 1H), 1.74 (d, J = 6.4 Hz, 3H). | 468 |
| 91 | 20 | 2-(2-Methyl-5-((2R,4S)-2-((((R)-1-(naphthalen-1-yl)ethyl)amino)methyl)chroman-4-yl)phenoxy)acetic acid hydrochloride 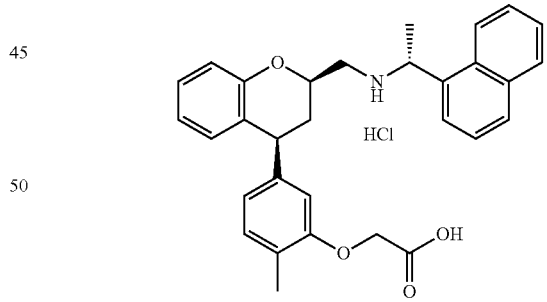 ¹HNMR (400 MHz, DMSO-d₆): δ 12.93 (bs, 1H), 9.95 (bs, 1H), 9.56 (bs, 1H), 8.23 (m, 1H), 8.04-8.00 (m, 3H), 7.67-7.61 (m, 3H), 7.11-7.08 (m, 2H), 6.85 (d, J = 7.6 Hz, 1H), 6.77 (t, J = 7.2 Hz, 1H), 6.68 (t, J = 7.6 Hz, 2H), 6.61 (d, J = 7.6 Hz, 1H), 5.49-5.48 (m, 1H), 4.68 (m, 1H), 4.62 (s, 2H), 4.18-4.14 (m, 1H), 3.28 (m, 2H), 2.20 (m, 1H), 2.16 (s, 3H), 1.97-1.88 (m, 1H), 1.76 (d, J = 6.8 Hz, 3H) | 482.1 |

TABLE 7-continued

| Ex. No. | Ester Ex. No. | Structure | Mass (m/z) |
|---|---|---|---|
| 92 | 21 | 2-(3-Methyl-5-((2R,4S)-2-((((R)-1-(naphthalen-1-yl)ethyl)amino)methyl)chroman-4-yl)phenoxy)acetic acid hydrochloride 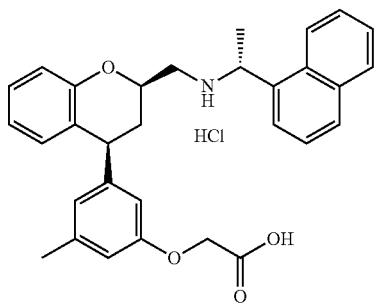 $^1$HNMR (400 MHz, DMSO-$d_6$): δ 12.96 (bs, 1H), 10.09 (bs, 1H), 9.67 (bs, 1H), 8.29 (d, J = 8.0 Hz, 1H), 8.08-8.00 (m, 3H), 7.67-7.59 (m, 3H), 7.11 (t, J = 7.6 Hz, 1H), 6.84 (d, J = 7.6 Hz, 1H), 6.78 (t, J = 7.6 Hz, 1H), 6.62-6.57 (m, 4H), 5.49 (m, 1H), 4.67 (m, 1H), 4.60 (s, 2H), 4.15 (m, 1H), 3.28-3.21 (m, 2H), 2.22 (s, 3H), 2.18 (m, 1H), 1.92 (m, 1H), 1.77 (d, J = 6.8 Hz, 3H). | 481.55 |
| 93a | 22a | 2-(2-Fluoro-5-((2R,4R)-2-((((R)-1-(naphthalen-1-yl)ethyl)amino)methyl)chroman-4-yl)phenoxy)acetic acid hydrochloride 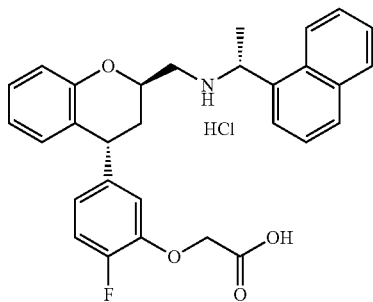 $^1$HNMR (400 MHz, DMSO-$d_6$): δ 13.02 (bs, 1H), 9.67 (bs, 1H), 9.46 (bs, 1H), 8.24 (d, J = 8.4 Hz, 1H), 8.01-7.95 (m, 3H), 7.65-7.57 (m, 3H), 7.21-7.06 (m, 2H), 6.93-6.77 (m, 4H), 6.36 (m, 1H), 5.40 (m, 1H), 4.72 (s, 2H), 4.28-4.22 (m, 2H), 3.39-3.29 (m, 1H), 3.13 (m, 1H), 2.07-1.97 (m, 2H), 1.68 (d, J = 6.8 Hz, 3H). | 486.0 |
| 93b | 22b | 2-(2-Fluoro-5-((2R,4S)-2-((((R)-1-(naphthalen-1-yl)ethyl)amino)methyl)chroman-4-yl)phenoxy)acetic acid hydrochloride 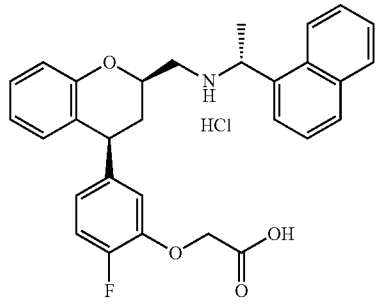 $^1$HNMR (400 MHz, DMSO-$d_6$): δ 12.92 (bs, 1H), 9.64 (bs, 1H), 9.43 (bs, 1H), 8.29 (d, J = 8.4 Hz, 1H), 8.05-7.99 (m, 3H), 7.67-7.61 (m, 3H), 7.20-7.13 (m, 2H), 6.94 (dd, J = 8.0 Hz & J = 1.6 Hz, 1H), 6.85-6.72 (m, 3H), 6.58 (d, J = 7.6 Hz, 1H), 5.48 (m, 1H), 4.71 (s, 2H), 4.65 (m, 1H), 4.22 (m, 1H), 3.37-3.21 (m, 2H), 2.18 (m, 1H), 1.98 (m, 1H), 1.74 (d, J = 6.8 Hz, 3H). | |
| 94 | 23 | 2-(2-Fluoro-3-((2R,4R)-2-((((R)-1-(naphthalen-1-yl)ethyl)amino)methyl)chroman-4-yl)phenoxy)acetic acid hydrochloride 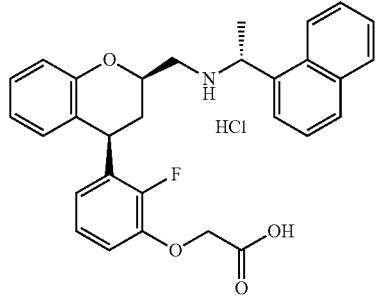 $^1$H NMR (400 MHz, DMSO-$d_6$): δ 13.07 (bs, 1H), 9.90 (bs, 1H), 9.52 (bs, 1H), 8.28 (d, J = 8.0 Hz, 1H), 8.04-8.00 (m, 3H), 7.67-7.59 (m, 3H), 7.14 (t, J = 7.6 Hz, 1H), 7.05 (t, J = 8.0 Hz, 1H), 6.96 (t, J = 8.0 Hz, 1H), 6.87 (d, J = 8.0 Hz, 1H), 6.81 (t, J = 7.2 Hz, 1H), 6.72 (s, 1H), 6.61 (d, J = 7.2 Hz, 1H), 5.47 (m, 1H), 4.76 (s, 2H), 4.70 (m, 1H), 4.53 (m, 1H), 3.38-3.33 (m, 1H), 3.26 (m, 1H), 2.27-2.22 (m, 1H), 1.98 (m, 1H), 1.75 (d, J = 6.4 Hz, 3H). | 486.0 |

TABLE 7-continued

| Ex. No. | Ester Ex. No. | Structure | Mass (m/z) |
|---|---|---|---|
| 95a, | 24a | 2-(3-Fluoro-5-((2R,4R)-2-((((R)-1-(naphthalen-1-yl)ethyl)amino)methyl)chroman-4-yl)phenoxy)acetic acid hydrochloride 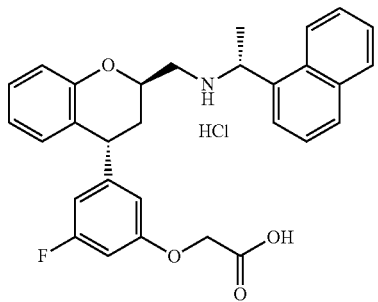 <br> $^1$H NMR (400 MHz, DMSO-d$_6$): δ 12.92 (bs, 1H), 9.64 (bs, 1H), 9.43 (bs, 1H), 8.24 (d, J = 8.4 Hz, 1H), 8.04-7.93 (m, 3H), 7.65-7.57 (m, 3H), 7.22 (t, J = 15.2 Hz, 1H), 6.96-6.88 (m, 3H), 6.66 (d, J = 10.8 Hz, 1H), 6.41 (s, 2H), 5.41 (m, 1H), 4.64 (s, 2H), 4.32-4.26 (m, 2H), 3.39-3.29 (m, 1H), 3.16 (m, 1H), 2.04 (m, 2H), 1.70 (d, J = 6.4 Hz, 3H). | 486.0 |
| 96 | 25 | 2-(4-Fluoro-3-((2R,4R)-2-((((R)-1-(naphthalen-1-yl)ethyl)amino)methyl)chroman-4-yl)phenoxy)acetic acid hydrochloride 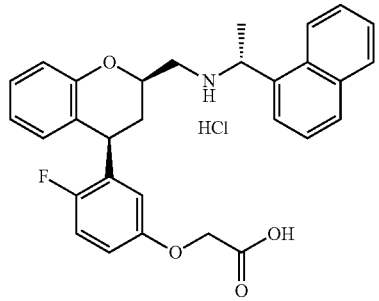 <br> $^1$HNMR (400 MHz, DMSO-d$_6$): δ 12.97 (bs, 1H), 9.87 (bs, 1H), 9.49 (bs, 1H), 8.29 (d, J = 8.4 Hz, 1H), 8.04-7.99 (m, 3H), 7.67-7.59 (m, 3H), 7.14-7.10 (m, 2H), 6.89-6.75 (m, 4H), 6.62 (d, J = 7.2 Hz, 1H), 5.48 (m, 1H), 4.68 (m, 1H), 4.60 (s, 2H), 4.46 (m, 1H), 3.38-3.24 (m, 2H), 2.18 (m, 1H), 2.08 (m, 1H), 1.73 (d, J = 6.4 Hz, 3H). | 486.1 |
| 95b | 24b | 2-(3-Fluoro-5-((2R,4S)-2-((((R)-1-(naphthalen-1-yl)ethyl)amino)methyl)chroman-4-yl)phenoxy)acetic acid hydrochloride 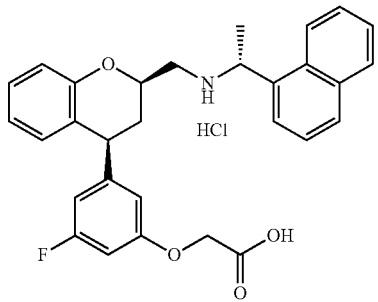 <br> $^1$HNMR (400 MHz, DMSO-d$_6$): δ 13.05 (bs, 1H), 9.95 (bs, 1H), 9.55 (bs, 1H), 8.29 (d, J = 8.0 Hz, 1H), 8.04-8.00 (m, 3H), 7.67-7.59 (m, 3H), 7.14 (t, J = 7.2 Hz, 1H), 6.86 (dd, J = 8.0, 0.8 Hz, 1H), 6.81 (dt, J = 7.6, 0.8 Hz, 1H), 6.71 (td, J = 10.8, J = 2.4 Hz, 1H), 6.65-6.57 (m, 3H), 5.48 (m, 1H), 4.68 (s, 2H), 4.62 (m, 1H), 4.26 (m, 1H), 3.39-3.31 (m, 1H), 3.18 (m, 1H), 2.22 (m, 1H), 1.95 (m, 1H), 1.72 (d, J = 6.4 Hz, 3H). | 486.0 |
| 97 | 26 | 2-Methyl-2-(3-((2R,4S)-2-((((R)-1-(naphthalen-1-yl)ethyl)amino)methyl)chroman-4-yl)phenoxy)propanoic acid hydrochloride 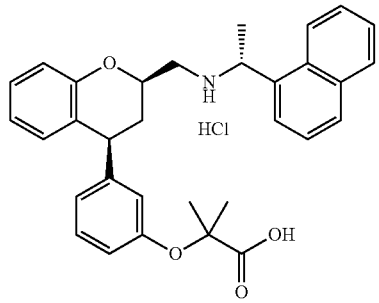 <br> $^1$HNMR (400 MHz, DMSO-d$_6$): δ 13.03 (bs, 1H), 9.36 (bs, 1H), 9.3 (bs, 1H), 8.28 (d, J = 8.4 Hz, 1H), 8.05 (t, J = 7.4 Hz, 1H), 7.95 (d, J = 4.4 Hz, 1H), 7.68-7.59 (m, 3H), 7.28-7.20 (m, 2H), 7.15-7.12 (m, 1H), 7.02 (s, 1H), 6.87 (d, J = 8 Hz, 1H), 6.83-6.79 (m, 1H), 6.69-6.60 (m, 3H), 5.48 (m, 1H), 4.62 (m, 1H), 4.22-4.19 (m, 1H), 3.24-3.20 (m, 2H), 2.23-2.19 (m, 1H), 1.91-1.85 (m, 1H), 1.75 (d, J = 6.4 Hz, 3H), 1.38 (s, 3H), 1.22 (s, 3H). | 505.5 |

TABLE 7-continued

| Ex. No. | Ester Ex. No. | Structure | Mass (m/z) |
|---|---|---|---|
| 98a | 27a | 4-((2R,4R)-2-((((R)-1-(Naphthalen-1-yl)ethyl)amino)methyl)chroman-4-yl)benzoic acid hydrochloride<br><br>$^1$H NMR (400 MHz, DMSO-d$_6$): δ 12.89 (bs, 1H), 9.48 (bs, 1H), 9.21 (bs, 1H), 8.24-8.22 (d, J = 8.4 Hz, 1H), 8.00-7.91 (m, 2H), 7.85-7.81 (m, 2H), 7.64-7.58 (m, 3H), 7.33-7.31 (d, J = 8.4 Hz, 1H), 7.26-7.21 (t, J = 8.8 Hz, 1H), 7.13-7.11 (d, J = 8 Hz, 2H), 6.97-6.81 (m, 3H), 5.39-5.38 (m, 1H), 4.37 (m, 1H), 4.18-4.1 (m, 1H), 3.37-3.30 (m, 2H), 2.15-1.95 (m, 2H), 1.67-1.66 (d, J = 6.4 Hz, 3H). | 437.60 |
| 98b | 27b | 4-((2R,4S)-2-((((R)-1-(Naphthalen-1-yl)ethyl)amino)methyl)chroman-4-yl)benzoic acid hydrochloride<br><br>$^1$H NMR (400 MHz, DMSO-d$_6$): δ 12.90 (bs, 1H), 9.82 (bs, 1H), 9.46 (bs, 1H), 8.30-8.28 (d, J = 8.4 Hz, 1H), 8.05-7.98 (m, 3H), 7.92-7.90 (d, J = 8.4 Hz, 2H), 7.68-7.60 (m, 3H), 7.31-7.29 (d, J = 8 Hz, 2H), 7.17-7.13 (t, J = 7.6 Hz, 1H), 6.90-6.88 (d, J = 7.6 Hz, 1H), 6.82-6.78 (t, J = 7.2 Hz, 1H), 6.56-6.55 (d, J = 7.6 Hz, 1H), 5.48-5.47 (m, 1H), 4.67-4.63 (m, 1H), 4.39-4.34 (m, 1H), 3.38-3.24 (m, 2H), 2.27-2.23 (m, 1H), 1.98-1.92 (m, 1H), 1.76-1.74 (d, J = 6.8 Hz, 3H). | 437.60 |
| 99a, | 28a | 2-Methyl-4-((2R,4R)-2-((((R)-1-(naphthalen-1-yl)ethyl)amino)methyl)chroman-4-yl)benzoic acid hydrochloride<br><br>$^1$HNMR (400 MHz, DMSO-d6): δ 12.80 (bs, 1H), 9.60 (bs, 1H), 9.40-9.30 (bs, 1H), 8.24-8.22 (d, J = 8.4 Hz, 1H), 8.02-7.97 (m, 2H), 7.88-7.86 (d, J = 6.8 Hz, 1H), 7.72-7.70 (m, 2H), 7.65-7.57 (m, 3H), 7.25-7.20 (m, 1H), 6.97-6.83 (m, 4H), 5.39-5.38 (m, 1H), 4.31 (m, 1H), 4.25 (m, 1H), 3.28 (m, 1H), 3.20-3.10 (m, 1H), 2.41 (s, 3H), 2.20-1.90 (m, 2H), 1.69-1.67 (d, J = 6.8 Hz, 3H). | 452.1 |
| 99b | 28b | 2-Methyl-4-((2R,4S)-2-((((R)-1-(naphthalen-1-yl)ethyl)amino)methyl)chroman-4-yl)benzoic acid hydrochloride<br><br>$^1$HNMR (400 MHz, DMSO-d6): δ 12.77 (bs, 1H), 9.69 (bs, 1H), 9.34 (bs, 1H), 8.30-8.28 (d, J = 8 Hz, 1H), 8.06-8.02 (t, J = 7.6 Hz, 2H), 7.93-7.92 (d, J = 7.2 Hz, 1H), 7.81-7.79 (d, J = 7.6 Hz, 1H), 7.69-7.61 (m, 3H), 7.17-7.08 (m, 3H), 6.90-6.88 (d, J = 8.4 Hz, 1H), 6.82-6.79 (t, J = 7.2 Hz, 1H), 6.59-6.57 (d, J = 7.6 Hz, 1H), 5.49-5.48 (m, 1H), 4.65-4.61 (m, 1H), 4.32-4.27 (m, 1H), 3.38-3.23 (m, 2H), 2.46 (s, 3H), 2.24-2.20 (m, 1H), 2.0-1.91 (m, 1H), 1.75 (d, J = 6.4 Hz, 3H). | 452.1 |

TABLE 7-continued

| Ex. No. | Ester Ex. No. | Structure | Mass (m/z) |
|---|---|---|---|
| 100a, | 29a | 4-((2R,4R)-2-((((R)-1-(Naphthalen-1-yl)ethyl)amino)methyl)chroman-4-yl)-2-(trifluoromethyl)benzoic acid hydrochloride<br><br>$^1$HNMR (400 MHz, DMSO-d$_6$): δ 13.56 (bs, 1H), 9.72 (bs, 1H), 9.47 (bs, 1H), 8.25 (d, J = 8.8 Hz, 1H), 8.01 (m, 3H), 7.76 (d, J = 8 Hz, 1H), 7.64-7.56 (m, 3H), 7.55 (s, 1H), 7.29-7.21 (m, 2H), 7.09-6.82 (m, 3H), 5.40-5.39 (m, 1H), 4.48 (m, 1H), 4.26-4.21 (m, 1H), 3.35 (m, 1H), 3.18-3.16 (m, 1H), 2.14-2.04 (m, 2H), 1.71 (d, J = 6.4 Hz, 3H). | 505.5 |
| 100b | 29b | 4-((2R,4S)-2-((((R)-1-(Naphthalen-1-yl)ethyl)amino)methyl)chroman-4-yl)-2-(trifluoromethyl)benzoic acid hydrochloride<br><br>$^1$HNMR (400 MHz, DMSO-d$_6$): δ 13.57 (bs, 1H), 10.17 (bs, 1H), 9.76 (bs, 1H), 8.25 (d, J = 8.8 Hz, 1H), 8.10 (d, J = 7.2 Hz, 1H), 8.01 (t, J = 8.8 Hz, 2H), 7.80 (d, J = 8 Hz, 1H), 7.67-7.59 (m, 4H), 7.55 (d, J = 8.4 Hz, 1H), 7.17 (t, J = 7.6 Hz, 1H), 6.89 (d, J = 7.6 Hz, 1H), 6.82 (t, J = 7.6 Hz, 1H), 6.55 (d, J = 7.6 Hz, 1H), 5.49 (m, 1H), 4.71-4.68 (m, 1H), 4.50-4.46 (m, 1H), 3.27 (m, 1H), 3.20-3.16 (m, 1H), 2.31-2.26 (m, 1H), 1.99-1.90 (m, 1H), 1.76 (d, J = 6.4 Hz, 3H). | 505.5 |
| 101 | 30 | 2,6-Difluoro-4-((2R,4S)-2-((((R)-1-(naphthalen-1-yl)ethyl)amino)methyl)chroman-4-yl)benzoic acid hydrochloride<br><br>$^1$HNMR (400 MHz, DMSO-d6): δ 13.80 (bs, 1H), 9.91 (bs, 1H), 9.54 (bs, 1H), 8.31-8.29 (d, J = 8.4 Hz, 1H), 8.05-8.00 (m, 3H), 7.69-7.60 (m, 3H), 7.19-7.15 (t, J = 7.2 Hz, 1H), 7.07-7.05 (m, 2H), 6.89-6.87 (d, J = 8 Hz, 1H), 6.85-6.81 (t, J = 7.6 Hz, 1H), 6.63-6.61 (d, J = 7.6 Hz, 1H), 5.50-5.48 (m, 1H), 4.65-4.63 (m, 1H), 4.40-4.35 (m, 1H), 3.35-3.23 (m, 2H), 2.32-2.22 (m, 1H), 2.01-1.96 (m, 1H), 1.76-1.74 (d, J = 6.8 Hz, 3H). | 473.3 |
| 102a, | 31a | 3-Methoxy-4-((2R,4R)-2-((((R)-1-(naphthalen-1-yl)ethyl)amino)methyl)chroman-4-yl)benzoic acid hydrochloride<br><br>$^1$HNMR (400 MHz, DMSO-d6): δ 13.00 (bs, 1H), 9.60-9.50 (bs, 1H), 9.30-9.20 (bs, 1H), 8.23-8.21 (d, J = 8 Hz, 1H), 8.01-7.97 (m, 2H), 7.90-7.88 (d, J = 6.8 Hz, 1H), 7.63-7.58 (m, 3H), 7.51-7.50 (d, J = 1.6 Hz, 1H), 7.42-7.40 (d, J = 7.6 Hz, 1H), 7.23-7.21 (m, 1H), 6.97-6.95 (d, J = 8 Hz, 1H), 6.90-6.89 (m, 2H), 6.52-6.50 (d, J = 8 Hz, 1H), 5.40-5.30 (m, 1H), 4.52-4.51 (m, 1H), 4.18-4.15 (m, 1H), 3.91 (s, 3H), 3.40-3.16 (m, 2H), 2.07-1.93 (m, 2H), 1.69 (d, J = 6.4 Hz, 3H). | 468.1 |

TABLE 7-continued

| Ex. No. | Ester Ex. No. | Structure | Mass (m/z) |
|---|---|---|---|
| 102b | 31b | 3-Methoxy-4-((2R,4S)-2-((((R)-1-(naphthalen-1-yl)ethyl)amino)methyl)chroman-4-yl)benzoic acid hydrochloride | 468.1 |

$^1$HNMR (400 MHz, DMSO-d6): δ 13.10 (bs, 1H), 9.80-9.70 (bs, 1H), 9.50-9.40 (bs, 1H), 8.29-8.27 (d, J = 8 Hz, 1H), 8.05-8.01 (m, 2H), 7.94-7.92 (d, J = 6.8 Hz, 1H), 7.70-7.60 (m, 3H), 7.55-7.50 (m, 2H), 7.15-7.07 (m, 2H), 6.88-6.86 (d, J = 7.6 Hz, 1H), 6.81-6.77 (t, J = 7.2 Hz, 1H), 6.57-6.55 (d, J = 7.6 Hz, 1H), 5.48-5.46 (m, 1H), 4.68-4.66 (m, 2H), 3.83 (s, 3H), 3.35-3.31 (m, 1H), 3.10-3.05 (m, 1H), 2.19-2.16 (m, 1H), 2.10-1.95 (m, 1H), 1.74 (d, J = 6.8 Hz, 3H).

| 103 | 32 | 3-Fluoro-4-((2R,4R)-2-((((R)-1-(naphthalen-1-yl)ethyl)amino)methyl)chroman-4-yl)benzoic acid hydrochloride | 454.3 |

$^1$H NMR (400 MHz, DMSO-d$_6$): δ 13.29 (bs, 1H), 9.63 (bs, 1H), 9.33 (bs, 1H), 8.29-8.27 (d, J = 8.4 Hz, 1H), 8.05-8.01 (m, 2H), 7.94-7.92 (d, J = 6.8 Hz, 1H), 7.77-7.74 (dd, J = 8 Hz, 1H), 7.68-7.62 (m, 4H), 7.34-7.32 (m, 1H), 7.19-7.15 (t, J = 8 Hz, 1H), 6.91-6.89 (d, J = 8 Hz, 1H), 6.84-6.81 (t, J = 7.6 Hz, 1H), 6.62-6.60 (d, J = 8 Hz, 1H), 5.49-5.47 (m, 1H), 4.68-4.59 (m, 2H), 3.51-3.25 (m, 2H), 2.28-2.23 (m, 1H), 2.01-1.98 (m, 1H), 1.74-1.73 (d, J = 6.4 Hz, 3H).

| Ex. No. | Ester Ex. No. | Structure | Mass (m/z) |
|---|---|---|---|
| 104 | 33 | 2-Fluoro-4-((2R,4S)-2-((((R)-1-(naphthalen-1-yl)ethyl)amino)methyl)chroman-4-yl)benzoic acid hydrochloride | 456.0 |

$^1$H NMR (400 MHz, DMSO-d6): δ 13.10 (bs, 1H), 9.80 (bs, 1H), 9.40 (bs, 1H), 8.30-8.28 (d, J = 8.8 Hz, 1H), 8.05-7.97 (m, 3H), 7.86-7.82 (t, J = 8 Hz, 1H), 7.68-7.61 (m, 3H), 7.16-7.09 (m, 3H), 6.90-6.88 (d, J = 8.4 Hz, 1H), 6.82-6.80 (t, J = 7.6 Hz, 1H), 6.60-6.58 (d, J = 7.6 Hz, 1H), 5.48-5.40 (m, 1H), 4.64-4.60 (m, 1H), 4.40-4.36 (m, 1H), 3.40-3.30 (m, 2H), 2.27-2.23 (m, 1H), 2.08-1.93 (m, 1H), 1.75-1.73 (m, 3H).

| 105a, | 34a | 2-(4-((2R,4R)-2-((((R)-1-(Naphthalen-1-yl)ethyl)amino)methyl)chroman-4-yl)phenoxy)acetic acid hydrochloride | 467.8 |

$^1$H NMR (400 MHz, DMSO-d$_6$): δ 12.99 (bs, 1H), 9.55 (bs, 1H), 9.35 (bs, 1H), 8.25 (d, J = 8.4 Hz, 1H), 8.02-7.90 (m, 3H), 7.65-7.57 (m, 3H), 7.21-7.08 (m, 2H), 6.94-6.80 (m, 6H), 5.40 (m, 1H), 4.65 (S, 2H), 4.39-4.21 (m, 2H), 3.40-3.16 (m, 2H), 2.05-2.02 (m, 1H), 1.97-1.91 (m, 1H), 1.69 (d, J = 6.8 Hz, 3H).

TABLE 7-continued

| Ex. No. | Ester Ex. No. | Structure | Mass (m/z) |
|---|---|---|---|
| 105b | 34b | 2-(4-((2R,4S)-2-((((R)-1-(Naphthalen-1-yl)ethyl)amino)methyl)chroman-4-yl)phenoxy)acetic acid hydrochloride | 467.8 |

¹H NMR (400 MHz, DMSO-d₆): δ 12.84 (bs, 1H), 9.77 (bs, 1H), 9.41 (bs, 1H), 8.30 (d, J = 8.4 Hz, 1H), 8.05 (t, J = 8.4 Hz, 2H), 7.98 (d, J = 7.2 Hz, 1H), 7.68-7.60 (m, 3H), 7.14-7.08 (m, 3H), 6.88-6.85 (m, 3H), 6.81 (t, J = 6.4 Hz & 1.2 Hz, 1H), 6.60 (d, J = 7.6 Hz, 1H), 5.48-5.47 (m, 1H), 4.65 (s, 2H), 4.61 (m, 1H), 4.22-4.17 (m, 1H), 3.31-3.24 (m, 2H), 2.20-2.16 (m, 1H), 1.95-1.85 (m, 1H), 1.76 (d, J = 6.8 Hz, 3H).

| Ex. No. | Ester Ex. No. | Structure | Mass (m/z) |
|---|---|---|---|
| 106a, | 35a | 2-(2-Fluoro-4-((2R,4R)-2-((((R)-1-(naphthalen-1-yl)ethyl)amino)methyl)chroman-4-yl)phenoxy)acetic acid hydrochloride | 486.0 |

¹HNMR (400 MHz, DMSO-d6): δ 13.10 (bs, 1H), 9.60 (bs, 1H), 9.20 (bs, 1H), 8.25-8.23 (d, J = 8 Hz, 1H), 8.02-7.98 (m, 2H), 7.89-7.87 (d, J = 6.8 Hz, 1H), 7.70-7.58 (m, 3H), 7.23-7.19 (m, 1H), 6.99-6.85 (m, 5H), 6.67-6.65 (d, J = 8.8 Hz, 1H), 5.50-5.40 (m, 1H), 4.72 (s, 2H), 4.24-4.14 (m, 2H), 3.25-3.20 (m, 2H), 2.10-1.90 (m, 2H), 1.69-1.68 (d, J = 6.4 Hz, 3H).

| Ex. No. | Ester Ex. No. | Structure | Mass (m/z) |
|---|---|---|---|
| 106b | 35b | 2-(2-Fluoro-4-((2R,4S)-2-((((R)-1-(naphthalen-1-yl)ethyl)amino)methyl)chroman-4-yl)phenoxy)acetic acid hydrochloride | 486.0 |

¹HNMR (400 MHz, DMSO-d6): δ 13.09 (bs, 1H), 9.67 (bs, 1H), 9.34 (bs, 1H), 8.30-8.27 (d, J = 8.4 Hz 1H), 8.05-8.01 (t, J = 8 Hz, 2H), 7.95-7.93 (d, J = 7.2 Hz, 1H), 7.68-7.60 (m, 3H), 7.16-7.12 (t, J = 8 Hz, 1H), 7.04-7.01 (m, 2H), 6.95-6.93 (d, J = 8.8 Hz, 1H), 6.87-6.85 (d, J = 8.4 Hz, 1H), 6.83-5.72 (t, J = 7.6 Hz, 1H), 6.61-6.59 (d, J = 7.6H, 1H), 5.47 (m, 1H), 4.75 (s, 2H), 4.60-4.58 (m, 1H), 4.15-4.14 (m, 1H), 3.37-3.33 (m, 2H), 2.21-2.16 (m, 1H), 1.97-1.88 (m, 1H), 1.74 (d, J = 6.8 Hz, 3H).

| Ex. No. | Ester Ex. No. | Structure | Mass (m/z) |
|---|---|---|---|
| 107a, | 36a | 2-(4-((2R,4R)-2-((((R)-1-(Naphthalen-1-yl)ethyl)amino)methyl)chroman-4-yl)phenyl)acetic acid hydrochloride | 451.6 |

¹H NMR (400 MHz, DMSO-d₆): δ 12.3 (bs, 1H), 9.4 (bs, 1H), 9.1 (bs, 1H), 8.24-8.22 (d, J = 8.4 Hz, 1H), 8.02-7.98 (m, 2H), 7.86-7.84 (d, J = 7.2 Hz, 1H), 7.68-7.59 (m, 3H), 7.32-7.09 (m, 3H), 6.96-6.82 (m, 5H), 5.39 (m, 1H), 4.26 (m, 2H), 3.55 (s, 2H), 3.44-3.29 (m, 2H), 2.17-2.07 (m, 1H), 1.98-1.95 (m, 1H), 1.69 (d, J = 6.4 Hz, 3H).

TABLE 7-continued

| Ex. No. | Ester Ex. No. | Structure | Mass (m/z) |
|---|---|---|---|
| 107b | 36b | 2-(4-((2R,4S)-2-((((R)-1-(Naphthalen-1-yl)ethyl)amino)methyl)chroman-4-yl)phenyl)acetic acid hydrochloride | 451.6 |

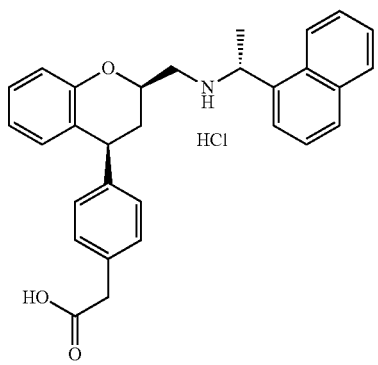

¹H NMR (400 MHz, DMSO-d$_6$): δ 12.32 (bs, 1H), 9.59 (bs, 1H), 9.29 (bs, 1H), 8.29-8.27 (d, J = 8 Hz, 1H), 8.05-8.01 (t, J = 7.2 Hz, 2H), 7.93-7.92 (d, J = 6.8 Hz, 1H), 7.70-7.60 (m, 3H), 7.23-7.21 (d, J = 8 Hz, 2H), 7.15-7.11 (m, 3H), 6.89-6.87 (d, J = 7.2 Hz, 1H), 6.81-6.78 (t, J = 7.6 Hz, 1H), 6.60-6.58 (d, J = 7.6 Hz, 1H), 5.48-5.45 (m, 1H), 4.64-4.59 (m, 1H), 4.26-4.22 (m, 1H), 3.55 (s, 2H), 3.44-3.29 (m, 2H), 2.22-2.17 (m, 1H), 1.97-1.88 (m, 1H), 1.72 (d, J = 6.4 Hz, 3H).

| Ex. No. | Ester Ex. No. | Structure | Mass (m/z) |
|---|---|---|---|
| 108a | 37a | 2-Methyl-2-(4-((2R,4R)-2-((((R)-1-(naphthalen-1-yl)ethyl)amino)methyl)chroman-4-yl)phenyl)propanoic acid hydrochloride | 479.4 |

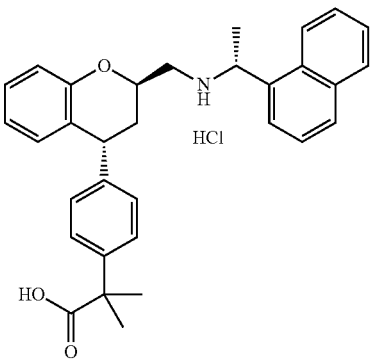

¹H NMR (400 MHz, DMSO-d$_6$): δ 12.31 (bs, 1H), 9.49 (bs, 1H), 9.25 (bs, 1H), 8.24-8.22 (d, J = 8.4 Hz, 1H), 8.00-7.88 (m, 3H), 7.70-7.50 (m, 3H), 7.28-7.12 (m, 3H), 6.96-6.86 (m, 5H), 5.40-5.38 (m, 1H), 4.25 (m, 2H), 3.43-3.29 (m, 2H), 2.07-1.91 (m, 2H), 1.69 (d, J = 6.4 Hz, 3H), 1.46 (s, 6H).

| Ex. No. | Ester Ex. No. | Structure | Mass (m/z) |
|---|---|---|---|
| 108b | 37b | 2-Methyl-2-(4-((2R,4S)-2-((((R)-1-(naphthalen-1-yl)ethyl)amino)methyl)chroman-4-yl)phenyl)propanoic acid hydrochloride | 479.4 |

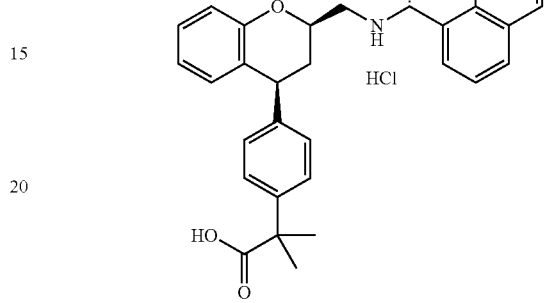

¹HNMR (400 MHz, DMSO-d$_6$): δ 12.31 (bs, 1H), 9.80 (bs, 1H), 9.45 (bs, 1H), 8.29-8.27 (d, J = 8.4 Hz, 1H), 8.05-7.98 (m, 2H), 7.86-7.85 (d, J = 6.8 Hz 1H), 7.66-7.61 (m, 3H), 7.30-7.28 (d, J = 8.4 Hz, 2H), 7.18-7.12 (m, 3H), 6.88-6.86 (d, J = 7.6 Hz, 1H), 6.81-6.77 (t, J = 7.6 Hz, 1H), 6.59-6.57 (d, J = 7.6 Hz, 1H), 5.48-5.47 (m, 1H), 4.63 (m, 1H), 4.26-4.22 (m, 1H), 3.37-3.31 (m, 1H), 3.24-3.14 (m, 1H), 2.18-2.14 (m, 1H), 1.93-1.85 (m, 1H), 1.75 (d, J = 6.4 Hz, 3H), 1.44 (s, 6H).

| Ex. No. | Ester Ex. No. | Structure | Mass (m/z) |
|---|---|---|---|
| 109 | 38 | 3-Methyl-4-((2R,4S)-2-((((R)-1-(naphthalen-1-yl)ethyl)amino)methyl)chroman-4-yl)benzoic acid hydrochloride | 452.1 |

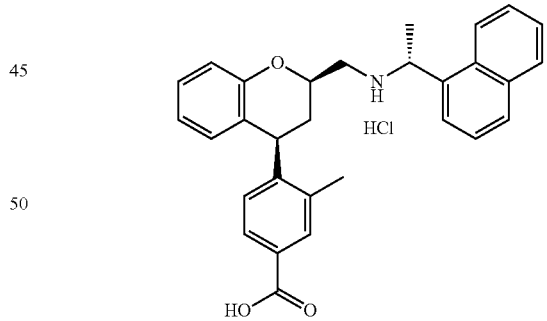

¹HNMR (400 MHz, DMSO-d6): δ 12.92 (bs, 1H), 9.82 (bs, 1H), 9.51 (bs, 1H), 8.30-8.28 (d, J = 8.4 Hz, 1H), 8.03-7.98 (m, 3H), 7.80 (s, 1H), 7.69-7.60 (m, 4H), 7.16-7.12 (t, J = 7.6 Hz, 1H), 6.98 (s, 1H), 6.89-6.87 (d, J = 8 Hz, 1H), 6.81-6.77 (t, J = 7.2 Hz, 1H), 6.53-6.51 (d, J = 8.8 Hz, 1H), 5.42 (m, 1H), 4.58-4.54 (m, 2H), 3.29-3.23 (m, 1H), 3.15-3.13 (m, 1H), 2.45 (s, 3H), 2.25-2.24 (m, 1H), 1.90-1.80 (m, 1H), 1.71 (d, J = 6.4 Hz, 3H).

TABLE 7-continued

| Ex. No. | Ester Ex. No. | Structure | Mass (m/z) |
|---|---|---|---|
| 110 | 39 | 2-Fluoro-5-((2S,4R)-2-((((R)-1-(naphthalen-1-yl)ethyl)amino)methyl)chroman-4-yl)benzoic acid hydrochloride | 456.1 |

$^1$H NMR (400 MHz, DMSO-d$_6$): δ 13.30 (bs, 1H), 10.04 (bs, 1H), 9.27 (bs, 1H), 8.28 (d, J = 8.4 Hz, 1H), 8.04-7.98 (m, 3H), 7.68-7.59 (m, 4H), 7.46-7.42 (m, 1H), 7.29-7.24 (m, 1H), 7.17 (t, J = 7.6 Hz, 1H), 6.92 (d, J = 8.4 Hz, 1H), 6.82 (t, J = 8.0 Hz, 1H), 6.57 (d, J = 7.8 Hz, 1H), 5.46 (m, 1H), 4.61-4.56 (m, 1H), 4.39-4.34 (m, 1H), 3.11 (m, 2H), 2.21-2.16 (m, 1H), 1.98-1.88 (m, 1H), 1.76 (d, J = 6.8 Hz, 3H).

| Ex. No. | Ester Ex. No. | Structure | Mass (m/z) |
|---|---|---|---|
| 111 | 40 | 3-((2S,4R)-2-((((R)-1-(Naphthalen-1-yl)ethyl)amino)methyl)chroman-4-yl)benzoic acid hydrochloride | 437.73 |

$^1$H NMR (400 MHz, DMSO-d6): δ 13.05 (bs, 1H), 10.08 (bs, 1H), 9.28 (bs, 1H), 8.28 (d, J = 8.4 Hz, 1H), 8.04-7.99 (m, 3H), 7.84-7.81 (m, 1H), 7.74-7.60 (m, 4H), 7.46-7.44 (m, 2H), 7.15 (t, J = 8.0 Hz, 1H), 6.93 (d, J = 8.0 Hz, 1H), 6.81 (t, J = 7.6 Hz, 1H), 6.56 (d, J = 8.0 Hz, 1H), 5.46 (m, 1H), 4.63-4.58 (m, 1H), 4.39-4.34 (m, 1H), 3.38-3.34 (m, 1H), 3.14-3.12 (m, 1H), 2.23-2.19 (m, 1H), 1.99-1.90 (m, 1H), 1.76 (d, J = 6.4 Hz, 3H).

| Ex. No. | Ester Ex. No. | Structure | Mass (m/z) |
|---|---|---|---|
| 112a | 41a | 2-Methyl-5-((2S,4R)-2-((((R)-1-(naphthalen-1-yl)ethyl)amino)methyl)chroman-4-yl)benzoic acid hydrochloride | 451.92 |

$^1$H NMR (400 MHz, DMSO-d6): δ 12.85 (bs, 1H), 9.9 (bs, 1H), 9.3 (bs, 1H), 8.29 (d, J = 8.4 Hz, 1H), 8.05 (t, J = 9.2 Hz & 8 Hz, 1H), 7.98 (d, J = 7.2 Hz, 2H), 7.68-7.60 (m, 4H), 7.25 (s, 2H), 7.16 (t, J = 7.6 Hz & 7.2 Hz, 1H), 6.92 (dd, J = 8.4 Hz & 1.2 Hz, 1H), 6.81 (t, J = 7.6 Hz & 1.2 Hz, 1H), 6.57 (d, J = 7.6 Hz, 1H), 5.47-5.46 (m, 1H), 4.60-4.58 (m, 1H), 4.32-4.27 (m, 1H), 3.34 (m, 1H), 3.17-3.13 (m, 1H), 2.49 (s, 3H), 2.17 (m, 1H), 1.95 (m, 1H), 1.76 (d, J = 6.8 Hz, 3H).

| Ex. No. | Ester Ex. No. | Structure | Mass (m/z) |
|---|---|---|---|
| 112b | 41b | 2-Methyl-5-((2S,4S)-2-((((R)-1-(naphthalen-1-yl)ethyl)amino)methyl)chroman-4-yl)benzoic acid hydrochloride | 451.92 |

$^1$H NMR (400 MHz, DMSO-d6): δ 12.8 (bs, 1H), 9.6 (bs, 1H), 9.2 (bs, 1H), 8.21 (d, J = 8.4 Hz, 1H), 8.03 (t, J = 8.8 Hz, 2H), 7.89 (d, J = 7.2 Hz, 1H), 7.66-7.58 (m, 3H), 7.45 (d, J = 1.6 Hz, 1H), 7.26-7.21 (m, 2H), 7.15 (dd, J = 8 Hz, J = 2 Hz, 1H), 6.98 (t, J = 7.6 Hz, 1H), 6.93 (t, J = 7.6 Hz, 2H), 5.39 (m, 1H), 4.32 (m, 1H), 4.27-4.22 (m, 1H), 3.34 (m, 1H), 3.05-3.04 (m, 1H), 2.49 (s, 3H), 2.11-2.06 (m, 1H), 2.05-1.98 (m, 1H), 1.67 (d, J = 6.8 Hz, 3H).

TABLE 7-continued

| Ex. No. | Ester Ex. No. | Structure | Mass (m/z) |
|---|---|---|---|
| 113a, | 42a | 2-(4-((2S,4R)-2-((((R)-1-(Naphthalen-1-yl)ethyl)amino)methyl)chroman-4-yl)phenoxy)acetic acid hydrochloride | 466.8 |

¹H NMR (400 MHz, DMSO-d6): δ 12.97 (bs, 1H), 10.04 (bs, 1H), 9.23 (bs, 1H), 8.28 (d, J = 8.4 Hz, 1H), 8.04-7.97 (m, 3H), 7.68-7.59 (m, 3H), 7.14-7.07 (m, 3H), 6.89-6.84 (m, 2H), 6.80 (t, J = 7.6 Hz, 2H), 6.58 (d, J = 7.6 Hz, 1H), 5.45 (m, 1H), 4.64 (s, 2H), 4.60-4.56 (m, 1H), 4.20-4.16 (m, 1H), 3.16-3.09 (m, 2H), 2.16-2.08 (m, 1H), 1.94-1.85 (m, 1H), 1.76 (d, J = 6.8 Hz, 3H).

| 113b | 42b | 2-(4-((2S,4S)-2-((((R)-1-(Naphthalen-1-yl)ethyl)amino)methyl)chroman-4-yl)phenoxy)acetic acid hydrochloride | 466.8 |

¹H NMR (400 MHz, DMSO-d6): δ 12.97 (bs, 1H), 9.77 (bs, 1H), 9.25 (bs, 1H), 8.24 (d, J = 8.4 Hz, 1H), 8.02-7.89 (m, 3H), 7.65-7.58 (m, 3H), 7.26-7.14 (m, 2H), 6.96-6.85 (m, 6H), 5.40 (m, 1H), 4.63 (s, 2H), 4.33-4.30 (m, 1H), 4.21 (m, 1H), 3.40-3.04 (m, 2H), 2.06-1.96 (m, 2H), 1.68 (d, J = 6.8 Hz, 3H).

| Ex. No. | Ester Ex. No. | Structure | Mass (m/z) |
|---|---|---|---|
| 114 | 45 | 4-((2R,4S)-2-((((R)-1-(4-Fluoro-3-methoxyphenyl)ethyl)amino)methyl)chroman-4-yl)-2-methylbenzoic acid hydrochloride | 450.1 |

¹HNMR (400 MHz, DMSO-d₆): δ 12.25 (bs, 1H), 9.70 (bs, 2H), 7.81 (d, J = 8 Hz, 1H), 7.61-7.60 (m, 1H), 7.30 (t, J = 8.4 Hz, 1H), 7.15-7.08 (m, 4H), 6.91 (d, J = 8 Hz, 1H), 6.79 (t, J = 7.6 Hz, 1H), 6.58 (d, J = 7.6 Hz, 1H), 4.53 (m, 2H), 4.27-4.25 (m, 1H), 3.87 (s, 3H), 3.09 (m, 1H), 2.95 (m, 1H), 2.46 (s, 3H), 2.23 (m, 1H), 1.94-1.85 (m, 1H), 1.65 (d, J = 6.8 Hz, 3H).

| 115 | 46 | 3-((2R,4S)-2-((((R)-1-(4-Fluoro-3-methoxyphenyl)ethyl)amino)methyl)chroman-4-yl)-2-methylbenzoic acid hydrochloride | 450.1 |

¹HNMR (400 MHz, DMSO-d₆): δ 12.78 (bs, 1H), 9.73-9.63 (bs, 2H), 7.59-7.50 (dd, J = 13.6 Hz, 7.2 Hz, 2H), 7.31 (t, J = 8.4 Hz, 1H), 7.21 (m, 3H), 7.02 (d, J = 8 Hz, 1H), 6.93 (d, J = 8.4 Hz, 1H), 6.80 (t, J = 7.2 Hz, 1H), 6.53 (m, 1H), 4.55-4.47 (m, 3H), 3.83 (s, 3H), 2.95-2.93 (m, 1H), 2.56-2.51 (m, 1H), 2.50 (s, 3H), 2.33-2.27 (m, 1H), 1.79-1.77 (m, 1H), 1.65 (d, J = 6.8 Hz, 3H)

TABLE 7-continued

| Ex. No. | Ester Ex. No. | Structure | Mass (m/z) |
|---|---|---|---|
| 116 | 47 | 5-((2R,4S)-2-((((R)-1-(4-Fluoro-3-methoxyphenyl)ethyl)amino)methyl)chroman-4-yl)-2-methyl benzoic acid hydrochloride 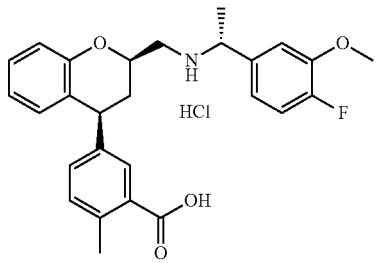 ¹HNMR (400 MHz, DMSO-d$_6$): δ 12.84 (bs, 1H), 9.78 (bs, 1H), 9.70 (bs, 1H), 7.65 (d, J = 8.4 Hz, 2H), 7.30-7.26 (m, 3H), 7.15-7.08 (m, 2H), 6.91 (d, J = 8 Hz, 1H), 6.80 (t, J = 7.2 Hz, 1H), 6.56 (d, J = 7.6 Hz, 1H), 4.55-4.53 (m, 1H), 4.48 (m, 1H), 4.29-4.25 (m, 1H), 3.87 (s, 3H), 3.11-3.10 (m, 1H), 2.95 (m, 1H), 2.46 (s, 3H), 2.25-2.18 (m, 1H), 1.89-1.83 (m, 1H), 1.65 (d, J = 6.4 Hz, 3H). | 450.1 |
| 117 | 48 | 3-((2R,4S)-2-((((R)-1-(4-Fluoro-3-methoxyphenyl)ethyl)amino)methyl)chroman-4-yl)-5-methylbenzoic acid hydrochloride 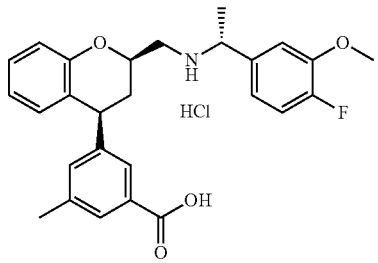 ¹HNMR (400 MHz, DMSO-d$_6$): δ 12.91 (bs, 1H), 9.71-9.66 (bs, 2H), 7.66 (s, 1H), 7.63 (d, J = 6.8 Hz, 1H), 7.54 (s, 1H), 7.31-7.27 (m, 2H), 7.16-7.09 (m, 2H), 6.92 (d, J = 8 Hz, 1H), 6.81 (t, J = 7.2 Hz, 1H), 6.58 (d, J = 7.6 Hz, 1H), 4.55-4.48 (m, 2H), 4.32-4.28 (m, 1H), 3.87 (s, 3H), 3.11 (m, 1H), 2.97 (m, 1H), 2.33 (s, 3H), 2.23 (m, 1H), 1.94 (m, 1H), 1.67 (d, J = 6.4 Hz, 3H). | 450.1 |
| 118 | 49 | 3-((2R,4S)-2-((((R)-1-(4-Fluoro-3-methoxyphenyl)ethyl)amino)methyl)chroman-4-yl)-4-methylbenzoic acid hydrochloride 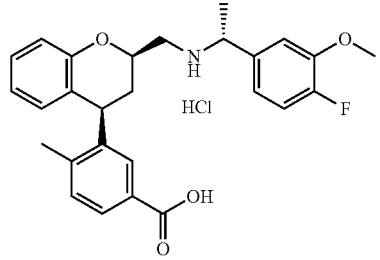 ¹HNMR (400 MHz, DMSO-d$_6$): δ 12.8 (bs, 1H), 9.8 (bs, 1H), 9.68 (bs, 1H), 7.71 (dd, J = 7.2 Hz, 7.6 Hz, 2H), 7.45 (m, 1H), 7.31-7.24 (m, 2H), 7.16-7.13 (m, 2H), 6.94 (d, J = 8 Hz, 1H), 6.80-6.76 (t, J = 7.2 Hz, 1H), 6.54 (d, J = 6.8 Hz, 1H), 4.58-4.48 (m, 3H), 3.88 (s, 3H), 3.11-3.10 (m, 1H), 2.95 (m, 1H), 2.46 (s, 3H), 2.32-2.27 (m, 1H), 1.79 (m, 1H), 1.62 (d, J = 6.4 Hz, 3H). | 450.1 |
| 119a | 43a | 5-((2R,4R)-2-((((R)-1-(4-Fluoronaphthalen-1-yl)ethyl)amino)methyl)chroman-4-yl)-2-methyl benzoic acid hydrochloride 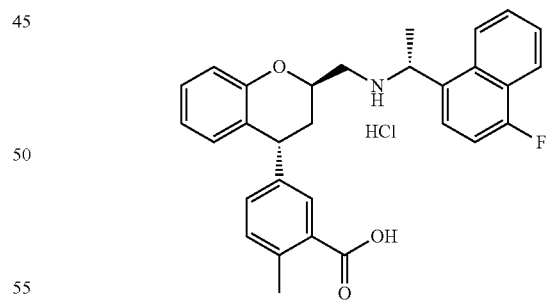 ¹HNMR (400 MHz, DMSO-d$_6$): δ 12.81 (bs, 1H), 9.45 (bs, 1H), 9.23 (bs, 1H), 8.33-8.30 (m, 1H), 8.15-8.13 (d, J = 8.4 Hz, 1H), 7.90-7.88 (m, 1H), 7.80-7.73 (m, 2H), 7.55-7.43 (m, 2H), 7.23-7.21 (m, 2H), 7.11-7.09 (m, 1H), 6.97-6.90 (m, 3H), 5.40-5.36 (m, 1H), 4.32 (m, 1H), 4.22-4.20 (m, 1H), 3.37-3.10 (m, 2H), 2.48 (s, 3H), 2.08-1.94 (m, 2H), 1.72-1.68 (d, J = 7.6 Hz, 3H). | 470.56 |

TABLE 7-continued

| Ex. No. | Ester Ex. No. | Structure | Mass (m/z) |
|---|---|---|---|
| 119b | 43b | 5-((2R,4S)-2-((((R)-1-(4-Fluoronaphthalen-1-yl)ethyl)amino)methyl)chroman-4-yl)-2-methyl benzoic acid hydrochloride 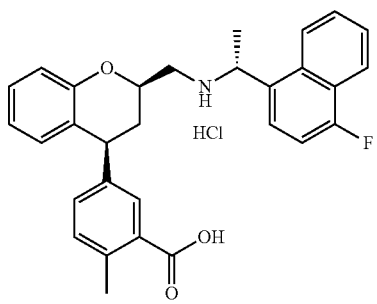 <sup>1</sup>H NMR (400 MHz, DMSO-d<sub>6</sub>): δ 12.85 (bs, 1H), 9.86 (bs, 1H), 9.47 (bs, 1H), 8.30-8.28 (d, J = 8 Hz, 1H), 8.18-8.16 (d, J = 7.2 Hz, 1H), 7.86-7.84 (m, 1H), 7.79-7.72 (m, 2H), 7.59 (s, 1H), 7.51-7.46 (m, 1H), 7.27 (s, 2H), 7.15-7.11 (t, J = 8 Hz, 1H), 6.88-6.86 (d, J = 8 Hz, 1H), 6.81-6.76 (t, J = 7.6 Hz, 1H), 6.55-6.53 (d, J = 7.6 Hz, 1H), 5.38-5.36 (m, 1H), 4.62-4.45 (m, 1H), 4.32-4.27 (m, 1H), 3.37-3.33 (m, 1H), 3.24-3.14 (m, 1H), 2.48 (s, 3H), 2.24-2.19 (m, 1H), 1.97-1.88 (m, 1H), 1.71-1.70 (d, J = 6.4 Hz, 3H). | 470.56 |
| 120a | 44a | 3-((2R,4S)-2-((((R)-1-(4-Fluoronaphthalen-1-yl)ethyl)amino)methyl)chroman-4-yl)-2-methoxybenzoic acid hydrochloride 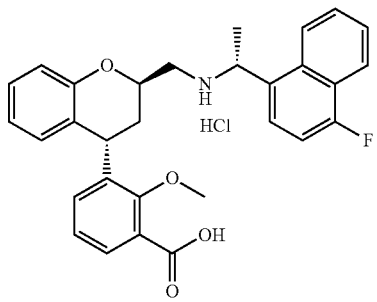 <sup>1</sup>H NMR (400 MHz, DMSO-d<sub>6</sub>): δ 13.1 (bs, 1H), 9.76 (bs, 1H), 9.5 (bs, 1H), 8.33-8.31 (d, J = 8.4 Hz, 1H), 8.14-8.12 (d, J = 7.6 Hz, 1H), 8.00-7.98 (m, 1H), 7.74-7.70 (m, 2H), 7.56-7.45 (m, 2H), 7.22-7.12 (m, 2H), 7.04-7.00 (t, J = 7.6 Hz, 1H), 6.95-6.87 (m, 3H), 5.36 (m, 1H), 4.51-4.50 (m, 1H), 4.29-4.26 (m, 1H), 3.86 (s, 3H), 3.30-3.17 (m, 2H), 2.08-2.04 (m, 1H), 1.89-1.85 (m, 1H), 1.76 (d, J = 6.4 Hz, 3H). | 485.9 |
| 120b | 44b | 3-((2R,4R)-2-((((R)-1-(4-fluoronaphthalen-1-yl)ethyl)amino)methyl)chroman-4-yl)-2-methoxybenzoic acid hydrochloride 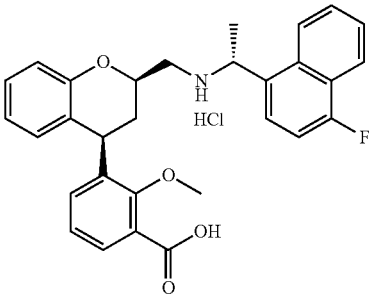 <sup>1</sup>H NMR (400 MHz, DMSO-d<sub>6</sub>): δ 12.95 (bs, 1H), 10.14 (bs, 1H), 9.76 (bs, 1H), 8.38-8.36 (d, J = 8.0 Hz, 1H), 8.17-8.09 (m, 2H), 7.77-7.70 (m, 2H), 7.61-7.58 (m, 1H), 7.53-7.48 (dd, J = 8.8 Hz, 1.2 Hz, 1H), 7.14-7.10 (m, 3H), 6.87-6.85 (d, J = 8 Hz, 1H), 6.80-6.77 (t, J = 7.6 Hz, 1H), 6.56-6.54 (d, J = 7.2 Hz, 1H), 5.50-5.40 (m, 1H), 4.80-4.70 (m, 2H), 3.80 (s, 3H), 3.38-3.22 (m, 2H), 2.23 (m, 1H), 1.90 (m, 1H), 1.77-1.75 (d, J = 6.4 Hz, 3H) | |

Example-121

2-Fluoro-5-((2S,4R)-2-(2-(((R)-1-(naphthalen-1-yl)ethyl)amino)ethyl)chroman-4-yl)benzoic Acid Hydrochloride

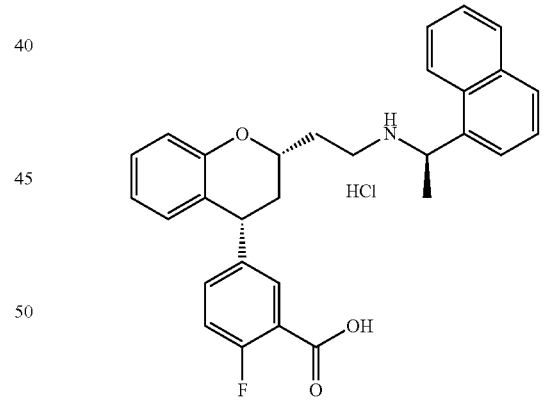

To a solution of Example-50 (0.15 g, 0.31 mmol) in methanol (6 mL), THF (6 mL) and water (1 mL) lithium hydroxide monohydrate (0.026 g, 0.620 mmol) was added. The reaction mixture was stirred at 65° C. for 4 h. The progress of reaction was monitored by TLC. Methanol was distilled off under vacuum then cooled to 0° C. and acidified with dilute HCl solution [pH=3 to 4]. The resultant white solid was filtered, washed and dried under vacuum to give white solid (110 mg, 78%).

Further, HCl salt of these amino compounds were prepared by following the similar hydrochloride salt procedure as described in Example-72a, 72b.

m/z-470; ¹HNMR (400 MHz, DMSO-d₆): δ 13.25 (bs, 1H), 9.98 (bs, 1H), 9.27 (bs, 1H), 8.28-8.26 (d, J=8.4 Hz, 1H), 8.03-7.98 (m, 3H), 7.66-7.59 (m, 4H), 7.44-7.41 (m, 1H), 7.29-7.25 (dd, J=8.8 & 2 Hz, 1H), 7.09-7.05 (t, J=7.2 Hz, 1H), 6.76-6.70 (m, 2H), 6.55-6.53 (d, J=7.6 Hz, 1H), 5.38-5.36 (m, 1H), 4.33-4.26 (m, 2H), 3.30-3.24 (m, 1H), 3.10-2.90 (m, 1H), 2.20-2.10 (m, 3H), 1.85-1.74 (m, 1H), 1.69-1.67 (d, J=6.8 Hz, 3H).

The below examples 122 to 129 given Table-8 were prepared by following the similar ester hydrolysis procedures as described in Example-121 by taking appropriate ester compound of Example-51 to 58.

Further, HCl salt of these amino compounds were prepared by following the similar hydrochloride salt procedure as described in Example-72a, 72b;

TABLE 8

| Ex. No. | Ester Ex. No. | Structure | Mass (m/z) |
|---|---|---|---|
| 122 | 51 | 2-Fluoro-5-((2R,4S)-2-(2-(((R)-1-(naphthalen-1-yl)ethyl)amino)ethyl)chroman-4-yl)benzoic acid hydrochloride | 470.42 |

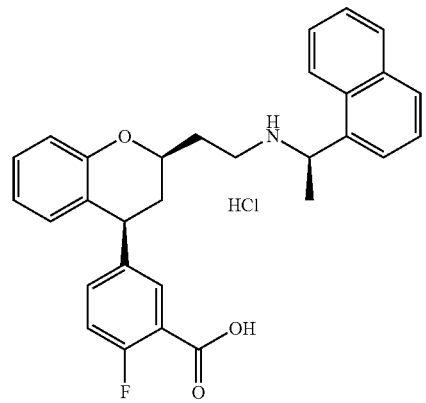 [SMILES: C[C@@H](NCC[C@H]1C[C@@H](c2ccc(F)c(C(=O)O)c2)c2ccccc2O1)c1cccc2ccccc12 ; Cl]

¹H NMR (400 MHz, DMSO-d6): δ 13.3-12.9 (bs, 1H), 9.40-9.30 (bs, 1H), 9.40 (bs, 1H), 8.29-8.27 (d, J = 8.4 Hz, 1H), 8.03-7.95 (m, 3H), 7.70-7.50 (m, 4H), 7.45-7.40 (m, 1H), 7.30-7.20 (t, 1H), 7.10-7.06 (m, 1H), 6.77-6.6.71 (m, 2H), 6.55-6.6.53 (d, J = 7.6 Hz, 1H), 5.45-5.40 (m, 1H), 4.32-4.29 (m, 2H), 3.30-3.15 (m, 2H), 2.20-2.10 (m, 3H), 1.80-1.77 (m, 1H), 1.70-1.68 (d, J = 6 Hz, 3H).

| 123 | 52 | 2-Methyl-5-((2S, 4R)-2-(2-(((R)-1-(naphthalen-1-yl)ethyl)amino)ethyl)chroman-4-yl)benzoic acid hydrochloride | 466.10 |

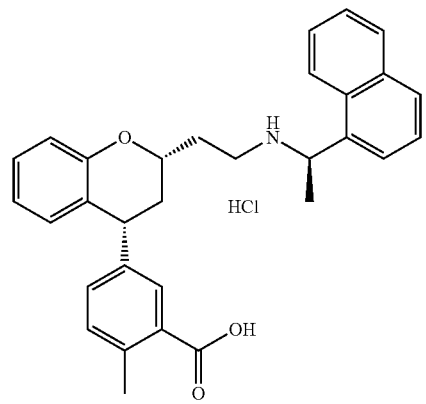 [SMILES: Cc1ccc([C@H]2C[C@@H](CCN[C@H](C)c3cccc4ccccc34)Oc3ccccc32)cc1C(=O)O ; Cl]

¹HNMR (400 MHz, DMSO-d₆): δ 12.65 (bs, 1H), 9.95 (bs, 1H), 9.25 (bs, 1H), 8.25-8.23 (d, J = 8.4 Hz, 1H), 8.02-7.98 (t, J = 7.6 Hz, 2H), 7.83-7.81 (d, J = 6.8 Hz, 1H), 7.66-7.58 (m, 4H), 7.27-7.22 (m, 2H), 7.08-7.04 (t, J = 7.6 Hz, 1H), 6.75-6.69 (m, 2H), 6.53-6.52 (d, J = 7.6 Hz, 1H), 5.35-5.33 (m, 1H), 4.26-4.02 (m, 2H), 3.29-3.23 (m, 1H), 3.05-2.98 (m, 1H ), 2.45 (s, 3H), 2.16-2.11 (m, 1H), 2.08-2.02 (m, 2H), 1.82-1.73 (m, 1H), 1.68-1.66 (d, J = 6.4 Hz, 3H)

TABLE 8-continued

| Ex. No. | Ester Ex. No. | Structure | Mass (m/z) |
|---|---|---|---|
| 124 | 53 | 2-Methyl-5-((2R,4S)-2-(2-(((R)-1-(naphthalen-1-yl)ethyl)amino)ethyl)chroman-4-yl)benzoic acid hydrochloride | 466.36 |

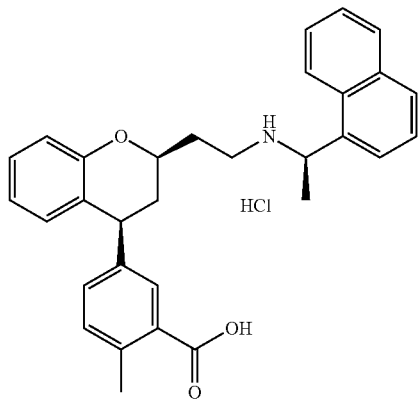 [SMILES: Cc1ccc([C@@H]2C[C@H](CCN[C@H](C)c3cccc4ccccc34)Oc3ccccc32)cc1C(=O)O ; Cl]

¹HNMR (400 MHz, DMSO-d₆): δ 12.84 (bs, 1H), 9.68 (bs, 1H), 9.16 (bs, 1H), 8.29-8.27 (d, J = 8.4 Hz, 1H), 8.03-7.99 (m, 2H), 7.85-7.93 (d, J = 7.2 Hz, 1H), 7.67-7.59 (m, 4H), 7.27-7.26 (m, 2H), 7.09-7.05 (t, J = 7.2 Hz, 1H), 6.75-6.70 (m, 2H), 6.55-6.53 (d, J = 7.6 Hz, 1H), 5.38-5.37 (m, 1H), 4.28-4.22 (m, 2H), 3.29-3.26 (m, 1H), 3.24-3.14 (m, 1H), 2.46 (s, 3H), 2.16-2.07 (m, 3H), 1.84-1.75 (m, 1H), 1.70-1.69 (d, J = 6.4 Hz, 3H)

| 125 | 54 | 2-Methoxy-3-((2R,4R)-2-(2-(((R)-1-(naphthalen-1-yl)ethyl)amino)ethyl)chroman-4-yl)benzoic acid hydrochloride | 482.1 |

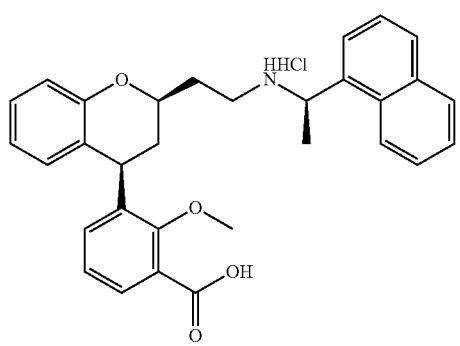

¹HNMR (400 MHz, DMSO-d6): δ 13.3 (bs, 1H), 9.80 (bs, 1H), 9.30 (bs, 1H), 8.29-8.27 (d, J = 8.4 Hz, 1H), 8.03-7.97 (m, 3H), 7.66-7.58 (m, 4H), 7.15-7.03 (m, 3H), 6.75-6.70 (m, 2H), 6.54-6.52 (d, J = 7.6 Hz, 1H), 5.45-5.40 (m, 1H), 4.62 (m, 1H), 4.40-4.32 (m, 1H), 3.62 (s, 3H), 3.24-3.22 (m, 1H), 3.15-3.11 (m, 1H), 2.14-2.08 (m, 3H), 1.90-1.75 (m, 1H), 1.71-1.69 (d, J = 6.8 Hz, 3H)

TABLE 8-continued

| Ex. No. | Ester Ex. No. | Structure | Mass (m/z) |
|---|---|---|---|
| 126 | 55 | 5-((2S, 4R)-2-(2-(((R)-1-(4-Fluoronaphthalen-1-yl)ethyl)amino)ethyl)chroman-4-yl)-2-methylbenzoic acid hydrochloride | 484.1 |

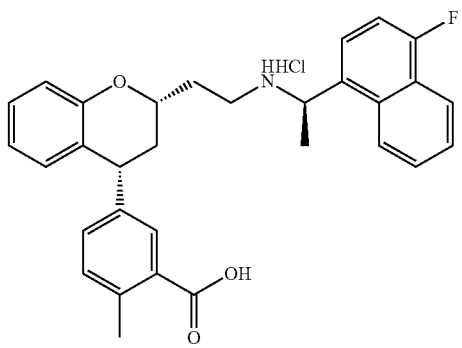

$^1$H NMR (400 MHz, DMSO-d6): δ 12.84 (bs, 1H), 9.81 (bs, 1H), 9.20 (bs, 1H), 8.37-8.35 (d, J = 8.4 Hz, 1H), 8.16-8.14 (m, 1H), 7.99-7.95 (m, 1H), 7.77-7.70 (m, 2H), 7.61 (s, 1H), 7.53-7.48 (m, 1H), 7.25 (s, 2H), 7.08-7.04 (m, 1H), 6.75-6.68 (m, 2H), 6.54-6.52 (d, J = 8.0 Hz, 1H), 5.36-5.35 (m, 1H), 4.28-4.21 (m, 2H), 3.28-3.26 (m, 1H), 3.01-2.99 (m, 1H), 2.49 (s, 3H), 2.17-2.06 (m, 3H), 1.85-1.76 (m, 1H), 1.70-1.68 (d, J = 6.8 Hz, 3H)

| 127 | 56 | 5-((2R,4S)-2-(2-(((R)-1-(4-Fluoronaphthalen-1-yl)ethyl)amino)ethyl)chroman-4-yl)-2-methylbenzoic acid hydrochloride | 484.1 |

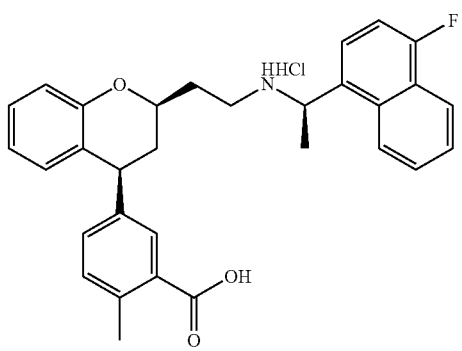

$^1$H NMR (400 MHz, DMSO-d6): δ 12.8 (bs, 1H), 9.8 (bs, 1H), 9.20 (bs, 1H), 8.37-8.35 (d, J = 8.4 Hz, 1H), 8.16-8.14 (m, 1H), 8.01-7.97 (m, 1H), 7.77-7.70 (m, 2H), 7.61 (s, 1H), 7.54-7.49 (m, 1H), 7.25 (s, 2H), 7.08-7.04 (m, 1H), 6.75-6.70 (m, 2H), 6.55-6.53 (d, J = 8 Hz, 1H), 5.35-5.32 (m, 1H), 4.29-4.21 (m, 2H), 3.23-3.21 (m, 1H), 3.13-3.11 (m, 1H), 2.49 (s, 3H), 2.15-2.07 (m, 3H), 1.90-1.75 (m, 1H) 1.70-1.68 (d, J = 6.8 Hz, 3H)

TABLE 8-continued

| Ex. No. | Ester Ex. No. | Structure | Mass (m/z) |
|---|---|---|---|
| 128 | 57 | 5-((2S, 4R)-2-(2-(((R)-1-(4-Fluoro-3-methoxyphenyl)ethyl)amino)ethyl)chroman-4-yl)-2-methylbenzoic acid hydrochloride | 463.9 |

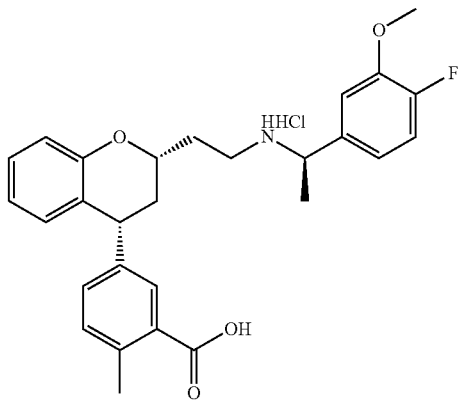

$^1$H NMR (400 MHz, DMSO-d6): δ 12.84 (bs, 1H), 9.50 (bs, 1H), 9.30 (bs, 1H), 7.62 (s, 1H), 7.57-7.54 (d, J = 8.4, 1H), 7.32-7.26 (m, 3H), 7.15-7.05 (m, 2H), 6.76-6.72 (m, 2H), 6.54-6.52 (d, J = 7.6 Hz, 1H), 4.41-4.39 (m, 1H), 4.27-4.23 (m, 2H), 3.86 (s, 3H), 3.08-3.01 (m, 1H), 2.95-2.88 (m, 1H), 2.45 (s, 3H), 2.16-2.11 (m, 1H), 2.01-1.99 (m, 2H), 1.80-1.76 (m, 1H), 1.58-1.56 (d, J = 6.4 Hz, 3H)

| Ex. No. | Ester Ex. No. | Structure | Mass (m/z) |
|---|---|---|---|
| 129 | 58 | 5-((2R,4S)-2-(2-(((R)-1-(4-Fluoro-3-methoxyphenyl)ethyl)amino)ethyl)chroman-4-yl)-2-methylbenzoic acid hydrochloride | 463.9 |

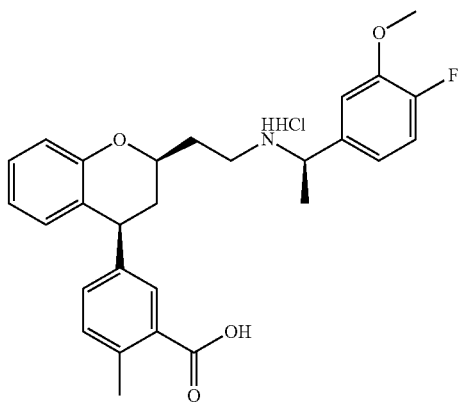

$^1$H NMR (400 MHz, DMSO-d6): δ 12.84 (bs, 1H), 9.7 (bs, 1H), 9.3 (bs, 1H), 7.63 (s, 1H), 7.60-7.58 (d, J = 8.4 Hz, 1H), 7.31-7.25 (m, 3H), 7.14-7.05 (m, 2H), 6.76-6.70 (m, 2H), 6.55-6.53 (d, J = 7.6 Hz, 1H), 4.42-4.40 (m, 1H), 4.27-4.22 (m, 2H), 3.85 (s, 3H), 3.07-3.01 (m, 1H), 2.91-2.88 (m, 1H), 2.44 (s, 3H), 2.17-2.12 (m, 1H), 2.07-2.01 (m, 2H), 1.85-1.76 (m, 1H), 1.59-1.57 (d, J = 6.4 Hz, 3H)

Example-130

2-Fluoro-5-((2S,4S)-2-(3-(((R)-1-(naphthalen-1-yl)ethyl)amino)propyl)chroman-4-yl)benzoic Acid Hydrochloride

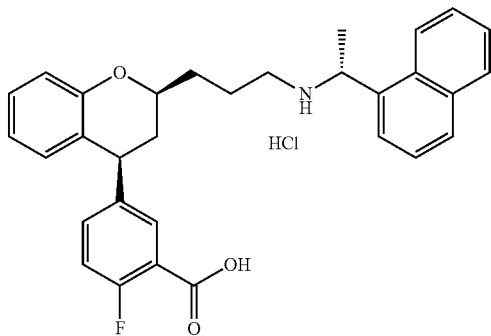 [SMILES: C[C@@H](NCCC[C@H]1C[C@@H](c2ccc(F)c(C(=O)O)c2)c2ccccc2O1)c1cccc2ccccc12 ; Cl]

To a solution of Example-59 (0.120 g, 0.24 mmol) in methanol (6 mL), THF (6 mL) and water (1 mL), lithium hydroxide monohydrate (0.028 g, 1.2 mmol) was added. The reaction mixture was stirred at 65° C. for 4 h. The progress of reaction was monitored by TLC. Solvent was distilled off under vacuum then cooled to 0° C. and acidified with dilute HCl solution [pH=3 to 4], the resultant solid was filtered and it was triturated with ethereal HCl and evaporated to dryness to give title compound as off white solid. (90 mg, 70%).

m/z: 484.3; $^1$H NMR (400 MHz, DMSO-d6): δ 13.3 (bs, 1H), 9.71 (bs, 1H), 9.22 (bs, 1H), 8.26-8.24 (d J=8.4 Hz, 1H), 8.02-7.98 (m, 3H), 7.83 (m, 1H), 7.65-7.57 (m, 4H), 7.44-7.41 (m, 1H), 7.30-7.25 (dd, J=8.8, 2 Hz, 1H), 7.09-7.05 (t, J=7.6 Hz, 1H), 6.69-6.67 (d, J=7.6 Hz, 1H), 6.54-6.52 (d, J=7.6 Hz, 1H), 5.34-5.32 (m, 1H), 4.30-4.27 (m, 1H), 4.12-4.11 (m, 1H), 3.09-3.00 (m, 1H), 2.89-2.86 (m, 1H), 2.13-2.09 (m, 1H), 1.88-1.66 (m, 8H).

The below examples 131 to 137 given Table-9 were prepared by following the above similar procedures as described in Example-130 by taking appropriate ester compound of Example-60 to 66.

Further, HCl salt of these amino compounds were prepared by following the similar hydrochloride salt procedure as described in Example-72a, 72b.

TABLE 9

| Ex. No. | Ester Ex. No. | Structure | Mass (m/z) |
|---|---|---|---|
| 131 | 60 | 2-Fluoro-5-((2R,4R)-2-(3-(((R)-1-(naphthalen-1-yl)ethyl)amino)propyl)chroman-4-yl)benzoic acid hydrochloride<br>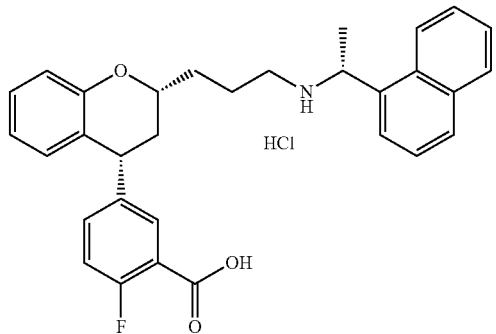 [SMILES: C[C@@H](NCCC[C@@H]1C[C@H](c2ccc(F)c(C(=O)O)c2)c2ccccc2O1)c1cccc2ccccc12 ; Cl]<br>$^1$HNMR (400 MHz, DMSO-d$_6$): δ 13.6 (bs, 1H), 9.75 (bs, 1H), 9.20 (bs, 1H), 8.29-8.27 (d, J = 8.4 Hz, 1H), 8.01-7.96 (m, 3H), 7.65-7.59 (m, 4H), 7.41-7.40 (m, 1H), 7.29-7.24 (dd, J = 8.4 & 2 Hz, 1H), 7.07-7.03 (t, J = 7.2 Hz, 1H), 6.756.71 (dd, J = 8.4 & 1.2 Hz, 1H), 6.56-6.51 (m, 2H), 5.34-5.32 (m, 1H), 4.32-4.27 (m, 1H), 4.13-4.08 (m, 1H), 3.05-3.03 (m, 1H), 2.89-2.86 (m, 1H), 2.13-2.08 (m, 1H), 1.95-1.82 (m, 2H), 1.77-1.65 (m, 6H). | 484.36 |
| 132 | 61 | 2-Methyl-5-((2S, 4S)-2-(3-(((R)-1-(naphthalen-1-yl)ethyl)amino)propyl)chroman-4-yl)benzoic acid hydrochloride<br>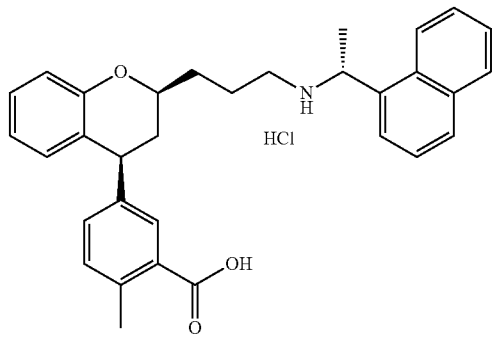 [SMILES: Cc1ccc([C@@H]2C[C@H](CCCN[C@H](C)c3cccc4ccccc34)Oc3ccccc32)cc1C(=O)O ; Cl] | 479.3 |

TABLE 9-continued

| Ex. No. | Ester Ex. No. | Structure | Mass (m/z) |
|---|---|---|---|
| | | ¹HNMR (400 MHz, DMSO-d₆): δ 12.84 (bs, 1H), 9.95, (bs, 1H), 9.35 (bs, 1H), 8.28-8.26 (d, J = 8 Hz, 1H), 8.05-7.97 (m, 3H), 7.64-7.57 (m, 4H), 7.27-7.22 (m, 2H), 7.08-7.03 (t, J = 7.6 Hz, 1H), 6.74-6.67 (m, 2H), 6.53-6.51 (d, J = 7.6 Hz, 1H), 5.34-5.33 (m, 1H), 4.25-4.21 (m, 1H), 4.13-4.09 (m, 1H), 3.10-2.95 (m, 1H), 2.90-2.75 (m, 1H), 2.45 (s, 3H), 2.10-2.06 (m, 1H), 1.94-1.85 (m, 2H), 1.78-1.65 (m, 6H). | |
| 133 | 62 | 2-Methyl-5-((2R,4R)-2-(3-(((R)-1-(naphthalen-1-yl)ethyl) amino)propyl)chroman-4-yl)benzoic acid hydrochloride | 479.3 |

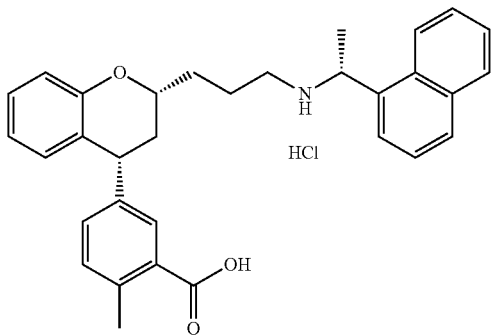 [SMILES: Cc1ccc([C@H]2C[C@@H](CCCN[C@H](C)c3cccc4ccccc34)Oc3ccccc32)cc1C(=O)O ; Cl]

¹HNMR (400 MHz, DMSO-d₆): δ 12.82 (bs, 1H), 9.83 (bs, 1H), 9.24 (bs, 1H), 8.29-8.27 (d, J = 8.4 Hz, 1H), 8.04-7.98 (m, 3H), 7.65-7.58 (m, 4H), 7.27-7.21 (m, 2H), 7.06-7.02 (t, J = 7.2 Hz, 1H), 6.73-6.69 (t, J = 8.4 Hz, 1H), 6.55-6.51 (m, 2H), 5.34-5.33 (m, 1H), 4.25-4.20 (m, 1H), 4.14-4.08 (m, 1H), 3.1-2.91 (m, 1H), 2.95-2.75 (m, 1H), 2.45 (s, 3H), 2.10-2.07 (m, 1H), 1.91-1.87 (m, 2H), 1.77-1.65 (m, 6H).

| 134 | 63 | 5-((2S, 4S)-2-(3-(((R)-1-(4-Fluoro-3-methoxyphenyl)ethyl) amino)propyl)chroman-4-yl)-2-methylbenzoic acid hydrochloride | 478.42 |

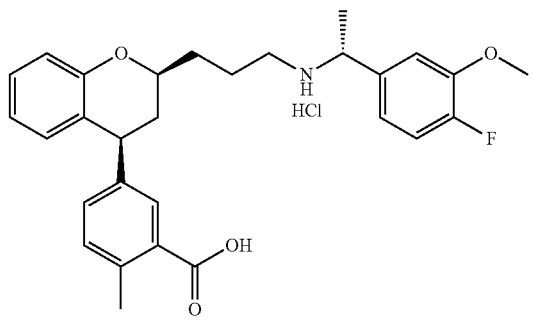 [SMILES: COc1cc([C@@H](C)NCCC[C@H]2C[C@@H](c3ccc(C)c(C(=O)O)c3)c3ccccc3O2)ccc1F ; Cl]

¹H NMR (400 MHz, DMSO-d₆): δ 12.84 (bs, 1H), 9.45 (bs, 1H), 9.25 (bs, 1H), 7.62 (s, 1H), 7.55 (dd, J = 8.4 Hz & J = 1.6 Hz, 1H), 7.30-7.25 (m, 3H), 7.13-7.05 (m, 2H), 6.75-6.71 (m, 2H), 6.54 (d, J = 7.6 Hz, 1H), 4.38-4.36 (m, 1H), 4.28-4.23 (m, 1H), 4.17-4.12 (m, 1H ), 3.84 (s, 3H), 2.86 (m, 1H), 2.67 (m, 1H), 2.5 (s, 3H), 2.14-2.09 (m, 1H), 1.91-1.89 (m, 1H), 1.82-1.73 (m, 2H), 1.70-1.67 (m, 2H), 1.58 (d, J = 6.8 Hz, 3H).

TABLE 9-continued

| Ex. No. | Ester Ex. No. | Structure | Mass (m/z) |
|---|---|---|---|
| 135 | 64 | 4-((2S, 4S)-2-(3-(((R)-1-(4-Fluoronaphthalen-1-yl)ethyl) amino)propyl)chroman-4-yl)-3-methylbenzoic acid hydrochloride | 498.5 |

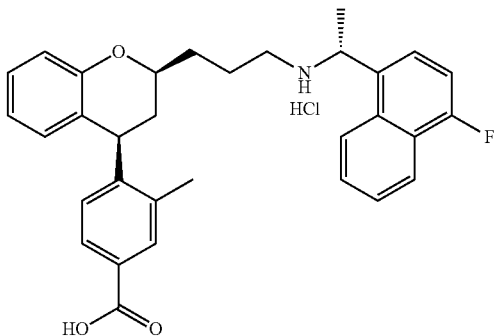 [SMILES: Cc1cc(C(=O)O)ccc1[C@@H]1C[C@H](CCCN[C@H](C)c2ccc(F)c3ccccc23)Oc2ccccc21 ; Cl]

$^1$HNMR (400 MHz, DMSO): δ 12.81 (bs, 1H), 9.77 (bs, 1H), 9.23 (bs, 1H), 8.37-8.35 (d, J = 8.0 Hz, 1H), 8.15-8.13 (d, J = 7.6 Hz, 1 H), 8.01-7.98 (m, 1H), 7.79-7.67 (m, 4H), 7.52-7.47 (dd, J = 8.4, 2 Hz, 1H), 7.08-7.04 (t, J = 7.6 Hz, 1H), 6.94 (s, 1H), 6.74-6.70 (t, J = 7.6 Hz, 1 H), 6.68-6.66 (d, J = 8.4 Hz, 1H), 6.48-6.47 (d, J = 7.2 Hz, 1H), 5.32-5.30 (m, 1H), 4.53-4.51 (m, 1H), 4.16 (m, 1H), 3.11-3.00 (m, 1H), 2.89-2.80 (m, 1H), 2.46 (s, 3H), 2.11-2.0 (m, 1H), 1.99-1.65 (m, 3H), 1.70-1.68 (m, 5H).

| Ex. No. | Ester Ex. No. | Structure | Mass (m/z) |
|---|---|---|---|
| 136 | 65 | 4-((2S, 4S)-2-(3-(((R)-1-(4-Fluoronaphthalen-1-yl)ethyl) amino)propyl)chroman-4-yl)benzoic acid hydrochloride | 484.0 |

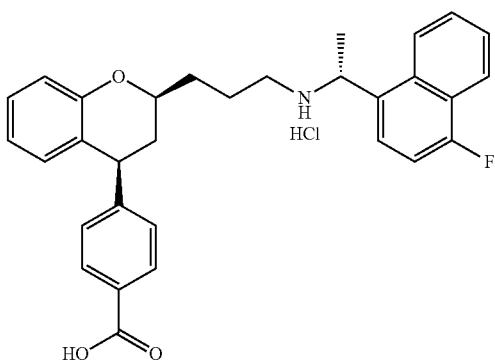 [SMILES: C[C@@H](NCCC[C@H]1C[C@@H](c2ccc(C(=O)O)cc2)c2ccccc2O1)c1ccc(F)c2ccccc12 ; Cl]

$^1$HNMR (400 MHz, DMSO-d$_6$): δ 12.90 (bs, 1H), 9.66 (bs, 1H), 9.20 (bs, 1H), 8.37-8.35 (d, J = 8.0 Hz, 1H), 8.15-8.14 (d, J = 7.2 Hz, 1H), 7.98-7.95 (m, 1H), 7.91-7.89 (d, J = 8 Hz, 2H), 7.76-7.68 (m, 2H), 7.52-7.48 (dd, J = 8.4, 2 Hz, 1H), 7.29-7.27 (d, J = 8 Hz, 2H), 7.09-7.07 (t, J = 7.2 Hz, 1H), 6.74-6.71 (t, J = 7.6 Hz, 1H), 6.68-6.66 (d, J = 8 Hz, 1H), 6.52-6.50 (d, J = 7.6 Hz, 1H), 5.32-5.31 (m, 1H), 4.33-4.29 (m, 1H), 4.15-4.12 (m, 1H), 3.15-3.00 (m, 1H), 2.90-2.80 (m, 1H), 2.14-2.08 (m, 1H), 1.90-1.75 (m, 3H), 1.69-1.67 (m, 5H).

TABLE 9-continued

| Ex. No. | Ester Ex. No. | Structure | Mass (m/z) |
|---|---|---|---|
| 137 | 66 | 5-((2S, 4S)-2-(3-(((R)-1-(4-Fluoronaphthalen-1-yl)ethyl)amino)propyl)chroman-4-yl)-2-methylbenzoic acid hydrochloride | 498.5 |

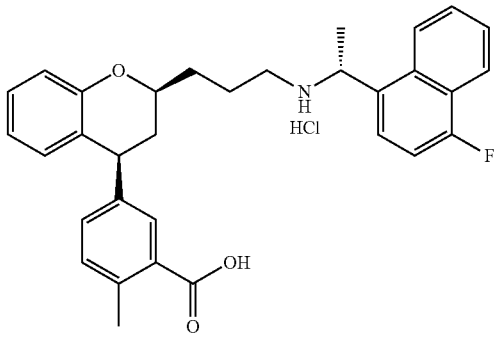 [SMILES: Cc1ccc([C@@H]2C[C@H](CCCN[C@H](C)c3ccc(F)c4ccccc34)Oc3ccccc32)cc1C(=O)O ; Cl]

$^1$H NMR (400 MHz, DMSO-d6): δ 12.84 (bs, 1H), 9.74 (bs, 1H), 9.24 (bs, 1 H), 8.37-8.35 (d, J = 8.4 Hz, 1H), 8.15-8.13 (d, J = 7.6 Hz, 1H), 8.01-7.97 (m, 1H), 7.76-7.69 (m, 2H), 7.61 (m, 1H), 7.52-7.47 (dd, J = 8.4, 2 Hz, 1H), 7.27-7.22 (m, 2H), 7.07-7.04 (t, J = 7.2 Hz, 1 H), 6.74-6.70 (t, J = 7.6 Hz, 1H), 6.67-6.65 (d, J = 8.0 Hz, 1H), 6.54-6.52 (d, J = 7.6 Hz, 1H), 5.32-5.31 (m, 1 H), 4.26-4.21 (m, 1H), 4.13-4.11 (m, 1H), 3.10-3.04 (m, 1 H), 2.89-2.87 (m, 1H), 2.46 (s, 3 H), 2.08-2.03 (m, 1 H), 1.90-1.70 (m, 3H), 1.68-1.63 (m, 5H).

Example-138

Methyl 2-(3-((2R,4S)-2-((((R)-1-(naphthalen-1-yl)ethyl)amino)methyl)chroman-4-yl)benzamido)acetate

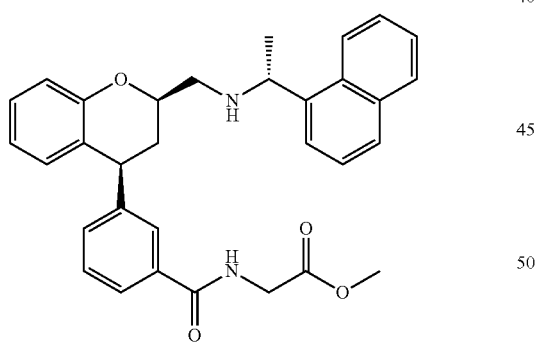

To a stirred solution of Example-73 (0.14 g, 0.295 mmol) in THF (10 mL), (3-(ethyliminomethyleneamino)-N,N-dimethylpropan-1-amine) (EDC) (0.062 g, 0.325 mmol), HOBT (0.05 g, 0.325 mmol) and N,N-Diisopropylethylamine (DIPEA) (0.153 g, 1.18 mmol) were added. The reaction mixture was stirred at 0° C. for 15 minutes. Then, to this solution glycine methyl ester hydrochloride (0.037 g, 0.295 mmol) was added. The reaction mixture was stirred at RT overnight. The progress of reaction was monitored by TLC. The reaction mixture was diluted with water (20 mL) and the compound extracted with ethyl acetate (20 mL×2). Combined organic layer was washed with water (20 mL) followed by brine solution (20 mL). The organic layer was dried over Na$_2$SO$_4$ and concentrated under reduced pressure to give crude product (0.14 g, 93% yield); m/z-509.1.

Example-139

Methyl 2-(2-methyl-5-((2R,4S)-2-((((R)-1-(naphthalen-1-yl)ethyl)amino)methyl)chroman-4-yl)benzamido)acetate

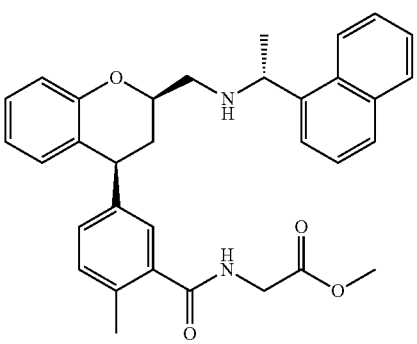 [SMILES: COC(=O)CNC(=O)c1cc([C@@H]2C[C@H](CN[C@H](C)c3cccc4ccccc34)Oc3ccccc32)ccc1C]

The title compound was prepared by following the similar procedure as described in Example-138 by using corresponding acid compound of Example-84b; m/z-523.1.

Example-140

2-(3-((2R,4S)-2-((((R)-1-(Naphthalen-1-yl)ethyl)amino)methyl)chroman-4-yl)benzamido)acetic Acid Hydrochloride

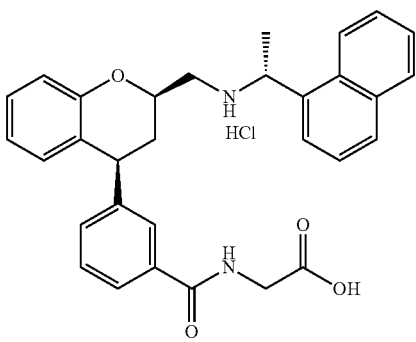 [SMILES: C[C@@H](NC[C@H]1C[C@@H](c2cccc(C(=O)NCC(=O)O)c2)c2ccccc2O1)c1cccc2ccccc12 ; Cl]

To a solution of Example-138 (0.15 g, 0.295 mmol) in methanol (5 mL), THF (5 mL) and water (2 mL) lithium hydroxide monohydrate (0.035 g, 1.47 mmol) was added. The reaction mixture was stirred at RT for overnight. The progress of reaction was monitored by TLC. Solvent was distilled off under vacuum then cooled to 0° C. and acidified with dilute HCl solution [pH=3 to 4]. Extracted the product with ethyl acetate (10 mL×2), washed with water (5 mL×2) followed by brine solution (5 mL), dried over sodium sulfate and concentrated under vacuum to get solid. Ethereal HCl (2 mL) was added and stirred for 10 min. The solvent was removed and the resultant solid washed with diethyl ether (2 mL) followed by n-pentane (2 mL), dried to get product as a hydrochloride salt. (0.1 g, 64% yield);

m/z 495.1; $^1$HNMR (400 MHz, DMSO-$d_6$): δ 12.5 (bs, 1H), 9.8 (bs, 1H), 9.5 (bs, 1H), 8.54-8.51 (m, 1H), 8.30-8.28 (m, 1H), 8.04-7.99 (m, 3H), 7.67-7.59 (m, 3H), 7.21-7.11 (m, 4H), 6.85-6.77 (m, 2H), 6.63-6.61 (m, 1H), 5.49 (d, J=6.4 Hz, 1H), 4.67 (d, J=6.3 Hz, 1H), 4.27-4.25 (m, 1H), 3.86 (d, J=6.2 Hz, 2H), 3.31 (m, 2H), 2.21-2.19 (m, 1H), 2.0-1.99 (m, 1H), 1.76 (d, J=6.4 Hz, 3H).

Example-141

2-(2-Methyl-5-((2R,4S)-2-((((R)-1-(naphthalen-1-yl)ethyl)amino)methyl)chroman-4-yl)benzamido)acetic Acid Hydrochloride

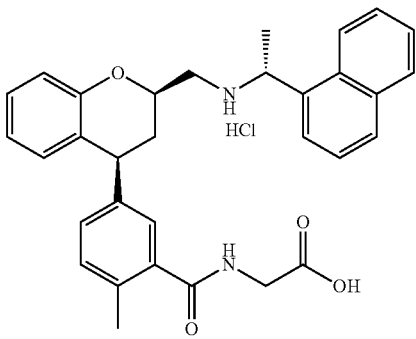 [SMILES: Cc1ccc([C@@H]2C[C@H](CN[C@H](C)c3cccc4ccccc34)Oc3ccccc32)cc1C(=O)NCC(=O)O ; Cl]

The title compound was prepared by following the similar procedure as described in Example-140 by using corresponding ester Example-139 and lithium hydroxide hydrate;

m/z 509.1; $^1$H NMR (400 MHz, DMSO-$d_6$): δ 9.8 (bs, 1H), 9.5 (bs, 1H), 8.54-8.51 (m, 1H), 8.30-8.28 (m, 1H), 8.04-7.99 (m, 3H), 7.67-7.59 (m, 3H), 7.21-7.11 (m, 3H), 6.85-6.77 (m, 2H), 6.63-6.61 (m, 1H), 5.49 (d, J=6.4 Hz, 1H), 4.67 (d, J=6.3 Hz, 1H), 4.27-4.25 (m, 1H), 3.86 (d, J=6.24 Hz, 2H), 3.37 (m, 2H), 2.45 (s, 3H), 2.21-2.19 (m, 1H), 2.0-1.99 (m, 1H), 1.76 (d, J=6.4 Hz, 3H).

Example-142

N,2-Dimethyl-5-((2R,4S)-2-((((R)-1-(naphthalen-1-yl)ethyl)amino)methyl)chroman-4-yl)benzamide Hydrochloride

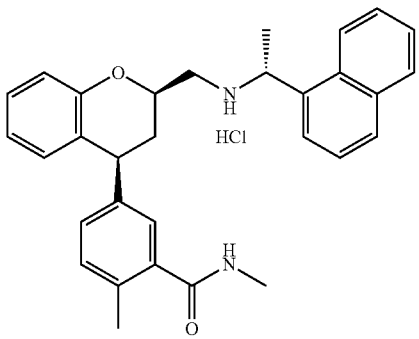 [SMILES: CNC(=O)c1cc([C@@H]2C[C@H](CN[C@H](C)c3cccc4ccccc34)Oc3ccccc32)ccc1C ; Cl]

To a solution of Example-84b (100 mg, 0.205 mmol) in DMF (3 mL), 1,1'-carbonyldiimidazole (CDI) (24.92 mg, 0.154 mmol) was added and stirred at RT for 15 minutes. To this reaction mixture methylamine hydrochloride (50 mg, 0.74 mmol) and triethylamine (0.02 mL, 0.143 mmol) were added and heated to 60° C. and further maintained for 24 h. The reaction progress was monitored by TLC. Reaction was quenched with ice water (3 mL) the resultant solid was filtered and washed with water (5 mL×2). Dry this solid at 45° C. Further, HCl salt of these amino compound was prepared by following the similar hydrochloride salt procedure as described in Example-72a, 72b (18.5 mg, 38.9%)

m/z-464.5; $^1$HNMR (400 MHz, DMSO-$d_6$): 9.78 (bs, 1H), 9.43 (bs, 1H), 8.31 (d, J=8.4 Hz, 1H), 8.13 (q, J=4.8 Hz, 1H), 8.05 (t, J=7.6 Hz, 2H), 7.99 (d, J=7.6 Hz, 1H), 7.71-7.60 (m, 2H), 7.20 (t, J=8 Hz, 1H), 7.16-7.11 (m, 3H), 6.88 (d, J=8 Hz, 1H), 6.81 (t, J=6.8 Hz & 8.4 Hz, 1H), 6.62 (d, J=7.6 Hz, 1H), 5.5-5.48 (m, 1H), 4.46-4.61 (m, 1H), 4.26-4.22 (m, 1H), 3.32 (m, 1H), 3.25 (m, 1H), 2.70 (s, 3H), 2.33 (s, 3H), 2.21-2.16 (m, 1H), 1.99-1.95 (m, 1H), 1.76 (d, J=6.8 Hz, 3H).

The below Examples 143 to 147 given Table-10 were prepared by following the above similar procedures as described in Example-142 by taking appropriate acid compound of Example-84b and appropriate amine;

Further, HCl salt of these amino compounds were prepared by following the similar hydrochloride salt procedure as described in Example-72a, 72b.

TABLE 10

| Ex. No. | Structure | Mass (m/z) |
|---|---|---|
| 143 | N,N,2-Trimethyl-5-((2R,4S)-2-((((R)-1-(naphthalen-1-yl)ethyl)amino)methyl)chroman-4-yl)benzamide hydrochloride | 478.6 |

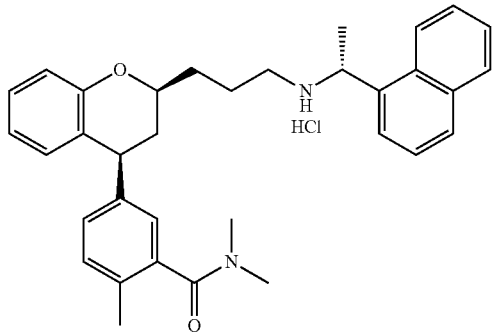 [SMILES: Cc1ccc([C@@H]2C[C@H](CCCN[C@H](C)c3cccc4ccccc34)Oc3ccccc32)cc1C(=O)N(C)C ; Cl]

¹HNMR (400 MHz, DMSO-d₆): 9.71 (bs, 1H), 9.34 (bs, 1H), 8.30 (d, J = 8.4 Hz, 1H), 8.05 (t, J = 7.6 Hz & 8 Hz, 2H), 7.96 (d, J = 7.6 Hz, 1H), 7.68-7.60 (m, 3H), 7.28 (d, J = 8 Hz, 1H), 7.16-7.11 (m, 2H), 6.94 (s, 1H), 6.88 (d, J = 8 Hz, 1H), 6.81 (d, J = 6.8 Hz, 1H), 6.59 (d, J = 7.6 Hz, 1H), 5.49-5.47 (m, 1H), 4.65-4.60 (m, 1H), 4.27-4.23 (m, 1H), 3.37 (m, 2H), 2.96 (s, 3H), 2.71 (s, 3H), 2.16 (s, 3H), 2.23-2.16 (m, 1H), 2.02-2.11 (m, 1H), 1.75 (d, J = 6.8 Hz, 3H).

| 144 | 2-Methyl-5-((2R,4S)-2-((((R)-1-(naphthalen-1-yl)ethyl)amino)methyl)chroman-4-yl)benzamide hydrochloride | 450.7 |

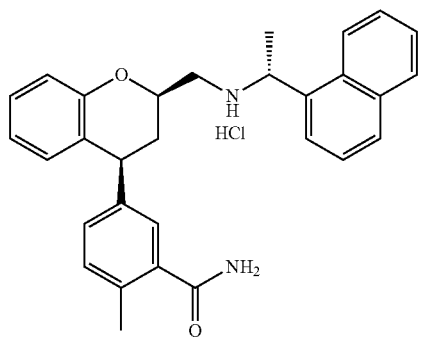 [SMILES: Cc1ccc([C@@H]2C[C@H](CN[C@H](C)c3cccc4ccccc34)Oc3ccccc32)cc1C(N)=O ; Cl]

¹HNMR (400 MHz, DMSO-d₆): 9.80 (bs, 1H), 9.44 (bs, 1H), 8.28 (d, J = 8.4 Hz, H), 8.05 (m, 3H), 7.68 (m, 3H), 7.61 (bs, 1H), 7.36 (bs, 1H), 7.19-7.09 (m, 4H), 6.88 (d, J = 6.8 Hz & 0.8 Hz, 1H), 6.81 (t, J = 6.8 Hz & 0.8 Hz, 1H), 6.63 (d, J = 7.6 Hz, 1H), 5.49-5.48 (m, 1H), 4.64 (m, 1H), 4.26-4.22 (m, 1H), 3.32-3.31 (m, 1H), 3.25-3.24 (m, 1H), 2.34 (s, 3H), 2.21-2.17 (m, 1H), 1.99-1.91 (m, 1H), 1.76 (d, J = 6.8 Hz, 3H).

TABLE 10-continued

| Ex. No. | Structure | Mass (m/z) |
|---|---|---|
| 145 | N-Ethyl-N, 2-dimethyl-5-((2R,4S)-2-((((R)-1-(naphthalen-1-yl)ethyl)amino)methyl)chroman-4-yl)benzamide hydrochloride 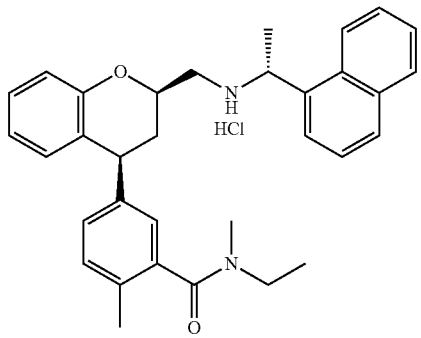 [SMILES: CCN(C)C(=O)c1cc([C@@H]2C[C@H](CN[C@H](C)c3cccc4ccccc34)Oc3ccccc32)ccc1C ; Cl] ¹HNMR (400 MHz, DMSO-d₆): 9.71 (bs, 1H), 9.35 (bs, 1H), 8.30 (d, J = 8.4 Hz, 1H), 8.05 (t, J = 7.6 Hz & 8 Hz, 2H), 7.96 (d, J = 7.6 Hz, 1H), 7.67-7.60 (m, 3H), 7.23-7.22 (m, 1H), 7.16-7.09 (m, 2H), 6.88 (d, J = 8 Hz, 2H), 6.81 (t, J = 7.6 Hz & 7.2 Hz, 1H) 6.59 (t, J = 6.4 Hz & 7.2 Hz, 1H), 5.49-5.47 (m, 1H), 4.62 (m, 1H), 4.26-4.24 (m, 1H), 3.39-3.37 (m, 2H), 2.92 (s, 2H), 2.55 (s, 3H), 2.33 (s, 3H), 2.16 (m, 1H), 1.98 (m, 1H), 1.75 (d, J = 6.8 Hz, 3H), 1.12 (t, J = 6 Hz, 3H). | 493.49 |
| 146 | N, N-Diethyl-2-methyl-5-((2R,4S)-2-((((R)-1-(naphthalen-1-yl)ethyl)amino)methyl)chroman-4-yl)benzamide hydrochloride 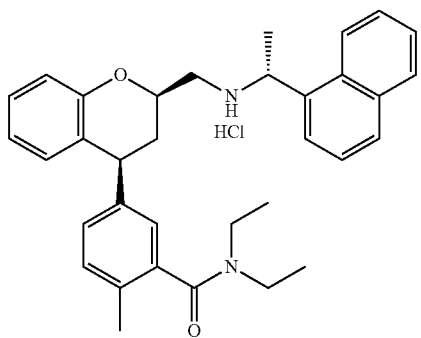 [SMILES: CCN(CC)C(=O)c1cc([C@@H]2C[C@H](CN[C@H](C)c3cccc4ccccc34)Oc3ccccc32)ccc1C ; Cl] ¹HNMR (400 MHz, DMSO-d₆): 9.69 (bs, 1H), 9.35 (bs, 1H), 8.30 (d, J = 8.4 Hz, 1H), 8.06 (t, J = 8 Hz, 2H), 7.94 (d, J = 7.2 Hz, 1H), 7.67-7.60 (m, 3H), 7.23 (d, J = 8 Hz, 1H), 7.21-7.12 (m, 2H), 6.88 (d, J = 7.2 Hz, 2H), 6.81 (t, J = 7.6 Hz & 7.2 Hz, 1H), 6.58 (d, J = 7.6 Hz, 1H), 5.48-5.47 (m, 1H), 4.62 (m, 1H), 4.28-4.24 (m, 1H), 3.39 (m, 4H), 3.27 (m, 1H), 3.05 (m, 1H), 2.19 (m, 1H), 2.16 (s, 3H), 1.96-1.92 (m, 1H), 1.75 (d, J = 6.8 Hz, 3H), 1.14 (m, 6H). | 493.49 |

TABLE 10-continued

| Ex. No. | Structure | Mass (m/z) |
|---|---|---|
| 147 | (2-Methyl-5-((2R,4S)-2-((((R)-1-(naphthalen-1-yl)ethyl)amino)methyl)chroman-4-yl)phenyl)(pyrrolidin-1-yl)methanone hydrochloride 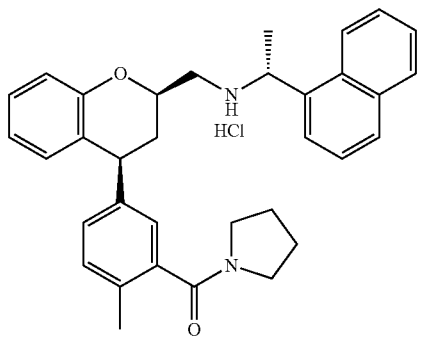 [SMILES: Cc1ccc([C@@H]2C[C@H](CN[C@H](C)c3cccc4ccccc34)Oc3ccccc32)cc1C(=O)N1CCCC1 ; Cl] <br> ¹HNMR (400 MHz, DMSO-d₆): 9.99 (bs, 1H), 9.58 (bs, 1H), 8.30 (d, J = 8.4 Hz, 1H), 8.04-8.00 (m, 3H), 7.67-7.59 (m, 3H), 7.22 (d, J = 8 Hz, 1H), 7.15-7.09 (m, 2H), 6.98 (s, 1H), 6.87 (d, J = 7.6 Hz, 1H), 6.81 (d, J = 1.2 Hz, 1H), 6.58 (d, J = 7.6 Hz, 1H), 5.50-5.47 (m, 1H ), 4.67 (m, 1H), 4.25-4.21 (m, 1H), 3.43-3.37 (m, 2H), 3.35-3.28 (m, 2H), 3.06-2.94 (m, 2H), 2.23-2.22 (m, 1H), 2.19 (s, 3H), 1.94-1.9 (m, 1H), 1.78 (d, J = 6.8 Hz, 3H), 1.73 (m, 4H). | 504.6 |

The below Examples 148 to 165 given Table-11 can be prepared by following the similar procedures as described herein above by taking appropriately substituted intermediates.

TABLE 11

| Ex. No. | Structure |
|---|---|
| 148 | 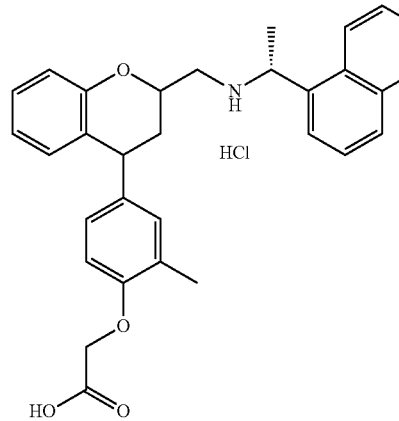 |
| 149 | 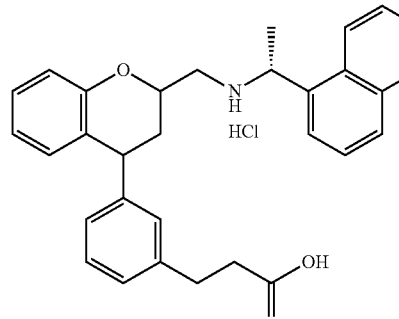 |
| 150 |  |
| 151 |  |

TABLE 11-continued

| Ex. No. | Structure |
|---|---|
| 152 | |
| 153 | |
| 154 | |
| 155 | 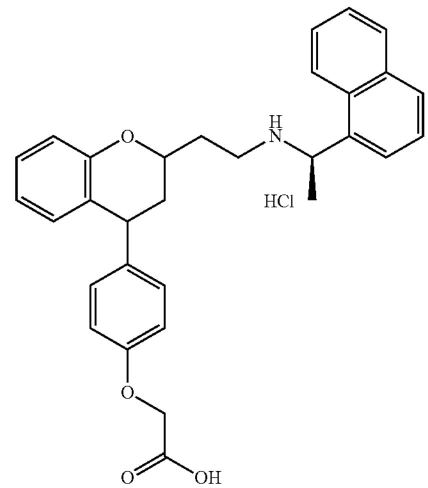 [SMILES: C[C@@H](NCCC1CC(c2ccc(OCC(=O)O)cc2)c2ccccc2O1)c1cccc2ccccc12 ; Cl] |
| 156 | 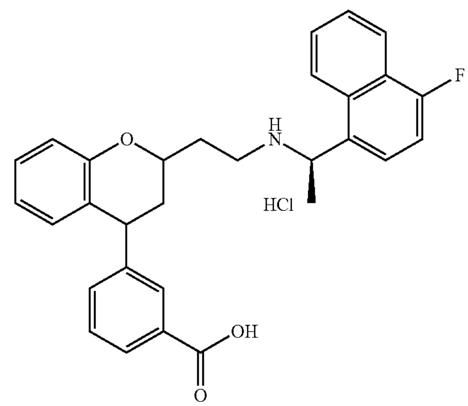 [SMILES: C[C@@H](NCCC1CC(c2cccc(C(=O)O)c2)c2ccccc2O1)c1ccc(F)c2ccccc12 ; Cl] |
| 157 | 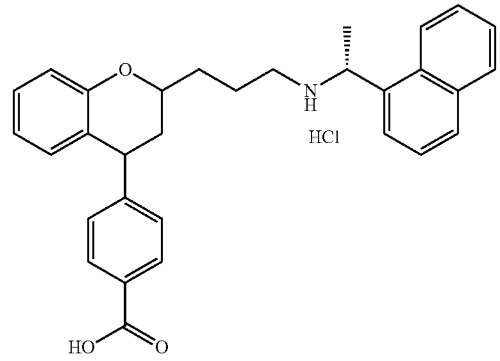 [SMILES: C[C@@H](NCCCC1CC(c2ccc(C(=O)O)cc2)c2ccccc2O1)c1cccc2ccccc12 ; Cl] |
| 158 | 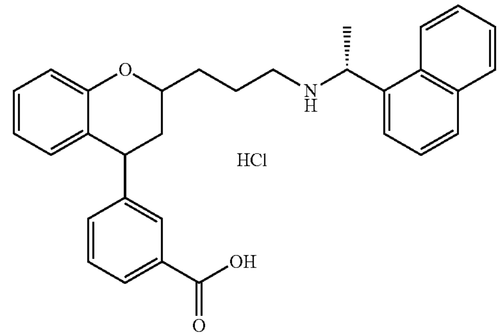 [SMILES: C[C@@H](NCCCC1CC(c2cccc(C(=O)O)c2)c2ccccc2O1)c1cccc2ccccc12 ; Cl] |

TABLE 11-continued

| Ex. No. | Structure |
|---|---|
| 159 | (chroman with 4-aryl bearing 3-methyl-4-carboxylic acid; 2-propyl chain linked via NH to (R)-1-(1-naphthyl)ethyl; HCl) |
| 160 | (chroman with 4-(3-carboxyphenyl); 2-propyl chain linked via NH to (R)-1-(4-fluoronaphth-1-yl)ethyl; HCl) |
| 161 | (chroman with 4-aryl bearing 2-methyl-3-carboxylic acid; 2-CH₂NH linked to (R)-1-(3-methoxy-4-fluorophenyl)ethyl; HCl) |
| 162 | (chroman with 4-aryl bearing 2,6-dimethyl-3-carboxylic acid; 2-CH₂NH linked to (R)-1-(3-methoxy-4-fluorophenyl)ethyl; HCl) |
| 163 | (chroman with 4-aryl bearing 2,6-difluoro-3-carboxylic acid; 2-CH₂NH linked to (R)-1-(3-methoxy-4-fluorophenyl)ethyl; HCl) |
| 164 | (chroman with 4-(2-fluoro-5-carboxyphenyl); 2-CH₂NH linked to (R)-1-(3-methoxy-4-fluorophenyl)ethyl; HCl) |
| 165 | (chroman with 4-aryl bearing 2-fluoro-3-(carboxymethoxy); 2-CH₂NH linked to (R)-1-(3-methoxy-4-fluorophenyl)ethyl; HCl) |

In-Vitro Pharmacological Activity

Certain illustrative compounds within the scope of the invention are screened for CaSR activity according to the procedure given below. The screening of the compounds may also be carried by other methods and procedures known to skilled in the art.

In-Vitro Assay Method of Calcimimetics Through Modulation of Calcium Sensing Receptor (CaSR):

The ability of the compounds to modulate Calcium sensing receptor is determined by measuring an increase in intracellular calcium $[Ca^{2+}]_i$. Stably transfected HEK293 cells expressing hCaSR_pTriEx-3 hygro vector are developed. Cells are grown overnight on a 96-well plate to 80% confluency in Ham's F12 containing 20% FBS at 37° C., 5% $CO_2$. Subsequently, cells are washed extensively with 20 mM HEPES buffer containing 126 mM $NaCl_2$, 1 mM $MgCl_2$ and 4 mM KCl to remove serum components that might interfere with the assay. Cells are loaded with calcium sensing Fluo4NW dye in HEPES base buffer containing 0.1% BSA and 1 mg/ml glucose for 30 minutes to measure changes in intracellular calcium. The activities of the compounds are measured in FLIPR using 0.3 mM $CaCl_2$ in 20 mM HEPES base buffer. The effectiveness of the compound to modulate receptor activity is determined by calculating the $EC_{50}$ responses for that compound in an 8-point assay and plotted using GraphPad Prism 5.

The compounds prepared were tested using the above assay procedure and the results obtained are given below. The $EC_{50}$ (nM) values of few representative compounds are set forth in Table-12.

The in-vitro activity data has been given in Table-12 for representative compounds.

TABLE 12

| Example number | $EC_{50}$ Range |
|---|---|
| 67, 72b, 73, 75, 81b, 83, 84b, 89b, 91, 93a, 93b, 99b, 102b, 104, 105b, 119b, 124, 136, 140 | Less than 20 nM |
| 88, 89a, 97, 101, 107b, 111, 146 | Between 20.01-50.00 nM |
| 81a, 98a, 98b, 108a, 108b, 114, 116, 145 | Between 50.01-200 nM |

Thus, the above in-vitro assay method shows that the compounds of the invention were found to exhibit agonistic activity for CaSR, thereby showing utility for treating diseases, disorders associated with the modulation of CaSR.

In-Vivo Activity in CKD Wistar Rats:

Animals were fed with 0.75% adenine diet for a period of 28 days for development of chronic kidney disease (CKD). After measurement of plasma PTH on day 28, animals were randomized based on plasma PTH (intact PTH) levels before using them for the study. Overnight fasted animals were bled retro-orbitally to collect basal blood sample (0.5 ml). Rats were dosed orally with vehicle and with test compounds where they formulated in PEG 300:PG:Captisol (20:15:65). Six to eight animals were used in each group then compounds of the invention were administered at 1 mg/kg dose. Post 2 h oral dosing animals were fed with feed and water ad libitum. Post treatment blood samples were collected by retro-orbital bleeding under light ether anesthesia at different time points for plasma PTH estimation. Plasma PTH was measured using sandwich ELISA kits (Immunotopics, USA). Percentage suppression of plasma PTH was calculated with respect to individual basal untreated values by using the following Formula $$\text{Percent suppression} = \frac{\text{Pre-treated individual value} - \text{Post-treated individual}}{\text{Pre-treated individual value}} \times 100$$

Compounds of the invention for example, Example No. 67, 72b, 84b, 89b, 119b, 124 were found to suppress plasma PTH levels greater than 80%.

Thus, the above in-vivo method shows that the compounds of the invention were found to exhibit suppress plasma PTH levels, thereby showing utility for treating diseases, disorders associated with the modulation of CaSR.

All patents, patent applications and other publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

The invention claimed is:
1. A compound of Formula (I):

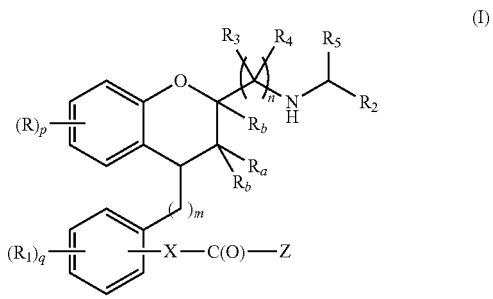

wherein,
$R_a$ is selected from hydrogen, halogen, substituted or unsubstituted alkyl, cyano, substituted or unsubstituted cycloalkyl and substituted or unsubstituted haloalkyl;

$R_b$, which may be same or different at each occurrence, is independently selected from hydrogen, halogen, substituted or unsubstituted alkyl, substituted or unsubstituted cycloalkyl and substituted or unsubstituted haloalkyl;

R, which may be same or different at each occurrence, is independently selected from halogen, hydroxy, substituted or unsubstituted alkyl, substituted or unsubstituted haloalkyl, substituted or unsubstituted alkenyl, substituted or unsubstituted alkynyl, substituted or unsubstituted cycloalkyl, $OR_6$, nitro, cyano, —C(O)$OR_6$, —(CH$_2$)$_r$—C(O)$OR_6$, —O—C(O)$OR_6$, —O(CH$_2$)$_r$—C(O)$OR_6$, —NR$_7$R$_8$, —(CH$_2$)$_r$NR$_7$R$_8$—, —C(O)R$_9$, —C(O)NR$_7$R$_8$, —(CH$_2$)$_r$—C(O)NR$_7$R$_8$, —NR$_7$C(O)R$_9$, —S(O)$_{0-2}$R$_6$, —S(O)$_2$NR$_7$R$_8$, and —NR$_7$S(O)$_2$R$_9$;

X is selected from a bond, —(CR$_c$R$_d$)$_r$—, —O—, —NR$_7$—, —NR$_7$(CR$_c$R$_d$)$_r$—, —O(CR$_c$R$_d$)$_r$—, —C(O) NR$_7$—, —C(O)NR$_7$(CR$_c$R$_d$)$_r$—, —(CR$_c$R$_d$)$_r$NR$_7$ (CR$_c$R$_d$)$_r$—, —(CR$_c$R$_d$)$_r$cycloalkylene-, cycloalkylene, -cycloalkylene(CR$_c$R$_d$)$_r$— and —O-cycloalkylene where cycloalkylene may be substituted or unsubstituted;

$R_c$ and $R_d$, which may be same or different at each occurrence, are independently selected from hydrogen, halogen, hydroxy, cyano, nitro, substituted or unsubstituted alkyl, substituted or unsubstituted haloalkyl and substituted or unsubstituted cycloalkyl; or $R_c$ and $R_d$, together with the carbon atom to which they are attached, may form a substituted or unsubstituted 3 to 7 membered saturated carbocyclic ring;

Z is —OR$_6$ or —NR$_{10}$R$_{11}$;

$R_1$, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, substituted or unsubstituted cycloalkyl, —OR$_6$, —C(O)R$_9$, —NR$_7$R$_8$, —(CH$_2$)$_r$NR$_7$R$_8$—, —(CH$_2$)$_r$—C(O)OR$_6$, —O—C(O) OR$_6$, —O(CH$_2$)$_r$—C(O)OR$_6$, —C(O)NR$_7$R$_8$, —(CH$_2$)$_r$—C(O)NR$_7$R$_8$, —NR$_7$C(O)R$_9$, —S(O)$_{0-2}$R$_7$, —S(O)$_2$NR$_7$R$_8$ and —NR$_7$S(O)$_2$R$_9$;

$R_2$ is selected from substituted or unsubstituted aryl, substituted or unsubstituted heteroaryl and substituted or unsubstituted heterocyclyl;

$R_3$ and $R_4$ may be same or different and are independently selected from hydrogen, halogen, substituted or unsubstituted alkyl, substituted or unsubstituted haloalkyl, substituted or unsubstituted alkenyl, substituted or unsubstituted alkynyl, substituted or unsubstituted alkoxy, substituted or unsubstituted haloalkoxy and substituted or unsubstituted cycloalkyl;

$R_5$ is substituted or unsubstituted alkyl;

$R_6$, which may be same or different at each occurrence, is independently selected from hydrogen, substituted or unsubstituted alkyl, substituted or unsubstituted haloalkyl, substituted or unsubstituted alkenyl, substituted or unsubstituted alkynyl, and substituted or unsubstituted aryl;

$R_7$ and $R_8$, which may be same or different at each occurrence, are independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; or $R_7$ and $R_8$, together with the nitrogen atom to which they are attached, may form a substituted or unsubstituted, saturated or unsaturated 3 to 12 membered cyclic ring, wherein the unsaturated cyclic ring may have one or two double bonds;

at each occurrence, $R_9$ is substituted or unsubstituted alkyl or substituted or unsubstituted aryl;

$R_{10}$ and $R_{11}$ may be same or different and are independently selected from hydrogen, substituted or unsubstituted alkyl, substituted or unsubstituted alkenyl, substituted or unsubstituted alkynyl, —(CR$_c$R$_d$)$_r$—C(O)OR$_6$, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; or $R_{10}$ and $R_{11}$, together with the nitrogen atom to which they are attached, may form a substituted or unsubstituted, saturated or unsaturated 3 to 12 membered cyclic ring, wherein the unsaturated cyclic ring may have one or two double bonds;

'n' is an integer ranging from 1 to 3, both inclusive;
'm' is an integer ranging from 0 to 3, both inclusive;
'p' is an integer ranging from 0 to 4, both inclusive;
'q' is an integer ranging from 0 to 3, both inclusive; and
'r' is an integer ranging from 1 to 3, both inclusive;
or its pharmaceutically acceptable salt thereof.

2. The compound of claim 1, having the Formula (II):

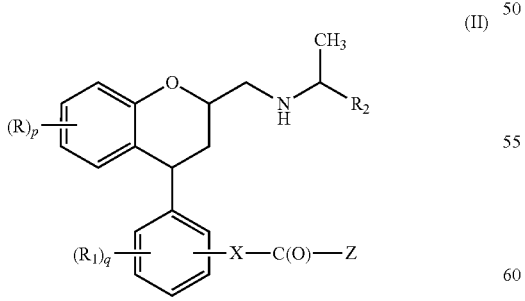

(II)

or its pharmaceutically acceptable salt thereof;
wherein,
$R_2$ is substituted or unsubstituted phenyl or substituted or unsubstituted naphthyl;
R, $R_1$, X, Z, 'p' and 'q' are as defined in claim 1.

3. The compound of claim 1, having the Formula (III):

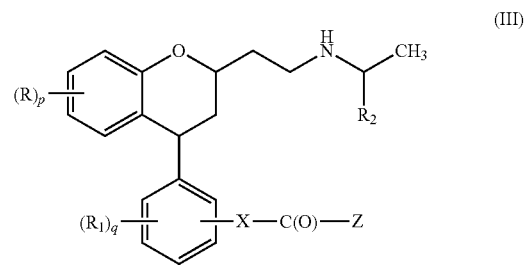

(III)

or its pharmaceutically acceptable salt thereof;
wherein,
$R_2$ is substituted or unsubstituted phenyl or substituted or unsubstituted naphthyl;
R, $R_1$, X, Z, 'p' and 'q' are as defined in claim 1.

4. The compound of claim 1, having the Formula (IV):

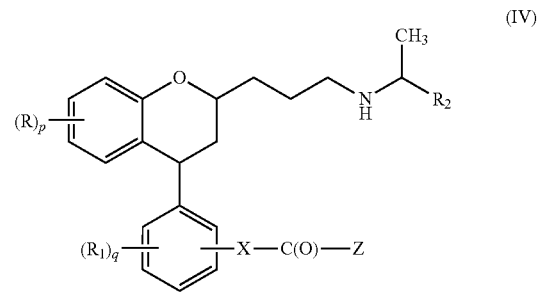

(IV)

or its pharmaceutically acceptable salt thereof;
wherein,
$R_2$ is substituted or unsubstituted phenyl or substituted or unsubstituted naphthyl;
R, $R_1$, X, Z, 'p' and 'q' are as defined in claim 1.

5. The compound of claim 1, having the Formula (V):

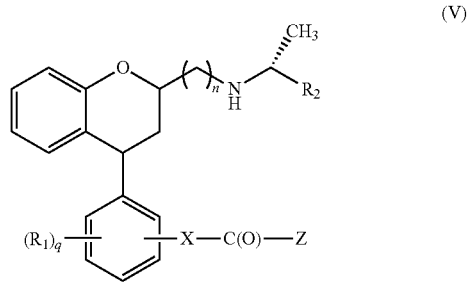

(V)

or its pharmaceutically acceptable salt thereof;
wherein,
$R_2$ is substituted or unsubstituted phenyl or substituted or unsubstituted naphthyl;
$R_1$, X, Z, 'n', and 'q' are as defined in claim 1.

6. The compound of claim 1, wherein 'm' is 0 or 1.
7. The compound of claim 1, wherein 'p' is 0 or 1.
8. The compound of claim 1, wherein 'q' is 0, 1 or 2.
9. The compound of claim 1, wherein $R_1$ is selected from halogen, substituted or unsubstituted alkyl, substituted or unsubstituted haloalkyl, substituted or unsubstituted cycloalkyl, cyano, —OR$_6$, —C(O)alkyl, wherein $R_6$ is hydrogen, substituted or unsubstituted alkyl, substituted or unsubstituted haloalkyl, or substituted or unsubstituted cycloalkyl; and 'q' is 0, 1, or 2.

10. The compound of claim 1, wherein $R_2$ is substituted or unsubstituted aryl wherein the aryl is substituted or unsubstituted phenyl or substituted or unsubstituted naphthyl.

11. The compound of claim 2, wherein the substituent(s) on phenyl or naphthyl may be one or more and are independently selected from halogen, hydroxyl, substituted or unsubstituted alkyl, substituted or unsubstituted haloalkyl, and substituted or unsubstituted alkoxy.

12. The compound of claim 1, wherein X is selected from a bond, —$(CR_cR_d)_r$—, —O—, —$NR_7$—, —$NR_7(CR_cR_d)_r$—, —$O(CR_cR_d)_r$—, —$C(O)NR_7$—, —$C(O)NR_7(CR_cR_d)_r$—, —$(CR_cR_d)_rNR_7(CR_cR_d)_r$—, —$(CR_cR_d)_r$-cycloalkylene-, cycloalkylene, -cycloalkylene$(CR_cR_d)_r$— and —O-cycloalkylene where cycloalkylene may be substituted or unsubstituted; $R_7$ is hydrogen or substituted or unsubstituted alkyl; $R_c$ and $R_d$ are hydrogen or alkyl and 'r' is 1, 2 or 3.

13. The compound of claim 1, wherein Z is —$OR_6$ wherein $R_6$ is selected from hydrogen, substituted or unsubstituted alkyl, substituted or unsubstituted haloalkyl, substituted or unsubstituted aryl or substituted or unsubstituted arylalkyl.

14. The compound of claim 1, wherein Z is $NR_{10}R_{11}$ wherein $R_{10}$ and $R_{11}$ may be same or different and are independently selected from hydrogen, substituted or unsubstituted alkyl, —$(CR_cR_d)_r$—C(O)OH, —$(CR_cR_d)_r$—C(O)O-alkyl, substituted or unsubstituted cycloalkyl, substituted or unsubstituted aryl or substituted or unsubstituted arylalkyl; or $R_{10}$ and $R_{11}$, together with the nitrogen atom to which they are attached, may form a saturated or unsaturated 3 to 12 membered cyclic ring, where the unsaturated cyclic ring may have one or two double bonds; wherein $R_c$ and $R_d$ are hydrogen or substituted or unsubstituted alkyl and 'r' is 1, 2 or 3.

15. The compound of claim 1, wherein $R_a$ is hydrogen; $R_b$ is hydrogen; $R_1$ is selected from halogen, substituted or unsubstituted alkyl, substituted or unsubstituted haloalkyl, substituted or unsubstituted cycloalkyl, cyano, —$OR_6$, —C(O)alkyl wherein $R_6$ is hydrogen, substituted or unsubstituted alkyl, substituted or unsubstituted haloalkyl, or substituted or unsubstituted cycloalkyl; 'q' is 0, 1, or 2; $R_2$ is substituted or unsubstituted aryl; $R_3$ is hydrogen; $R_4$ is hydrogen; $R_5$ is substituted or unsubstituted alkyl; X is selected from a bond, —$(CR_cR_d)_r$—, —O—, —$NR_7$—, —$NR_7(CR_cR_d)_r$—, —$O(CR_cR_d)_r$—, —$C(O)NR_7$—, —$C(O)NR_7(CR_cR_d)_r$— wherein $R_7$ is hydrogen or substituted or unsubstituted alkyl, $R_c$ and $R_d$ are hydrogen or substituted or unsubstituted alkyl, 'r' is 1, 2, or 3; Z is —$OR_6$ or $NR_{10}R_{11}$ wherein $R_6$ is selected from hydrogen, substituted or unsubstituted alkyl, substituted or unsubstituted haloalkyl, substituted or unsubstituted aryl or substituted or unsubstituted arylalkyl; $R_{10}$ and $R_{11}$ may be same or different and are independently selected from hydrogen, substituted or unsubstituted alkyl, —$(CR_cR_d)_r$—C(O)OH, —$(CR_cR_d)_r$—C(O)O-alkyl, substituted or unsubstituted cycloalkyl or $R_{10}$ and $R_{11}$ together may form a substituted or unsubstituted, saturated or unsaturated 3 to 12 membered cyclic ring, where the unsaturated cyclic ring may have one or two double bonds, 'n' is 1, 2 or 3; 'm' is 0 or 1; and 'p' is 0;

or its pharmaceutically acceptable salt thereof.

16. The compound of claim 5, wherein $R_1$ is selected from halogen, substituted or unsubstituted alkyl, substituted or unsubstituted haloalkyl, substituted or unsubstituted cycloalkyl, cyano, —$OR_6$, —C(O)alkyl wherein $R_6$ is hydrogen, substituted or unsubstituted alkyl, substituted or unsubstituted haloalkyl, or substituted or unsubstituted cycloalkyl; 'q' is 0, 1, or 2; $R_2$ is substituted or unsubstituted aryl; X is selected from a bond, —$(CR_cR_d)_r$—, —O—, —$NR_7$—, —$NR_7(CR_cR_d)_r$—, —$O(CR_cR_d)_r$—, —$C(O)NR_7$—, —$C(O)NR_7(CR_cR_d)_r$— wherein $R_7$ is hydrogen or substituted or unsubstituted alkyl, $R_c$ and $R_d$ are hydrogen or substituted or unsubstituted alkyl, 'r' is 1, 2, or 3; Z is —$OR_6$ or $NR_{10}R_{11}$ wherein $R_6$ is selected from hydrogen, substituted or unsubstituted alkyl, substituted or unsubstituted haloalkyl, substituted or unsubstituted aryl or substituted or unsubstituted arylalkyl; $R_{10}$ and $R_{11}$ may be same or different and are independently selected from hydrogen, substituted or unsubstituted alkyl, —$(CR_cR_d)_r$—C(O)OH, —$(CR_cR_d)_r$—C(O)O-alkyl, substituted or unsubstituted cycloalkyl or $R_{10}$ and $R_{11}$ together may form a substituted or unsubstituted, saturated or unsaturated 3 to 12 membered cyclic ring, where the unsaturated cyclic ring may have one or two double bonds; and 'n' is 1, 2 or 3;

or its pharmaceutically acceptable salt thereof.

17. The compound of claim 1, which is selected from:

Methyl 2-fluoro-5-((2R,4R)-2-((((R)-1-(naphthalen-1-yl)ethyl)amino)methyl)chroman-4-yl)benzoate;

Methyl 2-fluoro-5-((2R,4S)-2-((((R)-1-(naphthalen-1-yl)ethyl)amino)methyl)chroman-4-yl)benzoate;

Methyl-3-((2R,4S)-2-((((R)-1-(naphthalen-1-yl)ethyl)amino)methyl)chroman-4-yl)benzoate;

Methyl 2-methyl-3-((2R,4S)-2-((((R)-1-(naphthalen-1-yl)ethyl)amino)methyl)chroman-4-yl)benzoate;

Methyl 3-methyl-5-((2R,4S)-2-((((R)-1-(naphthalen-1-yl)ethyl)amino)methyl)chroman-4-yl)benzoate;

Methyl 4-methyl-3-((2R,4S)-2-((((R)-1-(naphthalen-1-yl)ethyl)amino)methyl)chroman-4-yl)benzoate;

Methyl 2-ethyl-5-((2R,4R)-2-((((R)-1-(naphthalen-1-yl)ethyl)amino)methyl)chroman-4-yl)benzoate;

Methyl 2-ethyl-5-((2R,4S)-2-((((R)-1-(naphthalen-1-yl)ethyl)amino)methyl)chroman-4-yl)benzoate;

Methyl 2-isopropyl-5-((2R,4S)-2-((((R)-1-(naphthalen-1-yl)ethyl)amino)methyl)chroman-4-yl)benzoate;

Methyl 2-cyclopropyl-5-((2R,4R)-2-((((R)-1-(naphthalen-1-yl)ethyl)amino)methyl)chroman-4-yl)benzoate;

Methyl 2-cyclopropyl-5-((2R,4S)-2-((((R)-1-(naphthalen-1-yl)ethyl)amino)methyl)chroman-4-yl)benzoate;

Methyl 2,6-difluoro-3-((2R,4R)-2-((((R)-1-(naphthalen-1-yl)ethyl)amino)methyl)chroman-4-yl)benzoate;

Methyl 4-fluoro-2-methyl-3-((2R,4R)-2-((((R)-1-(naphthalen-1-yl)ethyl)amino)methyl)chroman-4-yl)benzoate;

Methyl 4-fluoro-2-methyl-3-((2R,4S)-2-((((R)-1-(naphthalen-1-yl)ethyl)amino)methyl)chroman-4-yl)benzoate;

Methyl 2,3-dimethyl-5-((2R,4S)-2-((((R)-1-(naphthalen-1-yl)ethyl)amino)methyl)chroman-4-yl)benzoate;

Methyl 5-((2R,4S)-2-((((R)-1-(naphthalen-1-yl)ethyl)amino)methyl)chroman-4-yl)-2-(trifluoromethyl)benzoate;

Methyl 2-methyl-5-((2R,4R)-2-((((R)-1-(naphthalen-1-yl)ethyl)amino)methyl)chroman-4-yl)benzoate;

Methyl 2-methyl-5-((2R,4S)-2-((((R)-1-(naphthalen-1-yl)ethyl)amino)methyl)chroman-4-yl)benzoate;

Methyl 2-fluoro-3-((2R,4R)-2-((((R)-1-(naphthalen-1-yl)ethyl)amino)methyl)chroman-4-yl)benzoate;

Methyl 3-fluoro-5-((2R,4S)-2-((((R)-1-(naphthalen-1-yl)ethyl)amino)methyl)chroman-4-yl)benzoate;

Methyl 4-fluoro-3-((2R,4R)-2-((((R)-1-(naphthalen-1-yl)ethyl)amino)methyl)chroman-4-yl)benzoate;

Methyl 2-methoxy-5-((2R,4S)-2-((((R)-1-(naphthalen-1-yl)ethyl)amino)methyl)chroman-4-yl)benzoate;

Methyl 2-methoxy-3-((2R,4R)-2-((((R)-1-(naphthalen-1-yl)ethyl)amino)methyl)chroman-4-yl)benzoate;
Methyl 2-methoxy-3-((2R,4S)-2-((((R)-1-(naphthalen-1-yl)ethyl)amino)methyl)chroman-4-yl)benzoate;
Methyl 4-methoxy-3-((2R,4R)-2-((((R)-1-(naphthalen-1-yl)ethyl)amino)methyl)chroman-4-yl)benzoate;
Methyl 2-(2-methyl-5-((2R,4S)-2-((((R)-1-(naphthalen-1-yl)ethyl)amino)methyl)chroman-4-yl)phenoxy)acetate;
Methyl 2-(3-methyl-5-((2R,4S)-2-((((R)-1-(naphthalen-1-yl)ethyl)amino)methyl)chroman-4-yl)phenoxy)acetate;
Methyl 2-(2-fluoro-5-((2R,4R)-2-((((R)-1-(naphthalen-1-yl)ethyl)amino)methyl)chroman-4-yl)phenoxy)acetate;
Methyl 2-(2-fluoro-5-((2R,4S)-2-((((R)-1-(naphthalen-1-yl)ethyl)amino)methyl)chroman-4-yl)phenoxy)acetate;
Methyl 2-(2-fluoro-3-((2R,4R)-2-((((R)-1-(naphthalen-1-yl)ethyl)amino)methyl)chroman-4-yl)phenoxy)acetate;
Methyl 2-(3-fluoro-5-((2R,4R)-2-((((R)-1-(naphthalen-1-yl)ethyl)amino)methyl)chroman-4-yl)phenoxy)acetate;
Methyl 2-(3-fluoro-5-((2R,4S)-2-((((R)-1-(naphthalen-1-yl)ethyl)amino)methyl)chroman-4-yl)phenoxy)acetate;
Methyl 2-(4-fluoro-3-((2R,4R)-2-((((R)-1-(naphthalen-1-yl)ethyl)amino)methyl)chroman-4-yl)phenoxy)acetate;
Methyl 2-methyl-2-(3-((2R,4S)-2-((((R)-1-(naphthalen-1-yl)ethyl)amino)methyl)chroman-4-yl)phenoxy)propanoate;
Methyl 4-((2R,4R)-2-((((R)-1-(naphthalen-1-yl)ethyl)amino)methyl)chroman-4-yl)benzoate;
Methyl 4-((2R,4S)-2-((((R)-1-(naphthalen-1-yl)ethyl)amino)methyl)chroman-4-yl)benzoate;
Methyl 2-methyl-4-((2R,4R)-2-((((R)-1-(naphthalen-1-yl)ethyl)amino)methyl)chroman-4-yl)benzoate;
Methyl 2-methyl-4-((2R,4S)-2-((((R)-1-(naphthalen-1-yl)ethyl)amino)methyl)chroman-4-yl)benzoate;
Methyl 4-((2R,4R)-2-((((R)-1-(naphthalen-1-yl)ethyl)amino)methyl)chroman-4-yl)-2-(trifluoromethyl)benzoate;
Methyl 4-((2R,4S)-2-((((R)-1-(naphthalen-1-yl)ethyl)amino)methyl)chroman-4-yl)-2-(trifluoromethyl)benzoate;
Methyl 2,6-difluoro-4-((2R,4S)-2-((((R)-1-(naphthalen-1-yl)ethyl)amino)methyl)chroman-4-yl)benzoate;
Methyl 3-methoxy-4-((2R,4R)-2-((((R)-1-(naphthalen-1-yl)ethyl)amino)methyl)chroman-4-yl)benzoate;
Methyl 3-methoxy-4-((2R,4R)-2-((((R)-1-(naphthalen-1-yl)ethyl)amino)methyl)chroman-4-yl)benzoate;
Methyl 3-fluoro-4-((2R,4R)-2-((((R)-1-(naphthalen-1-yl)ethyl)amino)methyl)chroman-4-yl)benzoate;
Methyl 2-fluoro-4-((2R,4S)-2-((((R)-1-(naphthalen-1-yl)ethyl)amino)methyl)chroman-4-yl)benzoate;
Methyl 2-(4-((2R,4R)-2-((((R)-1-(naphthalen-1-yl)ethyl)amino)methyl)chroman-4-yl)phenoxy)acetate;
Methyl 2-(4-((2R,4S)-2-((((R)-1-(naphthalen-1-yl)ethyl)amino)methyl)chroman-4-yl)phenoxy)acetate;
Methyl 2-(2-fluoro-4-((2R,4R)-2-((((R)-1-(naphthalen-1-yl)ethyl)amino)methyl)chroman-4-yl)phenoxy)acetate;
Methyl 2-(2-fluoro-4-((2R,4S)-2-((((R)-1-(naphthalen-1-yl)ethyl)amino)methyl)chroman-4-yl)phenoxy)acetate;
Methyl 2-(4-((2R,4R)-2-((((R)-1-(naphthalen-1-yl)ethyl)amino)methyl)chroman-4-yl)phenyl)acetate;
Methyl 2-(4-((2R,4S)-2-((((R)-1-(naphthalen-1-yl)ethyl)amino)methyl)chroman-4-yl)phenyl)acetate;
Methyl 2-methyl-2-(4-((2R,4R)-2-((((R)-1-(naphthalen-1-yl)ethyl)amino)methyl)chroman-4-yl)phenyl)propanoate;
Methyl 2-methyl-2-(4-((2R,4S)-2-((((R)-1-(naphthalen-1-yl)ethyl)amino)methyl)chroman-4-yl)phenyl)propanoate;

Methyl 3-methyl-4-((2R,4S)-2-((((R)-1-(naphthalen-1-yl)ethyl)amino)methyl)chroman-4-yl)benzoate;
Methyl 2-fluoro-5-((2S,4R)-2-((((R)-1-(naphthalen-1-yl)ethyl)amino)methyl)chroman-4-yl)benzoate;
Methyl 3-((2S,4R)-2-((((R)-1-(naphthalen-1-yl)ethyl)amino)methyl)chroman-4-yl)benzoate;
Methyl 2-methyl-5-((2S,4R)-2-((((R)-1-(naphthalen-1-yl)ethyl)amino)methyl)chroman-4-yl)benzoate;
Methyl 2-methyl-5-((2S,4S)-2-((((R)-1-(naphthalen-1-yl)ethyl)amino)methyl)chroman-4-yl)benzoate;
Methyl 2-(4-((2S,4R)-2-((((R)-1-(naphthalen-1-yl)ethyl)amino)methyl)chroman-4-yl)phenoxy)acetate;
Methyl 2-(4-((2S,4S)-2-((((R)-1-(naphthalen-1-yl)ethyl)amino)methyl)chroman-4-yl)phenoxy)acetate;
Methyl 5-((2R,4R)-2-((((R)-1-(4-fluoronaphthalen-1-yl)ethyl)amino)methyl)chroman-4-yl)-2-methylbenzoate;
Methyl 5-((2R,4S)-2-((((R)-1-(4-fluoronaphthalen-1-yl)ethyl)amino)methyl)chroman-4-yl)-2-methylbenzoate;
Methyl 3-((2R,4R)-2-((((R)-1-(4-fluoronaphthalen-1-yl)ethyl)amino)methyl)chroman-4-yl)-2-methoxybenzoate;
Methyl 3-((2R,4S)-2-((((R)-1-(4-fluoronaphthalen-1-yl)ethyl)amino)methyl)chroman-4-yl)-2-methoxybenzoate;
Methyl 4-((2R)-2-((((R)-1-(4-fluoro-3-methoxyphenyl)ethyl)amino)methyl)chroman-4-yl)-2-methylbenzoate;
Methyl 3-((2R)-2-((((R)-1-(4-fluoro-3-methoxyphenyl)ethyl)amino)methyl)chroman-4-yl)-2-methylbenzoate;
Methyl 5-((2R)-2-((((R)-1-(4-fluoro-3-methoxyphenyl)ethyl)amino)methyl)chroman-4-yl)-2-methylbenzoate;
Methyl 3-((2R)-2-((((R)-1-(4-fluoro-3-methoxyphenyl)ethyl)amino)methyl)chroman-4-yl)-5-methylbenzoate;
Methyl 3-((2R)-2-((((R)-1-(4-fluoro-3-methoxyphenyl)ethyl)amino)methyl)chroman-4-yl)-4-methylbenzoate;
Methyl 2-fluoro-5-((2S,4R)-2-(2-(((R)-1-(naphthalen-1-yl)ethyl)amino)ethyl)chroman-4-yl)benzoate;
Methyl 2-fluoro-5-((2R,4S)-2-(2-(((R)-1-(naphthalen-1-yl)ethyl)amino)ethyl)chroman-4-yl)benzoate;
Methyl 2-methyl-5-((2S,4R)-2-(2-(((R)-1-(naphthalen-1-yl)ethyl)amino)ethyl)chroman-4-yl)benzoate;
Methyl 2-methyl-5-((2R,4S)-2-(2-(((R)-1-(naphthalen-1-yl)ethyl)amino)ethyl)chroman-4-yl)benzoate;
Methyl 2-methoxy-3-((2R,4R)-2-(2-(((R)-1-(naphthalen-1-yl)ethyl)amino)ethyl)chroman-4-yl)benzoate;
Methyl 5-((2S,4R)-2-(2-(((R)-1-(4-fluoronaphthalen-1-yl)ethyl)amino)ethyl)chroman-4-yl)-2-methylbenzoate;
Methyl 5-((2R,4S)-2-(2-(((R)-1-(4-fluoronaphthalen-1-yl)ethyl)amino)ethyl)chroman-4-yl)-2-methylbenzoate;
Methyl 5-((2S,4R)-2-(2-(((R)-1-(4-fluoro-3-methoxyphenyl)ethyl)amino)ethyl)chroman-4-yl)-2-methylbenzoate;
Methyl 5-((2R,4S)-2-(2-(((R)-1-(4-fluoro-3-methoxyphenyl)ethyl)amino)ethyl)chroman-4-yl)-2-methylbenzoate;
Methyl 2-fluoro-5-((2S,4S)-2-(3-(((R)-1-(naphthalen-1-yl)ethyl)amino)propyl)chroman-4-yl)benzoate;
Methyl 2-fluoro-5-((2R,4R)-2-(3-(((R)-1-(naphthalen-1-yl)ethyl)amino)propyl)chroman-4-yl)benzoate;
Methyl 2-methyl-5-((2S,4S)-2-(3-(((R)-1-(naphthalen-1-yl)ethyl)amino)propyl)chroman-4-yl)benzoate;
Methyl 2-methyl-5-((2R,4R)-2-(3-(((R)-1-(naphthalen-1-yl)ethyl)amino)propyl)chroman-4-yl)benzoate;
Methyl 5-((2S,4S)-2-(3-(((R)-1-(4-fluoro-3-methoxyphenyl)ethyl)amino)propyl)chroman-4-yl)-2-methylbenzoate;

Methyl 4-((2S,4S)-2-(3-(((R)-1-(4-fluoronaphthalen-1-yl)ethyl)amino)propyl)chroman-4-yl)-3-methylbenzoate;

Methyl 4-((2S,4S)-2-(3-(((R)-1-(4-fluoronaphthalen-1-yl)ethyl)amino)propyl)chroman-4-yl)benzoate;

Methyl 5-((2S,4S)-2-(3-(((R)-1-(4-fluoronaphthalen-1-yl)ethyl)amino)propyl)chroman-4-yl)-2-methylbenzoate;

2,6-Dimethyl-3-((2R,4S)-2-((((R)-1-(naphthalen-1-yl)ethyl)amino)methyl)chroman-4-yl)benzoic acid hydrochloride;

2,6-Dimethyl-3-((2R,4S)-2-(2-(((R)-1-(naphthalen-1-yl)ethyl)amino)ethyl)chroman-4-yl)benzoic acid hydrochloride;

2,6-Dimethyl-3-((2R,4R)-2-(3-(((R)-1-(naphthalen-1-yl)ethyl)amino)propyl)chroman-4-yl)benzoic acid hydrochloride;

2,6-Dimethyl-3-((2S,4S)-2-(3-(((R)-1-(naphthalen-1-yl)ethyl)amino)propyl)chroman-4-yl)benzoic acid hydrochloride;

3-((2S,4S)-2-(3-(((R)-1-(4-Fluoro-3-methoxyphenyl)ethyl)amino)propyl)chroman-4-yl)-2,6-dimethylbenzoic acid hydrochloride;

2-Fluoro-5-((2R,4R)-2-((((R)-1-(naphthalen-1-yl)ethyl)amino)methyl)chroman-4-yl)benzoic acid hydrochloride;

2-Fluoro-5-((2R,4S)-2-((((R)-1-(naphthalen-1-yl)ethyl)amino)methyl)chroman-4-yl)benzoic acid hydrochloride;

3-((2R,4S)-2-((((R)-1-(Naphthalen-1-yl)ethyl)amino)methyl)chroman-4-yl)benzoic acid hydrochloride;

2-Methyl-3-((2R,4S)-2-((((R)-1-(naphthalen-1-yl)ethyl)amino)methyl)chroman-4-yl)benzoic acid hydrochloride;

3-Methyl-5-((2R,4S)-2-((((R)-1-(naphthalen-1-yl)ethyl)amino)methyl)chroman-4-yl)benzoic acid hydrochloride;

4-Methyl-3-((2R,4S)-2-((((R)-1-(naphthalen-1-yl)ethyl)amino)methyl)chroman-4-yl)benzoic acid hydrochloride;

2-Ethyl-5-((2R,4R)-2-((((R)-1-(naphthalen-1-yl)ethyl)amino)methyl)chroman-4-yl)benzoic acid hydrochloride;

2-Ethyl-5-((2R,4S)-2-((((R)-1-(naphthalen-1-yl)ethyl)amino)methyl)chroman-4-yl)benzoic acid hydrochloride;

2-Isopropyl-5-((2R,4S)-2-((((R)-1-(naphthalen-1-yl)ethyl)amino)methyl)chroman-4-yl)benzoic acid hydrochloride;

2-Cyclopropyl-5-((2R,4R)-2-((((R)-1-(naphthalen-1-yl)ethyl)amino)methyl)chroman-4-yl)benzoic acid hydrochloride;

2-Cyclopropyl-5-((2R,4S)-2-((((R)-1-(naphthalen-1-yl)ethyl)amino)methyl)chroman-4-yl)benzoic acid hydrochloride;

2,6-Difluoro-3-((2R,4R)-2-((((R)-1-(naphthalen-1-yl)ethyl)amino)methyl)chroman-4-yl)benzoic acid hydrochloride;

4-Fluoro-2-methyl-3-((2R,4S)-2-((((R)-1-(naphthalen-1-yl)ethyl)amino)methyl)chroman-4-yl)benzoic acid hydrochloride;

4-Fluoro-2-methyl-3-((2R,4R)-2-((((R)-1-(naphthalen-1-yl)ethyl)amino)methyl)chroman-4-yl)benzoic acid hydrochloride;

2,3-Dimethyl-5-((2R,4S)-2-((((R)-1-(naphthalen-1-yl)ethyl)amino)methyl)chroman-4-yl)benzoic acid hydrochloride;

5-((2R,4S)-2-((((R)-1-(Naphthalen-1-yl)ethyl)amino)methyl)chroman-4-yl)-2-(trifluoromethyl)benzoic acid hydrochloride;

2-Methyl-5-((2R,4R)-2-((((R)-1-(naphthalen-1-yl)ethyl)amino)methyl)chroman-4-yl)benzoic acid hydrochloride;

2-Methyl-5-((2R,4S)-2-((((R)-1-(naphthalen-1-yl)ethyl)amino)methyl)chroman-4-yl)benzoic acid hydrochloride;

2-Fluoro-3-((2R,4R)-2-((((R)-1-(naphthalen-1-yl)ethyl)amino)methyl)chroman-4-yl)benzoic acid hydrochloride;

3-Fluoro-5-((2R,4S)-2-((((R)-1-(naphthalen-1-yl)ethyl)amino)methyl)chroman-4-yl)benzoic acid hydrochloride;

4-Fluoro-3-((2R,4R)-2-((((R)-1-(naphthalen-1-yl)ethyl)amino)methyl)chroman-4-yl)benzoic acid hydrochloride;

2-Methoxy-5-((2R,4S)-2-((((R)-1-(naphthalen-1-yl)ethyl)amino)methyl)chroman-4-yl)benzoic acid hydrochloride;

2-Methoxy-3-((2R,4S)-2-((((R)-1-(naphthalen-1-yl)ethyl)amino)methyl)chroman-4-yl)benzoic acid hydrochloride;

2-Methoxy-3-((2R,4R)-2-((((R)-1-(naphthalen-1-yl)ethyl)amino)methyl)chroman-4-yl)benzoic acid hydrochloride;

4-Methoxy-3-((2R,4R)-2-((((R)-1-(naphthalen-1-yl)ethyl)amino)methyl)chroman-4-yl)benzoic acid hydrochloride;

2-(2-Methyl-5-((2R,4S)-2-((((R)-1-(naphthalen-1-yl)ethyl)amino)methyl)chroman-4-yl)phenoxy)acetic acid hydrochloride;

2-(3-Methyl-5-((2R,4S)-2-((((R)-1-(naphthalen-1-yl)ethyl)amino)methyl)chroman-4-yl)phenoxy)acetic acid hydrochloride;

2-(2-Fluoro-5-((2R,4R)-2-((((R)-1-(naphthalen-1-yl)ethyl)amino)methyl)chroman-4-yl)phenoxy)acetic acid hydrochloride;

2-(2-Fluoro-5-((2R,4S)-2-((((R)-1-(naphthalen-1-yl)ethyl)amino)methyl)chroman-4-yl)phenoxy)acetic acid hydrochloride;

2-(2-Fluoro-3-((2R,4R)-2-((((R)-1-(naphthalen-1-yl)ethyl)amino)methyl)chroman-4-yl)phenoxy)acetic acid hydrochloride;

2-(3-Fluoro-5-((2R,4R)-2-((((R)-1-(naphthalen-1-yl)ethyl)amino)methyl)chroman-4-yl)phenoxy)acetic acid hydrochloride;

2-(3-Fluoro-5-((2R,4S)-2-((((R)-1-(naphthalen-1-yl)ethyl)amino)methyl)chroman-4-yl)phenoxy)acetic acid hydrochloride;

2-(4-Fluoro-3-((2R,4R)-2-((((R)-1-(naphthalen-1-yl)ethyl)amino)methyl)chroman-4-yl)phenoxy)acetic acid hydrochloride;

2-Methyl-2-(3-((2R,4S)-2-((((R)-1-(naphthalen-1-yl)ethyl)amino)methyl)chroman-4-yl)phenoxy)propanoic acid hydrochloride;

4-((2R,4R)-2-((((R)-1-(Naphthalen-1-yl)ethyl)amino)methyl)chroman-4-yl)benzoic acid hydrochloride;

4-((2R,4S)-2-((((R)-1-(Naphthalen-1-yl)ethyl)amino)methyl)chroman-4-yl)benzoic acid hydrochloride;

2-Methyl-4-((2R,4R)-2-((((R)-1-(naphthalen-1-yl)ethyl)amino)methyl)chroman-4-yl)benzoic acid hydrochloride;

2-Methyl-4-((2R,4S)-2-((((R)-1-(naphthalen-1-yl)ethyl)amino)methyl)chroman-4-yl)benzoic acid hydrochloride;

4-((2R,4R)-2-((((R)-1-(Naphthalen-1-yl)ethyl)amino)methyl)chroman-4-yl)-2-(trifluoromethyl)benzoic acid hydrochloride;

4-((2R,4S)-2-((((R)-1-(Naphthalen-1-yl)ethyl)amino)methyl)chroman-4-yl)-2-(trifluoromethyl)benzoic acid hydrochloride;

2,6-Difluoro-4-((2R,4S)-2-((((R)-1-(naphthalen-1-yl)ethyl)amino)methyl)chroman-4-yl)benzoic acid hydrochloride;

3-Methoxy-4-((2R,4R)-2-((((R)-1-(naphthalen-1-yl)ethyl)amino)methyl)chroman-4-yl)benzoic acid hydrochloride;

3-Methoxy-4-((2R,4S)-2-((((R)-1-(naphthalen-1-yl)ethyl)amino)methyl)chroman-4-yl)benzoic acid hydrochloride;

3-Fluoro-4-((2R,4R)-2-((((R)-1-(naphthalen-1-yl)ethyl)amino)methyl)chroman-4-yl)benzoic acid hydrochloride;

2-Fluoro-4-((2R,4S)-2-((((R)-1-(naphthalen-1-yl)ethyl)amino)methyl)chroman-4-yl)benzoic acid hydrochloride;

2-(4-((2R,4R)-2-((((R)-1-(Naphthalen-1-yl)ethyl)amino)methyl)chroman-4-yl)phenoxy)acetic acid hydrochloride;

2-(4-((2R,4S)-2-((((R)-1-(Naphthalen-1-yl)ethyl)amino)methyl)chroman-4-yl)phenoxy)acetic acid hydrochloride;

2-(2-Fluoro-4-((2R,4R)-2-((((R)-1-(naphthalen-1-yl)ethyl)amino)methyl)chroman-4-yl)phenoxy)acetic acid hydrochloride;

2-(2-Fluoro-4-((2R,4S)-2-((((R)-1-(naphthalen-1-yl)ethyl)amino)methyl)chroman-4-yl)phenoxy)acetic acid hydrochloride;

2-(4-((2R,4R)-2-((((R)-1-(Naphthalen-1-yl)ethyl)amino)methyl)chroman-4-yl)phenyl)acetic acid hydrochloride;

2-(4-((2R,4S)-2-((((R)-1-(Naphthalen-1-yl)ethyl)amino)methyl)chroman-4-yl)phenyl)acetic acid hydrochloride;

2-Methyl-2-(4-((2R,4R)-2-((((R)-1-(naphthalen-1-yl)ethyl)amino)methyl)chroman-4-yl)phenyl)propanoic acid hydrochloride;

2-Methyl-2-(4-((2R,4S)-2-((((R)-1-(naphthalen-1-yl)ethyl)amino)methyl)chroman-4-yl)phenyl)propanoic acid hydrochloride;

3-Methyl-4-((2R,4S)-2-((((R)-1-(naphthalen-1-yl)ethyl)amino)methyl)chroman-4-yl)benzoic acid hydrochloride;

2-Fluoro-5-((2S,4R)-2-((((R)-1-(naphthalen-1-yl)ethyl)amino)methyl)chroman-4-yl)benzoic acid hydrochloride;

3-((2S,4R)-2-((((R)-1-(Naphthalen-1-yl)ethyl)amino)methyl)chroman-4-yl)benzoic acid hydrochloride;

2-Methyl-5-((2S,4R)-2-((((R)-1-(naphthalen-1-yl)ethyl)amino)methyl)chroman-4-yl)benzoic acid hydrochloride;

2-Methyl-5-((2S,4S)-2-((((R)-1-(naphthalen-1-yl)ethyl)amino)methyl)chroman-4-yl)benzoic acid hydrochloride;

2-(4-((2S,4R)-2-((((R)-1-(Naphthalen-1-yl)ethyl)amino)methyl)chroman-4-yl)phenoxy)acetic acid hydrochloride;

2-(4-((2S,4S)-2-((((R)-1-(Naphthalen-1-yl)ethyl)amino)methyl)chroman-4-yl)phenoxy)acetic acid hydrochloride;

4-((2R,4S)-2-((((R)-1-(4-Fluoro-3-methoxyphenyl)ethyl)amino)methyl)chroman-4-yl)-2-methylbenzoic acid hydrochloride;

3-((2R,4S)-2-((((R)-1-(4-Fluoro-3-methoxyphenyl)ethyl)amino)methyl)chroman-4-yl)-2-methylbenzoic acid hydrochloride;

5-((2R,4S)-2-((((R)-1-(4-Fluoro-3-methoxyphenyl)ethyl)amino)methyl)chroman-4-yl)-2-methyl benzoic acid hydrochloride;

3-((2R,4S)-2-((((R)-1-(4-Fluoro-3-methoxyphenyl)ethyl)amino)methyl)chroman-4-yl)-5-methylbenzoic acid hydrochloride;

3-((2R,4S)-2-((((R)-1-(4-Fluoro-3-methoxyphenyl)ethyl)amino)methyl)chroman-4-yl)-4-methylbenzoic acid hydrochloride;

5-((2R,4R)-2-((((R)-1-(4-Fluoronaphthalen-1-yl)ethyl)amino)methyl)chroman-4-yl)-2-methyl benzoic acid hydrochloride;

5-((2R,4S)-2-((((R)-1-(4-Fluoronaphthalen-1-yl)ethyl)amino)methyl)chroman-4-yl)-2-methyl benzoic acid hydrochloride;

3-((2R,4S)-2-((((R)-1-(4-Fluoronaphthalen-1-yl)ethyl)amino)methyl)chroman-4-yl)-2-methoxybenzoic acid hydrochloride;

3-((2R,4R)-2-((((R)-1-(4-Fluoronaphthalen-1-yl)ethyl)amino)methyl)chroman-4-yl)-2-methoxybenzoic acid hydrochloride;

2-Fluoro-5-((2S,4R)-2-(2-(((R)-1-(naphthalen-1-yl)ethyl)amino)ethyl)chroman-4-yl)benzoic acid hydrochloride;

2-Fluoro-5-((2S,4S)-2-(2-(((R)-1-(naphthalen-1-yl)ethyl)amino)ethyl)chroman-4-yl)benzoic acid hydrochloride;

2-Methyl-5-((2S,4R)-2-(2-(((R)-1-(naphthalen-1-yl)ethyl)amino)ethyl)chroman-4-yl)benzoic acid hydrochloride;

2-Methyl-5-((2S,4S)-2-(2-(((R)-1-(naphthalen-1-yl)ethyl)amino)ethyl)chroman-4-yl)benzoic acid hydrochloride;

2-Methoxy-3-((2R,4R)-2-(2-(((R)-1-(naphthalen-1-yl)ethyl)amino)ethyl)chroman-4-yl)benzoic acid hydrochloride;

5-((2S,4R)-2-(2-(((R)-1-(4-Fluoronaphthalen-1-yl)ethyl)amino)ethyl)chroman-4-yl)-2-methylbenzoic acid hydrochloride;

5-((2R,4S)-2-(2-(((R)-1-(4-Fluoronaphthalen-1-yl)ethyl)amino)ethyl)chroman-4-yl)-2-methylbenzoic acid hydrochloride;

5-((2S,4R)-2-(2-(((R)-1-(4-Fluoro-3-methoxy phenyl)ethyl)amino)ethyl)chroman-4-yl)-2-methylbenzoic acid hydrochloride;

5-((2R,4S)-2-(2-(((R)-1-(4-Fluoro-3-methoxy phenyl)ethyl)amino)ethyl)chroman-4-yl)-2-methylbenzoic acid hydrochloride;

2-Fluoro-5-((2S,4S)-2-(3-(((R)-1-(naphthalen-1-yl)ethyl)amino)propyl)chroman-4-yl)benzoic acid hydrochloride;

2-Fluoro-5-((2R,4R)-2-(3-(((R)-1-(naphthalen-1-yl)ethyl)amino)propyl)chroman-4-yl)benzoic acid hydrochloride;

2-Methyl-5-((2S,4S)-2-(3-(((R)-1-(naphthalen-1-yl)ethyl)amino)propyl)chroman-4-yl)benzoic acid hydrochloride;

2-Methyl-5-((2R,4R)-2-(3-(((R)-1-(naphthalen-1-yl)ethyl)amino)propyl)chroman-4-yl)benzoic acid hydrochloride;

5-((2S,4S)-2-(3-(((R)-1-(4-Fluoro-3-methoxyphenyl)ethyl)amino)propyl)chroman-4-yl)-2-methylbenzoic acid hydrochloride;

4-((2S,4S)-2-(3-(((R)-1-(4-Fluoronaphthalen-1-yl)ethyl)amino)propyl)chroman-4-yl)-3-methylbenzoic acid hydrochloride;

4-((2S,4S)-2-(3-(((R)-1-(4-Fluoronaphthalen-1-yl)ethyl)amino)propyl)chroman-4-yl)benzoic acid hydrochloride;

5-((2S,4S)-2-(3-(((R)-1-(4-Fluoronaphthalen-1-yl)ethyl)amino)propyl)chroman-4-yl)-2-methylbenzoic acid hydrochloride;

Methyl 2-(3-((2R,4S)-2-((((R)-1-(naphthalen-1-yl)ethyl)amino)methyl)chroman-4-yl)benzamido)acetate;

Methyl 2-(2-methyl-5-((2R,4S)-2-((((R)-1-(naphthalen-1-yl)ethyl)amino)methyl)chroman-4-yl)benzamido)acetate;

2-(3-((2R,4S)-2-((((R)-1-(Naphthalen-1-yl)ethyl)amino)methyl)chroman-4-yl)benzamido)acetic acid hydrochloride;

2-(2-Methyl-5-((2R,4S)-2-((((R)-1-(naphthalen-1-yl)ethyl)amino)methyl)chroman-4-yl)benzamido)acetic acid hydrochloride;

N,2-Dimethyl-5-((2R,4S)-2-((((R)-1-(naphthalen-1-yl)ethyl)amino)methyl)chroman-4-yl)benzamide hydrochloride;

N,N,2-Trimethyl-5-((2R,4S)-2-((((R)-1-(naphthalen-1-yl)ethyl)amino)methyl)chroman-4-yl)benzamide hydrochloride;

2-Methyl-5-((2R,4S)-2-((((R)-1-(naphthalen-1-yl)ethyl)amino)methyl)chroman-4-yl)benzamide hydrochloride;

N-Ethyl-N,2-dimethyl-5-((2R,4S)-2-((((R)-1-(naphthalen-1-yl)ethyl)amino)methyl)chroman-4-yl)benzamide hydrochloride;

N,N-Diethyl-2-methyl-5-((2R,4S)-2-((((R)-1-(naphthalen-1-yl)ethyl)amino)methyl)chroman-4-yl)benzamide hydrochloride; and (2-Methyl-5-((2R,4S)-2-((((R)-1-(naphthalen-1-yl)ethyl)amino)methyl)chroman-4-yl)phenyl)(pyrrolidin-1-yl)methanone hydrochloride;

or its pharmaceutically acceptable salt thereof.

18. A pharmaceutical composition comprising one or more compounds of Formula (I) according to claim 1, and one or more pharmaceutically acceptable excipients.

19. A method of treating, managing and/or lessening the diseases or disorders, syndromes or conditions associated with the modulation of calcium sensing receptor (CaSR) in a subject in need thereof wherein the method comprises administering to the subject a therapeutically effective amount of a compound of claim 1 or a pharmaceutically acceptable salt thereof.

20. The method of claim 19, wherein the diseases, disorders, syndromes or conditions associated with the modulation of calcium sensing receptor (CaSR) are selected from hyperparathyroidism, chronic renal failure (with or without dialysis), chronic kidney disease (with or without dialysis) and their complications.

21. The method of claim 20, wherein hyperparathyroidism is primary hyperparathyroidism, secondary hyperparathyroidism or tertiary hyperparathyroidism.

22. The method of claim 19, wherein the diseases, disorders, syndromes or conditions associated with the modulation of CaSR receptors are selected from the group consisting of parathyroid adenoma, parathyroid hyperplasia, parathyroid carcinoma, vascular & valvular calcification, abnormal calcium homeostasis, hypercalcemia, abnormal phosphorous homeostasis, hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which $(Ca^{2+})_e$ ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastro-intestinal tract by augmenting gastric acidity.

23. A process for the preparation of compound of Formula (Ib):

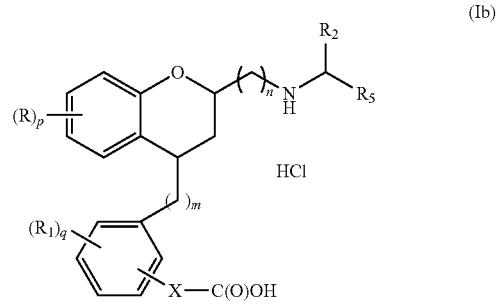

wherein X, R, $R_1$, $R_2$, $R_5$ 'm', 'n', 'p' and 'q' are as described in claim 1, the process comprising the steps of:

a) oxidizing a compound of Formula (15) by using suitable oxidation agents to give compound of Formula (16) in suitable solvent(s);

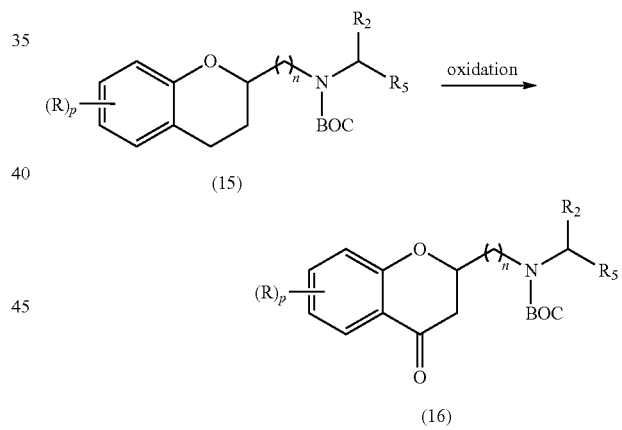

b) converting a compound of Formula (16) to compound of Formula (17) using PhNTf$_2$ (N-phenylbis(trifluoromethanesulfonimide) in presence of KHMDS (potassium hexamethyldisilazide);

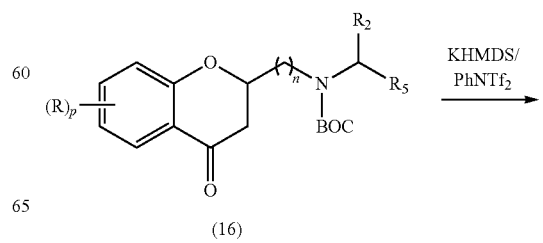

-continued

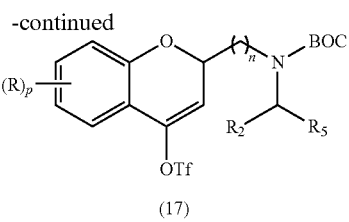
(17)

c) coupling of compound of Formula (17) with suitable aryl boronic acid or aryl boronic ester by following Suzuki coupling reaction to give compound of Formula (18) where Z is —OR$_6$ and R$_6$ is alkyl or benzyl;

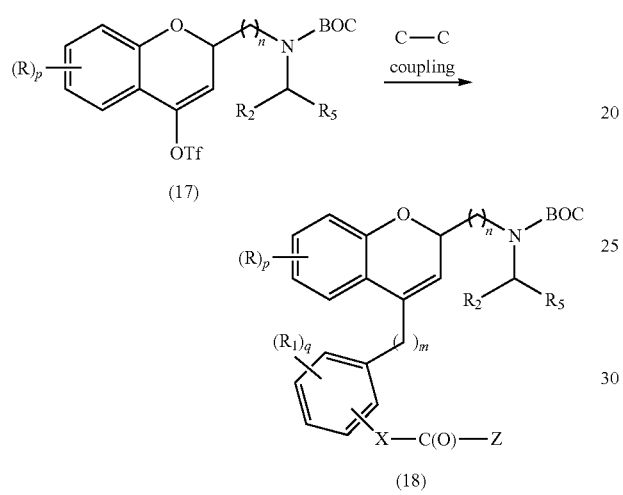

d) when Z is O-alkyl, then reducing the compound of Formula (18) with hydrogen over Palladium-Carbon to give ester compound of Formula (19) where Z is —O-alkyl;

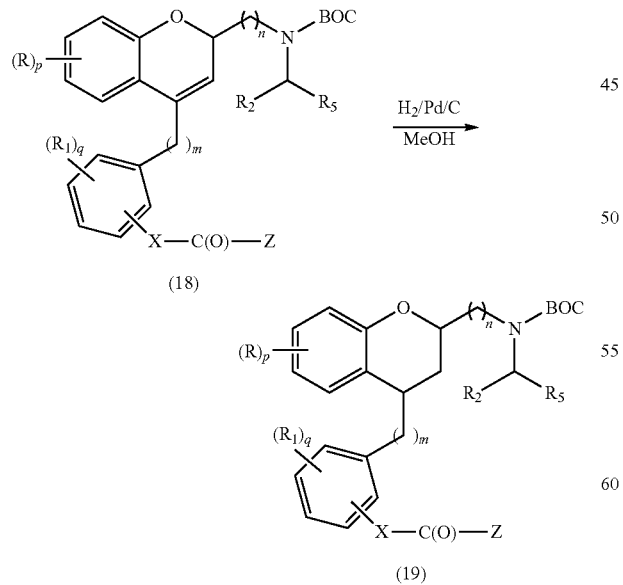

e) converting the compound of Formula (19) obtained in step d) to the compound of Formula (Ia);

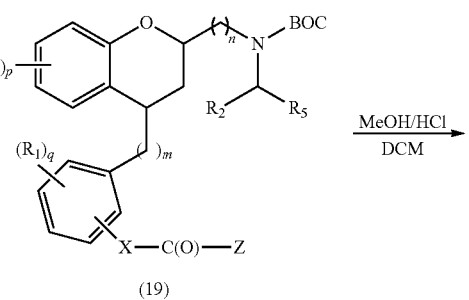
(19)

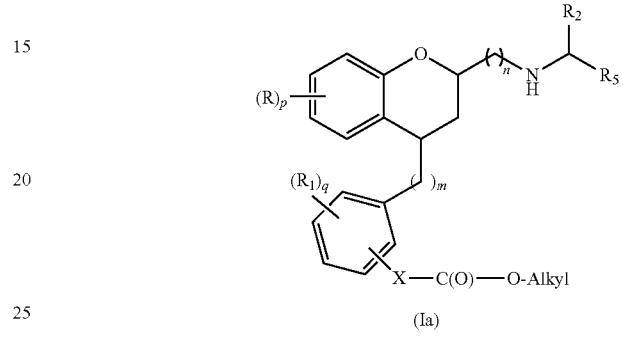
(Ia)

f) hydrolyzing the ester group in compound of Formula (Ia) to corresponding acid compound using suitable base and in suitable solvents;

g) converting the compound obtained in step f) to its hydrochloride salt having Formula (Ib);

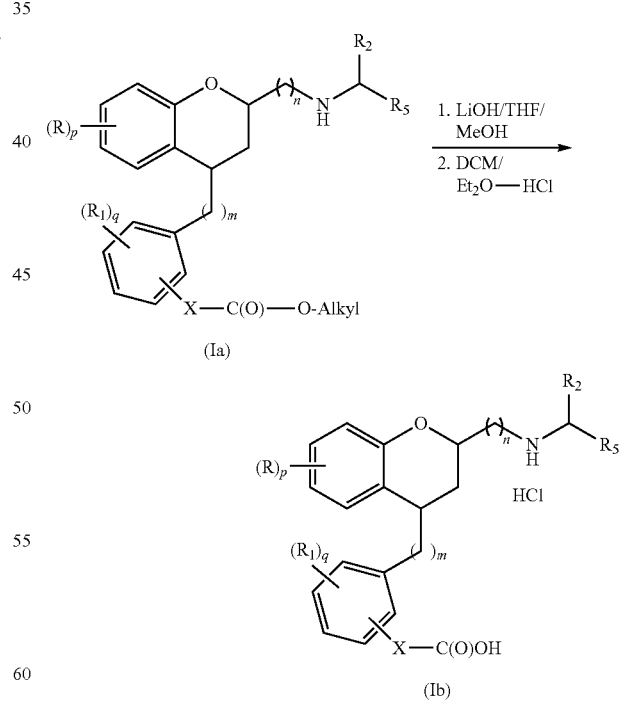

h) when Z is O-benzyl in compound of Formula (18), then reducing the compound of Formula (18) with hydrogen over Palladium-Carbon to give acid compound of Formula (19) where Z is OH;

189

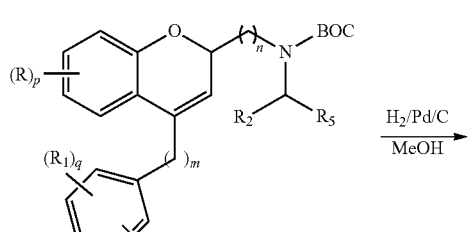

(18)

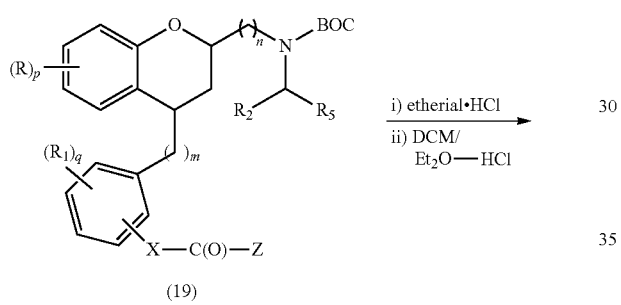

(19)

i) converting the compound of Formula (19) obtained in step h) to the compound of Formula (Ib);

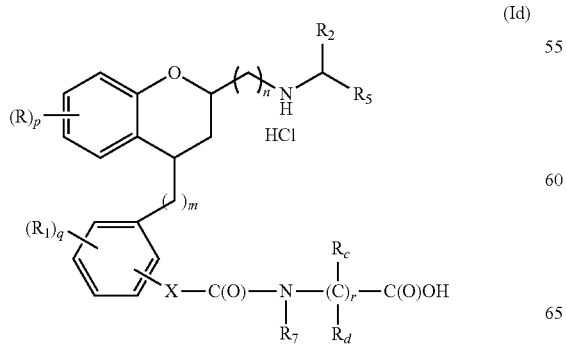

(19)

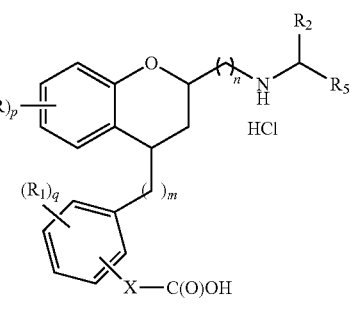

(Ib)

24. A process for the preparation of compound of Formula (Id):

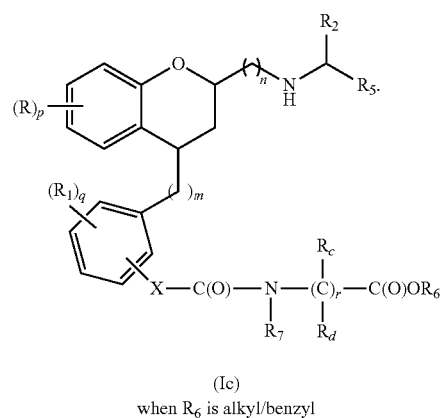

(Id)

190 wherein X, R, $R_1$, $R_2$, $R_5$, $R_7$, $R_c$, $R_d$ 'm', 'n', 'p', 'q' and 'r' are as described in claim 1, the process comprising the steps of:

a) coupling of acid compound of Formula (Ib) with suitable amines using suitable amide coupling reagents to give compound of Formula (Ic);

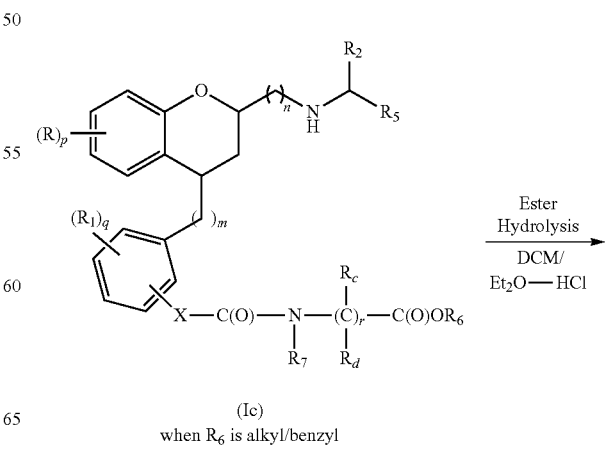

(Ib)

(Ic)
when $R_6$ is alkyl/benzyl b) hydrolyzing the amido ester group, if the compound of Formula (Ic) is an ester, to corresponding acid compound of Formula (Id) using suitable reagent and solvents (Ic)
when $R_6$ is alkyl/benzyl -continued

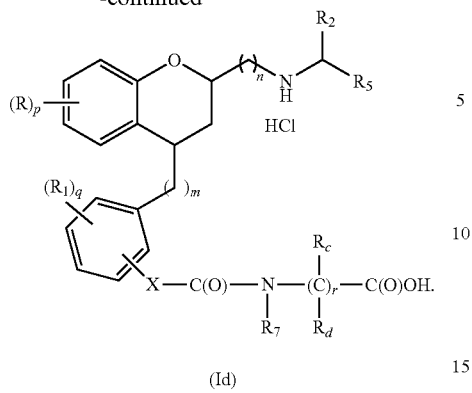

(Id)

25. A compound which is 2, 6-Dimethyl-3-((2R, 4S)-2-((((R)-1-(naphthalen-1-yl) ethyl) amino) methyl) chroman-4-yl)benzoic acid hydrochloride.

26. A compound which is 2-Methyl-5((2R,4S)-2-((((R)-1-(naphthalen-1-yl) ethyl)amino) methyl)chroman-4-yl)benzoic acid hydrochloride.

27. A compound which is 3-((2R,4S)-2-((((R)-1-(4-Fluoro-3-methoxyphenyl) ethyl) amino)methyl)chroman-4-yl)-5-methylbenzoic acid hydrochloride.

28. A compound which is 5-((2R,4 S)-2-((((R)-1-(4-Fluoronaphthalen-1-yl) ethyl) amino) methyl)chroman-4-yl)-2-methyl benzoic acid hydrochloride.

29. A compound which is 5-((2S,4R)-2-(2-(((R)-1-(4-Fluoro-3-methoxy phenyl) ethyl) amino) ethyl) chroman-4-yl)-2-methylbenzoic acid hydrochloride.

* * * * *